(12) United States Patent
Zhang et al.

(10) Patent No.: US 8,269,015 B2
(45) Date of Patent: Sep. 18, 2012

(54) 4-AZETIDINYL-1-HETEROARYL-CYCLO-HEXANE ANTAGONISTS OF CCR2

(75) Inventors: Xuqing Zhang, Audubon, PA (US); Heather Rae Hufnagel, Glenmoore, PA (US); Chaozhong Cai, North Wales, PA (US); James C. Lanter, Audubon, PA (US); Thomas P. Markotan, Morgantown, PA (US); Zhihua Sui, Spring House, PA (US)

(73) Assignee: Janssen Pharmaceutica N.V. (BE)

( * ) Notice: Subject to any disclaimer, the term of this patent is extended or adjusted under 35 U.S.C. 154(b) by 188 days.

(21) Appl. No.: 12/760,832

(22) Filed: Apr. 15, 2010

(65) Prior Publication Data
US 2010/0267688 A1    Oct. 21, 2010

Related U.S. Application Data

(60) Provisional application No. 61/169,876, filed on Apr. 16, 2009.

(51) Int. Cl.
C07D 401/00 (2006.01)
A01N 43/00 (2006.01)
(52) U.S. Cl. .................. 546/268.1; 514/210.1
(58) Field of Classification Search ................... None
See application file for complete search history.

(56) References Cited

U.S. PATENT DOCUMENTS

| | | | |
|---|---|---|---|
| 6,245,799 B1 | 6/2001 | Asselin et al. | |
| 6,255,315 B1 | 7/2001 | Patane et al. | |
| 2003/0004151 A1 | 1/2003 | Cherney et al. | |
| 2006/0069123 A1 | 3/2006 | Xia et al. | |
| 2010/0144695 A1 | 6/2010 | Zhang et al. | |
| 2010/0267668 A1 | 10/2010 | Zhang et al. | |
| 2010/0267689 A1 | 10/2010 | Zhang et al. | |

FOREIGN PATENT DOCUMENTS

| | | |
|---|---|---|
| EP | 1201239 | 5/2002 |
| WO | WO 2004/050024 | 6/2004 |
| WO | WO 2006/073592 | 7/2006 |
| WO | WO 2007/053498 | 5/2007 |
| WO | WO 2007/130712 | 11/2007 |

OTHER PUBLICATIONS

Silva, A. Mini-Rev.Med. Chem 2005 vol. 5, pp. 893-914.*
Vippagunta, S. Adv. Drug Deliv. Rev 2001 vol. 48, pp. 3-26.*
Dawson, et al, "Targeting Monocyte Chemoattractant Protein-1 Signalling in Disease", Expert Opin. Ther. Targets, 2003, vol. 7(1), pp. 35-48.
Seebach, et al, "Safe One-Pot Carbon-Carbon Bond Formation with Lithiated Nitrosamines Including Denitrosation by Sequential Reduction with Lithium a Aluminium Hydride and Raney-Nickel", Synthesis, 1979, vol. 6, pp. 423-424.
Gdaniec, et al., "Conformation and Stereodynamics of N,N-Dinitroso-2,4,6,8-tetraaryl-3,7-diazabicyclo [3.3.1] nonanes", J. Org. Chem., 1997 vol. 62, pp. 5619-5622.
Abdel-Magid, et al., "Reductive Amination of Aldehydes and Ketones with Sodium Triacetoxyborohydride. Studies on Direct and Indirect Reductive Amination Procedures", J. Org. Chem, 1996, vol. 61, pp. 3849-3862.
Chan, et al., "1,5-BIS (Trimethylsiloxy)-1,5-Dimethoxy-1-4-Pentadienes. Cyclopropance Synthesis Via Intramolecular Coupling", Tetrahedron Letters, 1982 vol. 23, No. 8, pp. 799-802.
Rollins, "Monocyte chemoattractant protein 1: a potential regulator of monocyte recruitment in inflammatory disease", 89Mol. Med. Today, 1996 vol. 2, pp. 198.
Das, B. et al. "A Highly Chemoselective Boc Protection of Amines using Sulfonic-Acid-Functionalized Silica as an Efficient Heterogeneous Recyclable Catalyst", Tetrahedron Lett. 2006, 47, 7551-7556.
Ingersoll, A. W. et. al., "Hippuric Acid", Organic Syntheses 1932, XII, vol. 12. pp. 40.
Xia M, Sui Z, "Recent Developments in CCR2 Antagonists", *Expert Opin. Ther. Patents*, 2009, 19(3), 295-303.

* cited by examiner

*Primary Examiner* — Janet Andres
*Assistant Examiner* — Heidi Reese
(74) *Attorney, Agent, or Firm* — Mary A. Appollina

(57) ABSTRACT

The present invention comprises compounds of Formula (I).

Formula (I)

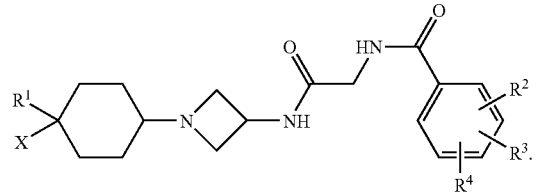

wherein: X, $R^1$, $R^2$, $R^3$, and $R^4$ are as defined in the specification. The invention also comprises a method of preventing, treating or ameliorating a syndrome, disorder or disease, wherein said syndrome, disorder or disease is type II diabetes, obesity and asthma. The invention also comprises a method of inhibiting CCR2 activity in a mammal by administration of a therapeutically effective amount of at least one compound of Formula (I).

17 Claims, No Drawings

4-AZETIDINYL-1-HETEROARYL-CYCLO-HEXANE ANTAGONISTS OF CCR2

CROSS-REFERENCE TO RELATED APPLICATIONS

This application claims priority from U.S. Provisional Application Ser. No. 61/169,876 filed Apr. 16, 2009, the contents of each of which are hereby incorporated by reference in their entirety.

FIELD OF THE INVENTION

The invention is directed to substituted dipiperidine compounds, which are antagonists to the chemoattractant cytokine receptor 2 (CCR2), pharmaceutical compositions, and methods for use thereof. More particularly, the CCR2 antagonists are substituted piperidyl acrylamide compounds useful for preventing, treating or ameliorating a CCR2 mediated syndrome, disorder or disease.

BACKGROUND OF THE INVENTION

CCR2 is a member of the GPCR family of receptors, as are all known chemokine receptors, and are expressed by monocytes and memory T-lymphocytes. The CCR2 signaling cascade involves activation of phospholipases (PLCβ2), protein kinases (PKC), and lipid kinases (PI-3 kinase).

Chemoattractant cytokines (i.e., chemokines) are relatively small proteins (8-10 kD), which stimulate the migration of cells. The chemokine family is divided into four subfamilies based on the number of amino acid residues between the first and second highly conserved cysteines.

Monocyte chemotactic protein-1 (MCP-1) is a member of the CC chemokine subfamily (wherein CC represents the subfamily having adjacent first and second cysteines) and binds to the cell-surface chemokine receptor 2 (CCR2). MCP-1 is a potent chemotactic factor, which, after binding to CCR2, mediates monocyte and lymphocyte migration (i.e., chemotaxis) toward a site of inflammation. MCP-1 is also expressed by cardiac muscle cells, blood vessel endothelial cells, fibroblasts, chondrocytes, smooth muscle cells, mesangial cells, alveolar cells, T-lymphocytes, marcophages, and the like.

After monocytes enter the inflammatory tissue and differentiate into macrophages, monocyte differentiation provides a secondary source of several proinflammatory modulators, including tumor necrosis factor-α (TNF-α), interleukin-1 (IL-1), IL-8 (a member of the CXC chemokine subfamily, wherein CXC represents one amino acid residue between the first and second cysteines), IL-12, arachidonic acid metabolites (e.g., $PGE_2$ and $LTB_4$), oxygen-derived free radicals, matrix metalloproteinases, and complement components.

Animal model studies of chronic inflammatory diseases have demonstrated that inhibition of binding between MCP-1 and CCR2 by an antagonist suppresses the inflammatory response. The interaction between MCP-1 and CCR2 has been implicated (see Rollins B J, Monocyte chemoattractant protein 1: a potential regulator of monocyte recruitment in inflammatory disease, *Mol. Med. Today,* 1996, 2:198; and Dawson J, et al., Targeting monocyte chemoattractant protein-1 signaling in disease, *Expert Opin. Ther. Targets,* 2003 Feb. 7 (1):35-48) in inflammatory disease pathologies such as psoriasis, uveitis, atherosclerosis, rheumatoid arthritis (RA), multiple sclerosis, Crohn's Disease, nephritis, organ allograft rejection, fibroid lung, renal insufficiency, type II diabetes and diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, Chronic Obstructive Pulmonary Disease (COPD), allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, and stomach.

Monocyte migration is inhibited by MCP-1 antagonists (either antibodies or soluble, inactive fragments of MCP-1), which have been shown to inhibit the development of arthritis, asthma, and uveitis. Both MCP-1 and CCR2 knockout (KO) mice have demonstrated that monocyte infiltration into inflammatory lesions is significantly decreased. In addition, such KO mice are resistant to the development of experimental allergic encephalomyelitis (EAE, a model of human MS), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in MCP-1 expression and the number of infiltrating macrophages.

MCP-1 has been implicated in the pathogenesis of seasonal and chronic allergic rhinitis, having been found in the nasal mucosa of most patients with dust mite allergies. MCP-1 has also been found to induce histamine release from basophils in vitro. During allergic conditions, both allergens and histamines have been shown to trigger (i.e., to up-regulate) the expression of MCP-1 and other chemokines in the nasal mucosa of people with allergic rhinitis, suggesting the presence of a positive feedback loop in such patients. There remains a need for small molecule CCR2 antagonists for preventing, treating or ameliorating a CCR2 mediated inflammatory syndrome, disorder or disease resulting from MCP-1 induced monocyte and lymphocyte migration to a site of inflammation. All documents cited herein are incorporated by reference.

SUMMARY OF THE INVENTION

The present invention comprises compounds of Formula (I):

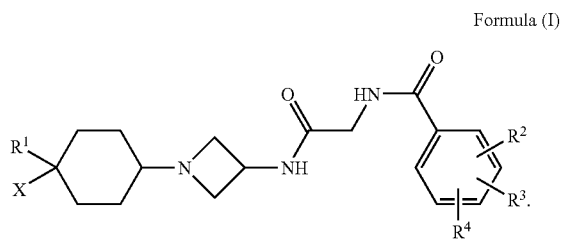

Formula (I)

wherein:
X is F, $NH_2$, or H;
$R^1$ is

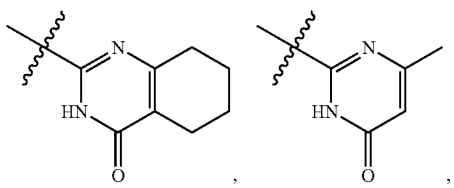

-continued

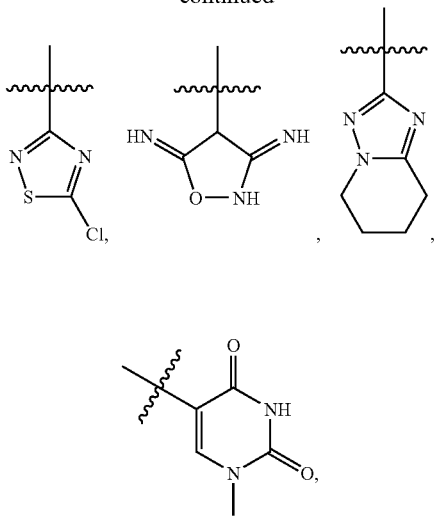

pyridyl, pyridyl-N-oxide, pyridin-2-onyl, indolyl, pyrazinyl, 3-H-thiazol-2-onyl, pyrimidyl, benzooxazolyl, oxazolyl, thiazolyl, isothiazolyl, pyrazolyl, imidazolyl, thiophenyl, furyl, [1,2,4]oxadiazolyl or [1,3,4]thiadiazolyl; wherein said pyridyl, pyridyl-N-oxide, pyrimidyl, pyrazolyl, imidazolyl, thiophenyl, or thiazolyl is optionally substituted with one substituent selected from the group consisting of $OC_{(1-4)}$ alkyl, $OC_{(3-6)}$cycloalkyl, $OCH_2CF_3$, $OCH_2Ph$, F, CN, Cl, $OCF_3$, $CF_3$, $CH_2CN$, $C_{(1-4)}$alkyl, $CH_2CF_3$, $N(C_{(1-4)}alkyl)_2$, $C_{(1-4)}alkylOH$, $Si(CH_3)_3$, —C≡CH, $SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, NHC(O)$CF_3$, $NHC_{(1-4)}$alkyl, $NHCO_2H$, $NHCO_2C_{(1-4)}$alkyl, $NHCOC_{(1-4)}$alkyl, $NHCONH_2$, $NHCONHC_{(1-4)}$alkyl, and Br; or said pyridyl may be substituted with one $OCH_3$ group and one $CH_3$; wherein said pyrimidyl is optionally substituted on any carbon atom with one $N(C_{(1-4)}alkyl)_2$ group; or said pyrimidinyl is substituted on any two carbon atoms with two substituents independently selected from the group consisting of OH, $OCH_3$, and $CH_3$; wherein said thiazolyl is substituted with $CO_2H$, $CONH_2$, $NHCO_2C_{(1-4)}$alkyl, or OH; or said thiazolyl is optionally substituted on two adjacent carbon atoms to form a fused bicyclic system benzothiazol-2-yl, wherein said benzothiazol-2-yl is optionally substituted with Br or $OCH_3$; wherein said pyridin-2-onyl is optionally substituted with one substituent selected from the group consisting of $CH_2CN$, $C_{(1-4)}$alkyl, $CH_2CF_3$, and $CH_2CH_2OH$, or said pyridin-2-onyl is substituted with 2 methyl groups; wherein said [1,2,4]oxadiazolyl is optionally substituted on any carbon atom with OH, $CCl_3$, or pyrrolidinyl;

$R^2$ is $C_{(1-4)}$alkyl, $NH_2$, $NO_2$, $NHCH_2CH_2OH$, $N(C_{(1-4)}alkyl)_2$, $N(SO_2CH_3)_2$, CN, F, Cl, Br, $CF_3$, $C_{(3-6)}$cycloalkyl, heterocyclyl, $OCF_3$, $OCF_2H$, $CF_2H$, or $OC_{(1-4)}$alkyl;

$R^3$ is H, F, Cl, $CF_3$, or $OC_{(1-4)}$alkyl; alternatively, $R^2$ and $R^3$ may be taken together with their attached phenyl to form a benzo[1,3]dioxolyl, 2,3-dihydro-benzofuranyl, or 2,3-dihydro-benzo[1,4]dioxinyl group;

$R^4$ is H, $OC_{(1-4)}$alkyl, or F;

and solvates, hydrates, tautomers, prodrugs, and pharmaceutically acceptable salts thereof.

DETAILED DESCRIPTION OF THE INVENTION

The present invention comprises compounds of Formula (I):

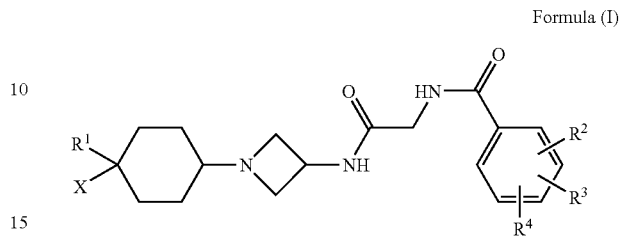

Formula (I)

wherein X, $R^1$, $R^2$, $R^3$ and $R^4$ are as defined above;

and solvates, hydrates, tautomers, prodrugs, and pharmaceutically acceptable salts thereof.

Another embodiment of the invention comprises compounds of Formula (Ia):

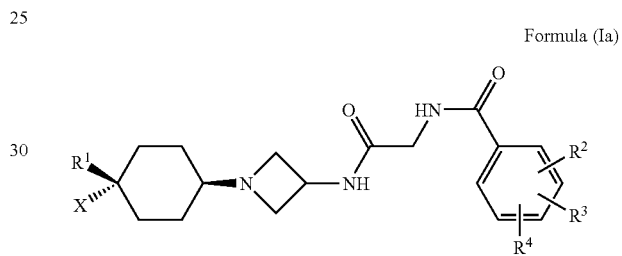

Formula (Ia)

wherein X, $R^1$, $R^2$, $R^3$ and $R^4$ are as defined above for Formula (I);

and solvates, hydrates, tautomers, prodrugs, and pharmaceutically acceptable salts thereof.

Another embodiment of the invention comprises compounds of Formula (I) and/or Formula (Ia) wherein:

X is F, or H;

$R^1$ is

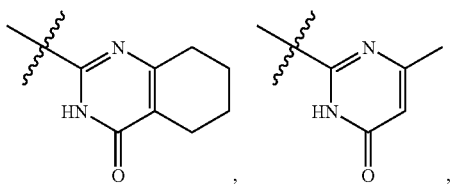

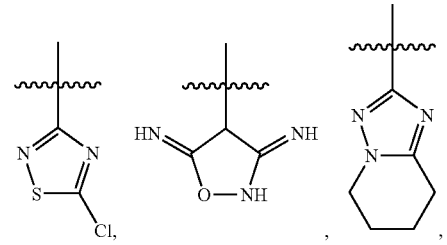

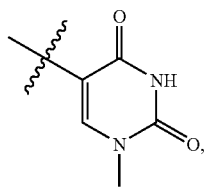

pyridyl, pyridyl-N-oxide, pyridin-2-onyl, indolyl, pyrazinyl, 3-H-thiazol-2-onyl, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, [1,2,4]oxadiazolyl or [1,3,4]thiadiazolyl; wherein said pyridyl, pyridyl-N-oxide, or thiazolyl is optionally substituted with one substituent selected from the group consisting of $OC_{(1-4)}$alkyl, $OC_{(3-6)}$cycloalkyl, $OCH_2CF_3$, $OCH_2Ph$, F, CN, $CH_2CN$, $C_{(1-4)}$alkyl, $CH_2CF_3$, $N(C_{(1-4)}alkyl)_2$, $C_{(1-4)}$alkylOH, $Si(CH_3)_3$, —C≡CH, $SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, $NHC(O)CH_3$, $NHC(O)CF_3$, $NHC_{(1-4)}$alkyl, and Br; or said pyridyl may be substituted with one $OCH_3$ group and one $CH_3$; wherein said pyrimidyl is optionally substituted on any carbon atom with one $N(C_{(1-4)}alkyl)_2$ group; or said pyrimidinyl is substituted on any two carbon atoms with one OH group and one $CH_3$; wherein said thiazolyl is substituted with $CO_2H$, $CONH_2$, $NHCO_2C_{(1-4)}$alkyl, or OH; or said thiazolyl is optionally substituted on two adjacent carbon atoms to form a fused bicyclic system benzothiazol-2-yl, wherein said benzothiazol-2-yl is optionally substituted with Br or $OCH_3$; wherein said pyridin-2-onyl is optionally substituted with one substituent selected from the group consisting of $CH_2CN$, $C_{(1-4)}$alkyl, $CH_2CF_3$, and $CH_2CH_2OH$, or said pyridin-2-onyl is substituted with 2 methyl groups; wherein said [1,2,4]oxadiazolyl is optionally substituted on any carbon atom with OH, $CCl_3$, or pyrrolidinyl;

$R^2$ is $C_{(1-4)}$alkyl, $NH_2$, $NO_2$, $NHCH_2CH_2OH$, $N(C_{(1-4)}alkyl)_2$, $N(SO_2CH_3)_2$, CN, F, Cl, Br, $CF_3$, pyrrolidinyl, $OCF_3$, $OCF_2H$, $CF_2H$, or $OC_{(1-4)}$alkyl;

$R^3$ is H, F, Cl, $CF_3$, or $OC_{(1-4)}$alkyl; alternatively, $R^2$ and $R^3$ may be taken together with their attached phenyl to form a benzo[1,3]dioxolyl group;

$R^4$ is H, $OCH_3$, or F;

and solvates, hydrates, tautomers, prodrugs, and pharmaceutically acceptable salts thereof.

Another embodiment of the invention comprises compounds of Formula (I) and/or Formula (Ia) wherein:

X is F, or H;

$R^1$ is

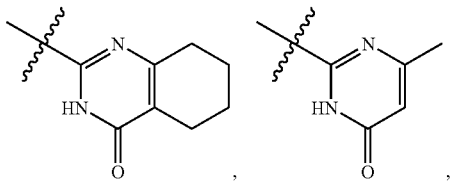

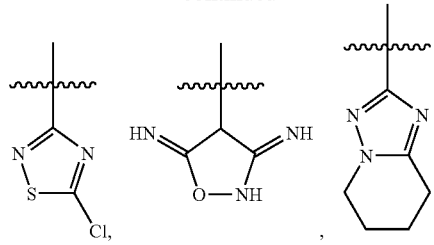

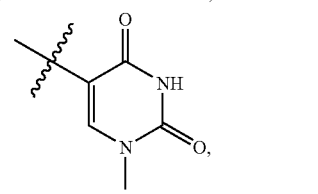

indolyl, pyridyl, pyridyl-N-oxide, pyridin-2-onyl, pyrimidyl, pyrazinyl, methyl substituted imidazolyl, methyl substituted pyrazolyl optionally substituted with Br, thiophenyl optionally substituted with Br, benzooxazolyl, oxazolyl, thiazolyl, [1,2,4]oxadiazolyl, isothiazolyl, or [1,3,4]thiadiazolyl; wherein said pyridyl, pyridyl-N-oxide, or thiazolyl is optionally substituted with one substituent selected from the group consisting of OH, $OC_{(1-4)}$alkyl, $NHC(O)CH_3$, $N(SO_2CH_3)_2$, $NHSO_2CH_3$, $NHC(O)CF_3$, $NHC_{(1-4)}$alkyl, $OC_{(3-6)}$cycloalkyl, $OCH_2CF_3$, $OCH_2Ph$, F, CN, $C_{(1-4)}$alkyl, $N(C_{(1-4)}alkyl)_2$, $C_{(1-4)}$alkylOH, $Si(CH_3)_3$, —C≡CH, $SCH_3$, $S(O)CH_3$, $SO_2CH_3$, pyrrolidinyl, $NH_2$, NHCN, and Br; or said pyridyl may be substituted with one $OCH_3$ group and one $CH_3$; wherein said pyrimidyl is optionally substituted on any carbon atom with one $N(C_{(1-4)}alkyl)_2$ group; or said pyrimidinyl is substituted on any two carbon atoms with one OH group and one $CH_3$; wherein said pyridin-2-onyl is optionally substituted with one substituent selected from the group consisting of $CH_2CN$, $C_{(1-4)}$alkyl, $CH_2CF_3$, and $CH_2CH_2OH$, or said pyridin-2-onyl is substituted with 2 methyl groups; wherein said thiazolyl is substituted with $CO_2H$, $CONH_2$, $NHCO_2C_{(1-4)}$alkyl, or OH; or said thiazolyl is optionally substituted on two adjacent carbon atoms to form a fused bicyclic system benzothiazol-2-yl, wherein said benzothiazol-2-yl is optionally substituted with Br or $OCH_3$; wherein said [1,2,4]oxadiazolyl is optionally substituted on any carbon atom with OH, $CCl_3$, or pyrrolidinyl;

$R^2$ is $NH_2$, $NO_2$, $NHCH_2CH_2OH$, $N(CH_3)_2$, $N(SO_2CH_3)_2$, CN, F, Cl, Br, $CF_3$, pyrrolidinyl, or $OCH_3$;

$R^3$ is H, F, Cl, $CF_3$, or $OCH_3$; alternatively, $R^2$ and $R^3$ may be taken together with their attached phenyl to form a benzo[1,3]dioxolyl group;

$R^4$ is H, or F;

and solvates, hydrates, tautomers, prodrugs, and pharmaceutically acceptable salts thereof.

Another embodiment of the invention comprises compounds of Formula (I) and/or Formula (Ia) wherein:

X is F, or H;

$R^1$ is

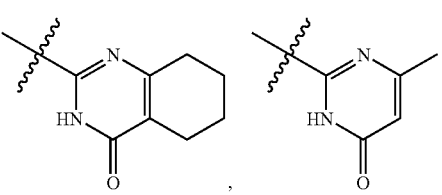

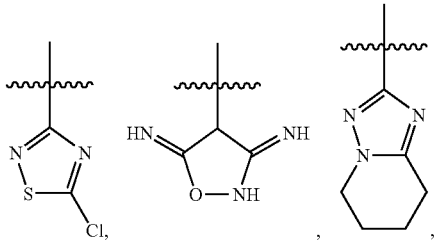

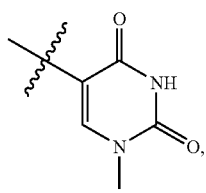

indolyl, pyrimidyl, pyridin-2-onyl, pyrazinyl, thiazolyl, [1,2,4]oxadiazolyl, or pyridyl, wherein said pyridyl is optionally substituted on any carbon atom with one substituent selected from the group consisting of OH, $OC_{(1-4)}$alkyl, $NHC(O)CH_3$, $N(SO_2CH_3)_2$, $NHSO_2CH_3$, $NHC(O)CF_3$, $NH_2$, $NHC_{(1-4)}$ alkyl, $N(CH_3)_2$, NHCN, $SO_2CH_3$; or said pyridyl is optionally substituted on any two carbon atoms with one OH group and one $CH_3$; wherein said pyrimidinyl is optionally substituted on any carbon atom with one $N(CH_3)_2$ group; or said pyrimidinyl is substituted on any two carbon atoms with one OH group and one $CH_3$; wherein said pyridin-2-onyl is optionally substituted with one substituent selected from the group consisting of $CH_2CN$, $C_{(1-4)}$alkyl, $CH_2CF_3$, and $CH_2CH_2OH$, or said pyridin-2-onyl is substituted with 2 methyl groups; wherein said thiazolyl is substituted with $CO_2H$, $CONH_2$, $NHCO_2C_{(1-4)}$alkyl, or OH; wherein said [1,2,4]oxadiazolyl is optionally substituted on any carbon atom with OH, $CCl_3$, or pyrrolidinyl;

$R^2$ is $CF_3$, CN, F, or Cl;
$R^3$ is H, Cl, $CF_3$, or F;
$R^4$ is H, or F;
and solvates, hydrates, tautomers, prodrugs, and pharmaceutically acceptable salts thereof.

Another embodiment of the invention comprises compounds of Formula (I) and/or Formula (Ia) wherein:
X is F, or H;
$R^1$ is

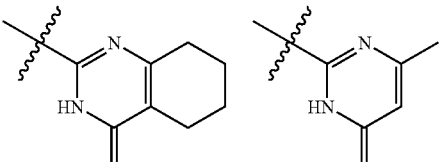

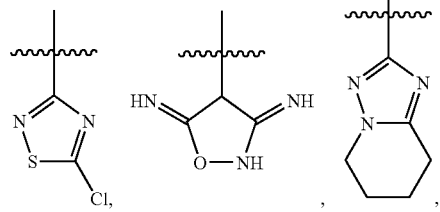

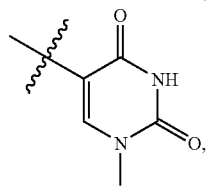

indolyl, pyrimidyl, pyridin-2-onyl, methylpyridin-2-onyl, pyrazinyl, thiazolyl, [1,2,4]oxadiazolyl, or pyridyl, wherein said pyridyl is optionally substituted on any carbon atom with one substituent selected from the group consisting of OH, $OCH_3$, $NHC(O)CH_3$, $N(SO_2CH_3)_2$, $NHSO_2CH_3$, $NHC(O)CF_3$, $NH_2$, $NHCH_3$, $N(CH_3)_2$, NHCN, $SO_2CH_3$; or said pyridyl is optionally substituted on any two carbon atoms with one OH group and one $CH_3$; wherein said pyrimidinyl is substituted on any carbon atom with one $N(CH_3)_2$ group; wherein said pyridin-2-onyl is N substituted with one substituent selected from the group consisting of $CH_2CN$, $C_{(1-4)}$ alkyl, $CH_2CF_3$, and $CH_2CH_2OH$, or said pyridin-2-onyl is substituted with 2 methyl groups; wherein said thiazolyl is substituted with $CO_2H$, $CONH_2$, $NHCO_2CH_3$, or OH; wherein said [1,2,4]oxadiazolyl is optionally substituted on any carbon atom with OH, $CCl_3$, or pyrrolidinyl;
$R^2$ is $CF_3$;
$R^3$ is H, or F;
$R^4$ is H;
and solvates, hydrates, tautomers, prodrugs, and pharmaceutically acceptable salts thereof.

Another embodiment of the invention is a compound which is selected from the group consisting of:

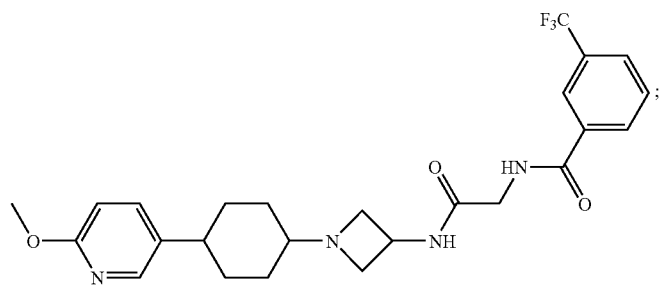

-continued
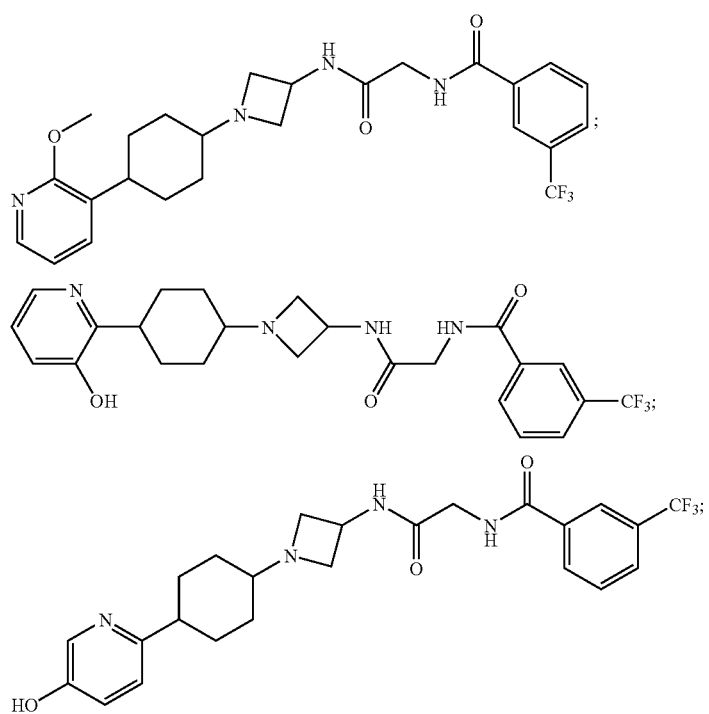
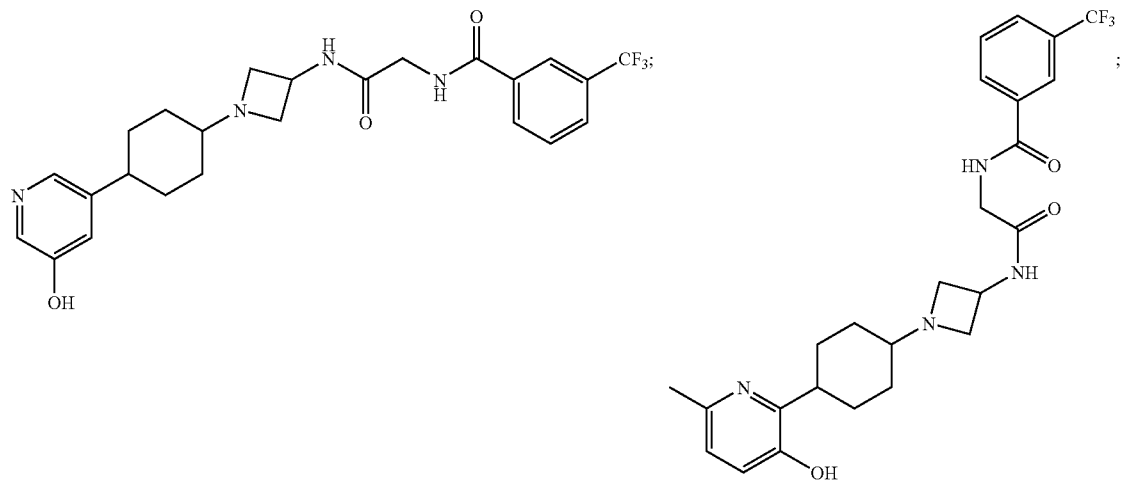
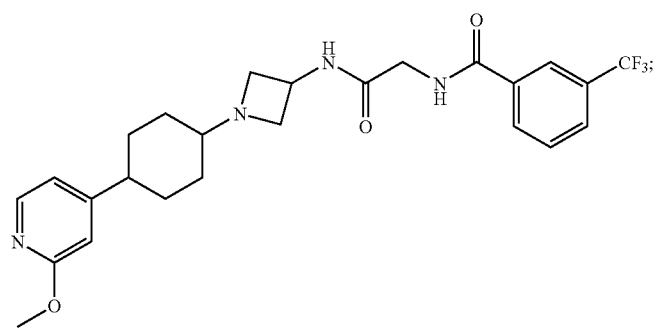

-continued
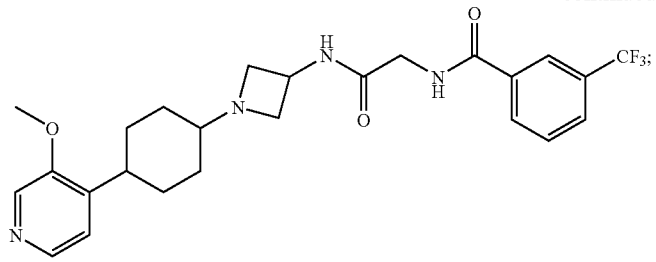
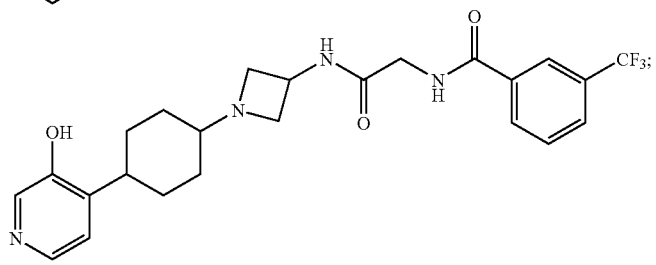
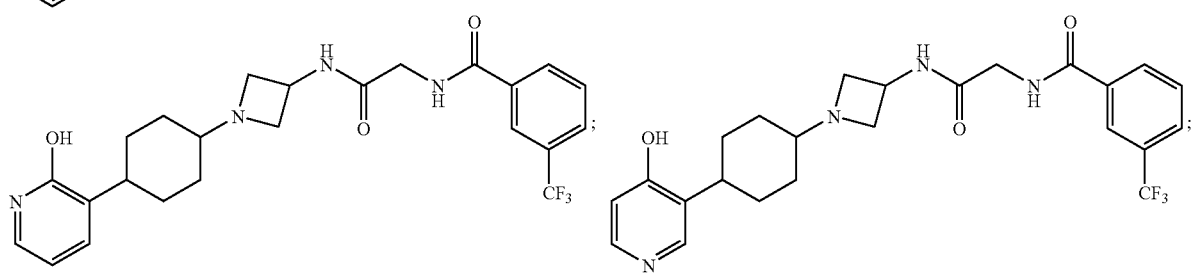
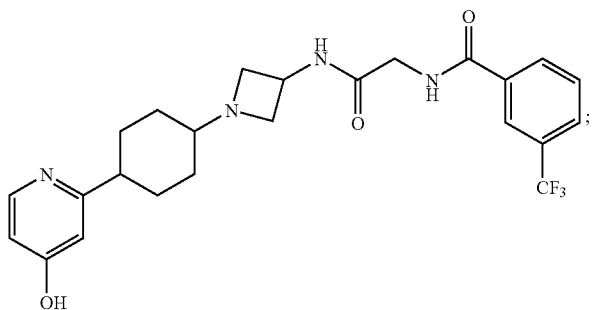
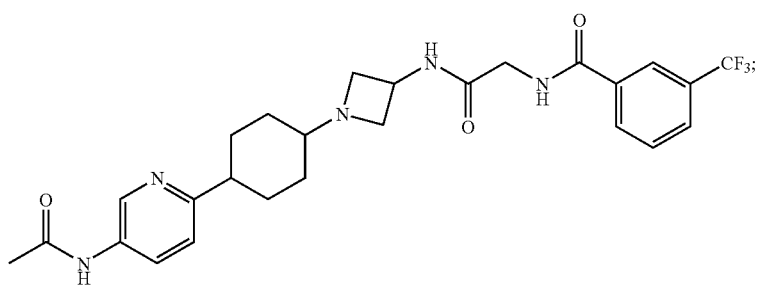
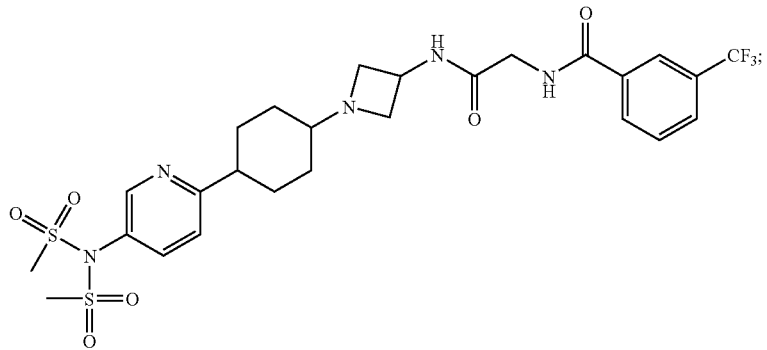

-continued
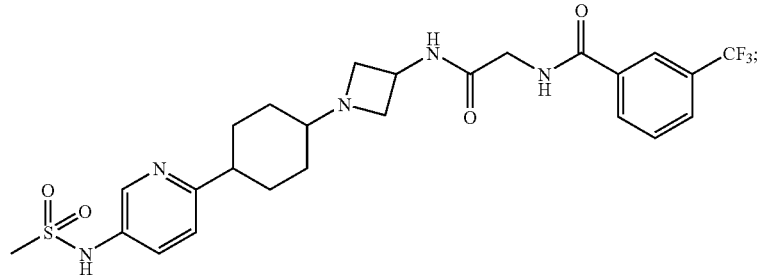
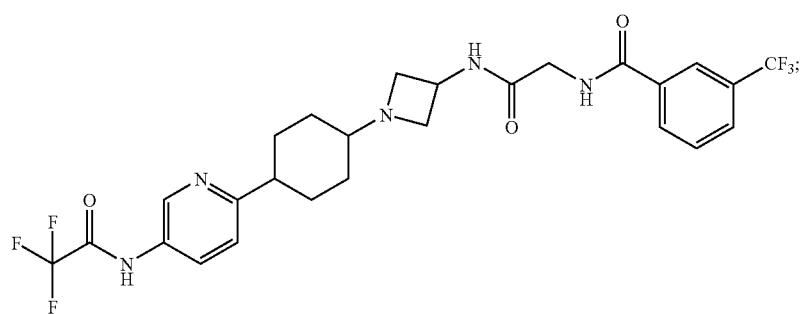
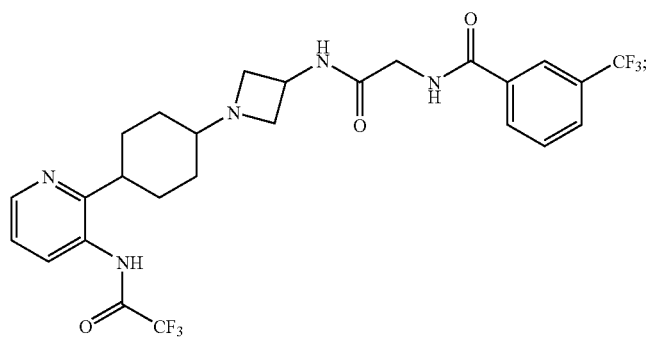
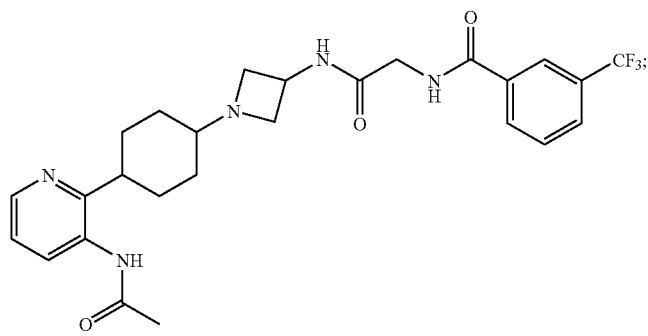
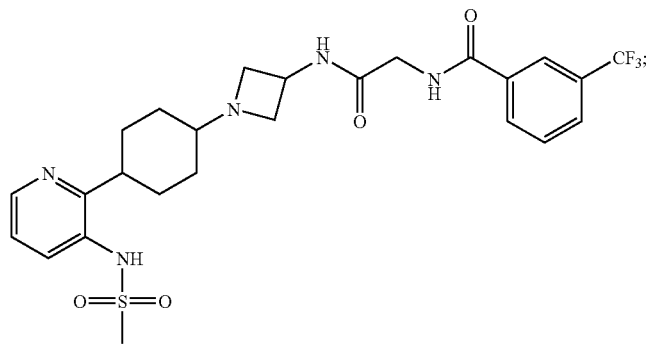

-continued
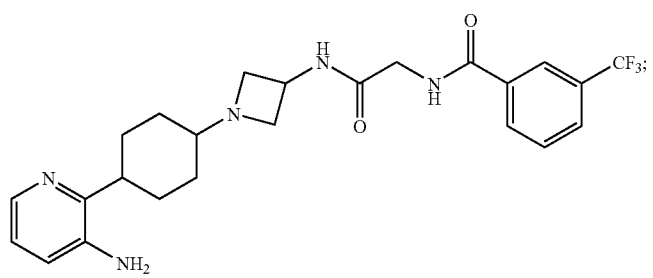
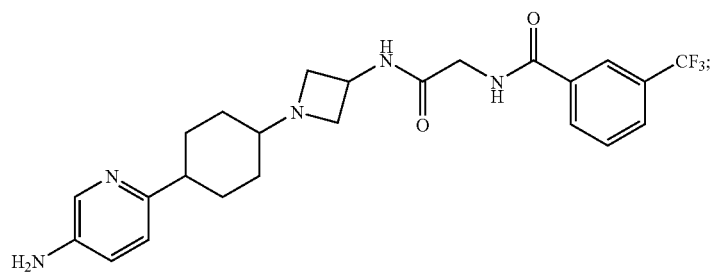
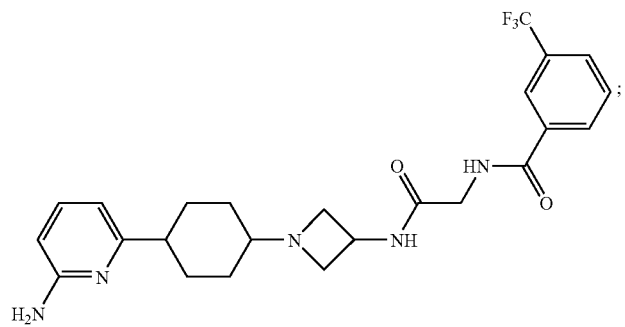
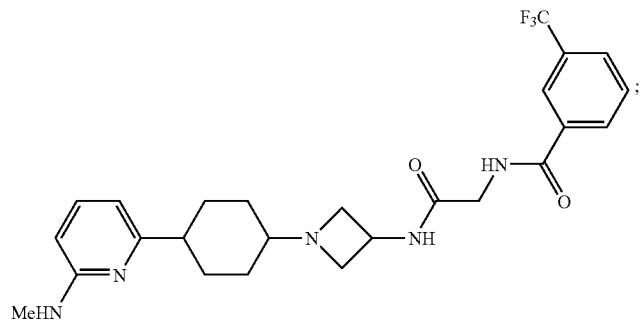
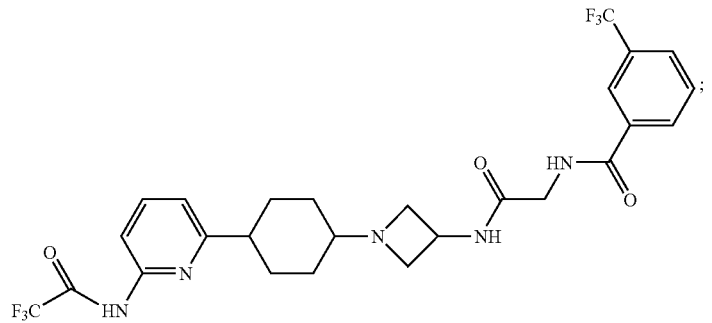

-continued
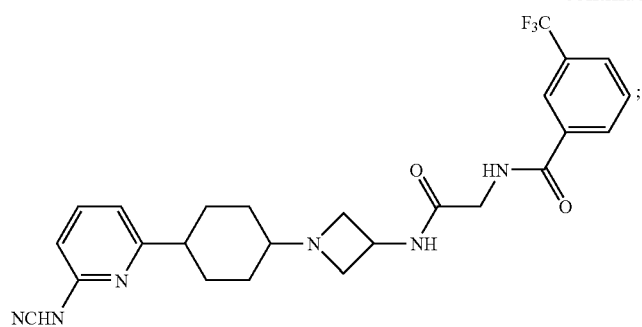
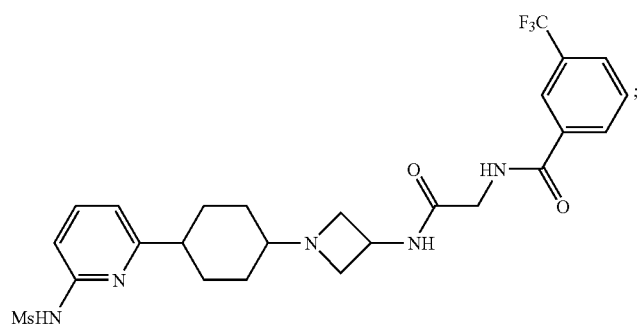
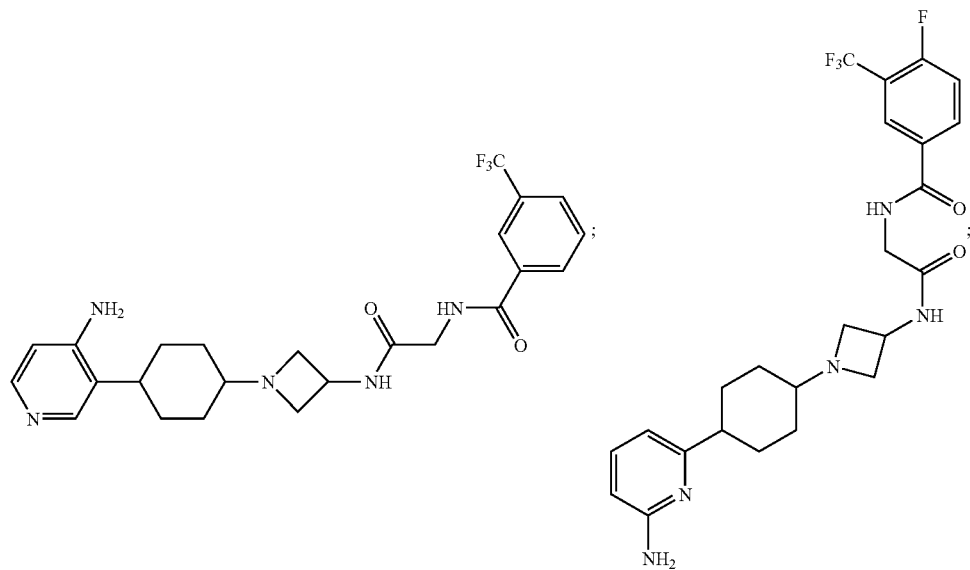
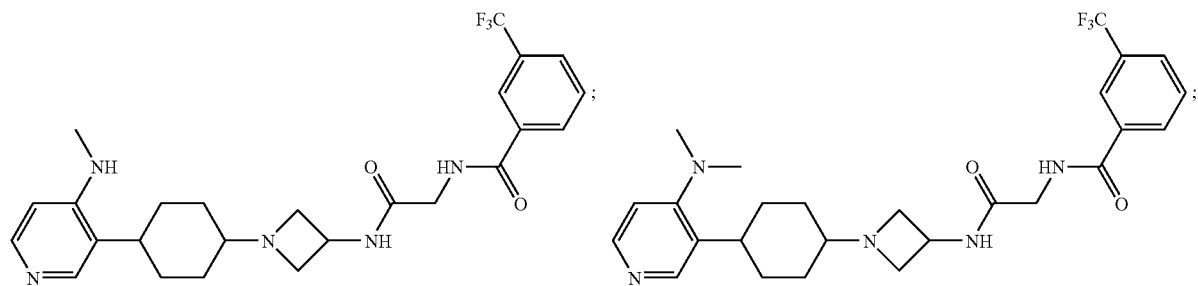

-continued
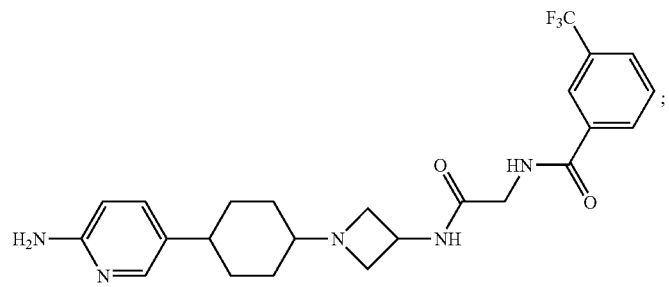
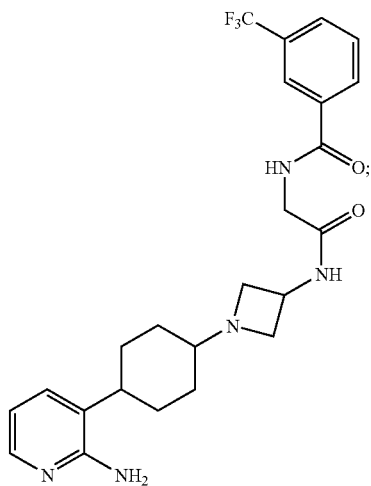
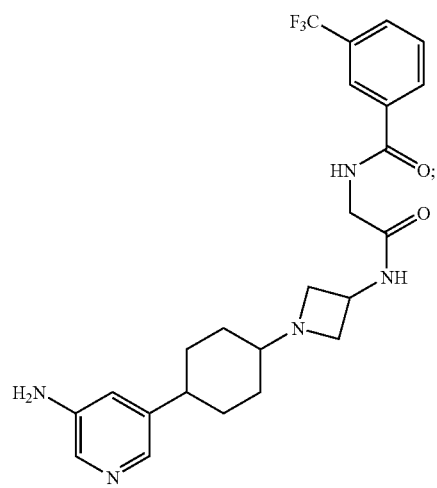
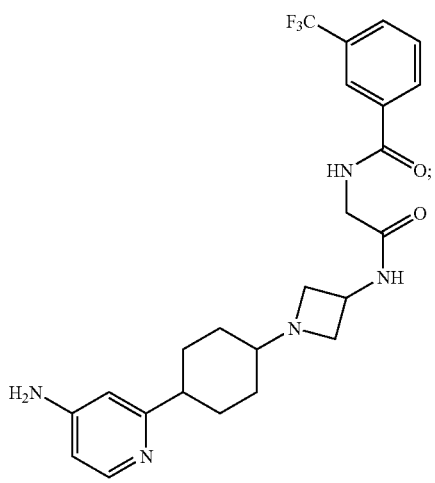
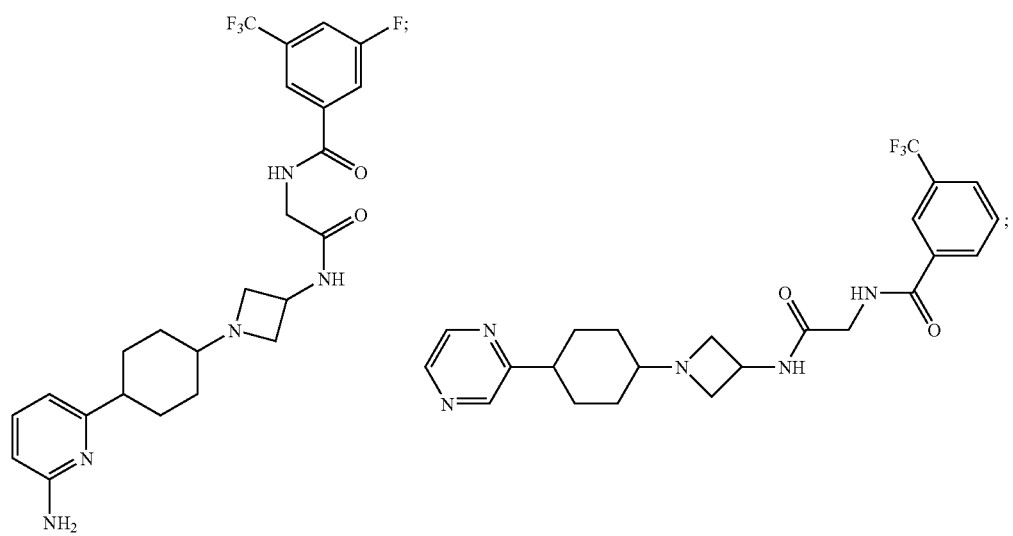

-continued
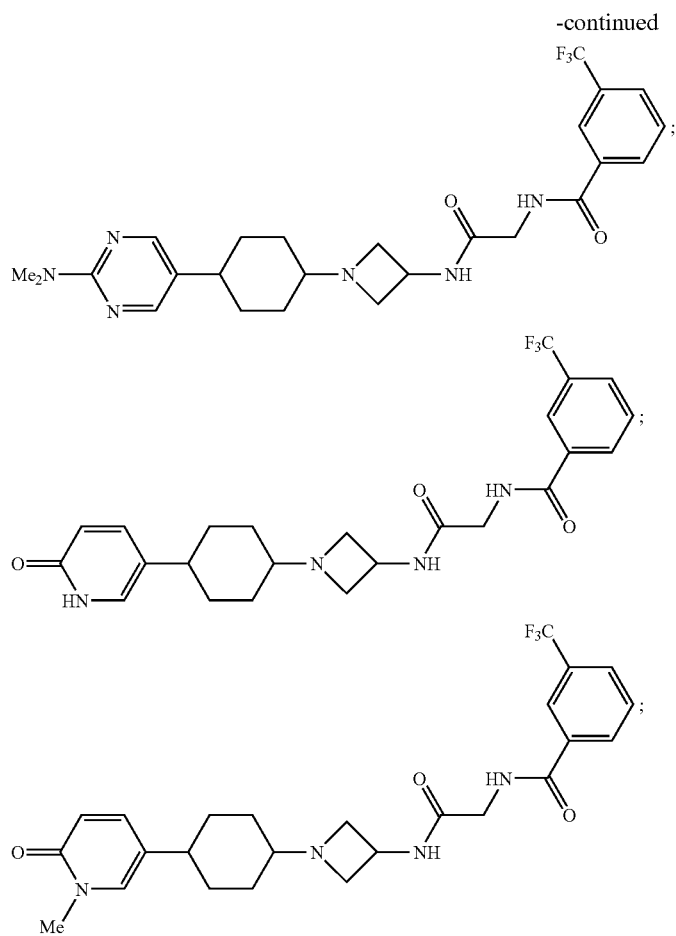
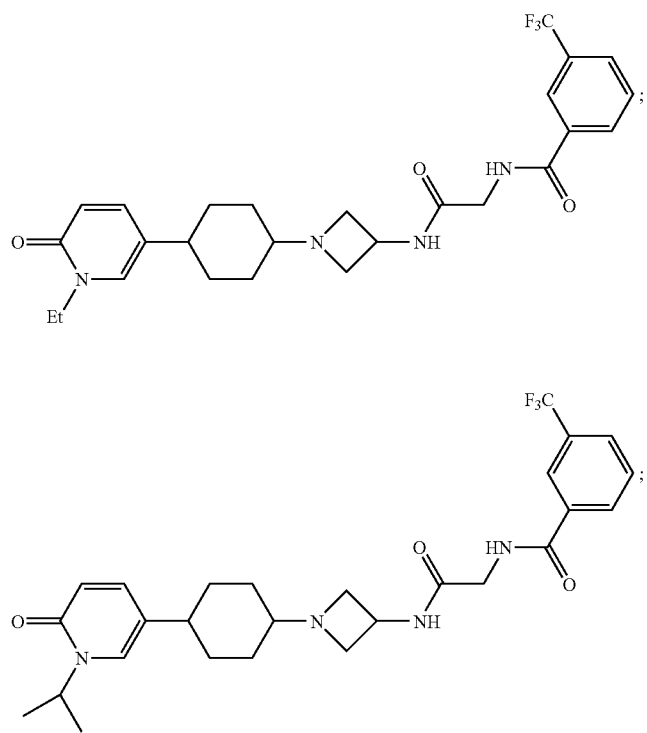

-continued
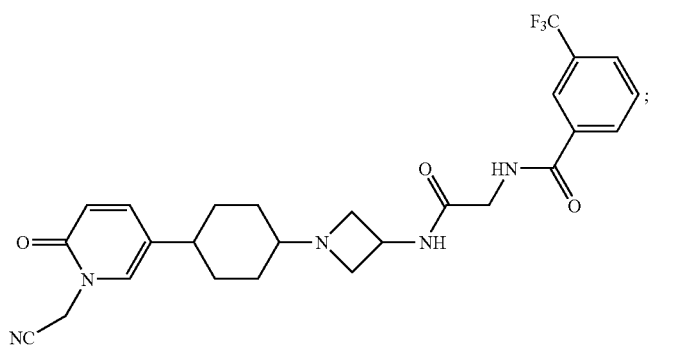
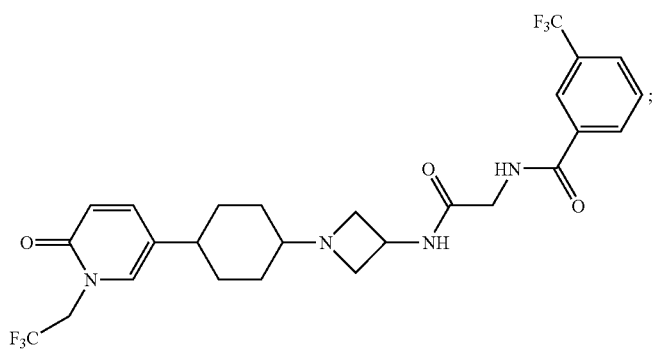
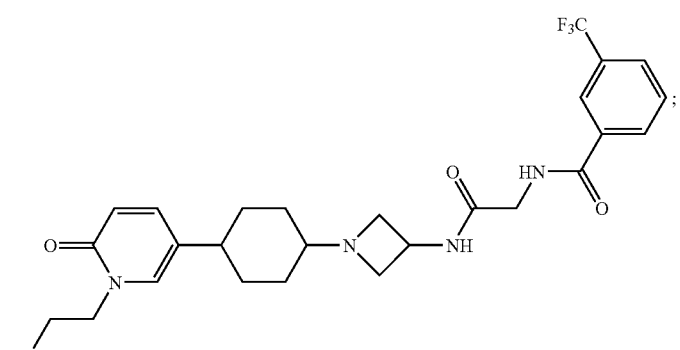
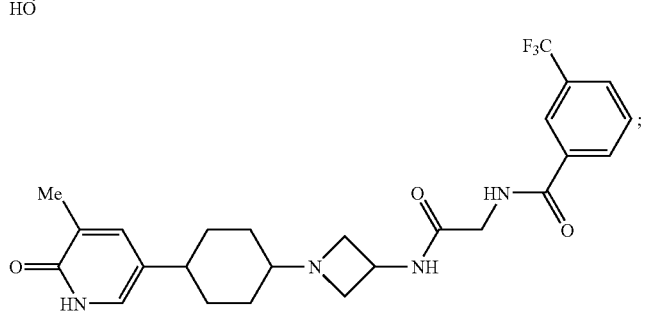
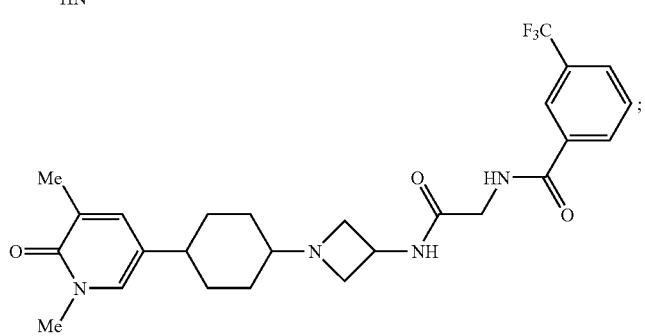

-continued
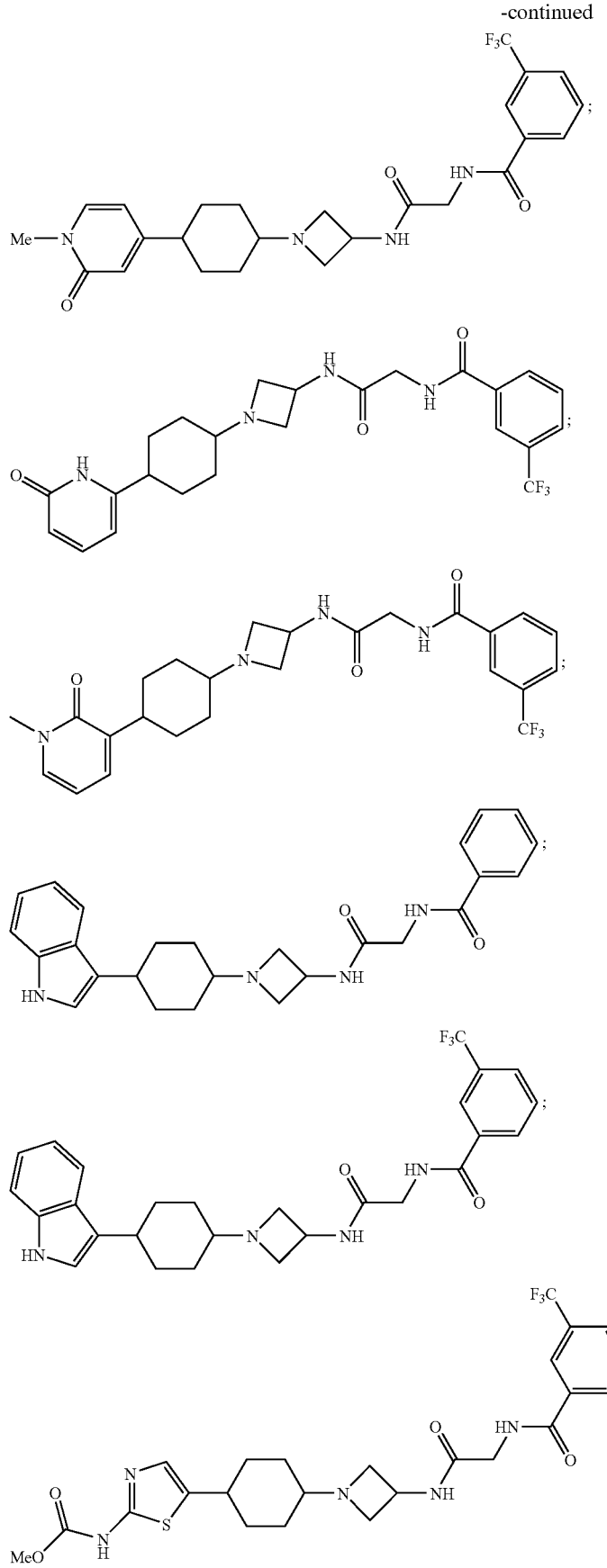

-continued
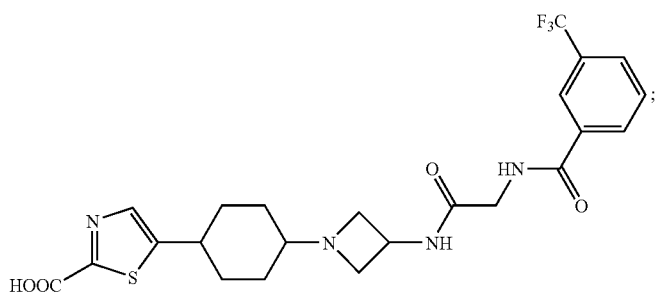
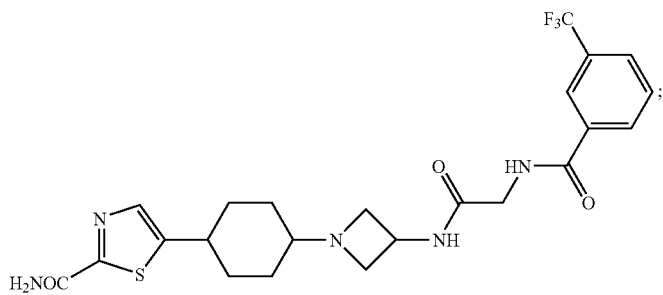
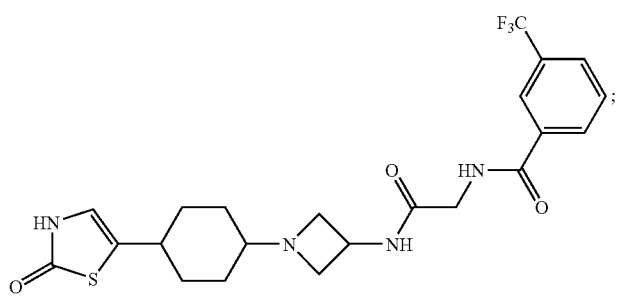
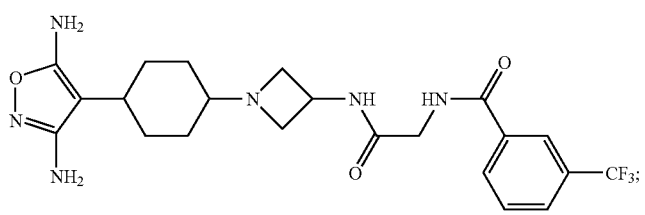
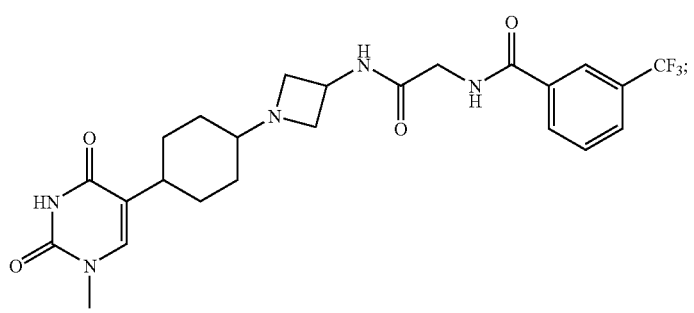
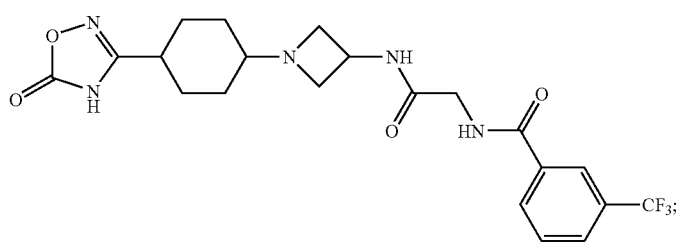

-continued
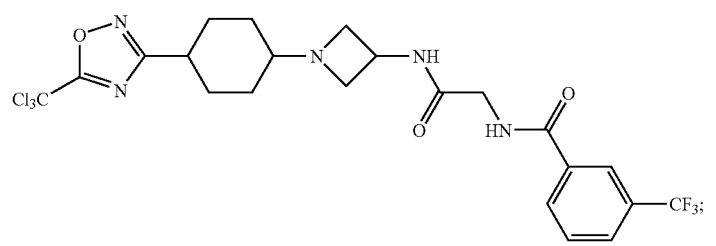
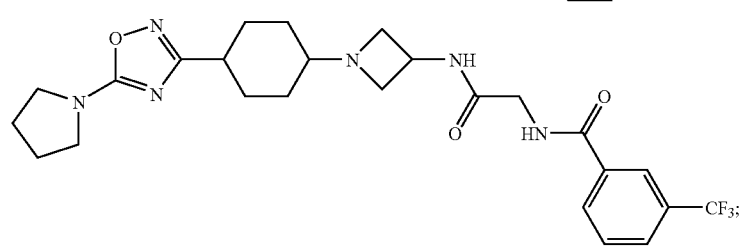
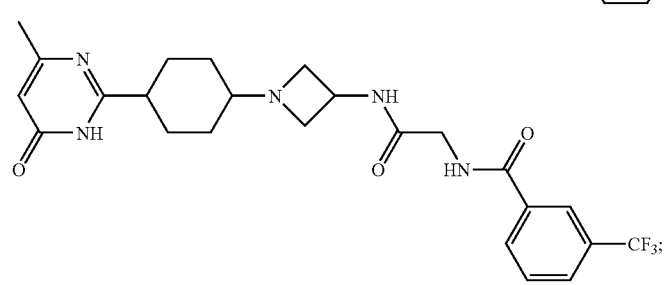
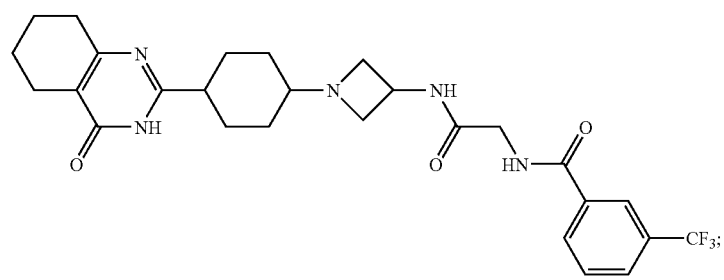
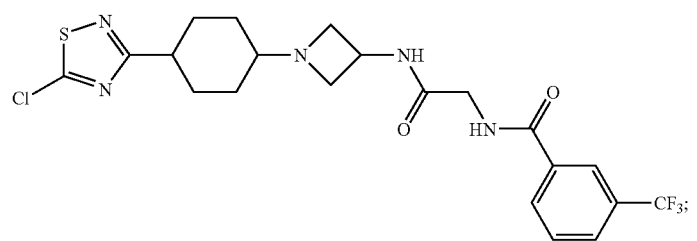
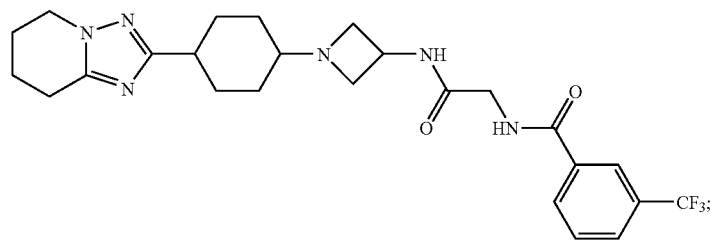

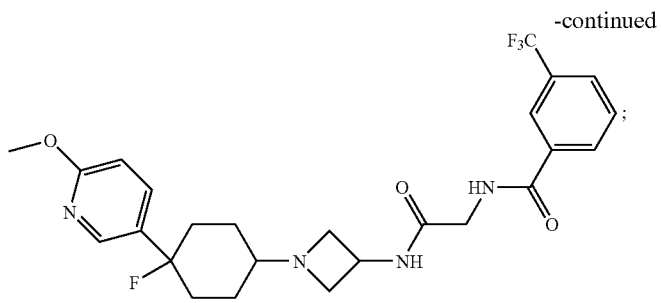
and solvates, hydrates, tautomers, prodrugs, and pharmaceutically acceptable salts thereof.
Another embodiment of the invention is a compound selected from the group consisting of:
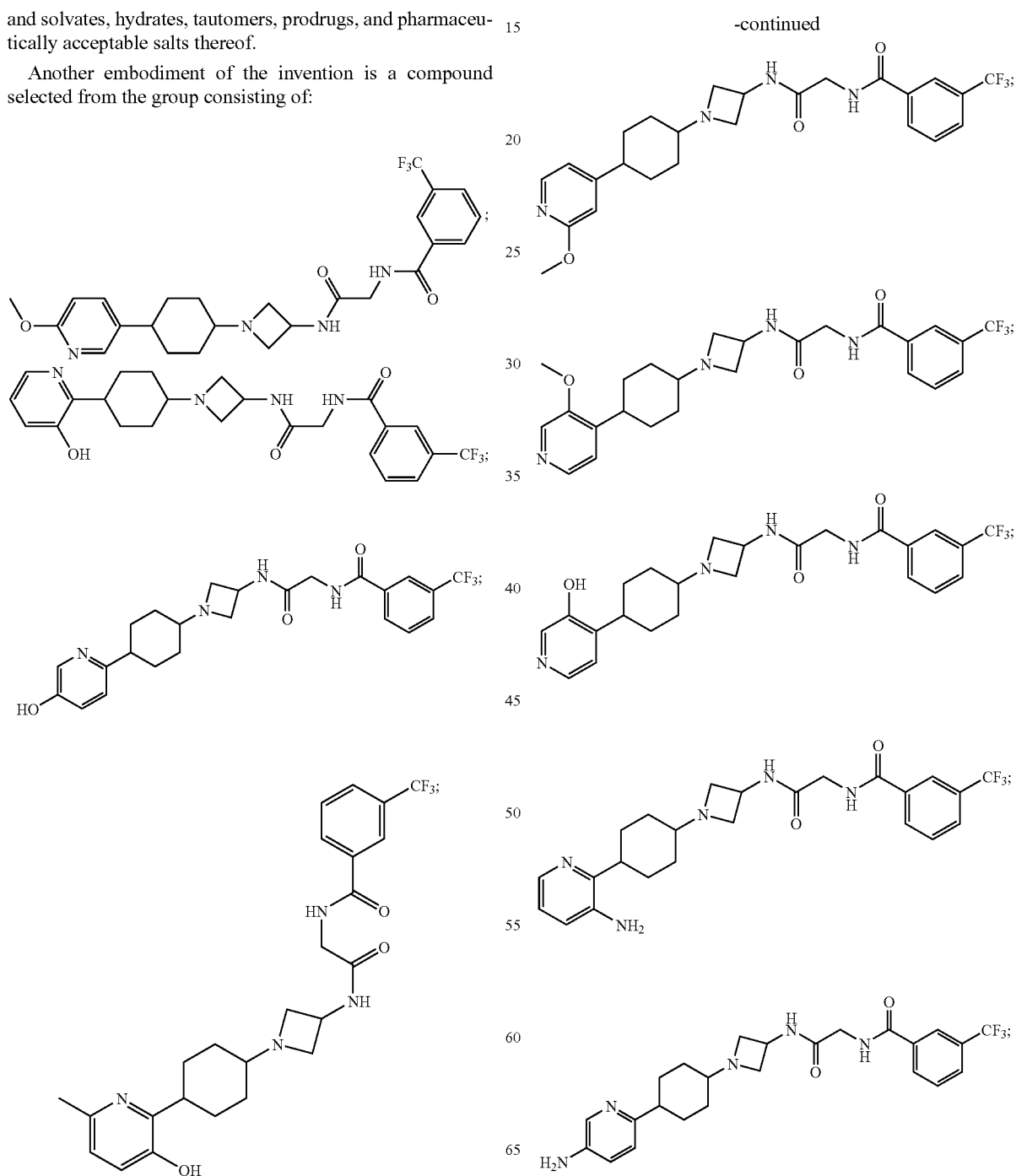

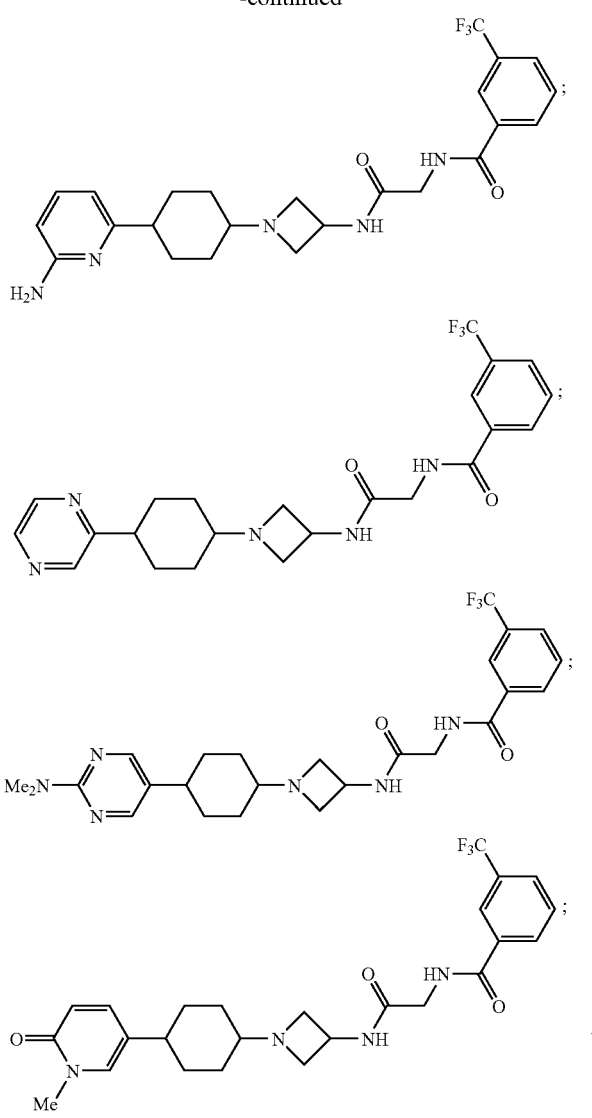
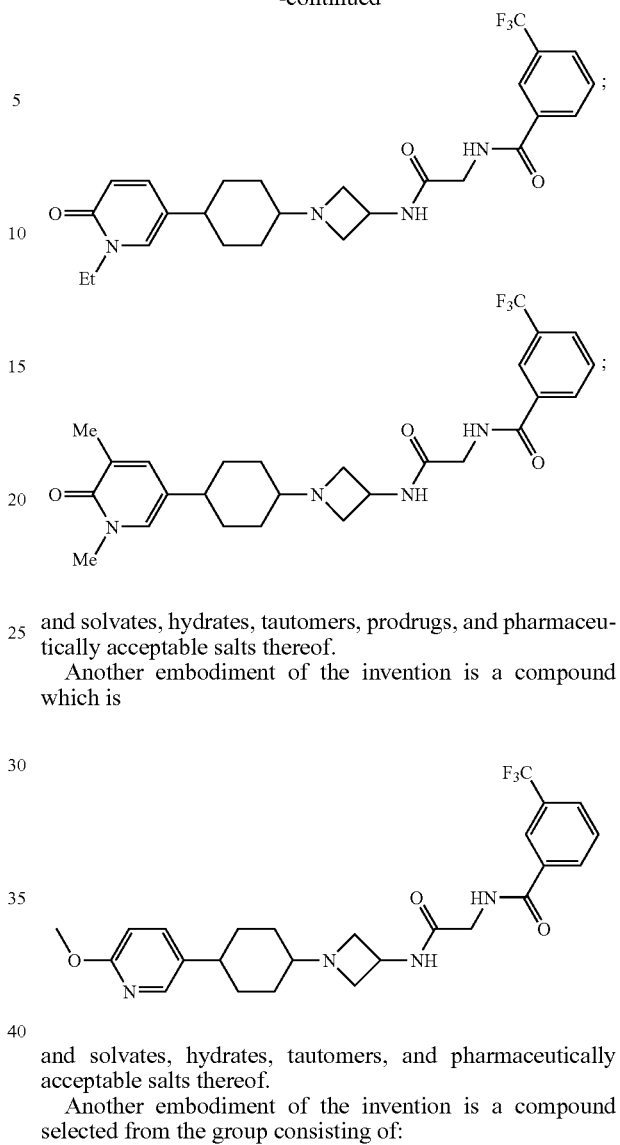
and solvates, hydrates, tautomers, prodrugs, and pharmaceutically acceptable salts thereof.
Another embodiment of the invention is a compound which is
and solvates, hydrates, tautomers, and pharmaceutically acceptable salts thereof.
Another embodiment of the invention is a compound selected from the group consisting of:
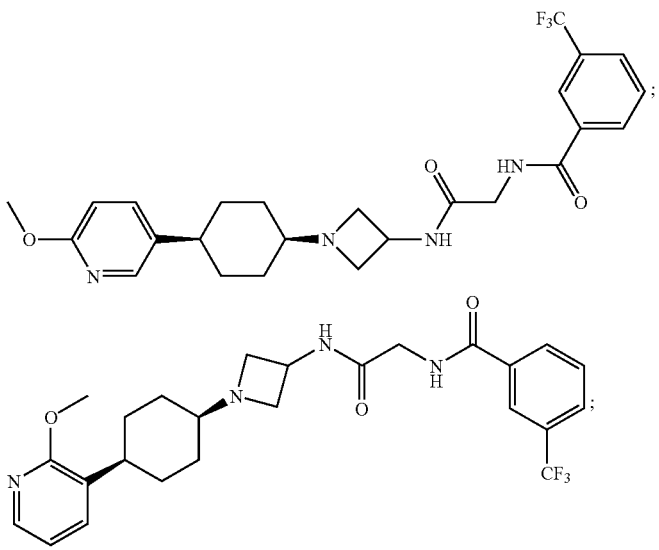

-continued
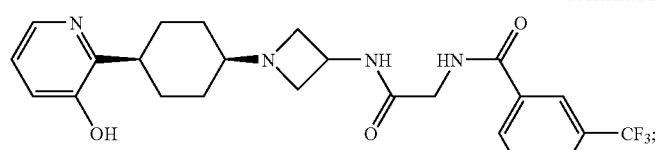
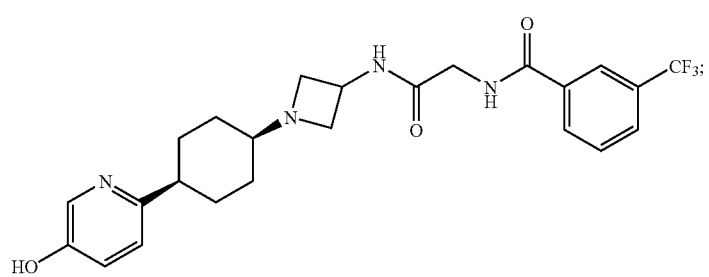
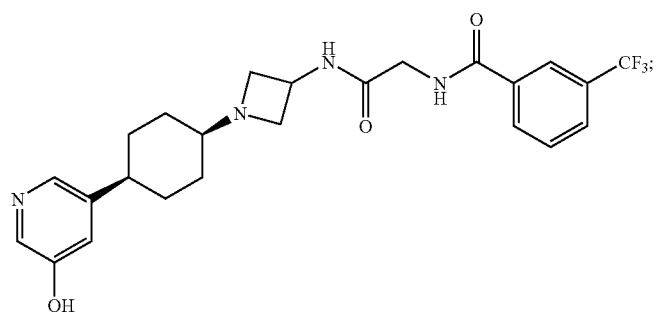
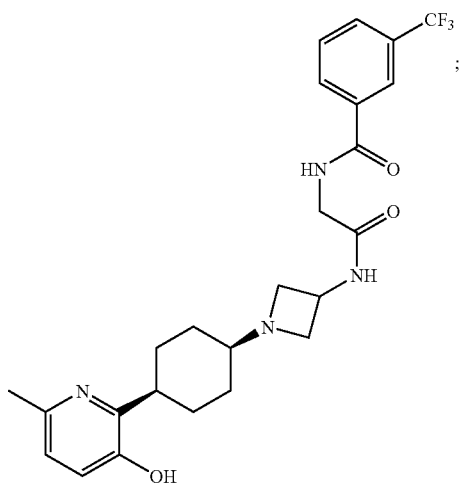
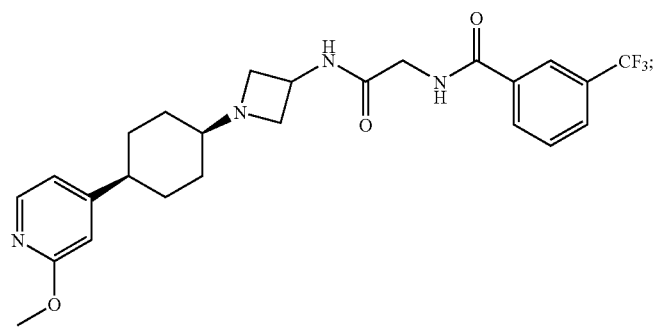
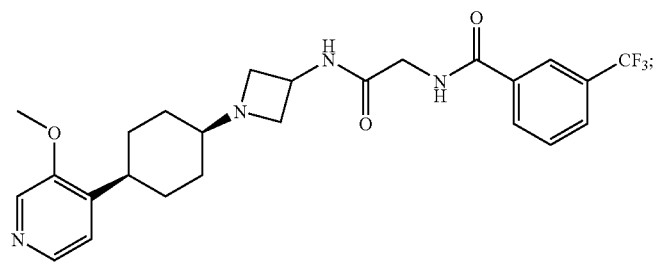

-continued
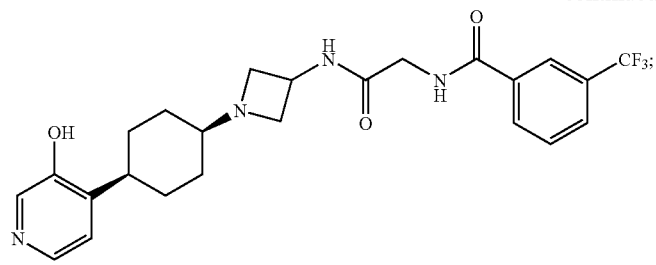
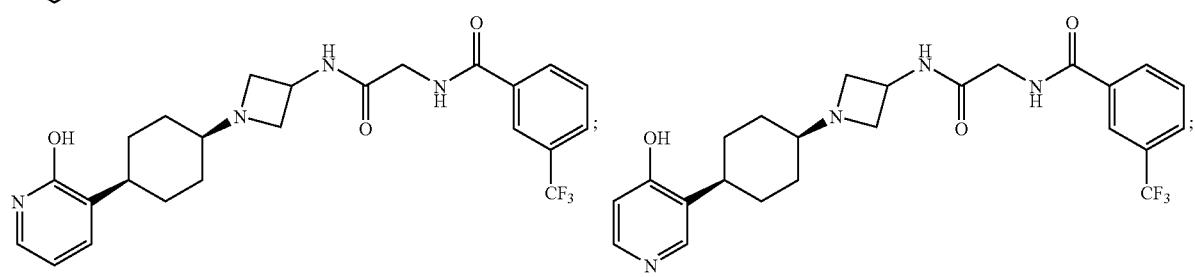
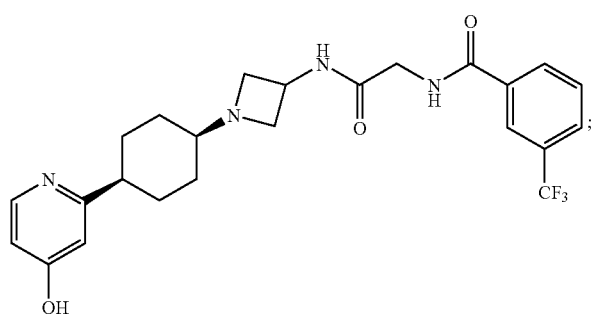
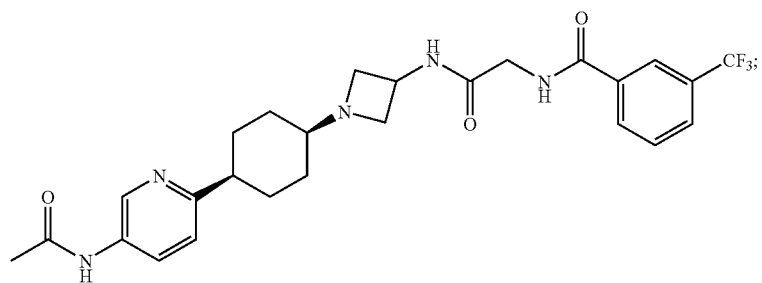
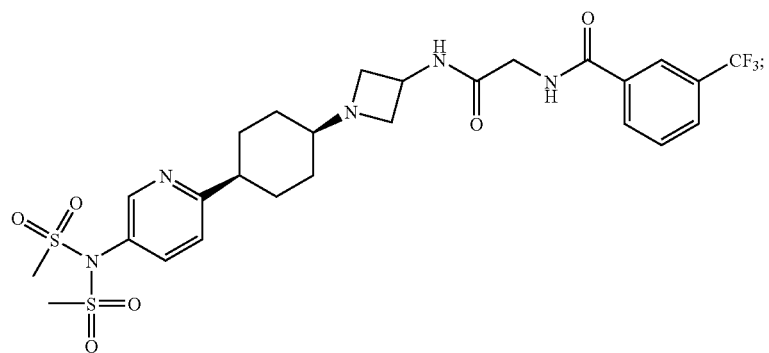

-continued
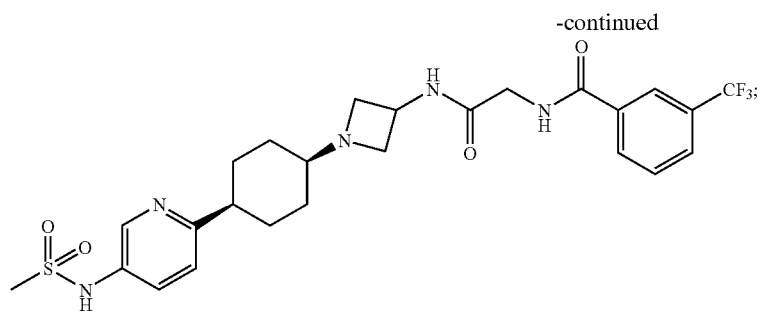
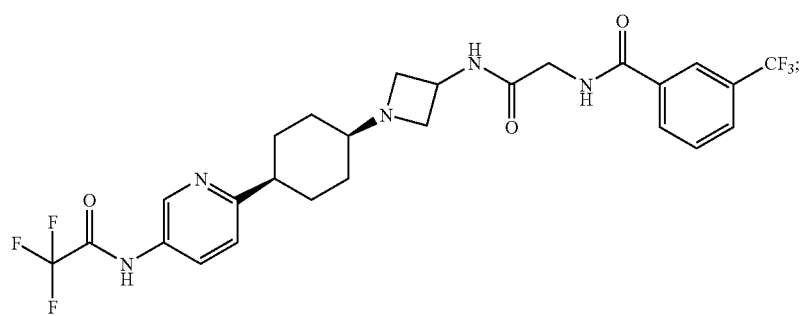
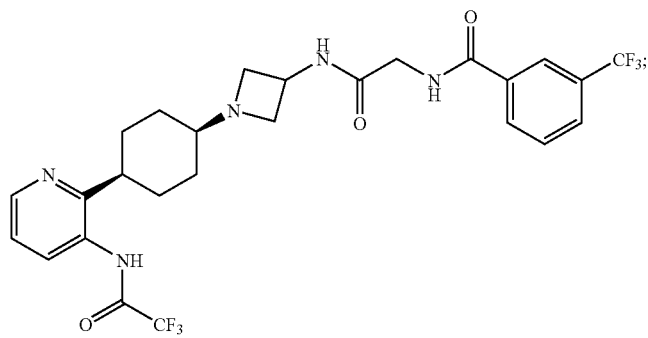
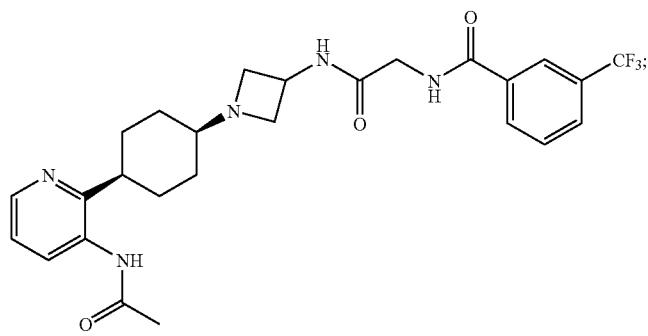
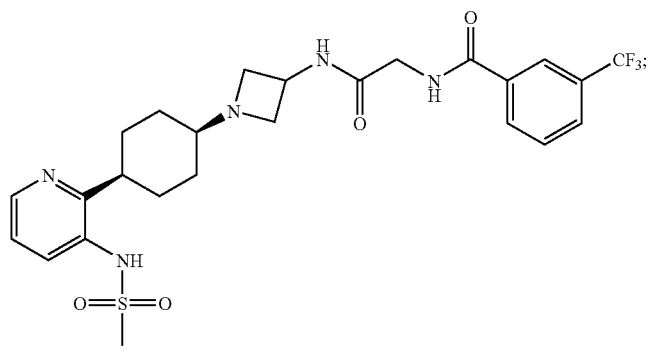

-continued
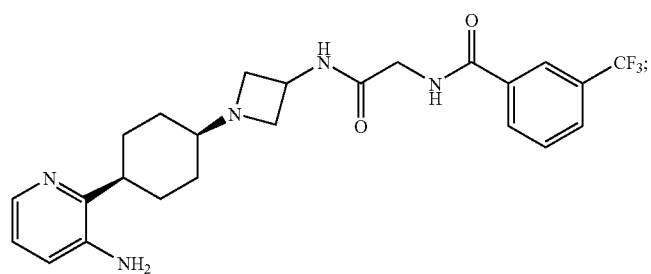
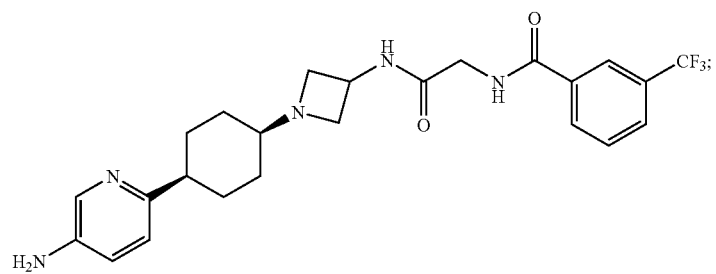
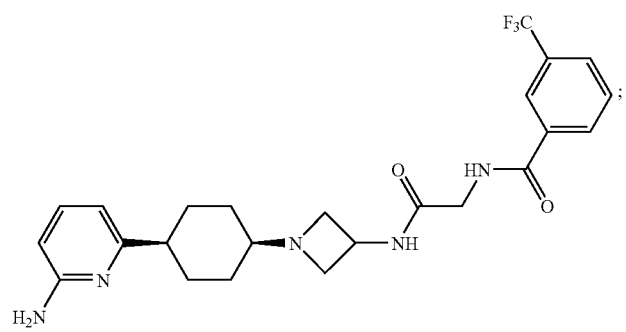
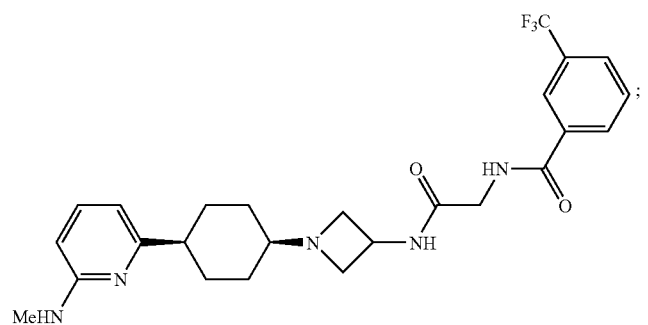
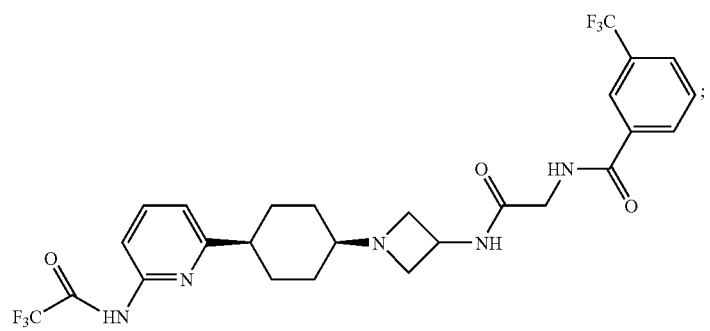

-continued
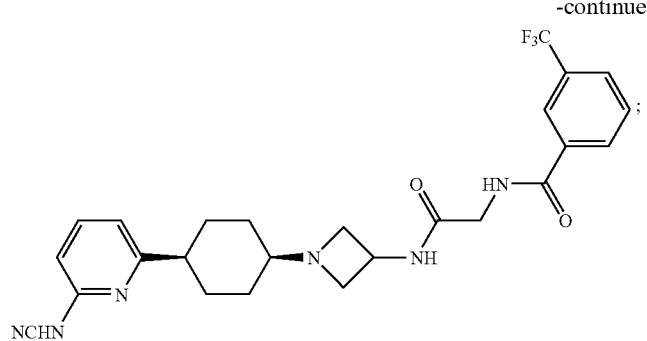
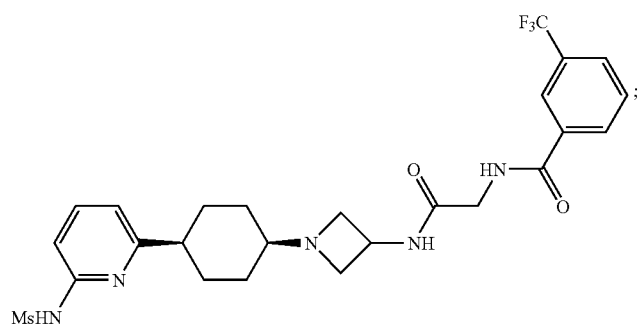
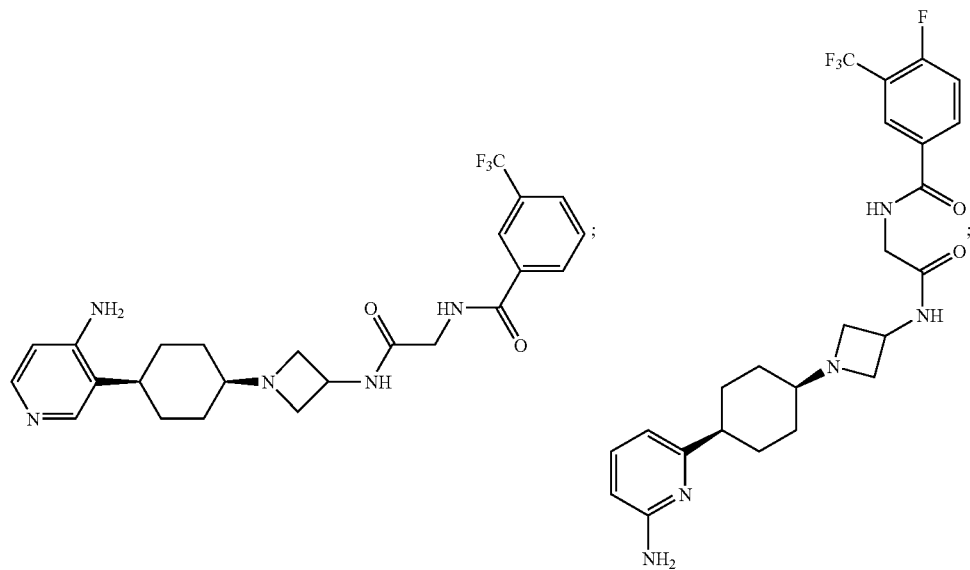
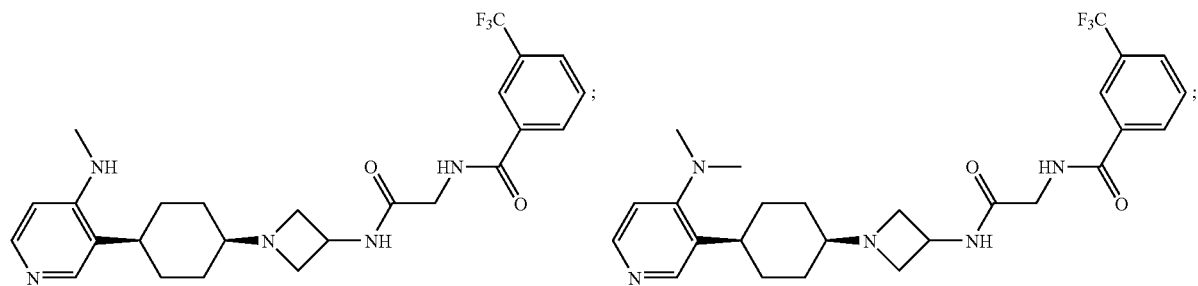

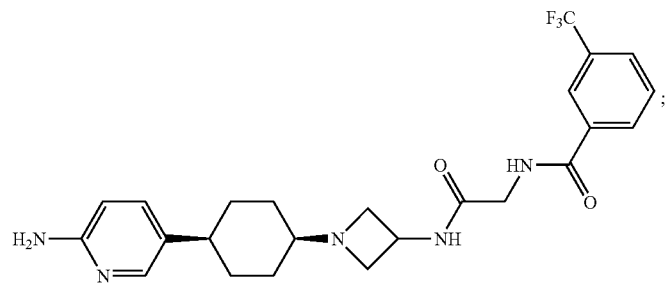
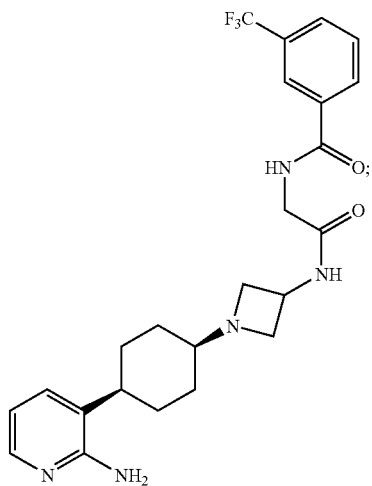
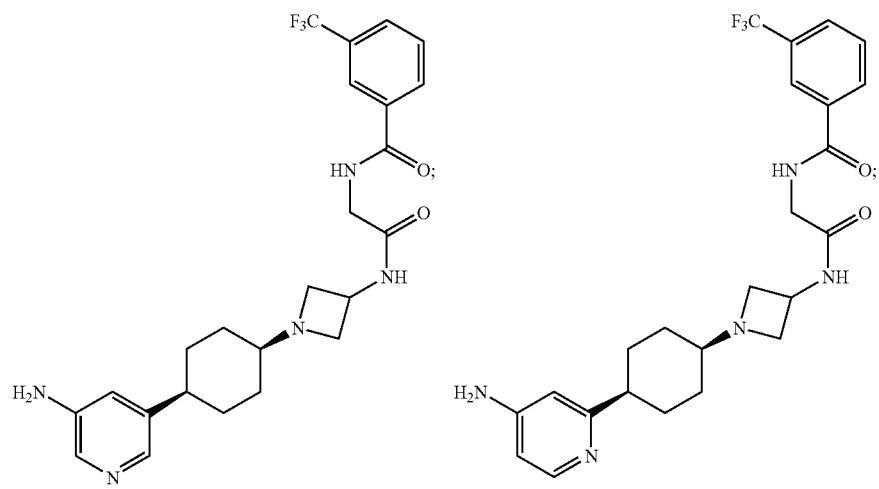
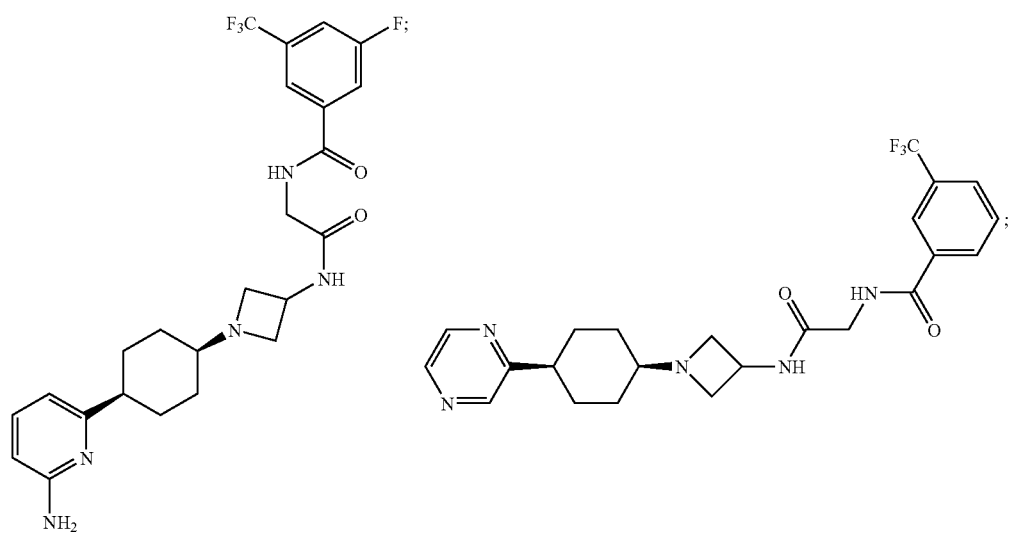

-continued
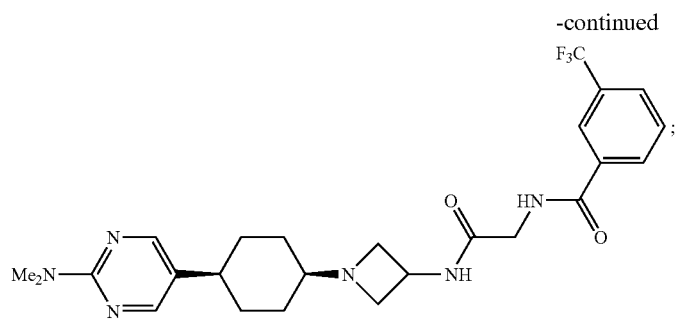
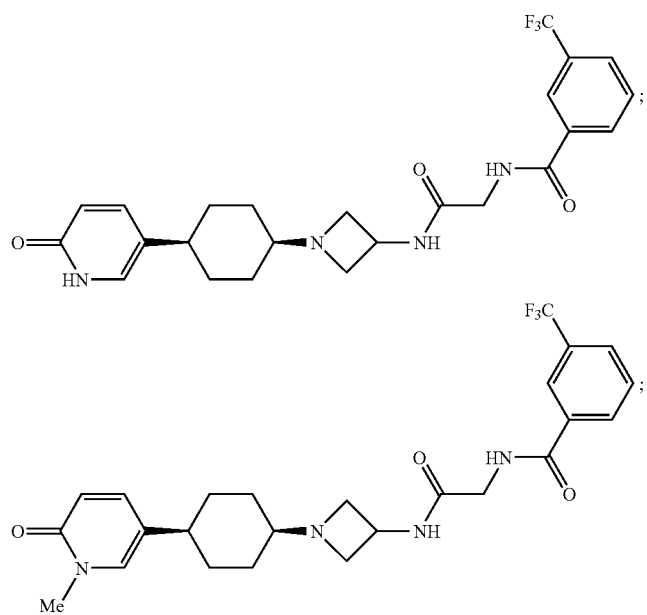
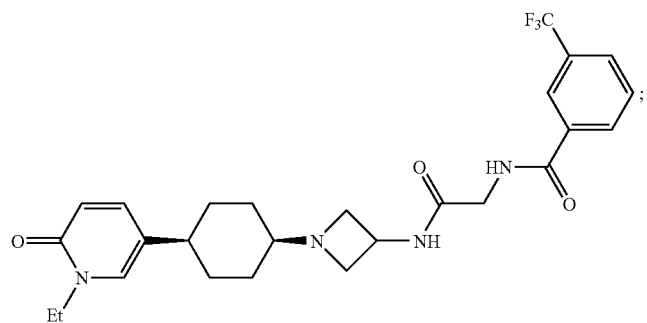
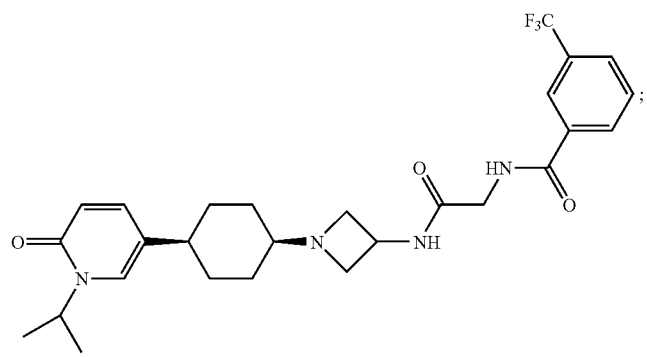

-continued
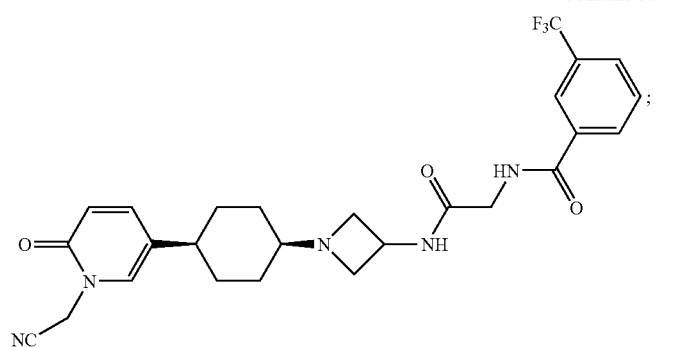
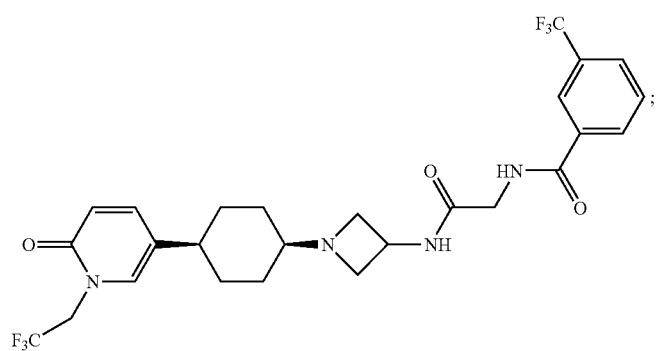
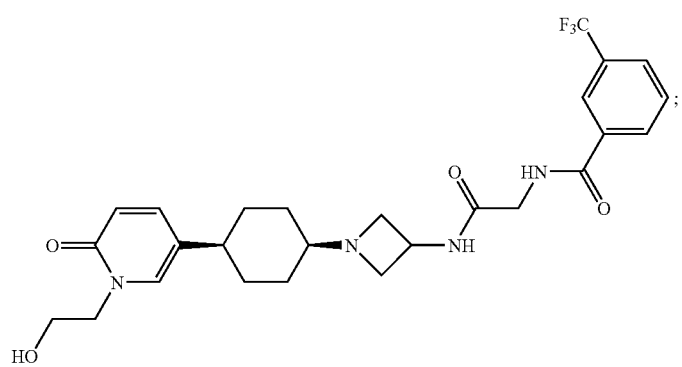
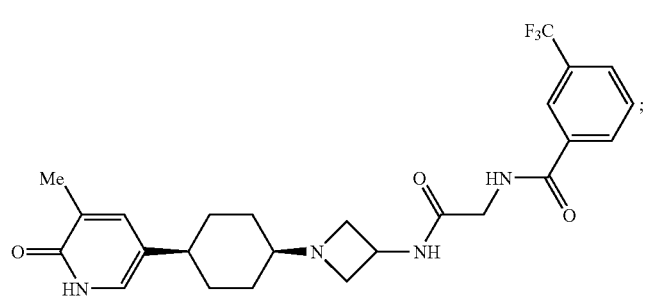
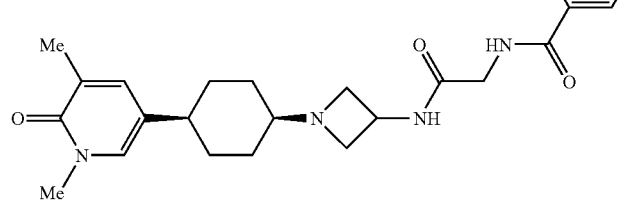

-continued
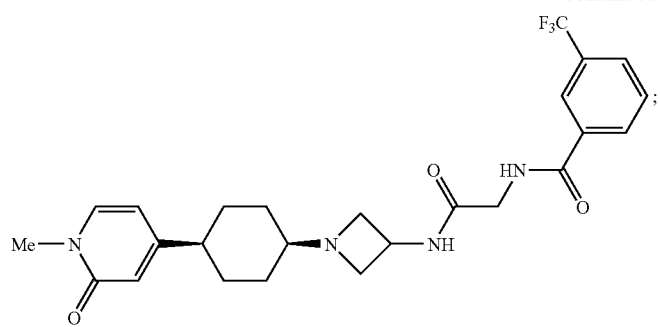
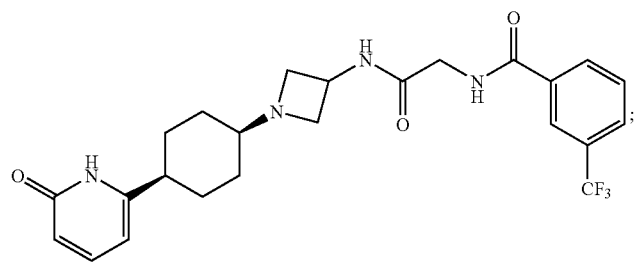
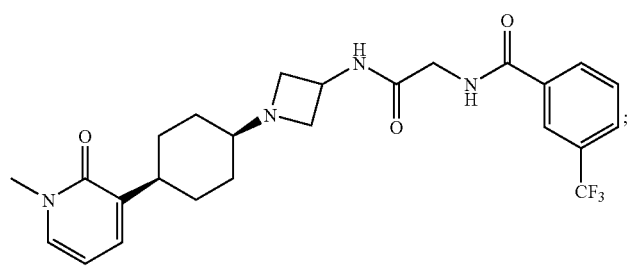
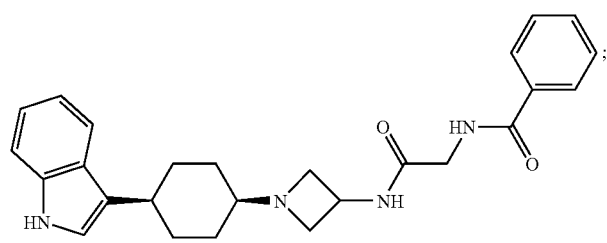
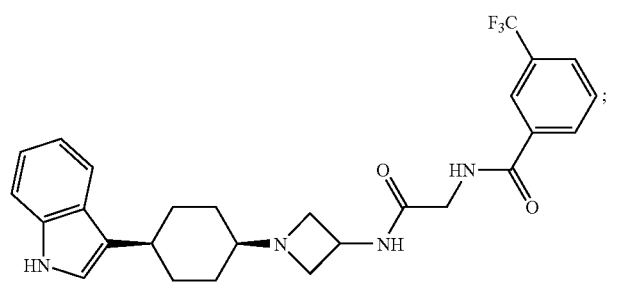
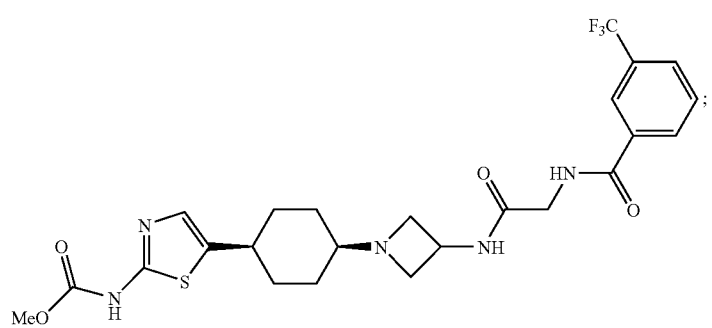

-continued
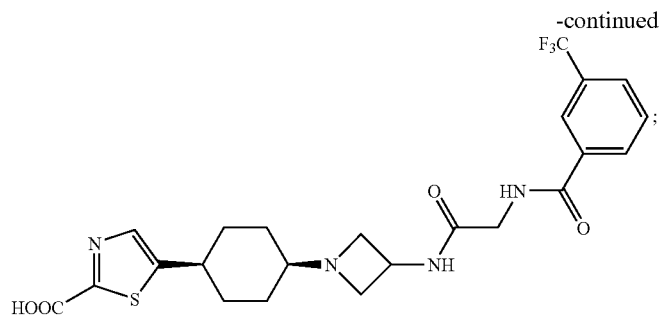
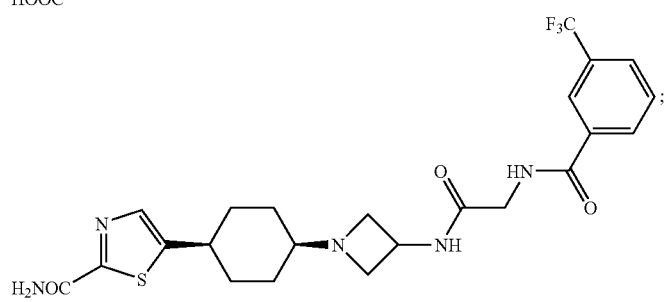
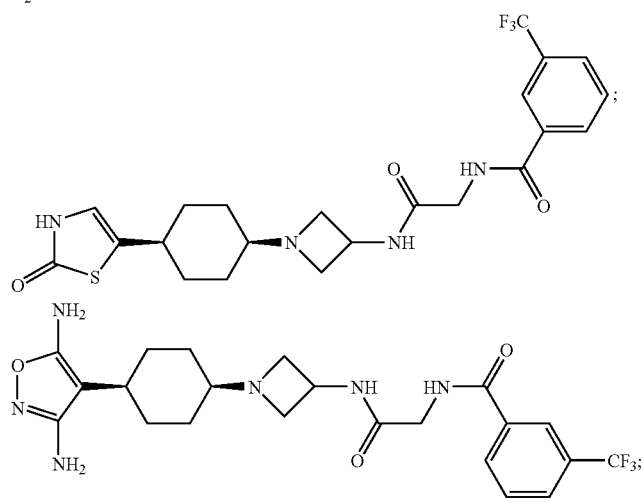
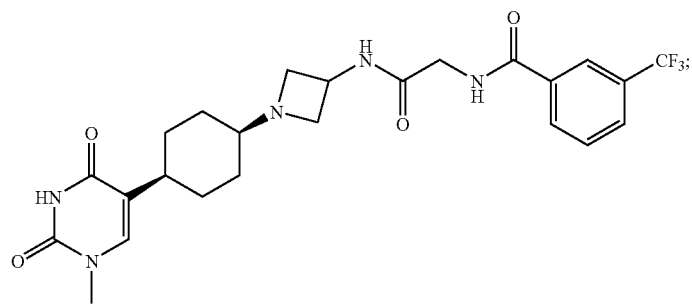
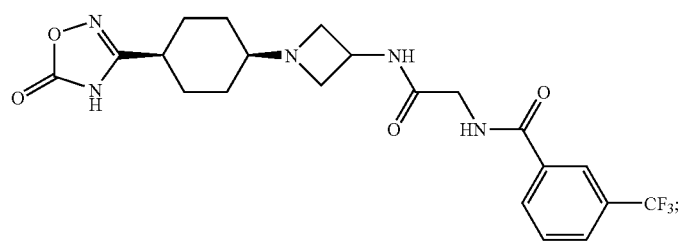

-continued
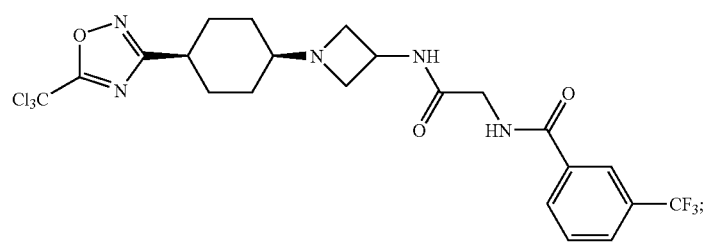
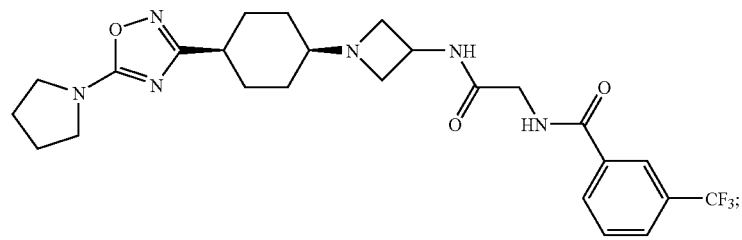
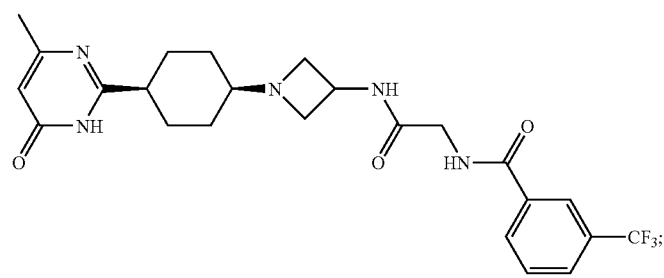
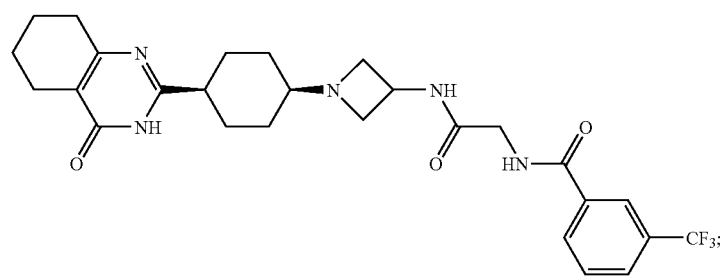
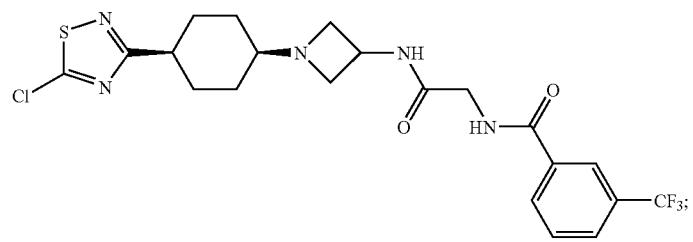
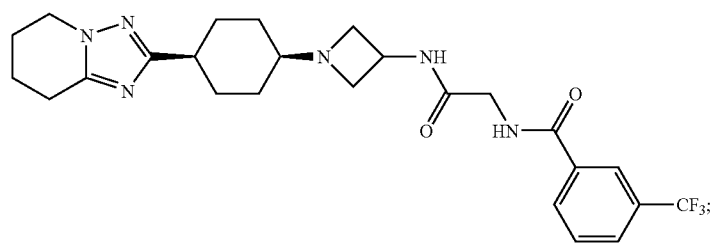

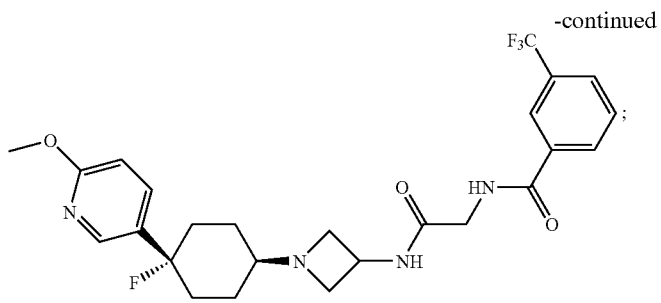

and solvates, hydrates, tautomers, prodrugs, and pharmaceutically acceptable salts thereof.

Another embodiment of the invention is the compound:

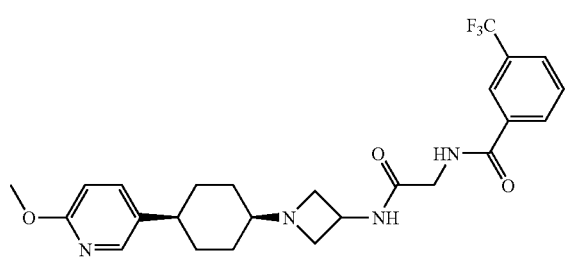

and solvates, hydrates, tautomers, prodrugs, and pharmaceutically acceptable salts thereof.

Another embodiment of the invention is a pharmaceutical composition, comprising a compound of Formula (I) and/or (Ia) and a pharmaceutically acceptable carrier.

Another embodiment of the invention is a pharmaceutical composition, comprising a compound listed in the Examples section of this specification and a pharmaceutically acceptable carrier.

The present invention also provides a method for preventing, treating or ameliorating a CCR2 mediated syndrome, disorder or disease comprising administering to a subject in need thereof a therapeutically effective amount of a compound of Formula (I) and/or (Ia) or a form, composition or medicament thereof. In one embodiment of the present invention, the CCR2 mediated syndrome, disorder or disease is an inflammatory syndrome, disorder or disease.

The present invention also provides a method for preventing, treating or ameliorating a CCR2 mediated inflammatory syndrome, disorder or disease wherein the syndrome, disorder or disease is associated with elevated MCP-1 expression or MCP-1 overexpression, or is an inflammatory condition that accompanies syndromes, disorders or diseases associated with elevated MCP-1 expression or MCP-1 overexpression comprising administering to a subject in need thereof a therapeutically effective amount of a compound of Formula (I) and/or (Ia) or a form, composition or medicament thereof.

The present invention also provides a method of preventing, treating or ameliorating a syndrome, disorder or disease, wherein said syndrome, disorder or disease is selected from the group consisting of: Chronic Obstructive Pulmonary Disease (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type II diabetes and diabetic complications, diabetic nephropathy, obesity, weight disorders, diabetic retinopathy, diabetic retinitis, diabetic microangiopathy, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof a therapeutically effective amount of a compound of Formula (I) and/or (Ia) or a form, composition or medicament thereof. Preferably, the syndrome, disorder or disease is selected from the group consisting of: ophthalmic disorders, rheumatoid arthritis, psoriasis, psoriatic arthritis, atopic dermatitis, chronic obstructive pulmonary disease, allergic rhinitis, asthma, allergic asthma, and periodontal diseases.

The invention also relates to methods of inhibiting CCR2 activity in a mammal by administration of an effective amount of at least one compound of Formula (I) and/or (Ia).

In another embodiment, the invention relates to a product made by the process of any of Examples from Example 1 to Example 64.

In another embodiment, the invention relates to a compound which is the less polar isomer of any of Examples #1-64. Preferably, the compound is the less polar isomer of Example #1.

In another embodiment, the invention relates to a process for the preparation of a compound of Formula (I), comprising reacting a compound of Formula (V)

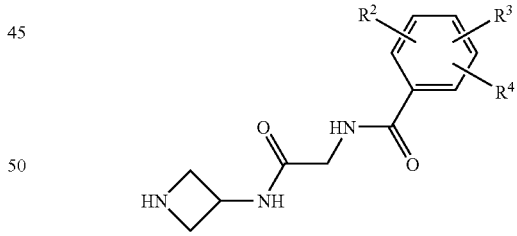

with a compound of Formula (VI)

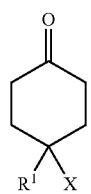

in the presence of a reducing agent to provide the compound of Formula (I).

In another embodiment, the invention relates to a product made by the above process.

In another embodiment, the invention relates to a process for the preparation of a compound of Formula (I), comprising reacting a compound of Formula (XIII)

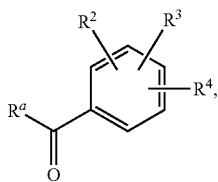
(XIII)

where $R_a$ is OH or Cl, with a compound of Formula (XII)

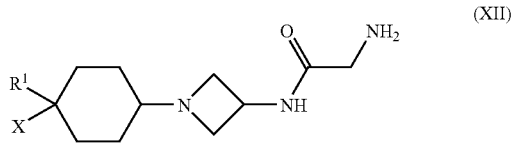
(XII)

in the presence of HOBt/EDCI or $Et_3N$ to provide the compound of Formula (I).

In another embodiment, the invention relates to a product made by the above process.

In another embodiment, the invention relates to the use of hCCR2 knock-in mice to identify antagonists of CCR2 for use in the treatment a disorder selected from asthma or obesity.

In another embodiment, the invention relates to the use of hCCR2 knock-in mice to identify antagonists of CCR2 as described in any of Examples 69, 70 or 71.

Definitions

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include, but are not limited to, cyclopropyl, cyclobutyl, cyclopentyl, cyclopentenyl, cyclohexyl, cyclohexenyl, cycloheptyl and cyclooctyl. Additional examples include $C_{(3-8)}$cycloalkyl, $C_{(5-8)}$cycloalkyl, $C_{(3-12)}$cycloalkyl, $C_{(3-20)}$cycloalkyl, decahydronaphthalenyl, and 2,3,4,5,6,7-hexahydro-1H-indenyl.

The term "oxo" refers to the functional group

The term "heterocyclyl" refers to a saturated or partially unsaturated monocyclic cycloalkyl ring radical wherein from 1 to 3 ring carbon atoms have been replaced with heteroatoms selected from N, O, or S. Said heteroatoms may exist in any allowed oxidation state. The radical may be derived from the removal of a hydrogen atom from a carbon or a nitrogen atom. Typical heterocyclyl radicals include, but are not limited to, 2H-pyrrolyl, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "heteroaromatic" or "heteroaryl" refers to 5- to 7-membered mono- or 8- to 10-membered bicyclic aromatic ring systems, containing from one to four heteroatoms selected from N, O, or S where the nitrogen and sulfur atoms can exist in any allowed oxidation state. Examples include, but are not limited to, benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroatom" refers to a nitrogen atom, an oxygen atom or a sulfur atom wherein the nitrogen and sulfur atoms can exist in any allowed oxidation states.

For use in medicines, the salts of the compounds of this invention refer to non-toxic "pharmaceutically acceptable salts." FDA approved pharmaceutically acceptable salt forms (Ref. International J. Pharm. 1986, 33, 201-217; J. Pharm. Sci., 1977, January, 66(1), p1) include pharmaceutically acceptable acidic/anionic or basic/cationic salts.

Throughout this specification, compounds are described as being separated, usually by silica gel column, although preporatory thin layer chromatography, or high or low pressure liquid choromatography may also be used. It is generally accepted that when eluting compounds through a silica gel-type separation medium, that the least polar compounds elute before the more polar compounds. Therefore, the term "less polar isomer", refers to the isomer that will elute first from a silica gel type separation medium.

Abbreviations

Herein and throughout this application, the following abbreviations may be used.

| | |
|---|---|
| BOC or Boc | tert-butyloxycarbonyl |
| Bu | butyl |
| DAST | diethylaminosulfur trifluoride |
| DBU | 1,8-diazabicyclo[5.4.0]undec-7-ene |
| DCC | dicyclohexylcarbodiimide |
| DCM | dicholomethane |
| DMF | dimethylformamide |
| EDCI | 1-ethyl-3-(3'-dimethylaminopropyl)carbodiimide |
| Et | ethyl |
| EtOAc | ethyl acetate |
| HOBt | hydroxybenzotriazole |
| IPA | isopropyl alcohol |
| Me | methyl |
| Ms | mesylate |
| OAc | acetate |
| $PdCl_2(dppf)$ | [1,1'-bis(diphenylphosphino)ferrocene]dichloropalladium(II) |

| | |
|---|---|
| PPh₃ | triphenylphosphine |
| iPr | isopropyl |
| PyBrop | bromo-tris-pyrrolidinophosphonium hexafluorophosphate |
| TEA | triethylamine |
| TFA | trifluoroacetic acid |
| THF | tetrahydrofuran |
| Ts | tosylate |

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, NH₃, NH₄OH, N-methyl-D-glucamine, piperidine, potassium, potassium-t-butoxide, potassium hydroxide (aqueous), procaine, quinine, sodium, sodium carbonate, sodium-2-ethylhexanoate (SEH), sodium hydroxide, triethanolamine, or zinc.

Methods of Use

The present invention is directed to a method for preventing, treating or ameliorating a CCR2 mediated syndrome, disorder or disease comprising administering to a subject in need thereof an effective amount of a compound of Formula (I) or (Ia) or a form, composition or medicament thereof.

Examples of a CCR2 mediated syndrome, disorder or disease for which the compounds of Formula (I) or (Ia) are useful include chronic obstructive pulmonary disorder (COPD), ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, type-I diabetes, type II diabetes and diabetic complications, diabetic nephropathy, diabetic retinopathy, diabetic retinitis, diabetic microangiopathy, overweight, obesity, obesity-associated insulin resistance, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach.

The term "administering" with respect to the methods of the invention, means a method for therapeutically or prophylactically preventing, treating or ameliorating a syndrome, disorder or disease as described herein by using a compound of Formula (I) or (Ia) or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be animal, typically a mammal, typically a human, which has been the object of treatment, observation or experiment. In one aspect of the invention, the subject is at risk of (or susceptible to) developing a syndrome, disorder or disease that is associated with elevated MCP-1 expression or MCP-1 overexpression, or a patient with an inflammatory condition that accompanies syndromes, disorders or diseases associated with elevated MCP-1 expression or MCP-1 overexpression.

The term "therapeutically effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "uveitis" generically refers to any inflammatory disease involving the eye. Uveitis can be divided into clinically distinct subtypes based on the part of the eye in which the inflammation is present (percentages correspond to patients known to fit these categories): anterior (51%), intermediate (13%), posterior (20%), or panuveitis (16%) and, according to the course of the disease, as either acute (16%), recurring (26%), or chronic (58%). Those with anterior uveitis (19%) eventually develop irreparable vision damage despite aggressive treatment such as unilateral blindness (9%), bilateral blindness (2%), or unilateral or bilateral vision impairment (8%). Most cases of uveitis are idiopathic, but known causes include infection (e.g., toxoplasmosis, cytomegalovirus, and the like) or development as a component of a systemic inflammatory and/or autoimmune disorder (e.g., juvenile RA, HLA-B27 associated spondyloarthropathies, sarcoidosis, and the like). (HLA-B27: Human Leukocyte Antigen B*27—is a class I surface antigen encoded by the B locus in the major histocompatibility complex (MHC) on chromosome 6 and presents micobial antigens to T cells. HLA-B27 is strongly associated with a certain set of autoimmune diseases referred to as the seronegative spondyloarthropathies.)

When employed as CCR2 inhibitors, the compounds of the invention may be administered in a therapeutically effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula (I) and/or (Ia) may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula (I) and/or (Ia) include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention. As used herein, the term "composition" is intended to encompass a product comprising the specified ingredients in the specified amounts, as well as any product which results, directly or indirectly, from combinations of the specified ingredients in the specified amounts.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in the Examples or Formula (I) or Formula (Ia) for use as a medicament, in particular, for use as a medicament for treating a CCR2 mediated syndrome disorder or disease.

In another embodiment, the invention relates to the use of a compound as described in the Examples of Formula (I) or Formula (Ia) for the preparation of a medicament for the treatment of a disease associated with an elevated or inappropriate CCR2 activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley &

Sons, 1991. The protecting groups may be removed at a convenient subsequent stage using methods known from the art.

General Reaction Scheme

Representative compounds of the present invention can be synthesized in accordance with the general synthetic methods described below. Compounds of Formula (I) can be prepared by methods known to those who are skilled in the art. The following reaction schemes are only meant to represent examples of the invention and are in no way meant to be a limit of the invention.

Compounds of Formula (I) may be prepared according to the processes outlined in Scheme 1.

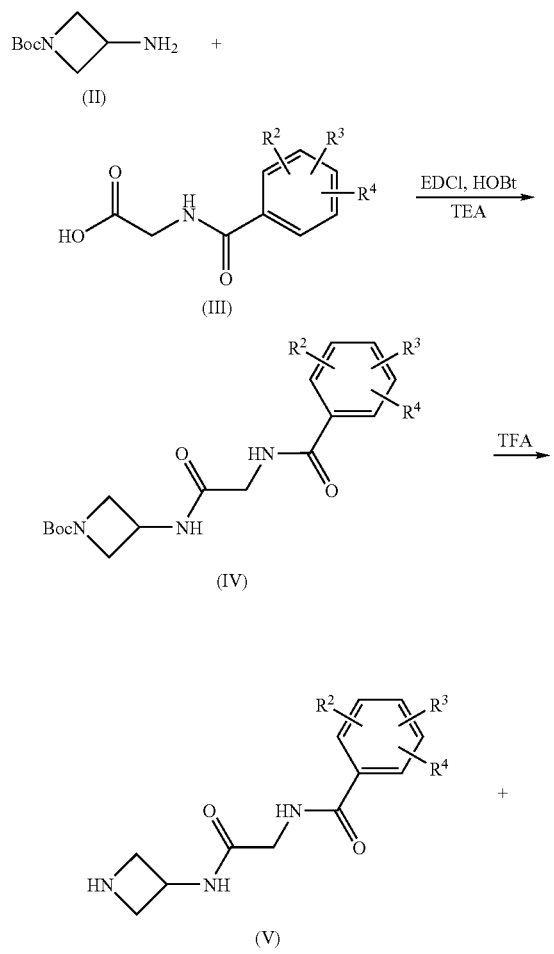

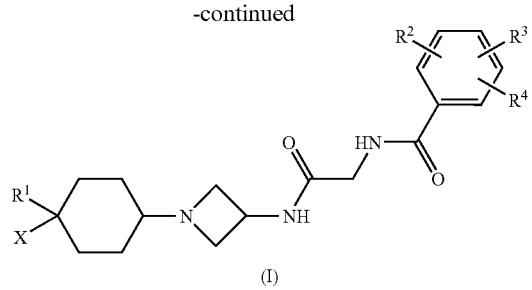

Scheme 1 illustrates a synthetic route leading to compounds of Formula (I). Commercially available azetidine (II) is reacted with acid (III), wherein (III) is prepared according to the procedure described by Ingersoll, A. W. et. al., Organic Syntheses 1932, XII, 40-2 substituting commercially available benzoyl chloride, in the presence of a coupling reagent such as EDCI/HOBt, PyBrop, or DCC, in an organic solvent such as THF, dichloromethane or 1,2-dichloroethane, at a temperature in the range of about 0° C. to about 25° C., to yield the corresponding amide (IV).

Amide (IV) is treated with an acid such as 1N HCl, 1N $H_2SO_4$ or trifluoroacetic acid in an organic solvent such as diethyl ether, THF, dichloromethane or dioxane, at a temperature in the range of about 0° C. to about 25° C. to yield amine (V).

Amine (V) is reacted with a suitably substituted ketone (VI), in the presence of a reducing reagent such as $NaBH_4$, $NaBH(CN)_3$ or $NaBH(OAc)_3$, in an organic base such as triethylamine, diethylpropylamine or N-methylmorpholine with or without molecule sieves, in an organic solvent such as dichloromethane, 1,2-dichloroethane or THF, at a temperature in the range of 0° C. to about 25° C., to yield the corresponding azetidine (I).

Alternatively, compounds of Formula (I) may be prepared according to the processes outlined in Scheme 2.

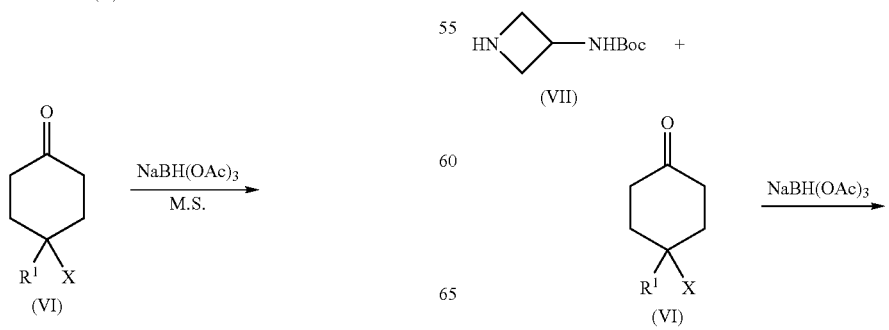

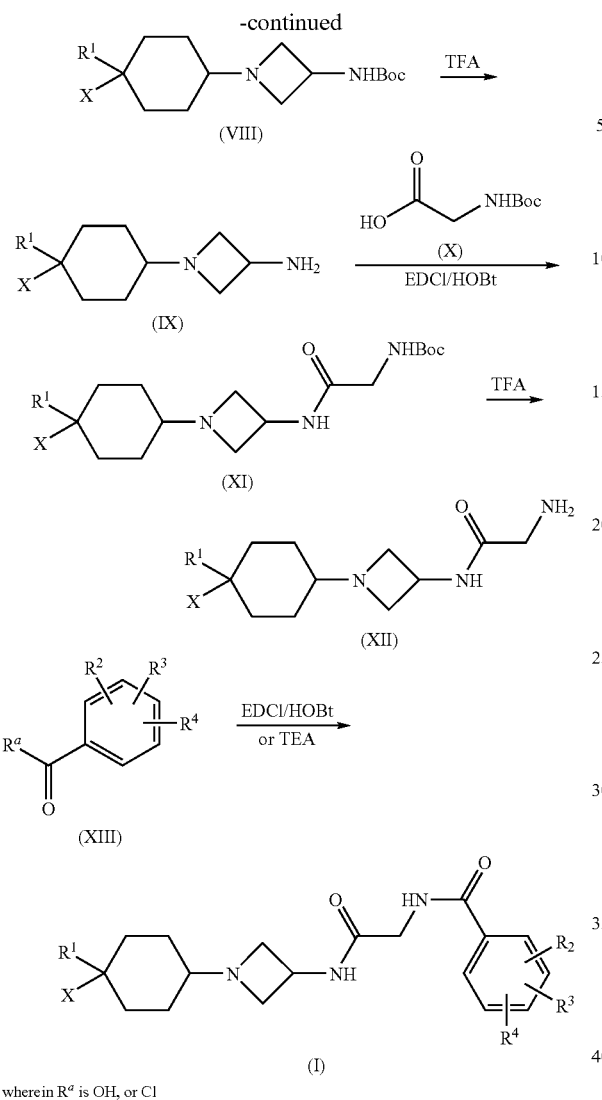

wherein $R^a$ is OH, or Cl

Commercially available azetidine (VII) is reacted with a suitably substituted ketone (VI), in the presence of a reducing reagent such as $NaBH_4$, $NaBH(CN)_3$ or $NaBH(OAc)_3$, in an organic base such as triethylamine, diethylpropylamine or N-methylmorpholine, with or without molecule sieves, in an organic solvent such as dichloromethane, 1,2-dichloroethane or THF at a temperature in the range of 0° C. to about 25° C., to yield the corresponding azetidine (VIII).

Azetidine (VIII) is treated with 1N HCl, 1N $H_2SO_4$ or trifluoroacetic acid in an organic solvent such as diethyl ether, THF, dioxane or dichloromethane, at a temperature in the range of about 0° C. to about 25° C., to yield the corresponding amine (IX).

Amine (IX) is reacted with acid (X), in the presence of a coupling reagent such as EDCI/HOBt, PyBrop or DCC, in an organic solvent such as THF, dichloromethane or 1,2-dichloroethane, at a temperature in the range of about 0° C. to about 25° C., to yield the corresponding azetidine (XI).

Azetidine (XI) is treated with 1N HCl or $H_2SO_4$ or trifluoroacetic acid, in an organic solvent such as diethyl ether, THF or dioxane, at a temperature in the range of about 0° C. to about 25° C., to yield the corresponding amine (XII).

Amine (XII) is reacted with acid (XIII). When $R^a$ is OH, the reaction is performed in the presence of a coupling reagent such as EDCI/HOBt, PyBrop or DCC, in an organic solvent such as THF, dichloromethaneor 1,2-dichloroethane, at a temperature in the range of about 0° C. to about 25° C. When $R^a$ is Cl, the reaction is performed in the presence of an organic base such triethylamine, diethylpropylamine or N-methylmorpholine, in an organic solvent such as THF, dichloromethane or 1,2-dichloroethane, at a temperature in the range of about 0° C. to about 25° C., to yield the corresponding azetidine (I).

Compounds of Formula (I) may be derived from ketone (VI). Preparation of (VI) is outlined in Scheme 3.

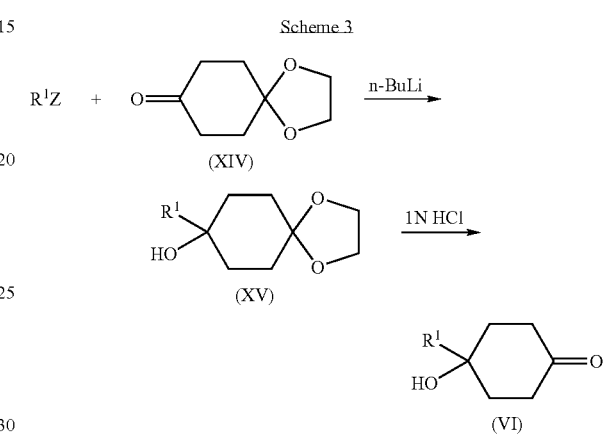

Z is H or halogen

Commercially available aryl halide or aryl alkane $R^1Z$ (where $R^1$ is as defined in Formula (I)) is reacted with commercially available ketone (XIV) in the presence of organometalic agent such as n-BuLi, i-PrMgBr or i-PrMgCl, in an organic solvent such as ether, THF or dioxane, at a temperature in the range of about −78° C. to about 0° C., to yield the corresponding ketal (XV).

Ketal (XV) is treated with an acid such as 1N HCl or 1N $H_2SO_4$ in an organic solvent such as acetone, acetonitrile or THF, at a temperature in the range of about 0° C. to about 25° C., to yield the corresponding ketone (VI).

Compounds of Formula (I) may be derived from ketone (XIX). Preparation of (XIX) is outlined in Scheme 4.

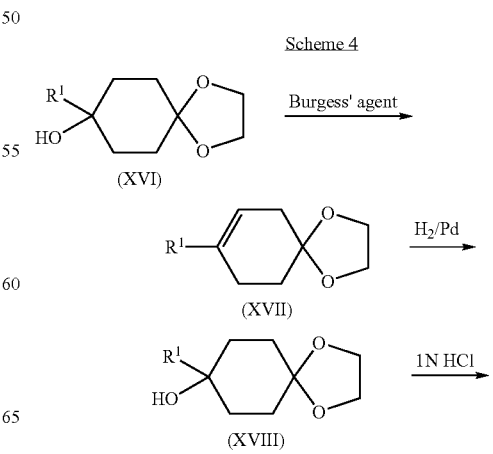

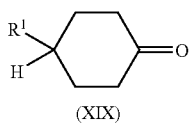

(XIX)

Ketal (XVI) is treated with a dehydrating agent such as Burgess' reagent, in an organic solvent such as ether, THF or dioxane, at a temperature in the range of about 0° C. to about 25° C., to yield the corresponding alkene (XVII).

Alkene (XVII) is treated with hydrogen gas under pressure from 5 to 50 psi catalyzed by 5-10% Pd/C, in an organic solvent such as methanol, at a temperature in the range of about 25° C. to about 50° C., to yield the corresponding alkane (XVIII).

Alkane (XVIII) is treated with 1N HCl or 1N $H_2SO_4$, in an organic solvent such as acetone, acetonitrile or THF, at a temperature in the range of about 0° C. to about 25° C., to yield the corresponding ketone (XIX).

Alternatively compound (XVII) may be prepared according to the processes outlined in Scheme 5.

Scheme 5

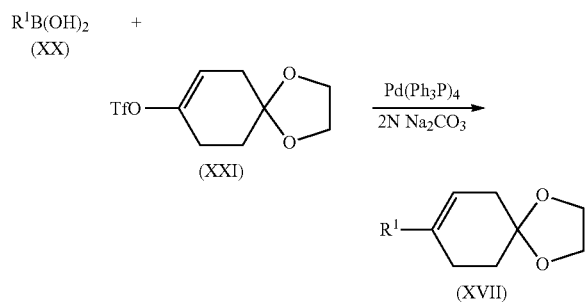

Z is halogen

Commercially available aryl boronic acid (XX), (wherein $R^1$ is as defined in Formula (I)) is reacted with vinyl triflate (XXI) prepared according to the procedure of Pearson, W. et. al., *J. Org. Chem.* 2004, 69, 9109-9122, in the presence of a catalyst such as $Pd(Ph_3P)_4$, $PdCl_2(Ph_3P)_2$ or $PdCl_2(dppf)$ and a base such as 2N $Na_2CO_3$ or $K_2CO_3$, in an organic solvent such as toluene, dioxane or THF, at a temperature in the range of about 80° C. to about 120° C., to yield the corresponding alkene (XVII).

Alternatively, commercially available aryl or heteroaryl halide $R^1Z$ is reacted with vinyl boronic ester (XXII) prepared according to Birch, A. M. et. al., PCT Int. Appl. 2006, WO 2006064189, in the presence of a catalyst such as $Pd(Ph_3P)_4$, $PdCl_2(Ph_3P)_2$ or $PdCl_2$ (dppf) and a base such as 2N $Na_2CO_3$ or $K_2CO_3$, in an organic solvent such as toluene, dioxane or THF, at a temperature in the range of about 80° C. to about 120° C., to yield the corresponding alkene (XVII).

Compounds of Formula (I) may be derived from ketone (XXIII). Ketone (XXIII) may be prepared according to the processes outlined in Scheme 6.

Scheme 6

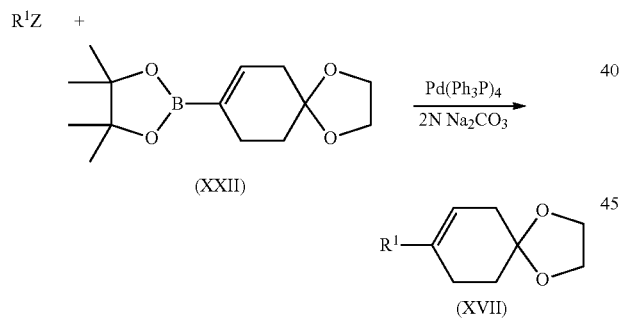

Ketal (XVI) is treated with a fluorinating agent such as DAST or trifluorosulfonyl fluoride, in an organic solvent such as dichloromethane, THF or dioxane, at a temperature in the range of about –78° C. to about 0° C., to yield the corresponding fluoride (XXIV). Fluoride (XXIV) is treated with an acid such as 1N HCl or 1N $H_2SO_4$, in an organic solvent such as acetone, acetonitrile or THF, at a temperature in the range of about 0° C. to about 25° C., to yield the corresponding ketone (XXIII).

Compounds of Formula (I) may be derived from ketone (XXV). Ketone (XXV) may be prepared according to the processes outlined in Scheme 7.

Scheme 7

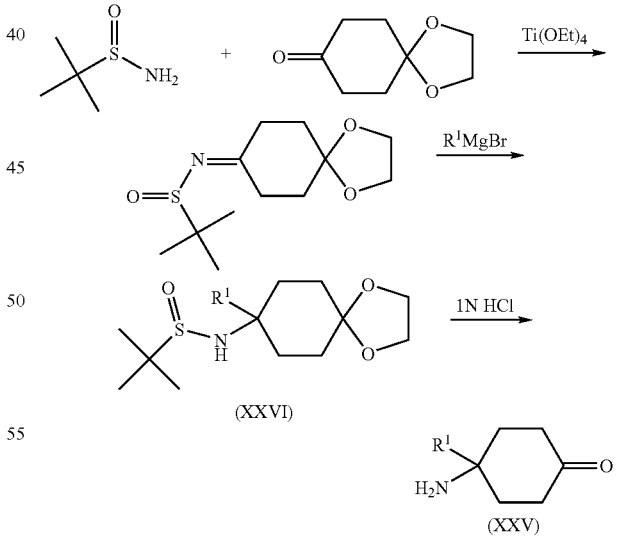

Commercially available 2-methyl-propane-2-sulfinic acid amide is reacted with commercially available 1,4-dioxa-spiro[4.5]decan-8-one in the presence of a coupling agent such as $Ti(OEt)_4$ or $CuSO_4$, in an organic solvent such as dichloromethane, THF or dioxane, at a temperature in the range of about 25° C. to about 80° C., to yield 2-methyl-propane-2-sulfinic acid (1,4-dioxa-spiro[4.5]dec-8-ylidene)-amide.

2-Methyl-propane-2-sulfinic acid (1,4-dioxa-spiro[4.5]dec-8-ylidene)-amide is treated with an organometalic agent such as $R^1$MgBr or $R^1$Li, in an organic solvent such as ether, THF or dioxane, at a temperature in the range of about −78° C. to about 25° C., to yield the corresponding sulfonamide (XXVI).

Sulfinamide (XXVI) is treated with an acid such as 1N HCl or 1N $H_2SO_4$ in an organic solvent such as acetone, acetonitrile or THF, at a temperature in the range of about 0° C. to about 25° C., to yield the corresponding ketone (XXV).

Compounds of Formula (I) where $R^1$ is linked with the cyclohexyl ring through N or O may be prepared according to the process outlined in Scheme 8.

Scheme 8

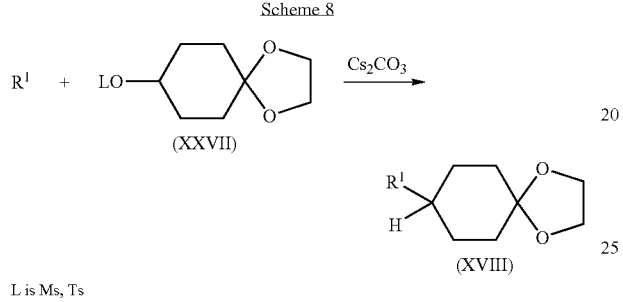

(XXVII)

(XVIII)

L is Ms, Ts

Commercially available OH or NH substituted $R^1$ is reacted with alkyl tosylate or alkyl mesylate (XXVII) in the presence of inorganic base such as $K_2CO_3$, $Cs_2CO_3$ or NaH, in an organic solvent such as DMF or THF, at a temperature in the range of about 25° C. to about 80° C., to yield the corresponding ketal (XVIII).

EXAMPLES

Representative compounds of the present invention can be synthesized in accordance with the general synthetic methods described below. Compounds of Formula (I) can be prepared by methods known to those who are skilled in the art. The following examples are only meant to represent examples of the invention and are in no way meant to be a limit of the invention.

Example 1

N-({1-[4-(6-Methoxy-pyridin-3-yl)-cyclohexyl]-azetidin-3-ylcarbamoyl}-methyl)-3-trifluoromethyl-benzamide Step A: 8-(6-Methoxy-pyridin-3-yl)-1,4-dioxa-spiro[4.5]decan-8-ol

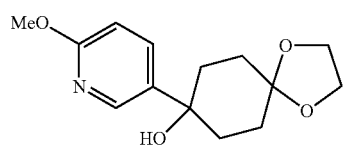

A solution of 5-bromo-2-methoxy-pyridine (Aldrich, 5.0 g, 26.6 mmol) in THF or ether (30 mL) at −78° C. was treated with n-BuLi (2.5 M in hexanes, 12 mL, 30 mmol) dropped slowly over 10 min. The reaction was stirred for an additional 20 min. at −78° C. A solution of 1,4-dioxa-spiro[4.5]decan-8-one (Aldrich, 4.37 g, 28 mmol) in THF (10 mL) was slowly dropped into the reaction. After addition, the reaction was stirred for an additional 2 hours at −78° C. The reaction was then quenched with water and warmed to room temperature. The solvent was removed in vacuo and the residue was partitioned between ethyl acetate and water. The organic layer was washed with brine, dried over anhydrous $Na_2SO_4$, filtered and concentrated to give a yellow solid, which was then purified by silica gel column on a CombiFlash® system (Teledyne Isco, Inc, Lincoln, Nebr.) using hexanes and ethyl acetate (from 10% ethyl acetate to 100% ethyl acetate) to afford the title compound as a yellow solid.

$^1$H NMR (400 MHz, $CDCl_3$) δ 8.28 (s, 1H), 7.75 (d, J=7.5 Hz, 1H), 6.72 (d, J=7.5 Hz, 1H), 3.95 (m, 4H), 2.35 (s, br, 1H), 2.10 (m, 1H), 1.85 (m, 2H), 1.65 (m, 2H).

Step B:
4-Hydroxy-4-(6-methoxy-pyridin-3-yl)-cyclohexanone

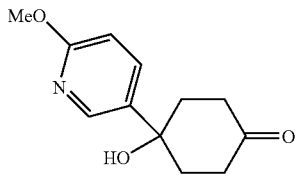

8-(6-Methoxy-pyridin-3-yl)-1,4-dioxa-spiro[4.5]decan-8-ol (4.00 g, 15.7 mmol) as prepared in the previous step was treated with 1N HCl (~16 mL) in acetone (20 mL) at room temperature for 4 hours. The reaction was neutralized with saturated $NaHCO_3$ solution and the solvent was removed. The residue was partitioned between ethyl acetate and water. The organic layer was washed with brine, dried over anhydrous $Na_2SO_4$, filtered and concentrated to give a yellow solid, which was purified by silica gel column on a CombiFlash® system using hexanes and ethyl acetate (from 10% ethyl acetate to 100% ethyl acetate) to afford the title compound as a pale yellow solid.

$^1$H NMR (400 MHz, $CDCl_3$) δ 8.30 (s, 1H), 7.75 (d, J=7.0 Hz, 1H), 6.75 (d, J=6.5 Hz, 1H), 3.90 (s, 4H), 2.91 (m, 2H), 2.35 (d, J=6.8 Hz, 2H), 2.22 (m, 4H).

Step C:
4-(6-Methoxy-pyridin-3-yl)-cyclohex-3-enone

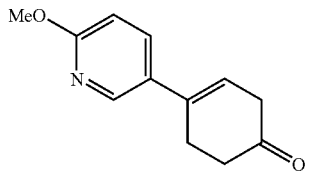

4-Hydroxy-4-(6-methoxy-pyridin-3-yl)-cyclohexanone (as prepared in the previous step, 750 mg, 3.40 mmol) in THF (5 mL) was treated with Burgess' reagent (Aldrich, 1.19 g, 5.0 mmol) at room temperature. The reaction was stirred for 10 hours. The solvent was removed in vacuo and the residue was partitioned between ethyl acetate and water. The organic layer was washed with brine, dried over anhydrous $Na_2SO_4$, filtered and concentrated to give yellow oil, which was then purified by silica gel column on a CombiFlash® system using hexanes and ethyl acetate (from 10% ethyl acetate to 100% ethyl acetate) to afford the title compound as white solid.

$^1$H NMR (400 MHz, CDCl$_3$) δ 8.25 (s, 1H), 7.61 (d, J=7.2 Hz, 1H), 6.72 (d, J=7.0 Hz, 1H), 6.02 (t, J=4.3 Hz, 1H), 3.90 (s, 3H), 3.08 (d, J=2.5 Hz, 2H), 2.81 (t, J=6.5 Hz, 2H), 2.62 (t, J=6.8 Hz, 2H).

Step D: 3-[2-(3-Trifluoromethyl-benzoylamino)-acetylamino]-azetidine-1-carboxylic acid tent-butyl ester

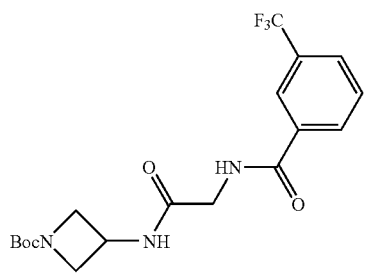

3-Amino-azetidine-1-carboxylic acid tert-butyl ester (AstaTech, 1.2 g, 6.97 mmol) and (3-trifluoromethyl-benzoylamino)-acetic acid (Bionet Building Blocks, 1.57 g, 6.36 mmol) were treated with EDCI (Aldrich, 1.57 g, 6.36 mmol), HOBT (Aldrich, 1.22 g, 6.36 mmol) in DCM (10 mL) at room temperature for 4 hours. The reaction solution was partitioned between DCM and water. The organic layer was washed with brine, dried over anhydrous Na$_2$SO$_4$, filtered and concentrated to give a yellow oil, and purified by silica gel column on a CombiFlash® system using hexanes and ethyl acetate (from 10% ethyl acetate to 100% ethyl acetate) to afford the title compound as a white solid.

$^1$H NMR (400 MHz, CDCl$_3$) δ 8.10 (s, 1H), 8.02 (d, J=6.6 Hz, 1H), 7.80 (d, J=6.8 Hz, 1H), 7.56 (t, J=6.5 Hz, 1H), 4.61 (m, 1H), 4.25 (t, J=7.2 Hz, 2H), 4.18 (d, J=5.5 Hz, 2H), 3.82 (t, J=7.5 Hz, 2H), 1.41 (s, 9H).

Step E: N-(Azetidin-3-ylcarbamoylmethyl)-3-trifluoromethyl-benzamide free base, HCl and TFA salt

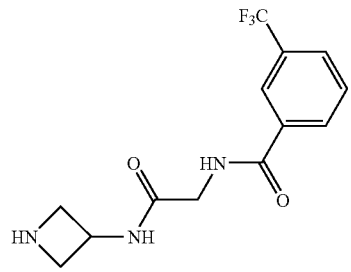

3-[2-(3-Trifluoromethyl-benzoylamino)-acetylamino]-azetidine-1-carboxylic acid tert-butyl ester (7.5 g, 18.7 mmol), as prepared in the previous step, was dissolved in 4N HCl in dioxane (5 mL) and MeOH (20 mL) at room temperature. The reaction was stirred for another 4 hours. The solvent was removed and the residue was dried to give the title compound as a HCl salt (yellow foam).

3-[2-(3-Trifluoromethyl-benzoylamino)-acetylamino]-azetidine-1-carboxylic acid tert-butyl ester (2.10 g, 5.24 mmol) was dissolved in 1:1 TFA and DCM mixed solution (10 mL) at room temperature. The reaction was stirred for another 2 hours. The solvent was removed and the residue was dried to give the title compound as a TFA salt containing extra TFA (colorless oil).

The free base was obtained by treating the salt in MeOH with solid Na$_2$CO$_3$ overnight. The solid was filtered and residue was dried to give the title compound for analytical characterization. The HCl or TFA salt was general used for the further reactions.

$^1$H NMR (400 MHz, CDCl$_3$) δ 8.10 (s, 1H), 8.05 (d, J=6.0 Hz, 1H), 7.78 (d, J=6.2 Hz, 1H), 7.55 (m, 2H), 4.78 (m, 1H), 4.15 (d, J=3.2 Hz, 2H), 3.95 (t, J=7.0 Hz, 2H), 3.52 (t, J=7.0 Hz, 2H).

Step F: N-({1-[4-(6-Methoxy-pyridin-3-yl)-cyclohex-3-enyl]-azetidin-3-ylcarbamoyl}-methyl)-3-trifluoromethyl-benzamide

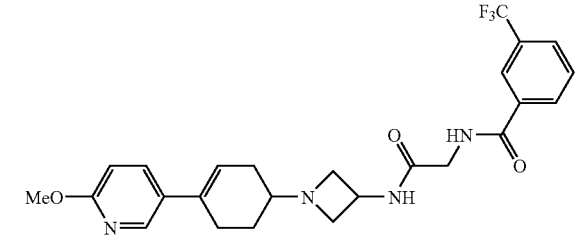

4-(6-Methoxy-pyridin-3-yl)-cyclohex-3-enone (as prepared in Step C, 1.02 g, 5.02 mmol) and N-(azetidin-3-ylcarbamoylmethyl)-3-trifluoromethyl-benzamide HCl salt (as prepared in the previous step, 2.54 g, 7.53 mmol) in DCM (15 mL) was treated with TEA (2.80 mL, 20 mmol) for 10 min followed by NaBH(OAc)$_3$ (Aldrich, 3.20 g, 15 mmol) for another 4 hours at room temperature. The reaction was quenched with saturated sodium bicarbonate. The organic layer was separated and the aqueous layer was extracted 3 times with chloroform/IPA "cocktail" (~3:1, v/v). The combined organic layers were dried over anhydrous Na$_2$SO$_4$, filtered and concentrated to give the crude product, which was then purified by a CombiFlash® system using ethyl acetate and 7N NH$_3$ in MeOH as eluent (from pure ethyl acetate to 5% 7N NH$_3$ in MeOH in ethyl acetate) to afford the title compound as white solids.

$^1$H NMR (400 MHz, CDCl$_3$) δ 8.15 (s, 1H), 8.10 (s, 1H), 8.05 (d, J=6.5 Hz, 1H), 7.75 (d, J=6.5 Hz, 1H), 7.60 (d, J=6.6 Hz, 1H), 7.55 (t, J=6.5 Hz, 1H), 7.40 (m, 1H), 7.02 (d, J=6.3 Hz, 1H), 6.70 (d, J=6.5 Hz, 1H), 5.92 (m, 1H), 4.58 (m, 1H), 4.20 (d, J=4.5 Hz, 2H), 3.90 (s, 3H), 3.65 (t, J=6.8 Hz, 2H), 3.05 (t, J=6.8 Hz, 2H), 2.45 (m, 1H), 2.30 (m, 2H), 1.92 (m, 2H), 1.45 (m, 1H), 1.28 (m, 1H).

Step G: N-({1-[4-(6-Methoxy-pyridin-3-yl)-cyclohexyl]-azetidin-3-ylcarbamoyl}-methyl)-3-trifluoromethyl-benzamide

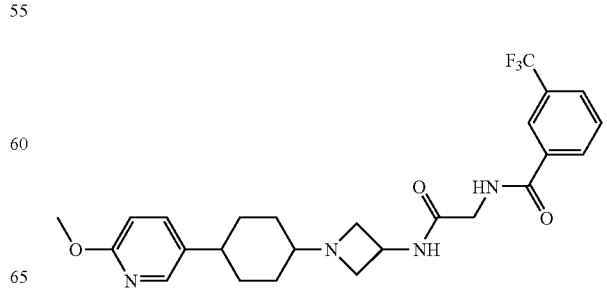

N-({1-[4-(6-Methoxy-pyridin-3-yl)-cyclohex-3-enyl]-azetidin-3-ylcarbamoyl}-methyl)-3-trifluoromethyl-benzamide (as prepared in the previous step, 500 mg, 1.02 mmol) from step B in MeOH (40 mL) was driven through an H-Cube® Continuous-flow Hydrogenation reactor (ThalesNano, Budapest, Hungary) under full hydrogen mode at room temperature using a 5% Pd/C cartridge. The resulting solution was concentrated and purified by silica gel column on a CombiFlash® system using ethyl acetate and 7N NH₃ in MeOH as eluent (from pure ethyl acetate to 5% 7N NH₃ in MeOH in ethyl acetate) to afford the two title compounds as white solids.

1a: Less Polar Isomer from Silica Gel Column

¹H NMR (400 MHz, CDCl₃) δ 8.21 (s, 1H), 8.05 (d, J=7.0 Hz, 2H), 7.85 (s, 1H), 7.80 (d, J=6.2 Hz, 1H), 7.60 (d, J=6.0 Hz, 1H), 7.50 (d, J=6.1 Hz, 1H), 7.36 (d, J=5.5 Hz, 1H), 6.76 (d, J=6.5 Hz, 1H), 4.55 (m, 1H), 4.25 (s, br, 2H), 4.01 (s, 3H), 3.65 (t, J=5.8 Hz, 2H), 2.90 (t, J=5.5 Hz, 2H), 2.48 (m, 1H), 1.85 (m, 2H), 1.70 (m, 2H), 1.45 (m, 4H).

1b: More Polar Isomer from Silica Gel Column

¹H NMR (400 MHz, CDCl₃) δ 8.10 (s, 1H), 8.02 (d, J=6.0 Hz, 1H), 8.00 (s, 1H), 7.78 (d, J=5.5 Hz, 1H), 7.60 (t, J=6.5 Hz, 1H), 6.80 (m, 1H), 6.67 (d, J=7.0 Hz, 1H), 4.55 (m, 1H), 4.19 9d, J=4.5 Hz, 2H), 3.65 (t, J=6.6 Hz, 2H), 3.02 (t, J=6.6 Hz, 2H), 2.38 (m, 1H), 1.90 (m, 4H), 1.36 (m, 2H), 1.15 (m, 2H).

Example 2

N-({1-[4-(2-Methoxy-pyridin-3-yl)-cyclohexyl]-azetidin-3-ylcarbamoyl}-methyl)-3-trifluoromethyl-benzamide Step A: 3-(1,4-Dioxa-spiro[4.5]dec-7-en-8-yl)-2-methoxy-pyridine

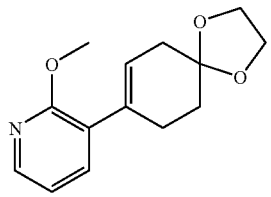

To a mixture of trifluoro-methanesulfonic acid 1,4-dioxa-spiro[4.5]dec-7-en-8-yl ester (prepared according to JOC, 69, 3943, 2004, 1.27 g, 3.47 mmol) and 2-methoxypyridine-3-boronic acid (Aldrich, 637 mg, 4.17 mmol) was added tetrakistriphenylphosphine palladium (120 mg, 0.10 mmol), dioxane (10 mL) and aqueous sodium carbonate (4.00 mL, 8.00 mmol, 2N). The reaction mixture was heated to 100° C. under argon for 16 hours and then cooled to room temperature and extracted with ethyl acetate. The organic layer was washed with brine, dried (Na₂SO₄) and concentrated in vacuo. The residue was purified by flash chromatography (SiO₂, 0-10% MeOH/CH₂Cl₂) to afford 3-(1,4-Dioxa-spiro[4.5]dec-7-en-8-yl)-2-methoxy-pyridine as a colorless oil.

¹H NMR (CHLOROFORM-d) δ: 8.04 (dd, J=4.9, 1.9 Hz, 1H), 7.44 (dd, J=7.3, 2.0 Hz, 1H), 6.83 (dd, J=7.2, 4.9 Hz, 1H), 5.80 (s, 1H), 3.99-4.07 (m, 4H), 3.70 (s, 3H), 2.62 (d, J=1.8 Hz, 2H), 2.46 (d, J=3.5 Hz, 2H), 1.89 (t, J=6.6 Hz, 2H).

Step B: 4-(2-Methoxy-pyridin-3-yl)-cyclohex-3-enone

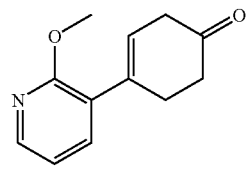

To a mixture of 3-(1,4-Dioxa-spiro[4.5]dec-7-en-8-yl)-2-methoxy-pyridine (as prepared in the previous step, 211 mg, 0.854 mmol) in acetonitrile was added aqueous HCl (5 mL, 5 mmol, 1M). The mixture was stirred at room temperature until HPLC indicated consumption of starting material. The reaction mixture was poured onto saturated sodium bicarbonate solution and extracted with ethyl acetate. The organic layer washed with brine, dried over anhydrous sodium sulfate and concentrated in vacuo. The residue was purified by flash chromatography (SiO₂, 0-10% MeOH/CH₂Cl₂) to afford 4-(2-methoxy-pyridin-3-yl)-cyclohex-3-enone.

LCMS (ESI, M/Z): 204 (MH+).

Step C: N-({1-[4-(2-Methoxy-pyridin-3-yl)-cyclohex-3-enyl]-azetidin-3-ylcarbamoyl}-methyl)-3-trifluoromethyl-benzamide

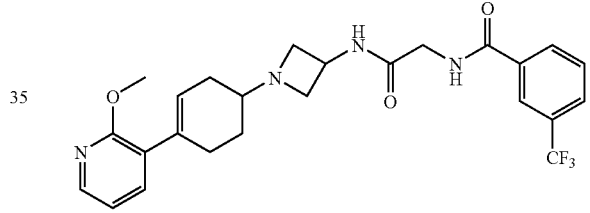

The title compound was prepared as a white solid from reductive amination of 4-(2-methoxy-pyridin-3-yl)-cyclohex-3-enone (as prepared in the previous step) and N-(azetidin-3-ylcarbamoylmethyl)-3-trifluoromethyl-benzamide using the procedure described in Step F of Example 1.

¹H NMR (CHLOROFORM-d) δ: 8.12 (s, 1H), 7.98-8.07 (m, 2H), 7.77 (d, J=7.8 Hz, 1H), 7.52-7.63 (m, 2H), 7.39 (dd, J=7.3, 1.8 Hz, 1H), 7.19-7.26 (m, 1H), 6.83 (dd, J=7.2, 4.9 Hz, 1H), 5.76-5.82 (m, 1H), 4.52-4.64 (m, 1H), 4.19 (d, J=4.8 Hz, 2H), 3.86-3.98 (m, 4H), 3.69 (d, J=8.1 Hz, 2H), 3.03 (s, 2H), 2.40 (d, J=3.0 Hz, 4H), 1.76-1.98 (m, 2H), 1.41 (none, 1H); LCMS (ESI, M/Z): 489 (MH+).

Step D: N-({1-[4-(2-Methoxy-pyridin-3-yl)-cyclohexyl]-azetidin-3-ylcarbamoyl}-methyl)-3-trifluoromethyl-benzamide

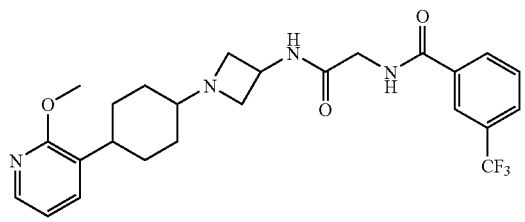

The title compound was prepared as a white solid from the hydrogenation of N-({1-[4-(2-methoxy-pyridin-3-yl)-cyclohex-3-enyl]-azetidin-3-ylcarbamoyl}-methyl)-3-trifluoromethyl-benzamide (as prepared in the previous step) using the procedure described in Step G of Example 1.

¹H NMR (CHLOROFORM-d) δ: 8.13 (s, 1H), 7.95-8.06 (m, 2H), 7.78 (d, J=7.8 Hz, 1H), 7.58 (t, J=7.6 Hz, 1H), 7.49 (br. s., 1H), 7.38 (d, J=1.8 Hz, 1H), 7.10-7.22 (m, 1H), 6.76-6.88 (m, 1H), 5.78 (br. s., 1H), 4.47-4.66 (m, 1H), 4.19 (dd, J=4.8, 1.8 Hz, 2H), 3.94 (s, 3H), 3.55-3.75 (m, 2H), 2.96-3.10 (m, 2H), 1.06-2.53 (series of m, 9H);
LCMS (ESI, M/Z): 491 (MH+).

Example 3

N-({1-[4-(3-Hydroxy-pyridin-2-yl)-cyclohexyl]-azetidin-3-ylcarbamoyl}-methyl)-3-trifluoromethyl-benzamide Step A: 2-(1,4-Dioxa-spiro[4.5]dec-7-en-8-yl)-pyridin-3-ol

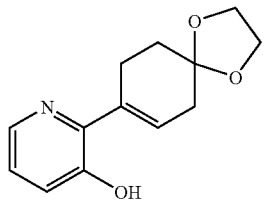

8-(4,4,5,5-Tetramethyl-[1,3,2]dioxaborolan-2-yl)-1,4-dioxa-spiro[4.5]dec-7-ene (prepared as described in PCT Int. Appl. WO2006064189, 0.292 g, 1.10 mmol), 2-iodo-3-hydroxypyridine (Aldrich, 0.177 g, 0.801 mmol), and tetrakis(triphenylphosphino)palladium(0) (Aldrich, 0.048 g, 0.042 mmol) were dissolved in 1,4-dioxane (9 mL), treated with 2M aqueous Na₂CO₃ (2.0 mL, 4.0 mmol), bubbled with argon for a few minutes, and heated to 100° C. under reflux condenser for 24 h. After cooling to ambient temperature, the reaction was diluted with water (30 mL), extracted thrice with dichloromethane, aqueous layer acidified to ca. pH 7, extracted twice more with dichloromethane, and the combined organic layers washed with brine, dried over Na₂SO₄, filtered, and concentrated in vacuo to give an orange oil. This was purified by thin layer chromatography on silica gel (EtOAc) to give the title compound as a yellow solid.

¹H NMR (400 MHz, CHLOROFORM-d) δ 8.16 (dd, J=4.5, 1.3 Hz, 1 H), 7.22 (dd, J=8.1, 1.3 Hz, 0 H), 7.07 (dd, J=8.2, 4.7 Hz, 1 H), 5.95-6.09 (m, 2 H), 4.03 (s, 4 H), 2.73 (dddd, J=6.4, 4.4, 2.2, 2.0 Hz, 2 H), 2.49 (d, J=2.8 Hz, 2 H), 1.96 (t, J=6.6 Hz, 2 H). ESI-MS (m/z): Calcd. For C₁₃H₁₅NO₃: 233. found: 234 (M+H).

Step B: 2-(1,4-Dioxa-spiro[4.5]dec-8-yl)-pyridin-3-ol

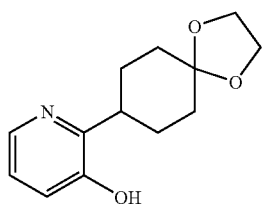

The title compound was prepared as a white solid from the hydrogenation of 2-(1,4-dioxa-spiro[4.5]dec-7-en-8-yl)-pyridin-3-ol (as prepared in the previous step) using the procedure described in Step G of Example 1.

¹H NMR (400 MHz, ACETONITRILE-d₃) δ 8.05 (dd, J=4.7, 1.4 Hz, 1 H), 7.19 (dd, J=8.1, 1.5 Hz, 1 H), 7.06 (dd, J=8.1, 4.5 Hz, 1 H), 3.86-3.99 (m, 4 H), 3.12 (tt, J=11.7, 3.7 Hz, 1 H), 1.72-1.94 (m, 6 H), 1.60-1.72 (m, 2 H). ESI-MS (m/z): Calcd. For C₁₃H₁₇NO₃: 235. found: 236 (M+H).

Step C: 4-(3-Hydroxy-pyridin-2-yl)-cyclohexanone

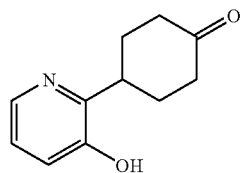

The title compound was prepared as a white solid from the deprotection of 2-(1,4-dioxa-spiro[4.5]dec-8-yl)-pyridin-3-ol (as prepared in the previous step) using the procedure described in Step B of Example 2.

¹H NMR (400 MHz, ACETONITRILE-d₃) δ 7.94 (dd, J=4.7, 1.4 Hz, 1 H), 7.28 (br. s., 1H), 7.07 (dd, J=8.1, 1.5 Hz, 1 H), 6.96 (dd, J=8.1, 4.5 Hz, 1 H), 3.46 (tt, J=11.2, 3.7 Hz, 1 H), 2.34-2.52 (m, 2 H), 2.22-2.34 (m, 2 H), 1.99-2.07 (m, 2 H), 1.88-1.99 (m, 2 H). ESI-MS (m/z): Calcd. For C₁₁H₁₃NO₂: 191. found: 192 (M+H).

Step D: N-({1-[4-(3-Hydroxy-pyridin-2-yl)-cyclohexyl]-azetidin-3-ylcarbamoyl}-methyl)-3-trifluoromethyl-benzamide

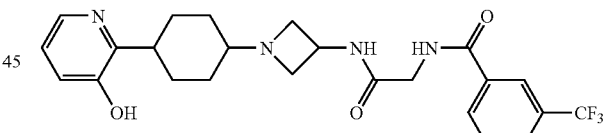

The title compounds were prepared as white solids from the reductive amination of 4-(3-hydroxy-pyridin-2-yl)-cyclohexanone (as prepared in the previous step) and N-(azetidin-3-ylcarbamoylmethyl)-3-trifluoromethyl-benzamide using the procedure described in Step F of Example 1.

¹H NMR (400 MHz, ACETONITRILE-d₃) δ 7.95 (s, 1 H), 7.89 (d, J=7.8 Hz, 1 H), 7.82 (dd, J=4.7, 1.4 Hz, 1 H), 7.66 (d, J=7.8 Hz, 1 H), 7.42-7.52 (m, 1 H), 7.33 (br. s., 1 H), 6.89 (dd, J=8.1, 1.3 Hz, 1 H), 6.83 (br. s., 1 H), 6.78 (dd, J=8.0, 4.7 Hz, 1H), 4.18 (m, J=6.9, 6.9, 6.9, 6.9, 6.8 Hz, 1 H), 3.75 (d, J=5.8 Hz, 2 H), 3.42 (t, J=6.8 Hz, 2 H), 2.82-2.89 (m, 1 H), 2.61-2.74 (m, 2 H), 2.18 (br. s., 1 H), 1.51 (br. s., 2 H), 1.15-1.38 (m, 4H). ESI-MS (m/z): Calcd. For C₂₄H₂₇N₄O₃F₃: 476. found: 477 (M+H).

Step E: N-({1-[4-(3-Hydroxy-pyridin-2-yl)-cyclohexyl]-azetidin-3-ylcarbamoyl}-methyl)-3-trifluoromethyl-benzamide hemisuccinate salt The product of the preceding step (0.556 g, 1.17 mmol) and succinic acid (0.069 g, 0.585 mmol) were dissolved in 2-propanol, concentrated to dryness in vacuo, dissolved in acetonitrile/water (100 mL), cooled to −78° C. (dry ice/acetone) until thoroughly frozen, and freeze-dried on a lyophilizer for 18 h giving the title compound as a fluffy, white, amorphous powder (672 mg).

$^1$H NMR (400 MHz, DMSO-$d_6$) δ ppm 9.63 (br. s., 1 H), 9.02 (t, J=5.8 Hz, 1 H), 8.41 (d, J=7.1 Hz, 1 H), 8.23 (s, 1 H), 8.19 (d, J=7.8 Hz, 1 H), 7.88-7.97 (m, 2 H), 7.75 (t, J=7.8 Hz, 1 H), 7.08 (dd, J=8.1, 1.5 Hz, 1 H), 6.99 (dd, J=8.0, 4.7 Hz, 1 H), 4.29 (m, 1 H), 3.88 (d, J=6.1 Hz, 2 H), 3.77 (spt, J=6.1 Hz, 0.5 H [2-PrOH]), 3.55 (t, J=6.8 Hz, 2 H), 3.02 (m, 1 H), 2.86 (br. s., 2 H), 2.31-2.42 (m, 3 H), 1.79-1.96 (m, 2 H), 1.67 (m, 2 H), 1.29-1.51 (m, 4 H), 1.04 (d, J=6.1 Hz, 3 H [2-PrOH]). ESI-MS (m/z): Calcd. For $C_{24}H_{27}N_4O_3F_3$: 476. found: 477 (M+H).

Example 4

N-({1-[4-(5-Hydroxy-pyridin-2-yl)-cyclohexyl]-azetidin-3-ylcarbamoyl}-methyl)-3-trifluoromethyl-benzamide hemisuccinate salt

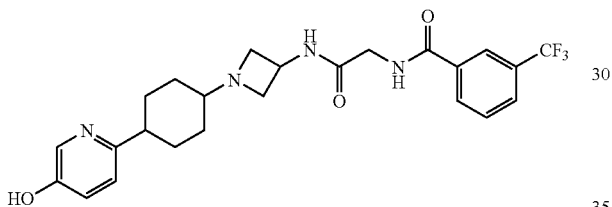

The title compound was prepared as described in Example 3: Steps A-E from 2-bromo-5-hydroxypyridine (Aldrich) as a white solid.

$^1$H NMR (400 MHz, DMSO-$d_6$) δ ppm 9.54 (br. s., 1 H), 9.00 (t, J=5.8 Hz, 1 H), 8.37 (d, J=7.3 Hz, 1 H), 8.23 (s, 1 H), 8.18 (d, J=7.8 Hz, 1 H), 8.02 (dd, J=2.7, 0.6 Hz, 1 H), 7.93 (d, J=7.8 Hz, 1 H), 7.74 (t, J=7.8 Hz, 1 H), 6.98-7.08 (m, 2 H), 4.28 (sxt, J=7.0 Hz, 1H), 3.88 (d, J=5.8 Hz, 2 H), 3.53 (t, J=6.7 Hz, 2 H), 2.76-2.91 (m, 2 H), 2.54-2.61 (m, 1 H), 2.39 (s, 2 H), 2.31-2.37 (m, 1 H), 1.72-1.90 (m, 2 H), 1.53-1.67 (m, 2 H), 1.33-1.50 (m, 4 H). ESI-MS (m/z): Calcd. For $C_{24}H_{27}N_4O_3F_3$: 476. found: 477 (M+H).

Example 5

N-({1-[4-(5-Hydroxy-pyridin-3-yl)-cyclohexyl]-azetidin-3-ylcarbamoyl}-methyl)-3-trifluoromethyl-benzamide

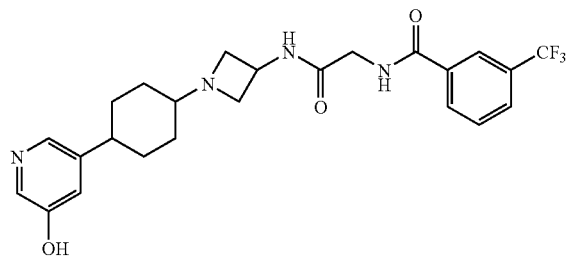

The title compound was prepared as described in Example 3: Steps A-D from 5-bromo-3-hydroxypyridine (Aldrich) as a white solid.

$^1$H NMR (400 MHz, METHANOL-$d_4$) δ ppm 8.22 (s, 1 H), 8.15 (d, J=7.8 Hz, 1 H), 7.93 (d, J=1.5 Hz, 1 H), 7.87 (d, J=8.1 Hz, 1 H), 7.70 (t, J=7.8 Hz, 1 H), 7.17 (t, J=2.3 Hz, 1 H), 7.10 (t, J=2.1 Hz, 1 H), 4.52 (quin, J=7.2 Hz, 1 H), 4.04 (s, 2 H), 3.55-3.67 (m, 1H), 2.47-2.57 (m, 1 H), 2.00-2.11 (m, 2 H), 1.71-1.93 (m, 4 H), 1.48-1.65 (m, 4 H), 1.33-1.48 (m, 2 H). ESI-MS (m/z): Calcd. For $C_{24}H_{27}N_4O_3F_3$: 476. found: 477 (M+H).

Example 6

N-({1-[4-(3-Hydroxy-6-methyl-pyridin-2-yl)-cyclohexyl]-azetidin-3-ylcarbamoyl}-methyl)-3-trifluoromethyl-benzamide

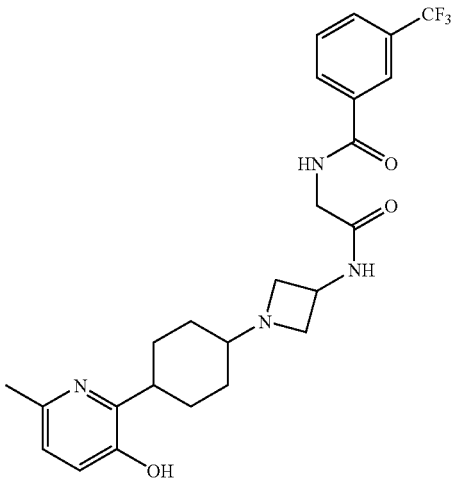

The title compound was prepared as described in Example 2: Steps A-D from 5-bromo-3-hydroxypyridine (Ryan Scientific) as a gold solid.

$^1$H NMR (400 MHz, CHLOROFORM-d) δ ppm 8.19 (s, 1 H), 8.11 (d, J=7.6 Hz, 1 H), 7.78 (d, J=8.1 Hz, 1 H), 7.59 (t, J=7.8 Hz, 1 H), 7.39 (br. s., 1 H), 7.05 (d, J=8.6 Hz, 1H), 6.89 (d, J=8.3 Hz, 1 H), 4.73 (s, 3 H), 4.25 (d, J=5.1 Hz, 2 H), 3.71 (m, 4 H), 2.39-2.45 (m, 2 H), 1.96-2.08 (m, 2 H), 1.81 (m, 2 H), 1.51-1.76 (m, 5 H). ESI-MS (m/z): Calcd. For $C_{25}H_{29}N_4O_3F_3$: 490. found: 491 (M+H).

Example 7

N-({1-[4-(2-Methoxy-pyridin-4-yl)-cyclohexyl]-azetidin-3-ylcarbamoyl}-methyl)-3-trifluoromethyl-benzamide

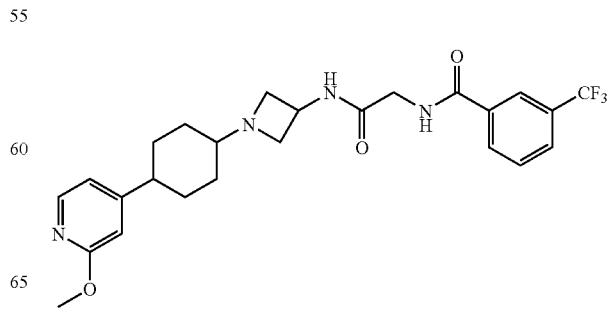

The title compound was prepared as described in Example 3: Steps A-D from 4-iodo-2-methoxypyridine (Aldrich) as a white solid.

¹H NMR (400 MHz, CHLOROFORM-d) δ ppm 8.15 (s, 1 H), 8.00-8.08 (m, 2 H), 7.77 (d, J=7.8 Hz, 1 H), 7.58 (t, J=7.8 Hz, 1 H), 7.44 (br. s., 1 H), 6.82 (d, J=5.1 Hz, 1 H), 6.64 (s, 1 H), 4.50-4.66 (m, 1 H), 4.19 (d, J=5.1 Hz, 2 H), 3.87-3.96 (m, 4 H), 3.63-3.82 (m, 2 H), 2.41-2.51 (m, 1 H), 1.79-1.97 (m, 3 H), 1.70 (m, 2 H), 1.36-1.63 (m, 5H). ESI-MS (m/z): Calcd. For $C_{25}H_{29}N_4O_3F_3$: 490. found: 491 (M+H).

Example 8

N-({1-[4-(3-Methoxy-pyridin-4-yl)-cyclohexyl]-azetidin-3-ylcarbamoyl}-methyl)-3-trifluoromethyl-benzamide

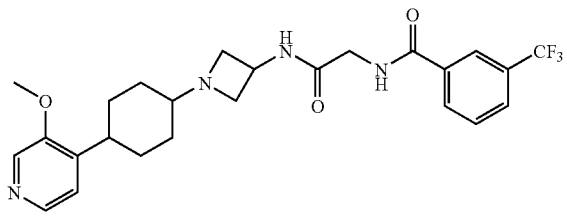

The title compound was prepared as described in Example 3: Steps A-D from 4-bromo-3-methoxypyridine (Aldrich) as a white solid.

¹H NMR (400 MHz, CHLOROFORM-d) δ ppm 8.22 (d, J=4.8 Hz, 1 H), 8.19 (s, 1 H), 8.13 (s, 1 H), 8.02 (d, J=7.8 Hz, 1 H), 7.78 (d, J=7.8 Hz, 1 H), 7.58 (t, J=7.8 Hz, 1 H), 7.42 (t, J=4.5 Hz, 1 H), 7.14-7.22 (m, 2 H), 4.56 (sxt, J=6.6 Hz, 1 H), 4.14-4.21 (m, 2H), 3.91 (s, 3 H), 3.60 (t, J=7.5 Hz, 2 H), 2.84-3.04 (m, 3 H), 2.30-2.37 (m, 1 H), 1.88 (m, 3 H), 1.64-1.77 (m, 3 H), 1.47-1.54 (m, 2 H). ESI-MS (m/z): Calcd. For $C_{25}H_{29}N_4O_3F_3$: 490. found: 491 (M+H).

Example 9

N-({1-[4-(3-Hydroxy-pyridin-4-yl)-cyclohexyl]-azetidin-3-ylcarbamoyl}-methyl)-3-trifluoromethyl-benzamide

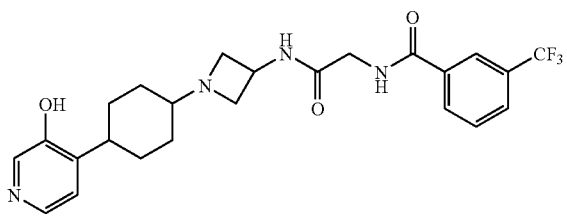

N-({1-[4-(3-Methoxy-pyridin-4-yl)-cyclohexyl]-azetidin-3-ylcarbamoyl}-methyl)-3-trifluoromethyl-benzamide (0.101 g, 0.206 mmol, as prepared in Example 8) was dissolved in anhydrous dichloromethane (10 mL) under Ar, treated with 0.83 N boron tribromide in dichloromethane (Aldrich, 2.00 mL, 1.66 mmol), and stirred at ambient temperature for 24 h. After quenching with saturated aqueous NaHCO₃, the reaction was stirred at ambient temperature for 30 mins and extracted thrice with 3:1 EtOAc/2-propanol. The combined organic layers were washed with brine, dried over Na₂SO₄, filtered, and concentrated in vacuo giving a gold gum that was purified by preparative thin layer chromatography on silica gel (15% MeOH in CH₂Cl₂, 0.6N in ammonia), giving the title compound as a pale yellow solid.

¹H NMR (400 MHz, DMSO-d₆) δ ppm 9.65 (s, 1 H), 9.01 (t, J=5.9 Hz, 1 H), 8.39 (d, J=7.3 Hz, 1 H), 8.23 (s, 1 H), 8.18 (d, J=7.8 Hz, 1 H), 8.05 (s, 1 H), 7.89-7.99 (m, 2 H), 7.74 (t, J=7.8 Hz, 1 H), 7.07 (d, J=5.1 Hz, 1 H), 4.28 (sxt, J=7.0 Hz, 1 H), 3.88 (d, J=5.8 Hz, 2 H), 3.51 (t, J=6.6 Hz, 2 H), 2.70-2.89 (m, 3 H), 2.26-2.38 (m, 1 H), 1.58-1.76 (m, 4 H), 1.31-1.50 (m, 4 H). ESI-MS (m/z): Calcd. For $C_{24}H_{27}N_4O_3F_3$: 476. found: 477 (M+H).

Example 10

N-({1-[4-(2-Hydroxy-pyridin-3-yl)-cyclohexyl]-azetidin-3-ylcarbamoyl}-methyl)-3-trifluoromethyl-benzamide Step A: 2-Benzyloxy-3-(1,4-dioxa-spiro[4.5]dec-7-en-8-yl)-pyridine

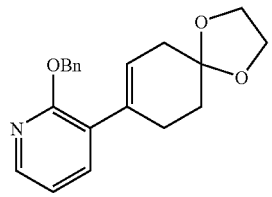

The title compound was prepared as described in Step A of Example 3 from 2-benzyloxy-3-bromo-pyridine (Alfa Aesar) as a white solid.

LCMS (ESI, M/Z): 324 (MH+).

Step B:
3-(1,4-Dioxa-spiro[4.5]dec-8-yl)-pyridin-2-ol

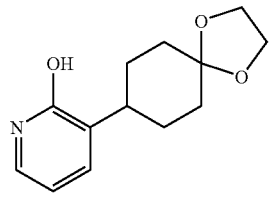

The title compound was prepared as a white solid from the hydrogenation of 2-benzyloxy-3-(1,4-dioxa-spiro[4.5]dec-7-en-8-yl)-pyridine (as prepared in the previous step) using the procedure described in Step G of Example 1.

LCMS (ESI, M/Z): 236 (MH+).

Step C: 4-(2-Hydroxy-pyridin-3-yl)-cyclohexanone

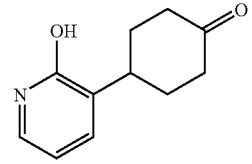

The title compound was prepared as a white solid from the deprotection of 3-(1,4-dioxa-spiro[4.5]dec-8-yl)-pyridin-2-ol (as prepared in the previous step) using the procedure described in Step B of Example 2.
LCMS (ESI, M/Z): 192 (MH+).

Step D: N-({1-[4-(2-Hydroxy-pyridin-3-yl)-cyclohexyl]-azetidin-3-ylcarbamoyl}-methyl)-3-trifluoromethyl-benzamide

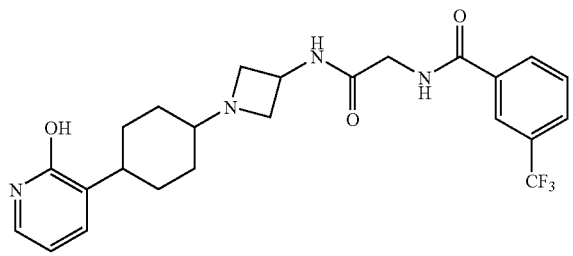

The title compounds were prepared as white solids from the reductive amination of 4-(2-hydroxy-pyridin-3-yl)-cyclohexanone (as prepared in the previous step) and N-(azetidin-3-ylcarbamoylmethyl)-3-trifluoromethyl-benzamide using the procedure described in Step F of Example 1.
LCMS (ESI, M/Z): 477 (MH+).

Example 11

N-({1-[4-(4-Hydroxy-pyridin-3-yl)-cyclohexyl]-azetidin-3-ylcarbamoyl}-methyl)-3-trifluoromethyl-benzamide Step A: 3-(1,4-Dioxa-spiro[4.5]dec-7-en-8-yl)-pyridin-4-ol

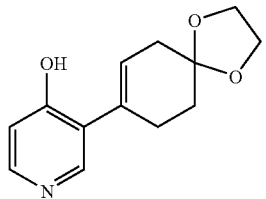

The title compound was prepared as described in Step A of Example 3 from 4-hydroxy-3-bromo-pyridine (SynChem) as a white solid.
$^1$H NMR (CHLOROFORM-d) δ: 7.89 (s, 1H), 7.79 (m, 1H), 6.76-6.90 (m, 1H), 5.89-6.04 (m, 1H), 3.99 (s, 4H), 2.55-2.72 (m, 2H), 2.42 (br. s., 2H), 1.87 (s, 2H). LCMS (ESI, M/Z): 234 (MH+).

Step B:
3-(1,4-Dioxa-spiro[4.5]dec-8-yl)-pyridin-4-ol

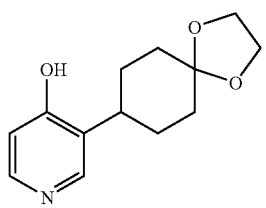

The title compound was prepared as a white solid from the hydrogenation of 3-(1,4-dioxa-spiro[4.5]dec-7-en-8-yl)-pyridin-4-ol (as prepared in the previous step) using the procedure described in Step G of Example 1.
$^1$H NMR (CHLOROFORM-d) δ: 7.81-7.94 (m, 2H), 6.98 (d, J=6.3 Hz, 1H), 3.88-4.04 (m, 4H), 2.92-3.10 (m, 1H), 1.80-2.02 (m, 4H), 1.52-1.80 (m, 4H). LCMS (ESI, M/Z): 236 (MH+).

Step C: 4-(4-Hydroxy-pyridin-3-yl)-cyclohexanone

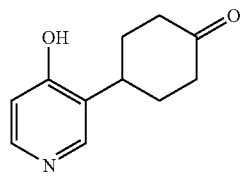

The title compound was prepared as a white solid from the deprotection of 3-(1,4-dioxa-spiro[4.5]dec-8-yl)-pyridin-4-ol (as prepared in the previous step) using the procedure described in Step B of Example 2.
LCMS (ESI, M/Z): 192 (MH+).

Step D: N-({1-[4-(4-Hydroxy-pyridin-3-yl)-cyclohexyl]-azetidin-3-ylcarbamoyl}-methyl)-3-trifluoromethyl-benzamide

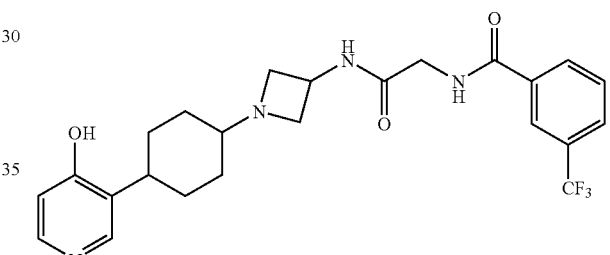

The title compound was prepared as a white solid from the reductive amination of 4-(4-hydroxy-pyridin-3-yl)-cyclohexanone (as prepared in the previous step) and N-(azetidin-3-ylcarbamoylmethyl)-3-trifluoromethyl-benzamide using the procedure described in Step F of Example 1.
LCMS (ESI, M/Z): 477 (MH+).

Example 12

N-({1-[4-(4-Hydroxy-pyridin-2-yl)-cyclohexyl]-azetidin-3-ylcarbamoyl}-methyl)-3-trifluoromethyl-benzamide Step A: 2-(1,4-Dioxa-spiro[4.5]dec-7-en-8-yl)-pyridin-4-ol

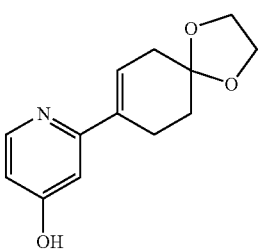

The title compound was prepared as described in Step A of Example 3 from 2-bromo-pyridin-4-ol (SynChem) as a white solid.

¹H NMR (CHLOROFORM-d) δ: 8.05-8.14 (m, 1H), 7.11 (s, 1H), 6.97-7.06 (m, 1H), 6.54-6.69 (m, 1H), 3.99 (s, 4H), 2.83-2.95 (m, 1H), 2.58-2.69 (m, 2H), 2.52 (d, J=1.8 Hz, 2H), 1.90 (s, 2H). LCMS (ESI, M/Z): 234 (MH+).

Step B:
2-(1,4-Dioxa-spiro[4.5]dec-8-yl)-pyridin-4-ol

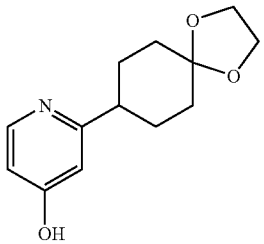

The title compound was prepared as a white solid from the hydrogenation of 2-(1,4-dioxa-spiro[4.5]dec-7-en-8-yl)-pyridin-4-ol (as prepared in the previous step) using the procedure described in Step G of Example 1.

¹H NMR (CHLOROFORM-d) δ: 8.07-8.16 (m, 1H), 7.07 (none, 2H), 3.50 (s, 4H), 2.82-3.01 (m, OH), 1.94-2.04 (m, 2H), 1.84 (s, 4H), 1.57-1.76 (m, 2H). LCMS (ESI, M/Z): 236 (MH+).

Step C: 4-(4-Hydroxy-pyridin-2-yl)-cyclohexanone

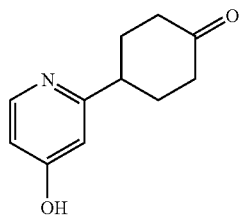

The title compound was prepared as a white solid from the deprotection of 2-(1,4-dioxa-spiro[4.5]dec-8-yl)-pyridin-4-ol (as prepared in the previous step) using the procedure described in Step B of Example 2.

¹H NMR (CHLOROFORM-d) δ: 8.34 (d, J=5.8 Hz, 1H), 6.71 (d, J=2.3 Hz, 1H), 6.65 (dd, J=5.8, 2.3 Hz, 1H), 2.66-2.81 (m, 1H), 1.60-2.04 (series of m, 8H). LCMS (ESI, M/Z): 192 (MH+).

Step D: N-({1-[4-(4-Hydroxy-pyridin-2-yl)-cyclohexyl]-azetidin-3-ylcarbamoyl}-methyl)-3-trifluoromethyl-benzamide

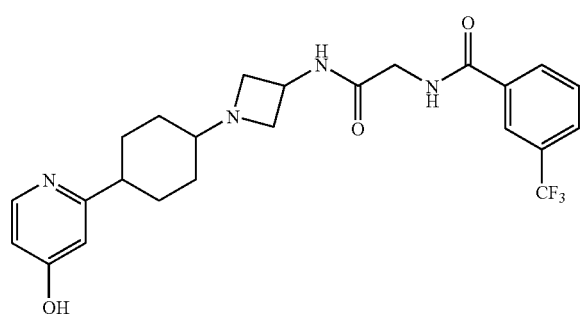

The title compound was prepared as a white solid from reductive amination of 4-(4-hydroxy-pyridin-2-yl)-cyclohexanone (as prepared in the previous step) and N-(azetidin-3-ylcarbamoylmethyl)-3-trifluoromethyl-benzamide using the procedure described in Step F of Example 1.

LCMS (ESI, M/Z): 477 (MH+).

Example 13

N-({1-[4-(5-Acetylamino-pyridin-2-yl)-cyclohexyl]-azetidin-3-ylcarbamoyl}-methyl)-3-trifluoromethyl-benzamide Step A: N-[6-(1,4-Dioxa-spiro[4.5]dec-8-yl)-pyridin-3-yl]-acetamide

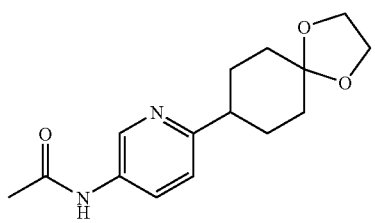

6-(1,4-Dioxa-spiro[4.5]dec-8-yl)-pyridin-3-ylamine (0.158 g, 0.675 mmol, prepared as described in Example 3: Steps A-B from 5-amino-2-bromopyridine, Aldrich) was dissolved in anhydrous dichloromethane (10 mL), treated with acetic anhydride (Aldrich, 0.080 mL, 0.846 mmol), and stirred at ambient temperature under Ar for 18 h. The reaction was quenched with saturated aqueous NaHCO₃, extracted thrice with dichloromethane, and the combined organic layers washed with brine, dried over Na₂SO₄, filtered, and the filtrate concentrated in vacuo giving the title compound as a pale solid.

¹H NMR (400 MHz, CHLOROFORM-d) δ ppm 8.41 (d, J=2.5 Hz, 1 H), 8.07 (dd, J=8.6, 2.5 Hz, 1 H), 7.42 (br. s., 1 H), 7.17 (d, J=8.6 Hz, 1 H), 3.98 (s, 4 H), 2.74 (m, 1 H), 2.19 (s, 3 H), 1.91-2.00 (m, 2 H), 1.77-1.91 (m, 4 H), 1.63-1.77 (m, 2 H). ESI-MS (m/z): Calcd. For $C_{15}H_{20}N_2O_3$: 276. found: 277 (M+H).

Step B: N-({1-[4-(5-Acetylamino-pyridin-2-yl)-cyclohexyl]-azetidin-3-ylcarbamoyl}-methyl)-3-trifluoromethyl-benzamide

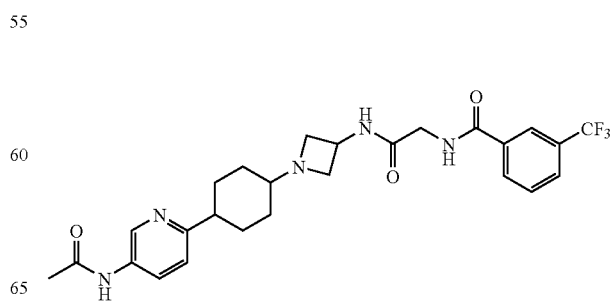

The title compound was prepared as described in Example 3: Steps C-D from N-[6-(1,4-dioxa-spiro[4.5]dec-8-yl)-pyridin-3-yl]-acetamide (as prepared in the previous step) to give a pale yellow solid.

$^1$H NMR (400 MHz, DMSO-d$_6$) δ ppm 10.07 (s, 1 H), 9.03 (t, J=5.9 Hz, 1 H), 8.57 (d, J=2.5 Hz, 1 H), 8.41 (d, J=7.3 Hz, 1 H), 8.23 (s, 1 H), 8.19 (d, J=7.8 Hz, 1 H), 7.86-7.98 (m, 2 H), 7.75 (t, J=7.7 Hz, 1 H), 7.17 (d, J=8.6 Hz, 1 H), 4.21-4.34 (m, 1 H), 3.88 (d, J=5.8 Hz, 2 H), 3.49-3.62 (m, 2 H), 2.83 (br. s., 1 H), 2.56-2.69 (m, 1 H), 2.05 (s, 3 H), 1.77-1.93 (m, 2 H), 1.62 (m, 2 H), 1.35-1.56 (m, 4 H). ESI-MS (m/z): Calcd. For C$_{26}$H$_{30}$N$_5$O$_3$F$_3$: 517. found: 518 (M+H).

Example 14

N-({1-[4-(5-bis-{Methanesulfonyl}-amino-pyridin-2-yl)-cyclohexyl]-azetidin-3-ylcarbamoyl}-methyl)-3-trifluoromethyl-benzamide Step A: N-[6-(1,4-Dioxa-spiro[4.5]dec-8-yl)-pyridin-3-yl]-methanesulfonamide and N-[6-(1,4-Dioxa-spiro[4.5]dec-8-yl)-pyridin-3-yl]-bis-(methanesulfonyl)-amide

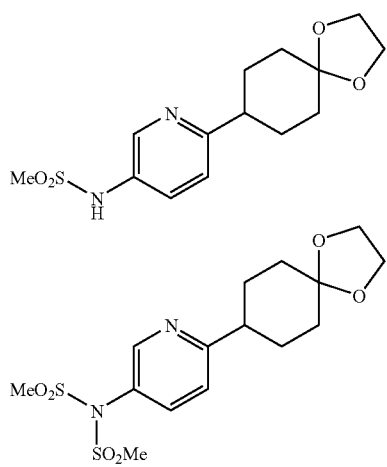

6-(1,4-Dioxa-spiro[4.5]dec-8-yl)-pyridin-3-ylamine (0.158 g, 0.675 mmol, prepared as described in Example 2: Steps A-B from 5-amino-2-bromopyridine) was dissolved in anhydrous dichloromethane (10 mL), treated with triethylamine (0.20 mL, 1.43 mmol) and methanesulfonyl chloride (Aldrich, 0.065 mL, 0.837 mmol), and stirred at ambient temperature under Ar for 2 d. The reaction was concentrated to dryness in vacuo and purified by preparative thin layer chromatography on silica gel (1:1 EtOAc:CH$_2$Cl$_2$) giving the slow-running mono-sulfonamide as white needles and the fast-running bis-sulfonamide as a white amorphous powder.

N-[6-(1,4-Dioxa-spiro[4.5]dec-8-yl)-pyridin-3-yl]-methanesulfonamide

ESI-MS (m/z): Calcd. For C$_{14}$H$_{20}$N$_2$O$_4$S: 312. found: 313 (M+H).

N-[6-(1,4-Dioxa-spiro[4.5]dec-8-yl)-pyridin-3-yl]-bis-(methanesulfonyl)-amide

ESI-MS (m/z): Calcd. For C$_{15}$H$_{22}$N$_2$O$_6$S$_2$: 390. found: 391 (M+H).

Step B: N-({1-[4-(5-bis-{Methanesulfonyl}-amino-pyridin-2-yl)-cyclohexyl]-azetidin-3-ylcarbamoyl}-methyl)-3-trifluoromethyl-benzamide

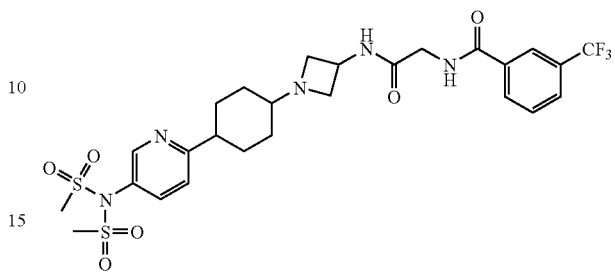

The title compound was prepared as described in Example 3: Steps C-D from N-[6-(1,4-dioxa-spiro[4.5]dec-8-yl)-pyridin-3-yl]-bis-(methanesulfonyl)-amide (as prepared in the previous step) and purified by preparative thin layer chromatography on silica gel (15% MeOH in CH$_2$Cl$_2$) giving a yellow-orange solid.

$^1$H NMR (400 MHz, DMSO-d$_6$) δ ppm 9.01 (t, J=5.9 Hz, 1 H), 8.59 (d, J=2.3 Hz, 1 H), 8.39 (d, J=7.3 Hz, 1 H), 8.23 (s, 1 H), 8.18 (d, J=7.8 Hz, 1 H), 7.93 (d, J=7.8 Hz, 1 H), 7.89 (dd, J=8.3, 2.5 Hz, 1 H), 7.74 (t, J=7.8 Hz, 1 H), 7.39 (d, J=8.3 Hz, 1 H), 4.27 (m, 1H), 3.88 (d, J=6.1 Hz, 2 H), 3.56 (s, 6 H), 3.49 (t, J=7.1 Hz, 2 H), 2.77 (m, 3 H), 2.31 (br. s., 1 H), 1.83-1.97 (m, 2 H), 1.58-1.69 (m, 2 H), 1.39-1.58 (m, 4 H). ESI-MS (m/z): Calcd. For C$_{26}$H$_{32}$N$_5$O$_6$F$_3$S$_2$: 631. found: 632 (M+H).

Example 15

N-({1-[4-(5-Methanesulfonyl-amino-pyridin-2-yl)-cyclohexyl]-azetidin-3-ylcarbamoyl}-methyl)-3-trifluoromethyl-benzamide

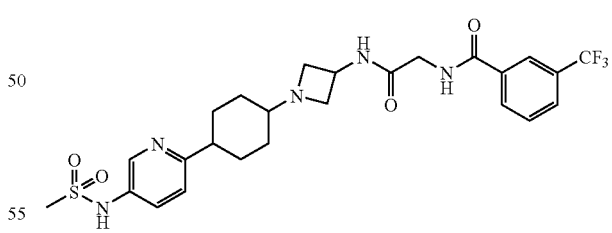

The title compound was prepared as described in Example 3: Steps C-D from N-[6-(1,4-dioxa-spiro[4.5]dec-8-yl)-pyridin-3-yl]-methanesulfonamide (as described in Example 14, Step A) and purified by preparative thin layer chromatography on silica gel (15% MeOH in CH$_2$Cl$_2$) giving a pale yellow solid.

¹H NMR (400 MHz, DMSO-d₆) δ ppm 9.81 (br. s., 1 H), 9.02 (t, J=5.8 Hz, 1 H), 8.39 (d, J=7.3 Hz, 1 H), 8.32 (d, J=2.5 Hz, 1 H), 8.23 (s, 1 H), 8.18 (d, J=8.1 Hz, 1 H), 7.93 (d, J=7.8 Hz, 1 H), 7.74 (t, J=7.8 Hz, 1 H), 7.53 (dd, J=8.5, 2.7 Hz, 1 H), 7.22 (d, J=8.3 Hz, 1 H), 4.27 (sxt, J=7.1 Hz, 1 H), 3.88 (d, J=5.8 Hz, 2 H), 3.50 (t, J=6.7 Hz, 2 H), 3.01 (s, 3H), 2.78 (t, J=6.4 Hz, 2 H), 2.56-2.70 (m, 1 H), 2.30 (br. s., 1 H), 1.75-1.93 (m, 2 H), 1.55-1.68 (m, 2 H), 1.35-1.55 (m, 4 H). ESI-MS (m/z): Calcd. For $C_{25}H_{30}N_5O_4F_3S$: 553. found: 554 (M+H).

Example 16

N-[(1-{4-[5-(2,2,2-Trifluoro-acetylamino)-pyridin-2-yl]-cyclohexyl}-azetidin-3-ylcarbamoyl)-methyl]-3-trifluoromethyl-benzamide Step A: N-[6-(1,4-Dioxa-spiro[4.5]dec-8-yl)-pyridin-3-yl]-2,2,2-trifluoro-acetamide

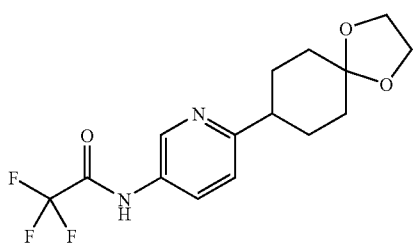

6-(1,4-Dioxa-spiro[4.5]dec-8-yl)-pyridin-3-ylamine (0.148 g, 0.632 mmol, prepared as described in Example 3: Steps A-B from 5-amino-2-bromopyridine) was dissolved in anhydrous dichloromethane (10 mL) under Ar, treated with trifluoroacetic anhydride (Aldrich, 0.100 mL, 0.720 mmol), and stirred at 50° C. under a reflux condenser for 3 d. The reaction was cooled to ambient temperature, diluted with dichloromethane, washed with saturated aqueous NaHCO₃, the aqueous layer extracted twice with dichloromethane, and the combined organic layers washed with brine, dried over Na₂SO₄, filtered, and the filtrate concentrated in vacuo giving the title compound as a pale yellow solid.
ESI-MS (m/z): Calcd. For $C_{15}H_{17}N_2O_3F_3$: 330. found: 331 (M+H)

Step B: N-[(1-{4-[5-(2,2,2-Trifluoro-acetylamino)-pyridin-2-yl]-cyclohexyl}-azetidin-3-ylcarbamoyl)-methyl]-3-trifluoromethyl-benzamide

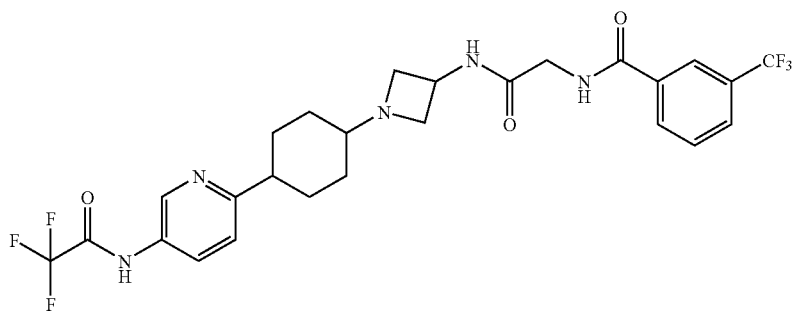

The title compound was prepared as described in Example 3: Steps C-D from N-[6-(1,4-dioxa-spiro[4.5]dec-8-yl)-pyridin-3-yl]-2,2,2-trifluoro-acetamide (as prepared in the previous step) and purified by preparative thin layer chromatography on silica gel (3:2:1 MeCN:CH₂Cl₂:MeOH) giving a pale yellow solid.
¹H NMR (400 MHz, CHLOROFORM-d) δ ppm 11.45 (br. s., 1 H), 9.07 (m, 1 H), 8.72 (d, J=2.5 Hz, 1 H), 8.45 (m, 1 H), 8.24 (s, 1 H), 8.20 (d, J=7.6 Hz, 1 H), 7.98 (dt, J=8.5, 2.9 Hz, 1 H), 7.94 (d, J=7.8 Hz, 1 H), 7.75 (t, J=7.6 Hz, 1 H), 7.33 (d, J=8.6 Hz, 1 H), 4.37 (m, 1 H), 3.83-3.94 (m, 3 H), 2.58-2.79 (m, 1H), 1.82-2.01 (m, 3 H), 1.39-1.74 (m, 5 H). ESI-MS (m/z): Calcd. For $C_{26}H_{27}N_5O_3F_6$: 571. found: 572 (M+H).

Example 17

N-[(1-{4-[3-(2,2,2-Trifluoro-acetylamino)-pyridin-2-yl]-cyclohexyl}-azetidin-3-ylcarbamoyl)-methyl]-3-trifluoromethyl-benzamide Step A: N-[2-(1,4-Dioxa-spiro[4.5]dec-8-yl)-pyridin-3-yl]-2,2,2-trifluoro-acetamide

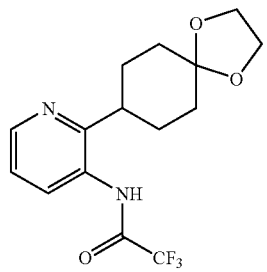

The title compound was prepared as described in Example 3: Steps A-B, and Example 16: Step A, from 3-amino-2-bromopyridine (Aldrich) as a white solid.
ESI-MS (m/z): Calcd. For $C_{15}H_{17}N_2O_3F_3$: 330. found: 331 (M+H)

Step B: N-[(1-{-4-[3-(2,2,2-Trifluoro-acetylamino)-pyridin-2-yl]-cyclohexyl}-azetidin-3-ylcarbamoyl)-methyl]-3-trifluoromethyl-benzamide

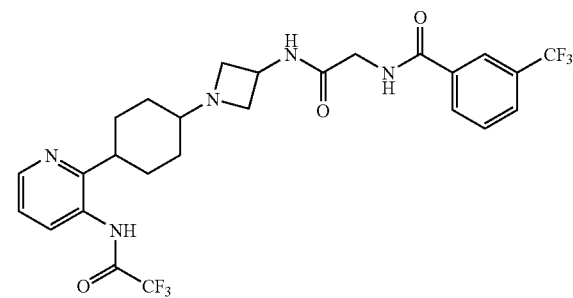

The title compound was prepared as described in Example 3: Steps C-D from N-[2-(1,4-dioxa-spiro[4.5]dec-8-yl)-pyridin-3-yl]-2,2,2-trifluoro-acetamide (as prepared in the previous step) and purified by preparative thin layer chromatography on silica gel (3:2:1 MeCN:CH$_2$Cl$_2$:MeOH) giving a light peach solid.

$^1$H NMR (400 MHz, DMSO-d$_6$) δ ppm 11.21 (br. s., 1 H), 9.08 (br. s., 1 H), 8.50-8.55 (m, 1 H), 8.39-8.50 (m, 1 H), 8.24 (s, 1 H), 8.20 (d, J=7.8 Hz, 1 H), 7.94 (d, J=7.6 Hz, 1H), 7.75 (t, J=7.8 Hz, 1 H), 7.68 (d, J=8.1 Hz, 1 H), 7.32 (dd, J=6.9, 5.2 Hz, 1 H), 4.20-4.55 (m, 1 H), 3.89 (d, J=5.6 Hz, 2 H), 2.83 (m, 1 H), 1.65-1.98 (m, 4 H), 1.16-1.64 (m, 4 H). ESI-MS (m/z): Calcd. For C$_{26}$H$_{27}$N$_5$O$_3$F$_6$: 571. found: 572 (M+H).

Example 18

N-({1-[4-(3-Acetylamino-pyridin-2-yl)-cyclohexyl]-azetidin-3-ylcarbamoyl}-methyl)-3-trifluoromethyl-benzamide Step A: N-[2-(1,4-Dioxa-spiro[4.5]dec-8-yl)-pyridin-3-yl]-acetamide

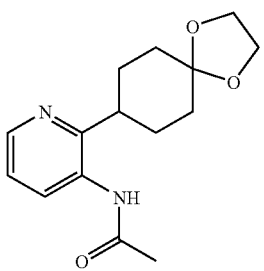

The title compound was prepared as described in Example 2: Steps A-B, and Example 13: Step A, from 3-amino-2-bromopyridine (Aldrich) as a white solid.

ESI-MS (m/z): Calcd. For C$_{15}$H$_{20}$N$_2$O$_3$: 276. found: 277 (M+H)

Step B: N-({1-[4-(3-Acetylamino-pyridin-2-yl)-cyclohexyl]-azetidin-3-ylcarbamoyl}-methyl)-3-trifluoromethyl-benzamide

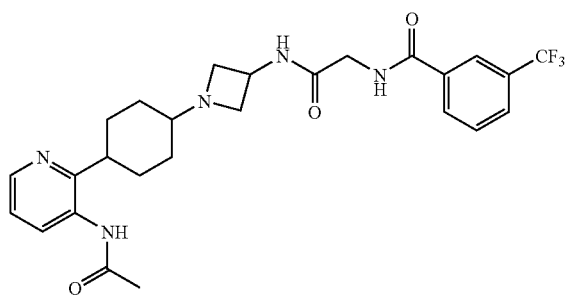

The title compound was prepared as described in Example 3: Steps C-D from N-[2-(1,4-dioxa-spiro[4.5]dec-8-yl)-pyridin-3-yl]-acetamide (as prepared in the previous step) and purified by preparative thin layer chromatography on silica gel (15% MeOH in CH$_2$Cl$_2$) giving a pale solid.

$^1$H NMR (400 MHz, DMSO-d$_6$) δ ppm 9.49 (s, 1 H), 9.03 (t, J=5.6 Hz, 1 H), 8.41 (d, J=6.8 Hz, 1 H), 8.33 (dd, J=4.5, 1.3 Hz, 1 H), 8.23 (s, 1 H), 8.19 (d, J=7.8 Hz, 1 H), 7.93 (d, J=7.6 Hz, 1 H), 7.75 (t, J=7.8 Hz, 1 H), 7.68 (dd, J=8.0, 1.1 Hz, 1 H), 7.17 (dd, J=8.0, 4.7 Hz, 1 H), 4.18-4.38 (m, 1 H), 3.89 (d, J=5.8 Hz, 2 H), 3.42-3.59 (m, 2 H), 2.94 (t, J=11.5 Hz, 1 H), 2.66-2.88 (m, 2 H), 2.22-2.41 (m, 1 H), 2.07 (s, 3 H), 1.90 (m, 2 H), 1.57-1.75 (m, 2 H), 1.33 (m, 4 H). ESI-MS (m/z): Calcd. For C$_{26}$H$_{30}$N$_5$O$_3$F$_3$: 517. found: 518 (M+H).

Example 19

N-({1-[4-(3-Methanesulfonylamino-pyridin-2-yl)-cyclohexyl]-azetidin-3-ylcarbamoyl}-methyl)-3-trifluoromethyl-benzamide Step A: N-[2-(1,4-Dioxa-spiro[4.5]dec-8-yl)-pyridin-3-yl]-methanesulfonamide

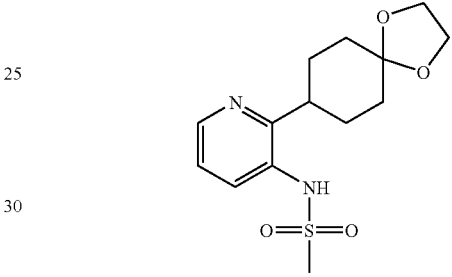

2-(1,4-Dioxa-spiro[4.5]dec-8-yl)-pyridin-3-ylamine (0.141 g, 0.603 mmol, prepared as described in Example 3: Steps A-B from 3-amino-2-bromopyridine) was dissolved in anhydrous dichloromethane (10 mL) under Ar, treated with methanesulfonyl chloride (0.155 mL, 1.48 mmol), a few drops of anhydrous pyridine, and stirred at ambient temperature for 24 h. The reaction was quenched with saturated aqueous NaHCO$_3$, the aqueous layer extracted thrice with dichloromethane, and the combined organic layers washed with brine, dried over Na$_2$SO$_4$, filtered, and the filtrate concentrated in vacuo giving the title compound as a very hygroscopic yellow solid. ESI-MS (m/z): Calcd. For C$_{14}$H$_{20}$N$_2$O$_4$S: 312. found: 313 (M+H)

Step B: N-({1-[4-(3-Methanesulfonylamino-pyridin-2-yl)-cyclohexyl]-azetidin-3-ylcarbamoyl}-methyl)-3-trifluoromethyl-benzamide

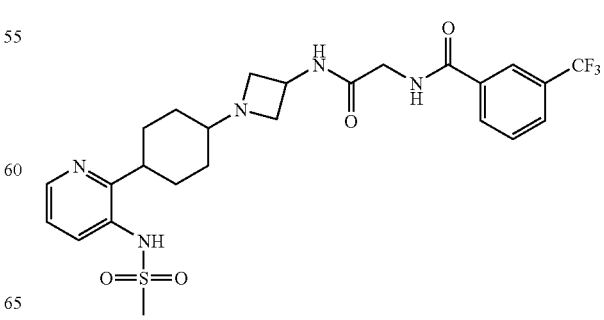

The title compound was prepared as described in Example 3: Steps C-D from N-[2-(1,4-dioxa-spiro[4.5]dec-8-yl)-pyridin-3-yl]-methanesulfonamide (as prepared in the previous step) as a pale solid.

$^1$H NMR (400 MHz, DMSO-d$_6$) δ ppm 9.03 (t, J=5.8 Hz, 1 H), 8.41 (dd, J=4.7, 1.6 Hz, 2H), 8.23 (s, 1 H), 8.19 (d, J=7.8 Hz, 1 H), 7.93 (d, J=7.8 Hz, 1 H), 7.75 (t, J=7.7 Hz, 1 H), 7.63 (dd, J=8.0, 1.6 Hz, 1 H), 7.21 (dd, J=8.0, 4.7 Hz, 1 H), 4.29 (sxt, J=6.8 Hz, 1 H), 3.89 (d, J=5.8 Hz, 2 H), 3.52 (m, 2 H), 3.16 (m, 1 H), 3.00 (s, 3 H), 2.82 (m, 2 H), 2.26-2.41 (m, 1 H), 1.83-2.00 (m, 2 H), 1.59-1.73 (m, 2 H), 1.37-1.51 (m, 2 H), 1.33 (m, 2H). ESI-MS (m/z): Calcd. For $C_{25}H_{30}N_5O_4F_3S$: 553. found: 554 (M+H).

Example 20

N-({1-[4-(3-Amino-pyridin-2-yl)-cyclohexyl]-azetidin-3-ylcarbamoyl}-methyl)-3-trifluoromethyl-benzamide

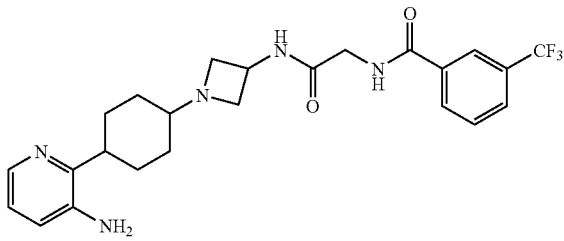

N-[(1-{4-[3-(2,2,2-Trifluoro-acetylamino)-pyridin-2-yl]-cyclohexyl}-azetidin-3-ylcarbamoyl)-methyl]-3-trifluoromethyl-benzamide (0.042 g, 0.073 mmol, as prepared in Example 17: Step B) was dissolved in methanol (3 mL), treated with a solution of powdered potassium carbonate (1.103, 0.730 mmol) in water (3 mL), and stirred at ambient temperature for 5 d, then heated to 70° C. under reflux condenser for 18 h. After removing the methanol in vacuo, the reaction was diluted with water and extracted thrice with 3:1 EtOAc/2-PrOH. The combined organic layers were washed with brine, dried over Na$_2$SO$_4$, filtered, and the filtrate concentrated in vacuo giving the title compound as a beige solid.

$^1$H NMR (400 MHz, MeOH-d$_4$) δ ppm 8.22 (s, 1 H), 8.15 (d, J=8.1 Hz, 1 H), 7.86 (d, J=7.8 Hz, 1 H), 7.77 (dd, J=4.5, 1.5 Hz, 1 H), 7.69 (t, J=7.8 Hz, 1 H), 7.04 (dd, J=8.1, 1.5 Hz, 1 H), 6.94 (dd, J=8.0, 4.7 Hz, 1 H), 4.44 (quin, J=6.7 Hz, 1H), 4.05 (s, 2 H), 3.64 (t, J=7.2 Hz, 2 H), 2.92-3.04 (m, 2 H), 2.84 (tt, J=10.8, 3.6 Hz, 1 H), 2.37-2.51 (m, 1 H), 1.92-2.08 (m, 2 H), 1.78 (m, 2 H), 1.47-1.65 (m, 4 H). ESI-MS (m/z): Calcd. For $C_{24}H_{28}N_5O_2F_3$: 475. found: 476 (M+H).

Example 21

N-({1-[4-(5-Amino-pyridin-2-yl)-cyclohexyl]-azetidin-3-ylcarbamoyl}-methyl)-3-trifluoromethyl-benzamide

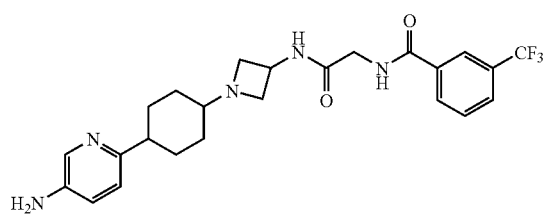

The title compound was prepared as described in Example 3: Steps A-D from 5-amino-2-bromopyridine (Aldrich) as a yellow solid.

$^1$H NMR (400 MHz, DMSO-d$_6$) δ ppm 9.11 (br. s., 1 H), 8.47-8.75 (m, 1 H), 8.25 (s, 1H), 8.21 (d, J=7.8 Hz, 1 H), 7.93 (d, J=7.8 Hz, 1 H), 7.83 (d, J=2.8 Hz, 1 H), 7.75 (t, J=7.8 Hz, 1 H), 7.00 (br. s., 1 H), 6.87 (dd, J=8.2, 2.7 Hz, 1 H), 5.04 (br. s., 2 H), 4.31-4.56 (m, 1 H), 3.97-4.23 (m, 1 H), 3.90 (d, J=5.8 Hz, 2 H), 2.54-2.62 (m, 1 H), 1.89 (m, 2 H), 1.35-1.75 (m, 6 H). ESI-MS (m/z): Calcd. For $C_{24}H_{28}N_5O_2F_3$: 475. found: 476 (M+H).

Example 22

N-({1-[4-(6-Amino-pyridin-2-yl)-cyclohexyl]-azetidin-3-ylcarbamoyl}-methyl)-3-trifluoromethyl-benzamide Step A: 6-(1,4-Dioxa-spiro[4.5]dec-7-en-8-yl)-pyridin-2-ylamine

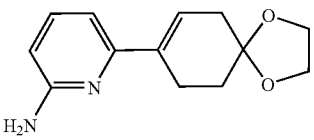

The title compound was prepared as described in Step A of Example 3 from 6-bromo-pyridin-2-ylamine (Aldrich) as a white solid.

$^1$H NMR (400 MHz, CDCl$_3$) δ 7.35 (t, J=6.5 Hz, 1H), 6.72 9d, J=6.2 Hz, 1H), 6.51 (m, 1H), 6.31 (d, J=6.2 Hz, 1H), 4.32 (s, br, 1H), 4.02 9s, 4H), 2.70 (m, 2H), 2.41 (s, 2H), 1.95 (t, J=5.8 Hz, 2H).

Step B:
6-(1,4-Dioxa-spiro[4.5]dec-8-yl)-pyridin-2-ylamine

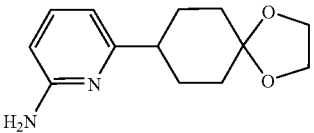

The title compound was prepared as a white solid from the hydrogenation of 6-(1,4-dioxa-spiro[4.5]dec-7-en-8-yl)-pyridin-2-ylamine (as prepared in the previous step) using the procedure described in Step G of Example 1.

ESI-MS (m/z): Calcd. For $C_{13}H_{18}N_2O_2$, 234. found: 235 (M+H).

Step C: 4-(6-Amino-pyridin-2-yl)-cyclohexanone

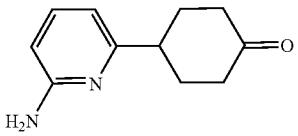

The title compound was prepared as a white solid from the deprotection of 6-(1,4-dioxa-spiro[4.5]dec-8-yl)-pyridin-2-ylamine (as prepared in the previous step) using the procedure described in Step B of Example 2.

ESI-MS (m/z): Calcd. For $C_{11}H_{14}N_2O$, 190. found: 191 (M+H).

Step D: N-({1-[4-(6-Amino-pyridin-2-yl)-cyclohexyl]-azetidin-3-ylcarbamoyl}-methyl)-3-trifluoromethyl-benzamide

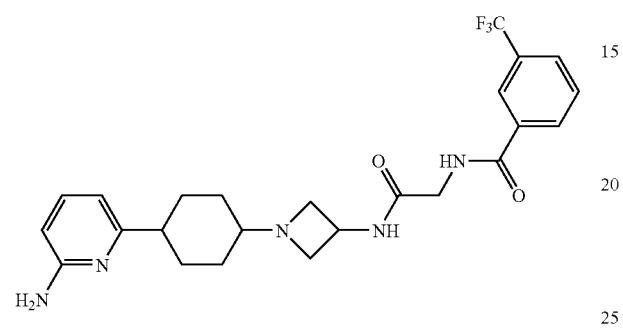

The title compounds were prepared as white solids from the reductive amination of 4-(6-amino-pyridin-2-yl)-cyclohexanone (as prepared in the previous step) and N-(azetidin-3-ylcarbamoylmethyl)-3-trifluoromethyl-benzamide using the procedure described in Step F of Example 1.

22a: Less Polar Isomer from Silica Gel Column
$^1$H NMR (MeOH) δ: 8.24 (s, 1H), 8.16 (d, J=7.8 Hz, 1H), 7.88 (d, J=7.8 Hz, 1H), 7.76 (d, J=6.8 Hz, 1H), 7.66-7.74 (m, 1H), 7.48 (dd, J=7.5, 1.6 Hz, 1H), 6.65 (dd, J=7.5, 5.2 Hz, 1H), 4.51 (t, J=6.9 Hz, 1H), 4.06 (s, 2H), 3.70 (t, J=7.6 Hz, 2H), 2.96 (t, J=7.7 Hz, 2H), 2.51-2.68 (m, 1H), 2.45 (br. s., 1H), 1.70-1.86 (m, 4H), 1.52-1.69 (m, 4H).

22b: More Polar Isomer from Silica Gel Column
$^1$H NMR (MeOH) δ: 8.24 (s, 1H), 8.16 (d, J=7.8 Hz, 1H), 7.89 (d, J=7.6 Hz, 1H), 7.75-7.80 (m, 1H), 7.67-7.75 (m, 1H), 7.49 (t, J=7.8 Hz, 1H), 6.61-6.74 (m, 1H), 4.52 (quin, J=7.3 Hz, 1H), 4.06 (s, 2H), 3.65-3.76 (m, 2H), 2.95-3.00 (m, 1H), 2.83 (t, J=6.8 Hz, 2H), 2.50-2.62 (m, 1H), 1.71-1.87 (m, 4H), 1.54-1.68 (m, 4H)

Example 23

N-({1-[4-(6-Methylamino-pyridin-2-yl)-cyclohexyl]-azetidin-3-ylcarbamoyl}-methyl)-3-trifluoromethyl-benzamide Step A: [6-(1,4-Dioxa-spiro[4.5]dec-7-en-8-yl)-pyridin-2-yl]-methyl-amine

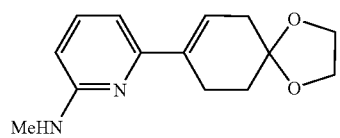

6-(1,4-Dioxa-spiro[4.5]dec-7-en-8-yl)-pyridin-2-ylamine (as prepared in Example 22, Step A, 2.5 g, 10.8 mmol) in DMF (10 mL) was treated with NaH (Aldrich, 95%, 550 mg, 21.6 mmol) at 0° C. The reaction was stirred for 20 min. and MeI (Aldrich, 810 μL, 12 mmol) was slowly added. The reaction was warmed to room temperature over 2 hours. MeOH (~1 mL) was added to quench the extra NaH. The reaction solution was partitioned between ethyl acetate and water. The organic layer was washed with brine, dried over anhydrous $Na_2SO_4$, filtered and concentrated to give a yellow oil, which was then purified by silica gel column on a CombiFlash® system using hexanes and ethyl acetate (from 10% ethyl acetate to 100% ethyl acetate) to afford the title compound as white solid.

$^1$H NMR (400 MHz, $CDCl_3$) δ 7.35 (t, J=6.5 Hz, 1H), 6.68 (d, J=6.6 Hz, 1H), 6.55 (m, 1H), 6.22 (d, J=6.5 Hz, 1H), 4.42 (s, br, 1H), 4.02 (s, 4H), 2.98 (d, J=4.5 Hz, 3H), 2.72 (t, J=4.6 Hz, 2H), 2.50 (s, 2H), 1.92 (t, J=6.2 Hz, 2H).

Step B: [6-(1,4-Dioxa-spiro[4.5]dec-8-yl)-pyridin-2-yl]-methyl-amine

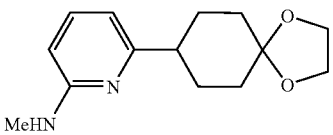

The title compound was prepared as a white solid from the hydrogenation of [6-(1,4-dioxa-spiro[4.5]dec-7-en-8-yl)-pyridin-2-yl]-methyl-amine (as prepared in the previous step) using the procedure described in Step G of Example 1.

ESI-MS (m/z): Calcd. For $C_{14}H_{20}N_2O_2$, 248. found: 249 (M+H).

Step C:
4-(6-Methylamino-pyridin-2-yl)-cyclohexanone

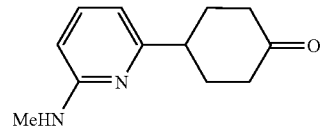

The title compound was prepared as a white solid from the deprotection of [6-(1,4-dioxa-spiro[4.5]dec-8-yl)-pyridin-2-yl]-methyl-amine (as prepared in the previous step) using the procedure described in Step B of Example 2.

ESI-MS (m/z): Calcd. For $C_{12}H_{16}N_2O$, 204. found: 205 (M+H).

Step D: N-({1-[4-(6-Methylamino-pyridin-2-yl)-cyclohexyl]-azetidin-3-ylcarbamoyl}-methyl)-3-trifluoromethyl-benzamide

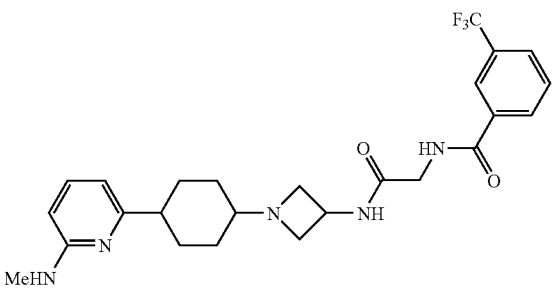

The title compounds were prepared as white solids from the reductive amination of 4-(6-methylamino-pyridin-2-yl)-cyclohexanone (as prepared in the previous step) and N-(azetidin-3-ylcarbamoylmethyl)-3-trifluoromethyl-benzamide using the procedure described in Step F of Example 1.

23a: Less Polar Isomer from Silica Gel Column,
$^1$H NMR (400 MHz, CDCl$_3$) δ 8.25 (s, br, 2H), 8.20 (s, 1H), 8.05 (d, J=6.5 Hz, 1H), 7.75 (d, J=6.6 Hz, 1H), 7.55 (t, J=6.6 Hz, 1H), 7.45 (t, J=7.5 Hz, 1H), 6.45 (d, J=6.8 Hz, 1H), 6.25 (d, J=6.8 Hz, 1H), 4.58 (m, 1H), 4.21 (d, J=4.0 Hz, 2H), 3.75 (t, J=6.0 Hz, 2H), 3.40 (t, J=6.0 Hz, 2H), 2.95 (d, J=3.5 Hz, 3H), 2.70 (s, 1H), 2.58 (m, 1H), 1.98 (m, 2H), 1.80 (m, 2H), 1.55 (4H).

23b: More Polar Isomer from Silica Gel Column
$^1$H NMR (400 MHz, CDCl$_3$) δ 8.20 (s, 1H), 8.10 (m, 1H), 7.85 (d, J=6.5 Hz, 2H), 7.75 (t, J=6.6 Hz, 1H), 7.70 (d, J=6.0 Hz, 1H), 7.55 (t, J=6.6 Hz, 1H), 4.58 (m, 1H), 4.21 (d, J=4.0 Hz, 2H), 3.80 (t, J=6.0 Hz, 2H), 3.40 (t, J=6.0 Hz, 2H), 2.85 (d, J=3.0 Hz, 3H), 2.60 (s, 1H), 2.48 (m, 1H), 1.98 (m, 2H), 1.50 (m, 2H), 1.35 (4H).

Example 24

N-[(1-{4-[6-(2,2,2-Trifluoro-acetylamino)-pyridin-2-yl]-cyclohexyl}-azetidin-3-ylcarbamoyl)-methyl]-3-trifluoromethyl-benzamide

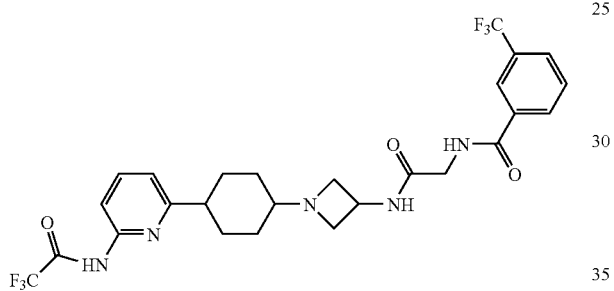

The title compound was prepared as a white solid from trifluoroacetylation of N-({1-[4-(6-amino-pyridin-2-yl)-cyclohexyl]-azetidin-3-ylcarbamoyl}-methyl)-3-trifluoromethyl-benzamide using the procedure described in Step A of Example 16.

$^1$H NMR (400 MHz, d$_4$-MeOH) δ 8.11 (s, 1H), 8.00 (d, J=6.6 Hz, 1H), 7.70 (d, J=6.5 Hz, 1H), 7.62 (t, J=6.0 Hz, 1H), 7.60 (d, J=6.1 Hz, 1H), 6.95 (d, J=6.0 Hz, 1H), 6.26 (d, J=6.0 Hz, 1H), 4.35 (m, 1H), 3.98 (s, 2H), 3.60 (t, J=7.0 Hz, 2H), 3.06 (t, J=6.1 Hz, 2H), 3.00 (m, 1H), 2.35 (m, 1H), 1.95 (m, 2H), 1.88 (m, 2H), 1.65 (m, 4H).

Example 25

N-({1-[4-(6-Cyanoamino-pyridin-2-yl)-cyclohexyl]-azetidin-3-ylcarbamoyl}-methyl)-3-trifluoromethyl-benzamide

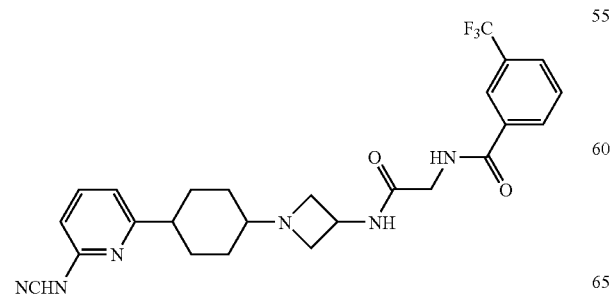

A solution of N-({1-[4-(6-amino-pyridin-2-yl)-cyclohexyl]-azetidin-3-ylcarbamoyl}-methyl)-3-trifluoromethyl-benzamide (120 mg, 0.25 mmol) in DMF (2 mL) was treated with NaH (95%, 10 mg, 0.40 mmol) at 0° C. The reaction was stirred for 20 min. and BrCN (Aldrich, 32 mg, 0.30 mmol) was slowly added. The reaction was warmed to room temperature over 2 hours. MeOH (~0.2 mL) was added to quenched extra NaH. The reaction solution was partitioned between DCM and water. The aqueous layer was extracted with a chloroform/IPA "cocktail" (3:1 v/v). The combined organic layers were washed with brine, dried over anhydrous Na$_2$SO$_4$, filtered and concentrated to give a yellow oil, which was purified by silica gel column on a CombiFlash® system using ethyl acetate and 7N NH$_3$ in MeOH as eluent (from pure ethyl acetate to 5% 7N NH$_3$ in MeOH in ethyl acetate) to afford the title compound as white solid.

$^1$H NMR (400 MHz, CDCl$_3$) δ 8.35 (s, br, 1H), 8.15 (s, 1H), 8.02 (d, J=6.5 Hz, 1H), 7.80 (m, 1H), 7.72 (d, J=6.6 Hz, 1H), 7.63 (m, 2H), 7.00 (d, J=6.0 Hz, 1H), 6.32 (d, J=6.2 Hz, 1H), 4.65 (m, 1H), 4.25 (m, 2H), 3.70 (t, J=6.5 Hz, 2H), 3.25 (m, 1H), 2.91 (t, J=6.1 Hz, 2H), 2.60 (m, 1H), 1.90 (m, 4H), 1.70 (m, 4H).

Example 26

N-({1-[4-(6-Methanesulfonylamino-pyridin-2-yl)-cyclohexyl]-azetidin-3-ylcarbamoyl}-methyl)-3-trifluoromethyl-benzamide

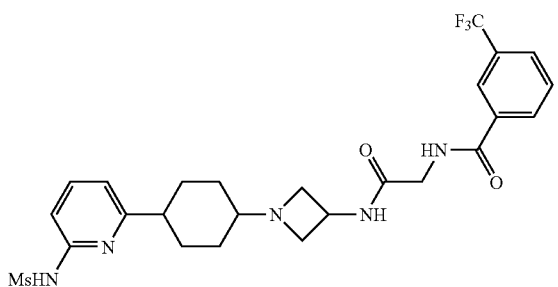

The title compound was prepared as a white solid from the mesylation of N-({1-[4-(6-amino-pyridin-2-yl)-cyclohexyl]-azetidin-3-ylcarbamoyl}-methyl)-3-trifluoromethyl-benzamide using the procedure described in Step A of Example 19.

$^1$H NMR (400 MHz, CDCl$_3$) δ 8.15 (s, 1H), 8.05 (m, 2H), 7.79 (d, J=6.2 Hz, 1H), 7.62 (d, J=3.6 Hz, 1H), 7.53 (t, J=6.6 Hz, 1H), 7.30 (s, 1H), 4.65 (m, 1H), 4.20 (m, 2H), 3.85 (m, 2H), 3.20 (s, 3H), 3.10 (m, 2H), 2.55 (m, 1H), 1.90 (m, 4H), 1.65 (m, 4H).

Example 27

N-({1-[4-(4-Amino-pyridin-3-yl)-cyclohexyl]-azetidin-3-ylcarbamoyl}-methyl)-3-trifluoromethyl-benzamide Step A: 3-(1,4-Dioxa-spiro[4.5]dec-7-en-8-yl)-pyridin-4-ylamine

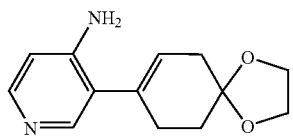

The title compound was prepared as described in Step A of Example 3 from 3-bromo-pyridin-4-ylamine (Aldrich) as a white solid.

$^1$H NMR (400 MHz, CDCl$_3$) δ 8.10 (d, J=5.6 Hz, 2H), 6.51 (s, 1H), 5.68 (m, 1H), 4.25 (s, br, 1H), 4.02 (s, 4H), 2.45 (m, 4H), 1.90 (t, J=7.0 Hz, 2H).

Step B:
3-(1,4-Dioxa-spiro[4.5]dec-8-yl)-pyridin-4-ylamine

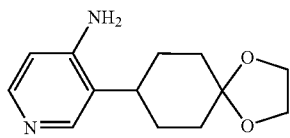

The title compound was prepared as a white solid from the hydrogenation of 3-(1,4-dioxa-spiro[4.5]dec-7-en-8-yl)-pyridin-4-ylamine (as prepared in the previous step) using the procedure described in Step G of Example 1.

ESI-MS (m/z): Calcd. For C$_{13}$H$_{18}$N$_2$O$_2$, 234. found: 235 (M+H).

Step C: 4-(4-Amino-pyridin-3-yl)-cyclohexanone

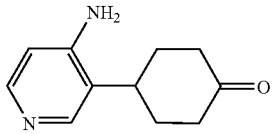

The title compound was prepared as a white solid from the deprotection of 3-(1,4-dioxa-spiro[4.5]dec-8-yl)-pyridin-4-ylamine (as prepared in the previous step) using the procedure described in Step B of Example 2.

ESI-MS (m/z): Calcd. For C$_{11}$H$_{14}$N$_2$O, 190. found: 191, (M+H).

Step D: N-({1-[4-(4-Amino-pyridin-3-yl)-cyclohexyl]-azetidin-3-ylcarbamoyl}-methyl)-3-trifluoromethyl-benzamide

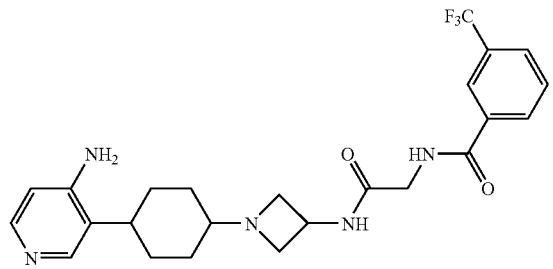

The title compounds were prepared as white solids from the reductive amination of 4-(4-amino-pyridin-3-yl)-cyclohexanone (as prepared in the previous step) and N-(azetidin-3-ylcarbamoylmethyl)-3-trifluoromethyl-benzamide using the procedure described in Step F of Example 1.

27a: Less Polar Isomer from Silica Gel Column, $^1$H NMR (400 MHz, d$_4$-MeOH) δ 8.12 (s, 1H), 8.06 (d, J=6.5 Hz, 1H), 8.02 (s, 1H), 7.95 (d, J=5.2 Hz, 1H), 7.78 (d, J=6.6 Hz, 1H), 7.60 (t, J=6.6 Hz, 1H), 7.32 (m, 1H), 6.60 (d, J=6.8 Hz, 1H), 4.45 (m, 1H), 4.05 (s, 2H), 3.65 (t, J=7.0 Hz, 2H), 2.95 (t, J=7.0 Hz, 2H), 2.45 (m, 1H), 2.40 (s, 1H), 1.95 (m, 2H), 1.80 (m, 2H), 1.55 (m, 4H).

27b: More Polar Isomer from Silica Gel Column $^1$H NMR (400 MHz, d$_4$-MeOH) δ 8.21 (s, 1H), 8.18 9d, J=6.1 Hz, 1H), 7.95 (s, 1H), 7.90 (d, J=6.5 Hz, 2H), 7.70 (t, J=6.6 Hz, 1H), 6.65 (d, J=6.8 Hz, 1H), 4.50 (m, 1H), 4.08 (s, 2H), 3.75 (t, J=7.0 Hz, 2H), 3.10 (t, J=7.0 Hz, 2H), 2.55 (m, 1H), 2.25 (m, 1H), 2.02 (m, 4H), 1.55 (m, 2H), 1.24 (m, 2H).

Example 28

N-({1-[4-(6-Amino-pyridin-2-yl)-cyclohexyl]-azetidin-3-ylcarbamoyl}-methyl)-4-fluoro-3-trifluoromethyl-benzamide

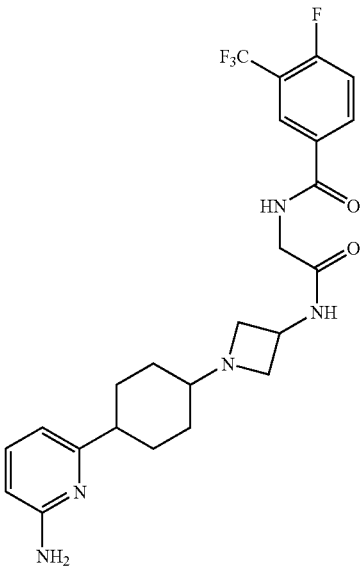

The title compounds were prepared as white solids from the reductive amination of 4-(6-amino-pyridin-2-yl)-cyclohexanone (as prepared in the Example 22, Step C) and N-(azetidin-3-ylcarbamoylmethyl)-4-fluoro-3-trifluoromethyl-benzamide (analog synthesis by following the procedure described in Organic Synthesis XII, 40-2, 1932) using the procedure described in Step F of Example 1.

$^1$H NMR (MeOH) δ: 8.17 (d, J=6.6 Hz, 1H), 8.10 (dd, J=8.7, 2.4 Hz, 1H), 7.37 (t, J=9.5 Hz, 1H), 7.28 (t, J=7.7 Hz, 1H), 6.45 (d, J=7.3 Hz, 1H), 6.27 (d, J=8.3 Hz, 1H), 4.37 (t, J=7.1 Hz, 1H), 3.93 (s, 2H), 3.55 (t, J=7.6 Hz, 2H), 2.83 (t, J=7.6 Hz, 2H), 2.35-2.46 (m, 1H), 2.20-2.34 (m, 1H), 1.70-1.85 (m, 2H), 1.61 (d, J=15.2 Hz, 2H), 1.46-1.55 (m, 2H), 1.34-1.46 (m, 2H).

Example 29

N-({1-[4-(4-Methylamino-pyridin-3-yl)-cyclohexyl]-azetidin-3-ylcarbamoyl}-methyl)-3-trifluoromethyl-benzamide and N-({1-[4-(4-Dimethylamino-pyridin-3-yl)-cyclohexyl]-azetidin-3-ylcarbamoyl}-methyl)-3-trifluoromethyl-benzamide

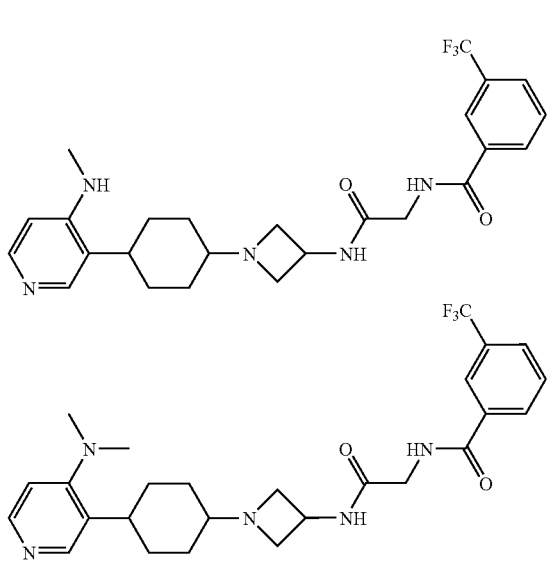

The title compounds were prepared as white solids from the NaH induced methylation of N-({1-[4-(4-amino-pyridin-3-yl)-cyclohexyl]-azetidin-3-ylcarbamoyl}-methyl)-3-trifluoromethyl-benzamide (as prepared in Example 27) using the procedure described in Step A of Example 23.

29a: More Polar Fraction from Silica Gel Column,
$^1$H NMR (400 MHz, CDCl$_3$) δ 8.15 (s, 1H), 8.12 (s, 1H), 8.06 (d, J=6.5 Hz, 2H), 8.02 (s, 1H), 7.75 (d, J=5.2 Hz, 1H), 7.59 (m, J=6.6 Hz, 2H), 6.50 (d, J=5.8 Hz, 1H), 4.65 (s, br, 1H), 4.48 (m, 1H), 4.20 (s, 2H), 3.55 (t, J=7.0 Hz, 2H), 2.95 (t, J=7.0 Hz, 2H), 2.55 (m, 1H), 2.30 (s, 1H), 2.28 (s, 3H), 1.95 (m, 2H), 1.80 (m, 2H), 1.55 (m, 4H).

29b: Less Polar Fraction from Silica Gel Column,
ESI-MS (m/z): Calcd. For C$_{26}$H$_{32}$F$_3$N$_5$O$_2$, 503. found: 504 (M+H).

Example 30

N-({1-[4-(6-Amino-pyridin-3-yl)-cyclohexyl]-azetidin-3-ylcarbamoyl}-methyl)-3-trifluoromethyl-benzamide Step A: 5-(1,4-Dioxa-spiro[4.5]dec-7-en-8-yl)-pyridin-2-ylamine

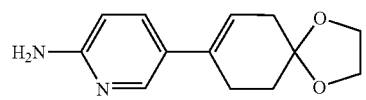

The title compound was prepared as described in Step A of Example 3 from 5-bromo-pyridin-2-ylamine (Aldrich) as a white solid.

$^1$H NMR (400 MHz, CDCl$_3$) δ 8.10 (s, 1H), 7.42 (d, J=6.2 Hz, 1H), 6.45 (d, J=6.5 Hz, 1H), 5.86 (m, 1H), 4.55 (s, br, 2H), 4.02 (s, 4H), 2.59 (t, J=3.5 Hz, 2H), 2.42 (s, 2H), 1.90 (t, J=6.0 Hz, 2H).

Step B: 5-(1,4-Dioxa-spiro[4.5]dec-8-yl)-pyridin-2-ylamine

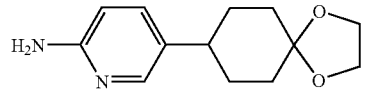

The title compound was prepared as a white solid from the hydrogenation of 5-(1,4-dioxa-spiro[4.5]dec-7-en-8-yl)-pyridin-2-ylamine (as prepared in the previous step) using the procedure described in Step G of Example 1.
ESI-MS (m/z): Calcd. For C$_{13}$H$_{18}$N$_2$O$_2$, 234. found: 235 (M+H).

Step C: 4-(6-Amino-pyridin-3-yl)-cyclohexanone

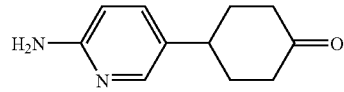

The title compound was prepared as a white solid from the deprotection of 5-(1,4-dioxa-spiro[4.5]dec-8-yl)-pyridin-2-ylamine (as prepared in the previous step) using the procedure described in Step B of Example 2.
ESI-MS (m/z): Calcd. For C$_{13}$H$_{18}$N$_2$O$_2$, 234. found: 235 (M+H).

Step D: N-({1-[4-(6-Amino-pyridin-3-yl)-cyclohexyl]-azetidin-3-ylcarbamoyl}-methyl)-3-trifluoromethyl-benzamide

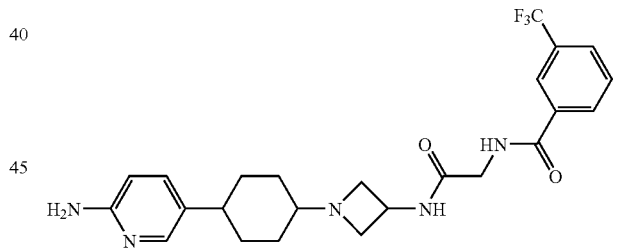

The title compounds were prepared as white solids from the reductive amination of 4-(6-amino-pyridin-3-yl)-cyclohexanone (as prepared in the previous step) and N-(azetidin-3-ylcarbamoylmethyl)-3-trifluoromethyl-benzamide using the procedure described in Step F of Example 1.

30a: Less Polar Isomer from Silica Gel Column,
$^1$H NMR (400 MHz, CDCl$_3$) δ 8.15 (s, 1H), 8.05 (d, J=6.8 Hz, 1H), 7.85 (s, 1H), 7.78 (d, J=6.5 Hz, 1H), 7.65 (t, J=6.5 Hz, 1H), 7.34 (d, J=6.5 Hz, 1H), 6.45 (d, J=5.5 Hz, 1H), 4.48 (m, 1H), 4.05 (d, J=4.5 Hz, 2H), 3.65 (t, J=6.5 Hz, 2H), 2.95 (t, J=6.5 Hz, 2H), 2.56 (m, 2H), 2.35 (m, 1H), 1.73 (m, 4H), 1.35 (m, 4H).

30b: More Polar Isomer from Silica Gel Column
$^1$H NMR (400 MHz, CDCl$_3$) δ 8.10 (s, 1H), 8.05 (d, J=6.5 Hz, 1H), 7.90 (m, 1H), 7.78 (d, J=6.6 Hz, 1H), 7.63 (t, J=6.6 Hz, 1H), 7.35 (d, J=6.0 Hz, 1H), 4.65 (m, 1H), 4.15 (d, J=3.5 Hz, 2H), 3.60 (m, J=6.5 Hz, 2H), 3.20 (m, J=6.1 Hz, 2H), 2.35 (m, 2H), 2.10 (m, 1H), 2.00 (m, 2H), 1.90 (m, 4H), 1.64 (m, 2H).

Example 31

N-({1-[4-(2-Amino-pyridin-3-yl)-cyclohexyl]-azetidin-3-ylcarbamoyl}-methyl)-3-trifluoromethyl-benzamide

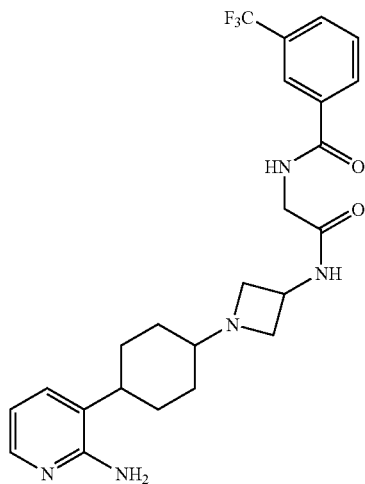

The title compound was prepared according to the procedure described in Example 3: Steps A-D from 3-bromo-pyridin-2-ylamine (Lancaster) as a yellow solid.

31a: Less Polar Isomer,
¹H NMR (MeOH) δ: 8.24 (s, 1H), 8.16 (d, J=7.8 Hz, 1H), 7.89 (d, J=7.8 Hz, 1H), 7.71 (t, J=8.0 Hz, 1H), 7.40 (t, J=7.8 Hz, 1H), 6.57 (d, J=7.6 Hz, 1H), 6.39 (d, J=8.1 Hz, 1H), 4.50 (quin, J=7.1 Hz, 1H), 4.06 (s, 2H), 3.68 (t, J=7.7 Hz, 2H), 2.96 (t, J=7.6 Hz, 2H), 2.46-2.62 (m, 1H), 2.42 (t, J=3.5 Hz, 1H), 1.84-1.98 (m, 2H), 1.68-1.81 (m, 2H), 1.49-1.68 (m, 4H).

31b: More Polar Isomer
¹H NMR (MeOH) δ: 8.24 (s, 1H), 8.16 (d, J=7.8 Hz, 1H), 7.88 (d, J=7.8 Hz, 1H), 7.71 (t, J=7.8 Hz, 1H), 7.39 (t, J=7.8 Hz, 1H), 6.57 (d, J=7.3 Hz, 1H), 6.39 (d, J=8.1 Hz, 1H), 4.49 (t, J=7.1 Hz, 1H), 4.06 (s, 2H), 3.68 (t, J=7.5 Hz, 2H), 2.96 (t, J=7.5 Hz, 2H), 2.52-2.60 (m, 1H), 2.42 (t, J=3.3 Hz, 1H), 1.83-1.99 (m, 2H), 1.72 (d, J=13.6 Hz, 2H), 1.63 (br. s., 2H), 1.44-1.60 (m, 2H)

Example 32

N-({1-[4-(5-Amino-pyridin-3-yl)-cyclohexyl]-azetidin-3-ylcarbamoyl}-methyl)-3-trifluoromethyl-benzamide

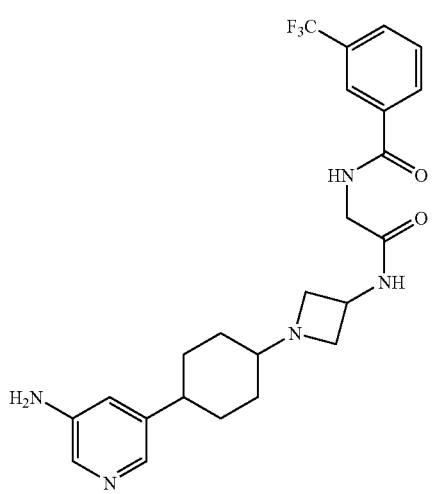

The title compound was prepared according to the procedure described in Example 3: Steps A-D from 5-bromo-pyridin-3-ylamine (Aldrich) as a yellow solid.

¹H NMR (MeOH) δ: 8.24 (s, 1H), 8.16 (d, J=7.8 Hz, 1H), 7.88 (d, J=7.8 Hz, 1H), 7.80 (s, 1H), 7.65-7.77 (m, 2H), 7.05 (s, 1H), 4.38-4.57 (m, 1H), 4.05 (s, 2H), 3.62-3.76 (m, 2H), 3.03 (br s, 2H), 2.95 (t, J=7.7 Hz, 2H), 2.38-2.47 (m, 2H), 1.79-1.92 (m, 2H), 1.74 (br. s., 2H), 1.50-1.67 (m, 4H).

Example 33

N-({1-[4-(4-Amino-pyridin-2-yl)-cyclohexyl]-azetidin-3-ylcarbamoyl}-methyl)-3-trifluoromethyl-benzamide

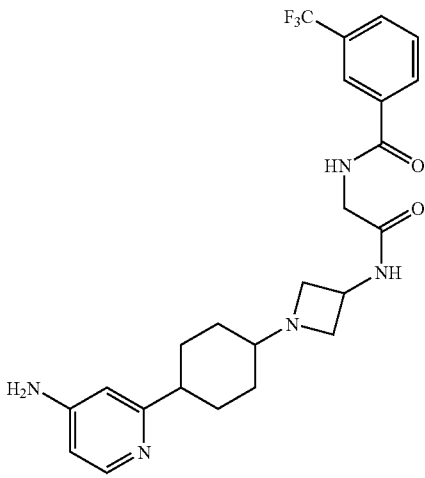

The title compound was prepared according to the procedure described in Example 3: Steps A-D from 2-bromo-pyridin-4-ylamine (Aldrich) as a yellow solid.

¹H NMR (MeOH) δ: 8.24 (s, 1H), 8.16 (d, J=7.8 Hz, 1H), 7.88 (d, J=8.6 Hz, 1H), 7.79 (d, J=2.8 Hz, 1H), 7.66-7.77 (m, 2H), 7.05 (t, J=2.0 Hz, 1H), 4.43-4.59 (m, 1H), 4.06 (s, 2H), 3.92 (br. s., 2H), 3.74 (t, J=7.8 Hz, 2H), 2.96-3.08 (m, 1H), 2.46-2.59 (m, 1H), 1.85 (d, J=12.1 Hz, 2H), 1.76 (d, J=12.6 Hz, 2H), 1.46-1.67 (m, 4H).

Example 34

N-({1-[4-(6-Amino-pyridin-2-yl)-cyclohexyl]-azetidin-3-ylcarbamoyl}-methyl)-3-fluoro-5-trifluoromethyl-benzamide

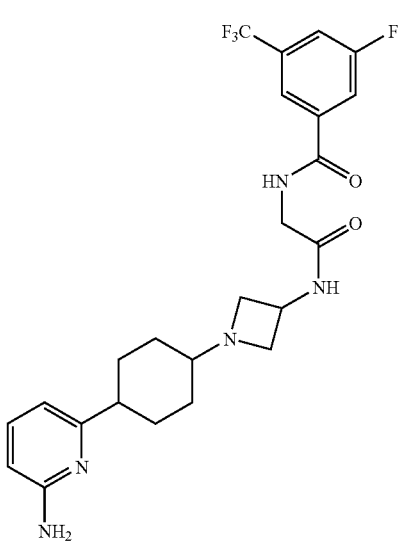

The title compounds were prepared as white solids from the reductive amination of 4-(6-amino-pyridin-2-yl)-cyclohexanone (as prepared in Example 22, Step C) and N-(azetidin-3-ylcarbamoylmethyl)-5-fluoro-3-trifluoromethyl-benzamide (analog synthesis by following the procedure described in Organic Synthesis XII, 40-2, 1932) using the procedure described in Step F of Example 1.

¹H NMR (MeOH) δ: 7.97 (br. s., 1H), 7.82 (d, J=9.3 Hz, 1H), 7.59 (d, J=8.3 Hz, 1H), 7.15-7.34 (m, 1H), 6.37 (d, J=6.8 Hz, 1H), 6.29 (d, J=8.1 Hz, 1H), 4.23-4.46 (m, 1H), 3.93 (s, 2H), 3.54-3.69 (m, 2H), 2.74-2.89 (m, 2H), 2.50 (d, J=7.3 Hz, 1H), 2.18 (s, 1H), 2.12 (br. s., 2H), 1.87 (br. s., 2H), 1.82 (br. s., 4H).

Example 35

N-{[1-(4-Pyrazin-2-yl-cyclohexyl)-azetidin-3-ylcarbamoyl]-methyl}-3-trifluoromethyl-benzamide Step A:
2-(1,4-Dioxa-spiro[4.5]dec-7-en-8-yl)-pyrazine

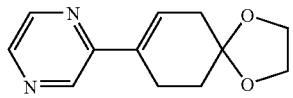

The title compound was prepared as described in Step A of Example 3 from 2-iodo-pyrazine (Aldrich) as a white solid.

ESI-MS (m/z): Calcd. For $C_{12}H_{14}N_2O_2$, 218. found: 219 (M+H).

Step B: 2-(1,4-Dioxa-spiro[4.5]dec-8-yl)-pyrazine

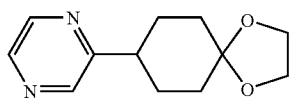

The title compound was prepared as a white solid from the hydrogenation of 2-(1,4-dioxa-spiro[4.5]dec-7-en-8-yl)-pyrazine (as prepared in the previous step) using the procedure described in Step G of Example 1.

ESI-MS (m/z): Calcd. For $C_{12}H_{16}N_2O_2$, 220. found: 221 (M+H).

Step C: 4-Pyrazin-2-yl-cyclohexanone

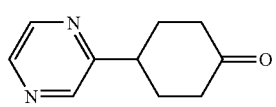

The title compound was prepared as a white solid from the de-protection of 2-(1,4-dioxa-spiro[4.5]dec-8-yl)-pyrazine (as prepared in the previous step) using the procedure described in Step B of Example 2.

¹H NMR (400 MHz, CDCl₃) δ 8.55 (d, J=6.0 Hz, 2H), 8.47 (s, 1H), 3.25 (m, 1H), 2.51 (m, 4H), 2.30 (m, 2H), 2.15 (m, 2H).

Step D: N-{[1-(4-Pyrazin-2-yl-cyclohexyl)-azetidin-3-ylcarbamoyl]-methyl}-3-trifluoromethyl-benzamide

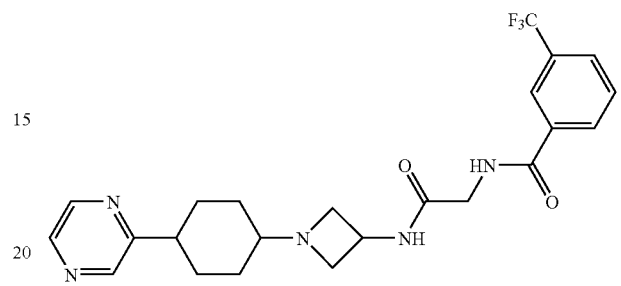

The title compounds were prepared as white solids from the reductive amination of 4-pyrazin-2-yl-cyclohexanone (as prepared in the previous step) and N-(azetidin-3-ylcarbamoylmethyl)-3-trifluoromethyl-benzamide using the procedure described in Step F of Example 1.

35a: Less Polar Isomer

¹H NMR (400 MHz, CDCl₃) δ 8.45 (m, 2H), 8.40 (s, 1H), 8.15 (s, 1H0, 8.05 (d, J=6.5 Hz, 1H), 7.75 (d, J=6.6 Hz, 1H), 7.55 (t, J=6.6 Hz, 1H), 4.50 (m, 1H), 4.20 (d, J=4.0 Hz, 2H), 3.60 (t, J=7.0 Hz, 2H), 3.05 (t, J=7.0 Hz, 2H), 2.80 (m, 1H), 2.40 (s, 1H), 2.02 (m, 4H), 1.70 (m, 2H), 1.45 (m, 2H).

35b: More Polar Isomer

¹H NMR (400 MHz, CDCl₃) δ 8.40 (m, 2H), 8.38 (s, 1H), 8.30 (s, 1H), 8.25 (d, J=6.5 Hz, 1H), 8.10 (s, 1H), 8.01 (d, J=6.5 Hz, 1H), 7.90 (d, J=6.6 Hz, 1H), 7.75 (t, J=6.6 Hz, 1H), 7.58 (t, J=6.6 Hz, 1H), 4.52 (m, 1H), 4.21 (d, J=4.0 Hz, 2H), 3.60 (t, J=7.0 Hz, 2H), 2.95 (t, J=7.0 Hz, 2H), 22.80 (m, 1H), 2.30 (s, br, 1H), 2.05 (m, 2H), 1.75 (m, 2H), 1.50 (m, 2H), 1.31 (m, 2H).

Example 36

N-({1-[4-(2-Dimethylamino-pyrimidin-5-yl)-cyclohexyl]-azetidin-3-ylcarbamoyl}-methyl)-3-trifluoromethyl-benzamide Step A: [5-(1,4-Dioxa-spiro[4.5]dec-7-en-8-yl)-pyrimidin-2-yl]-dimethyl-amine

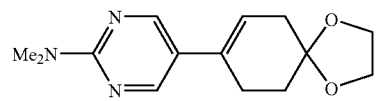

The title compound was prepared as described in Step A of Example 3 from (5-bromo-pyrimidin-2-yl)-dimethyl-amine (Aldrich) as a white solid.

ESI-MS (m/z): Calcd. For $C_{14}H_{19}N_3O_2$, 261. found: 262 (M+H).

Step B: [5-(1,4-Dioxa-spiro[4.5]dec-8-yl)-pyrimidin-2-yl]-dimethyl-amine

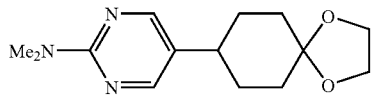

The title compound was prepared as a white solid from the hydrogenation of [5-(1,4-dioxa-spiro[4.5]dec-7-en-8-yl)-pyrimidin-2-yl]-dimethyl-amine (as prepared in the previous step) using the procedure described in Step G of Example 1.

$^1$H NMR (400 MHz, CDCl$_3$) δ 8.21 (s, 1H), 3.98 (s, 4H), 3.17 (s, 6H), 2.42 (m, 1H), 1.85 (m, 4H), 1.70 (m, 4H).

Step C: 4-(2-Dimethylamino-pyrimidin-5-yl)-cyclohexanone

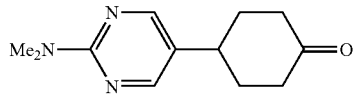

The title compound was prepared as a white solid from the de-protection of [5-(1,4-dioxa-spiro[4.5]dec-8-yl)-pyrimidin-2-yl]-dimethyl-amine (as prepared in the previous step) using the procedure described in Step B of Example 2.

$^1$H NMR (400 MHz, CDCl$_3$) δ 8.20 (s, 1H), 3.20 (s, 6H), 2.90 (m, 1H), 2.50 (m, 4H), 2.18 (m, 2H), 1.92 (m, 2H).

Step D: N-({1-[4-(2-Dimethylamino-pyrimidin-5-yl)-cyclohexyl]-azetidin-3-ylcarbamoyl}-methyl)-3-trifluoromethyl-benzamide

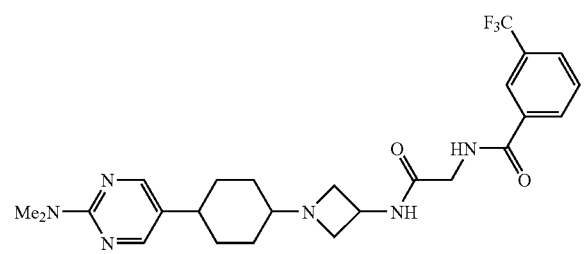

The title compounds were prepared as white solids from the reductive amination of 4-(2-dimethylamino-pyrimidin-5-yl)-cyclohexanone (as prepared in the previous step) and N-(azetidin-3-ylcarbamoylmethyl)-3-trifluoromethyl-benzamide using the procedure described in Step F of Example 1.

36a: Less Polar Isomer, $^1$H NMR (400 MHz, CDCl$_3$) δ 8.20 (s, 2H), 8.10 (s, 1H), 8.00 (d, J=6.5 Hz, 1H), 7.80 (d, J=6.6 Hz, 1H), 7.52 (m, 2H), 7.20 (m, 1H), 7.15 (d, J=5.1 Hz, 1H), 4.55 (m, 1H), 4.20 (d, J=4.0 Hz, 2H), 3.65 (t, J=7.0 Hz, 2H), 3.20 (s, 6H), 2.85 (t, J=7.0 Hz, 2H), 2.35 (m, 1H), 2.30 (s, 1H), 1.80 (m, 2H), 1.65 (m, 2H), 1.48 (m, 4H).

36b: More Polar Isomer $^1$H NMR (400 MHz, CDCl$_3$) δ 8.25 (s, 1H), 8.18 (s, 1H), 8.08 (d, J=6.5 Hz, 1H), 7.78 (d, J=6.6 Hz, 1H), 7.55 (m, 2H), 7.45 (m, 1H), 4.52 (m, 1H), 4.20 (d, J=4.0 Hz, 2H), 3.65 (t, J=7.0 Hz, 2H), 3.20 (s, 6H), 3.10 (t, J=7.0 Hz, 2H), 2.60 (m, 1H), 2.30 (s, 1H), 2.02 (m, 2H), 1.70 (m, 2H), 1.55 (m, 2H), 1.26 (m, 2H).

Example 37

N-({1-[4-(6-Oxo-1,6-dihydro-pyridin-3-yl)-cyclohexyl]-azetidin-3-ylcarbamoyl}-methyl)-3-trifluoromethyl-benzamide

Step A: 5-(1,4-Dioxa-spiro[4.5]dec-7-en-8-yl)-1H-pyridin-2-one

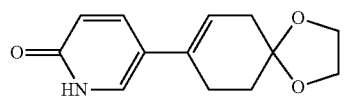

The title compound was prepared as described in Step A of Example 3 from 5-iodo-1H-pyridin-2-one (Aldrich) as a white solid.

$^1$H NMR (400 MHz, CDCl$_3$) δ 7.65 (d, J=6.5 Hz, 1H), 7.52 (d, J=6.2 Hz, 1H), 7.48 (d, J=5.0 Hz, 1H), 7.42 (t, J=6.2 Hz, 1H), 6.45 (t, J=4.5 Hz, 1H), 4.02 (s, 4H), 2.35 (m, 2H), 2.27 (m, 2H), 1.75 (m, 2H).

Step B: 5-(4-Oxo-cyclohex-1-enyl)-1H-pyridin-2-one

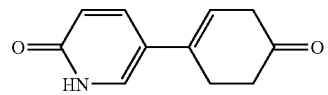

The title compound was prepared as a white solid from the de-protection of 5-(1,4-dioxa-spiro[4.5]dec-7-en-8-yl)-1H-pyridin-2-one (as prepared in the previous step) using the procedure described in Step B of Example 2.

$^1$H NMR (400 MHz, CDCl$_3$) δ 7.65 (d, J=6.8 Hz, 1H), 7.40 (s, 1H), 6.61 (s, J=7.0 Hz, 1H), 5.98 (m, 1H), 3.05 (s, 2H), 2.75 (t, J=5.8 Hz, 2H), 2.66 (t, J=6.3 Hz, 2H).

Step C: 5-(4-Oxo-cyclohexyl)-1H-pyridin-2-one

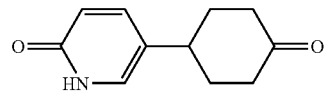

The title compound was prepared as a white solid from the hydrogenation of 5-(4-oxo-cyclohex-1-enyl)-1H-pyridin-2-one (as prepared in the previous step) using the procedure described in Step G of Example 1.

$^1$H NMR (400 MHz, CDCl$_3$) δ 8.10 (s, 1H), 7.52 (d, J=6.6 Hz, 1H), 7.23 (d, J=6.5 Hz, 1H), 2.55 (m, 4H), 2.25 (m, 1H), 1.67 (m, 4H).

Step D: N-({1-[4-(6-Oxo-1,6-dihydro-pyridin-3-yl)-cyclohexyl]-azetidin-3-ylcarbamoyl}-methyl)-3-trifluoromethyl-benzamide

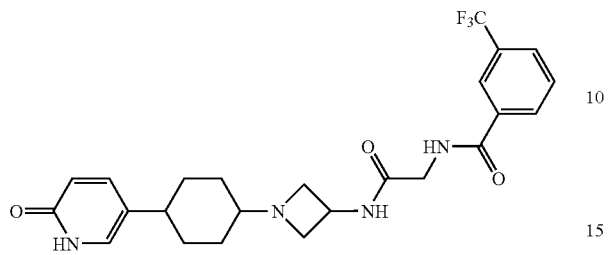

The title compounds were prepared as white solids from the reductive amination of 5-(4-oxo-cyclohexyl)-1H-pyridin-2-one (as prepared in the previous step) and N-(azetidin-3-ylcarbamoylmethyl)-3-trifluoromethyl-benzamide using the procedure described in Step F of Example 1.

37a: Less Polar Isomer, $^1$H NMR (400 MHz, CDCl$_3$) δ 8.25 (s, br, 1H), 8.20 (s, 1H), 8.09 (d, J=6.0 Hz, 1H), 7.78 (d, J=6.2 Hz, 1H), 7.61 (t, J=6.2 Hz, 1H), 7.45 (m, 1H), 7.40 (d, J=6.2 Hz, 1H), 7.18 (s, 1H), 6.52 (d, J=6.4 Hz, 1H), 4.55 (m, 1H), 4.21 (d, J=4.3 Hz, 2H), 3.58 (t, J=5.2 Hz, 2H), 2.99 (t, J=4.2 Hz, 2H), 2.35 (m, 2H), 1.80 (m, 2H), 1.65 (m, 2H), 1.48 (m, 4H).

37b: More Polar Isomer $^1$H NMR (400 MHz, CDCl$_3$) δ 9.35 (s, br, 1H), 8.15 (s, 1H), 8.05 (d, J=6.2 Hz, 1H), 7.80 (d, J=6.2 Hz, 1H), 7.60 (t, J=6.5 Hz, 1H), 7.40 (d, J=6.5 Hz, 1H), 7.10 (s, 1H), 6.55 (d, J=6.4 Hz, 1H), 4.58 (m, 1H), 4.15 (d, J=4.5 Hz, 2H), 3.68 (t, J=6.5 Hz, 2H), 3.25 (t, J=6.0 Hz, 2H), 2.36 (m, 1H), 2.32 (m, 1H), 1.80 (4, 2H), 1.56 (m, 2H), 1.32 (m, 2H).

Example 38

N-({1-[4-(1-Methyl-6-oxo-1,6-dihydro-pyridin-3-yl)-cyclohexyl]-azetidin-3-ylcarbamoyl}-methyl)-3-trifluoromethyl-benzamide Step A: 5-(1,4-Dioxa-spiro[4.5]dec-8-yl)-1H-pyridin-2-one

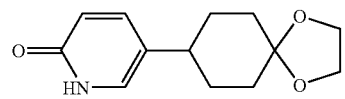

5-(1,4-Dioxa-spiro[4.5]dec-7-en-8-yl)-1H-pyridin-2-one from Step A of Example 37 (5.2 g, 22.1 mmol) in ethyl acetate (30 mL) was treated with 5% Pd/C (Aldrich, 2.6 g) at room temperature. The reaction mixture was then charged with a hydrogen balloon and stirred for 2 hours. The catalyst was removed by filtering the reaction through a pad of Celite. The filtrate was concentrated to give the crude product, which was then purified with a CombiFlash® system using silica gel column and 40% ethyl acetate in hexanes as eluent to give the title compound as a white solid.

ESI-MS (m/z): Calcd. For C$_{13}$H$_{17}$NO$_3$, 235. found: 236 (M+H), 258 (M+Na).

Step B: 5-(1,4-Dioxa-spiro[4.5]dec-8-yl)-1-methyl-1H-pyridin-2-one

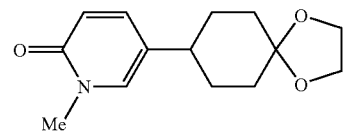

A solution of 5-(1,4-dioxa-spiro[4.5]dec-8-yl)-1H-pyridin-2-one (as prepared in the previous step, 750 mg, 3.19 mmol) in DMF (5 mL) was treated with Cs$_2$CO$_3$ (Aldrich, 1.56 g, 4.80 mmol) at room temperature for 10 min. MeI (Aldrich, 330 µL, 4.80 mmol) was added into the reaction solution and heated at 70° C. for 6 hours. The reaction solution was partitioned between ethyl acetate and water. The organic layer was washed with brine, dried over anhydrous Na$_2$SO$_4$, filtered and concentrated to give yellow oil, which was then purified by silica gel column on a CombiFlash® system using hexanes and ethyl acetate (from 10% ethyl acetate to 100% ethyl acetate) to afford the title compound as a white solid along with O-alylated product, 5-(1,4-dioxa-spiro[4.5]dec-8-yl)-2-methoxy-pyridine.

ESI-MS (m/z): Calcd. For C$_{14}$H$_{19}$NO$_3$, 249. found: 250 (M+H).

Step C: 1-Methyl-5-(4-oxo-cyclohexyl)-1H-pyridin-2-one

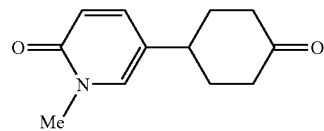

The title compound was prepared as a white solid from the de-protection of 5-(1,4-dioxa-spiro[4.5]dec-8-yl)-1-methyl-1H-pyridin-2-one (as prepared in the previous step) using the procedure described in Step B of Example 2.

$^1$H NMR (400 MHz, CDCl$_3$) δ 7.31 (d, J=6.5 Hz, 1H), 7.18 (s, 1H), 6.57 (d, J=6.5 Hz, 1H), 3.52 (s, 3H), 2.80 (m, 1H), 2.44 (d, J=6.0 Hz, 4H), 2.21 (m, 2H), 1.80 (m, 2H).

Step D: N-({1-[4-(1-Methyl-6-oxo-1,6-dihydro-pyridin-3-yl)-cyclohexyl]-azetidin-3-ylcarbamoyl}-methyl)-3-trifluoromethyl-benzamide

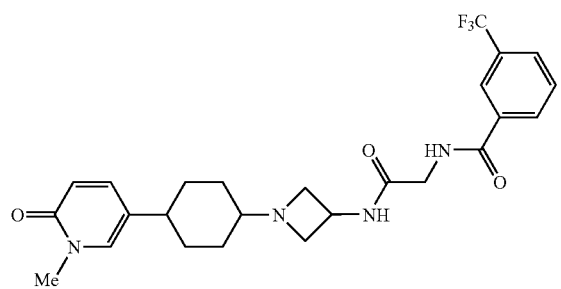

The title compounds were prepared as white solids from the reductive amination of 1-methyl-5-(4-oxo-cyclohexyl)-1H-pyridin-2-one (as prepared in the previous step) and N-(azetidin-3-ylcarbamoylmethyl)-3-trifluoromethyl-benzamide using the procedure described in Step F of Example 1.

38a: Less Polar Isomer $^1$H NMR (400 MHz, CDCl$_3$) δ 8.12 (s, 1H), 8.02 (d, J=6.2 Hz, 1H), 7.78 (d, J=6.5 Hz, 1H), 7.66 (s, 1H), 7.57 (t, J=6.5 Hz, 1H), 7.30 (d, J=6.6 Hz, 1H), 7.20 9s, br, 1H), 7.08 (s, 1H), 7.48 (d, J=6.7 Hz, 1H), 4.52 (m, 1H), 4.18 (d, J=4.5 Hz, 2H), 3.58 (t, J=6.0 Hz, 2H), 3.48 (s, 3H), 2.80 (t, J=6.0 Hz, 2H), 2.25 (m, 1H), 1.69 (m, 4H), 1.45 (m, 4H).

38b: More Polar Isomer $^1$H NMR (400 MHz, CDCl$_3$) δ 8.15 (s, 1H), 8.04 (d, J=6.2 Hz, 1H), 7.70 (d, J=6.5 Hz, 1H), 6.65 (s, 1H), 6.56 (t, J=7.0 Hz, 1H), 7.33 (s, br, 1H), 7.18 (d, J=6.8 Hz, 1H), 6.98 (s, 1H), 6.48 (d, J=6.6 Hz, 1H), 4.50 (m, 1H), 4.12 (d, J=4.5 Hz, 2H), 3.60 (d, J=7.1 Hz, 2H), 3.42 (s, 3H), 3.05 (t, J=7.0 Hz, 2H), 2.20 (m, 1H), 1.85 (m, 4H), 1.25 (m, 2H), 1.10 (m, 2H).

Example 39

N-({1-[4-(1-Ethyl-6-oxo-1,6-dihydro-pyridin-3-yl)-cyclohexyl]-azetidin-3-ylcarbamoyl}-methyl)-3-trifluoromethyl-benzamide Step A: 5-(1,4-Dioxa-spiro[4.5]dec-8-yl)-1-ethyl-1H-pyridin-2-one

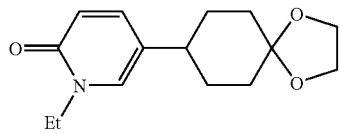

The title compound was prepared as a white solid from the ethylation of 5-(1,4-dioxa-spiro[4.5]dec-7-en-8-yl)-1H-pyridin-2-one with EtI (Aldrich) using the procedure described in Step B of Example 38.

$^1$H NMR (400 MHz, CDCl$_3$) δ 7.90 (s, 1H), 7.75 (d, J=6.0 Hz, 1H), 6.60 (d, J=6.2 Hz, 1H), 4.00 (q, J=6.5 Hz, 2H), 3.98 (m, 4H), 2.75 (m, 1H), 2.10 (m, 2H), 1.75 (m, 4H), 1.64 (m, 2H), 1.45 (t, J=6.5 Hz, 3H).

Step B: 1-Ethyl-5-(4-oxo-cyclohexyl)-1H-pyridin-2-one

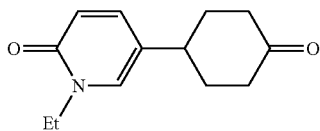

The title compound was prepared as a white solid from the deprotection of 5-(1,4-dioxa-spiro[4.5]dec-8-yl)-1-ethyl-1H-pyridin-2-one using the procedure described in Step B of Example 2.

$^1$H NMR (400 MHz, CDCl$_3$) δ 7.95 (s, 1H), 7.80 (d, J=6.5 Hz, 1H), 6.60 (d, J=6.8 Hz, 1H), 4.10 (q, J=7.0 Hz, 2H), 2.80 (m, 1H), 2.65 (m, 2H), 2.34 (m, 2H), 2.05 (m, 4H), 1.42 (t, J=7.0 Hz, 3H).

Step C: N-({1-[4-(1-Ethyl-6-oxo-1,6-dihydro-pyridin-3-yl)-cyclohexyl]-azetidin-3-ylcarbamoyl}-methyl)-3-trifluoromethyl-benzamide

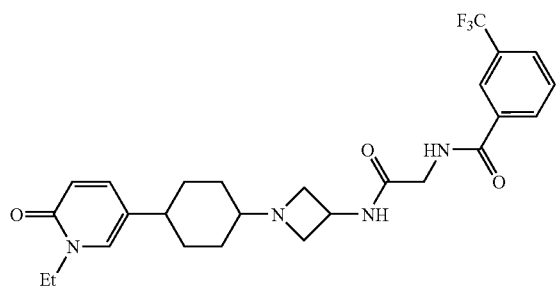

The title compounds were prepared as white solids from the reductive amination of 1-ethyl-5-(4-oxo-cyclohexyl)-1H-pyridin-2-one (as prepared in the previous step) and N-(azetidin-3-ylcarbamoylmethyl)-3-trifluoromethyl-benzamide using the procedure described in Step F of Example 1.

$^1$H NMR (400 MHz, d$_4$-MeOH) δ 8.18 (s, 1H), 8.08 (d, J=6.5 Hz, 1H), 7.78 (d, J=6.4 Hz, 1H), 7.60 (t, J=6.5 Hz, 1H), 7.15 (d, J=7.0 Hz, 2H), 7.02 (d, J=3.0 Hz, 2H), 6.05 (d, J=7.0 Hz, 1H), 4.51 (m, 1H), 4.25 (s, 2H), 4.10 (s, 2H), 3.98 (q, J=7.5 Hz, 2H), 3.60 (t, J=6.5 Hz, 2H), 3.05 (t, J=6.0 Hz, 2H), 2.48 (m, 1H), 2.45 (m, 1H), 1.75 (m, 4H), 1.55 (m, 4H), 1.32 (t, J=7.5 Hz, 3H).

Example 40

N-({1-[4-(1-Isopropyl-6-oxo-1,6-dihydro-pyridin-3-yl)-cyclohexyl]-azetidin-3-ylcarbamoyl}-methyl)-3-trifluoromethyl-benzamide Step A: 5-Iodo-1-isopropyl-1H-pyridin-2-one and 5-Iodo-2-isopropoxy-pyridine

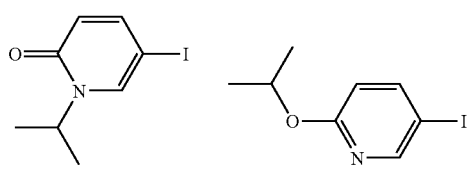

The title compounds were prepared as white solids from the iso-propylation of 5-iodo-1H-pyridin-2-one with i-PrI (Aldrich) using the procedure described in Step A of Example 38.

5-Iodo-1-isopropyl-1H-pyridin-2-one $^1$H NMR (400 MHz, CDCl$_3$) δ 7.60 (s, 1H), 7.48 (d, J=6.5 Hz, 1H), 6.38 (d, J=6.6 Hz, 1H), 5.02 (m, 1H), 1.42 (d, J=8.5 Hz, 6H).

5-Iodo-2-isopropoxy-pyridine $^1$H NMR (400 MHz, CDCl$_3$) δ 8.28 (s, 1H), 7.75 (d, J=6.8 Hz, 1H), 6.48 (d, J=6.5 Hz, 1H), 5.22 (m, 1H), 1.36 (d, J=6.5 Hz, 6H).

Step B: 5-(1,4-Dioxa-spiro[4.5]dec-7-en-8-yl)-1-isopropyl-1H-pyridin-2-one

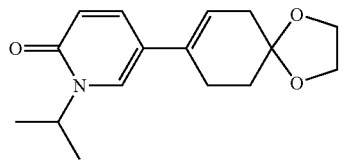

The title compound was prepared as a white solid as described in Step A of Example 3 from 5-iodo-1-isopropyl-1H-pyridin-2-one as prepared in the previous step.

$^1$H NMR (400 MHz, CDCl$_3$) δ 7.45 (d, J=6.4 Hz, 1H), 7.20 (s, 1H), 6.50 (d, J=7.0 Hz, 1H), 5.85 (m, 1H), 5.25 (m, 1H), 4.05 (s, 4H), 3.33 (m, 1H), 2.48 (m, 2H), 2.42 (s, 2H), 1.95 (t, J=5.5 Hz, 2H), 1.35 (d, J=7.2 Hz, 6H).

Step C: 1-Isopropyl-5-(4-oxo-cyclohexyl)-1H-pyridin-2-one

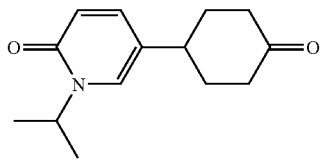

The title compound was prepared as a white solid from the hydrogenation of 5-(1,4-dioxa-spiro[4.5]dec-7-en-8-yl)-1-isopropyl-1H-pyridin-2-one (as prepared in the previous step) using the procedure described in Step G of Example 1 followed by de-protection of the corresponding ketal using the procedure described in Step B of Example 2.

ESI-MS (m/z): Calcd. For C$_{14}$H$_{19}$NO$_2$, 233. found: 234 (M+H).

Step D: N-({1-[4-(1-Isopropyl-6-oxo-1,6-dihydro-pyridin-3-yl)-cyclohexyl]-azetidin-3-ylcarbamoyl}-methyl)-3-trifluoromethyl-benzamide

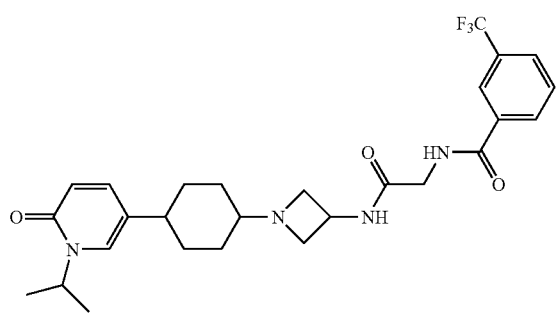

The title compounds were prepared as white solids from the reductive amination of 1-isopropyl-5-(4-oxo-cyclohexyl)-1H-pyridin-2-one (as prepared in the previous step) and N-(azetidin-3-ylcarbamoylmethyl)-3-trifluoromethyl-benzamide using the procedure described in Step F of Example 1.

40a: Less Polar Isomer

$^1$H NMR (400 MHz, d$_4$-MeOH) δ 8.25 (s, 1H), 8.18 (d, J=6.5 Hz, 1H), 7.90 (d, J=6.4 Hz, 1H), 7.72 (t, J=6.5 Hz, 1H), 7.51 (s, 1H), 7.48 (d, J=7.0 Hz, 1H), 6.51 (d, J=7.0 Hz, 1H), 5.25 (m, 1H), 4.55 (m, 1H), 4.15 (s, 2H), 3.75 (t, J=6.5 Hz, 2H), 3.02 (t, J=6.0 Hz, 2H), 2.48 (m, 1H), 1.75 (m, 4H), 1.55 (m, 4H), 1.38 (d, J=7.5 Hz, 6H).

40b: More Polar Isomer

$^1$H NMR (400 MHz, CDCl$_3$) δ 8.16 (s, 1H), 8.05 (d, J=6.5 Hz, 1H), 7.80 (d, J=6.1 Hz, 1H), 7.61 (d, J=6.6 Hz, 1H), 7.55 (t, J=6.6 Hz, 1H), 7.21 (d, J=6.0 Hz, 1H), 7.05 (s, 1H), 6.52 (d, J=6.5 Hz, 1H), 5.27 (m, 1H), 4.65 (m, 1H), 4.20 (d, J=3.5 Hz, 2H), 3.67 (t, J=6.5 Hz, 2H), 3.00 (m, J=6.1 Hz, 2H), 2.40 (m, 1H), 2.25 (m, 1H), 2.10 (m, 2H), 1.90 (m, 2H), 1.40 (m, 2H), 1.35 (d, J=7.0 Hz, 6H), 1.25 (m, 2H).

Example 41

N-({1-[4-(1-Cyanomethyl-6-oxo-1,6-dihydro-pyridin-3-yl)-cyclohexyl]-azetidin-3-ylcarbamoyl}-methyl)-3-trifluoromethyl-benzamide

Step A: (5-Iodo-2-oxo-2H-pyridin-1-yl)-acetonitrile

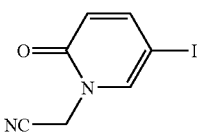

The title compound was prepared as a white solid from the alkylation of 5-iodo-1H-pyridin-2-one with CNCH$_2$I using the procedure described in Step A of Example 38.

$^1$H NMR (400 MHz, CDCl$_3$) δ 7.61 (s, 1H), 7.45 (d, J=6.6 Hz, 1H), 6.45 (d, J=6.6 Hz, 1H), 4.79 (s, 2H).

Step B: [5-(1,4-Dioxa-spiro[4.5]dec-7-en-8-yl)-2-oxo-2H-pyridin-1-yl]-acetonitrile

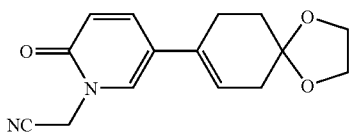

The title compound was prepared using the procedure described in Step A of Example 3 from (5-iodo-2-oxo-2H-pyridin-1-yl)-acetonitrile (Aldrich) as a white solid.

$^1$H NMR (400 MHz, CDCl$_3$) δ 7.35 (d, J=6.5 Hz, 1H), 7.30 (s, 1H), 6.58 (d, J=6.5 Hz, 1H), 5.89 (m, 1H), 4.85 (s, 2H), 4.01 (s, 4H), 2.50 (t, J=3.5 Hz, 2H), 2.45 (s, 2H), 1.92 (t, J=6.5 Hz, 2H).

Step C: [2-Oxo-5-(4-oxo-cyclohexyl)-2H-pyridin-1-yl]-acetonitrile

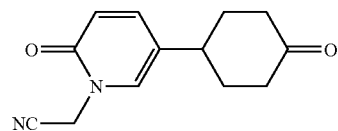

The title compound was prepared as a white solid from the hydrogenation of [5-(1,4-dioxa-spiro[4.5]dec-7-en-8-yl)-2-oxo-2H-pyridin-1-yl]-acetonitrile (as prepared in the previous step) using the procedure described in Step G of Example 1 followed by de-protection of the corresponding ketal using the procedure described in Step B of Example 2.

ESI-MS (m/z): Calcd. For $C_{13}H_{14}N_2O_2$, 230. found: 231 (M+H).

Step D: N-({1-[4-(1-Cyanomethyl-6-oxo-1,6-dihydro-pyridin-3-yl)-cyclohexyl]-azetidin-3-ylcarbamoyl}-methyl)-3-trifluoromethyl-benzamide

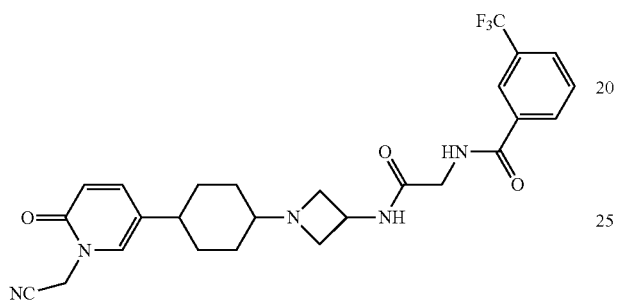

The title compounds were prepared as white solids from the reductive amination of [2-oxo-5-(4-oxo-cyclohexyl)-2H-pyridin-1-yl]-acetonitrile (as prepared in the previous step) and N-(azetidin-3-ylcarbamoylmethyl)-3-trifluoromethyl-benzamide using the procedure described in Step F of Example 1.

$^1$H NMR (400 MHz, $d_4$-MeOH) δ 8.18 (s, 1H), 8.11 (d, J=6.5 Hz, 1H), 7.88 (d, J=6.4 Hz, 1H), 7.70 (t, J=6.5 Hz, 1H), 7.45 (s, 1H), 7.37 (d, J=7.0 Hz, 1H), 6.41 (d, J=7.0 Hz, 1H), 4.80 (s, 2H), 4.45 (m, 1H), 4.03 (s, 2H), 3.65 (t, J=6.5 Hz, 2H), 2.98 (t, J=6.0 Hz, 2H), 2.38 (m, 1H), 1.80 (m, 4H), 1.50 (m, 4H).

Example 42

N-[(1-{4-[6-Oxo-1-(2,2,2-trifluoro-ethyl)-1,6-dihydro-pyridin-3-yl]-cyclohexyl}-azetidin-3-ylcarbamoyl)-methyl]-3-trifluoromethyl-benzamide Step A: 5-Iodo-1-(2,2,2-trifluoro-ethyl)-1H-pyridin-2-one and 5-Iodo-2-(2,2,2-trifluoro-ethoxy)pyridine

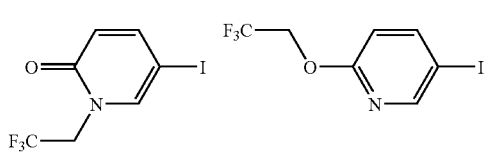

The title compounds were prepared as white solids from the alkylation of 5-iodo-1H-pyridin-2-one with $CF_3CH_2I$ (Aldrich) using the procedure described in Step A of Example 38.

5-Iodo-1-(2,2,2-trifluoro-ethyl)-1H-pyridin-2-one $^1$H NMR (400 MHz, $CDCl_3$) δ 7.51 (s, 1H), 7.45 (d, J=6.8 Hz, 1H), 6.42 (d, J=6.8 Hz, 1H), 4.55 (q, J=6.5 Hz, 2H).

5-Iodo-2-(2,2,2-trifluoro-ethoxy)-pyridine $^1$H NMR (400 MHz, $CDCl_3$) δ 8.30 (s, 1H), 7.85 (d, J=6.5 Hz, 1H), 6.68 9d, J=6.6 Hz, 1H), 4.71 (q, J=6.8 Hz, 2H).

Step B: 5-(1,4-Dioxa-spiro[4.5]dec-7-en-8-yl)-1-(2,2,2-trifluoro-ethyl)-1H-pyridin-2-one

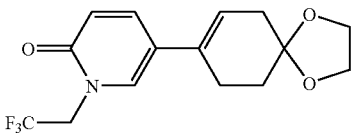

The title compound was prepared as described in Step A of Example 3 from 5-iodo-1-(2,2,2-trifluoro-ethyl)-1H-pyridin-2-one (as prepared in the previous step) as a white solid.

ESI-MS (m/z): Calcd. For $C_{15}H_{16}F_3NO_3$, 315. found: 316 (M+H).

Step C: 5-(1,4-Dioxa-spiro[4.5]dec-8-yl)-1-(2,2,2-trifluoro-ethyl)-1H-pyridin-2-one

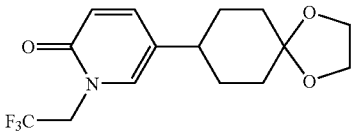

The title compound was prepared as a white solid from the hydrogenation of 5-(1,4-dioxa-spiro[4.5]dec-7-en-8-yl)-1-(2,2,2-trifluoro-ethyl)-1H-pyridin-2-one (as prepared in the previous step) using the procedure described in Step G of Example 1.

$^1$H NMR (400 MHz, $CDCl_3$) δ 7.48 (s, 1H), 7.40 (d, J=6.5 Hz, 1H), 6.36 (d, J=6.5 Hz, 1H), 4.42 (q, J=7.5 Hz, 2H), 3.95 (m, 4H), 2.70 (m, 1H), 2.105 (m, 2H), 1.70 (m, 4H), 1.55 (m, 2H).

Step D: 5-(4-Oxo-cyclohexyl)-1-(2,2,2-trifluoro-ethyl)-1H-pyridin-2-one

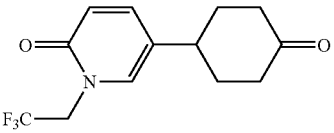

The title compound was prepared as a white solid from the de-protection of 5-(1,4-dioxa-spiro[4.5]dec-8-yl)-1-(2,2,2- trifluoro-ethyl)-1H-pyridin-2-one (as prepared in the previous step) using the procedure described in Step B of Example 2.

ESI-MS (m/z): Calcd. For $C_{13}H_{14}F_3NO_2$, 273. found: 274 (M+H).

Step E: N-[(1-{4-[6-Oxo-1-(2,2,2-trifluoro-ethyl)-1,6-dihydro-pyridin-3-yl]-cyclohexyl}-azetidin-3-yl-carbamoyl)-methyl]-3-trifluoromethyl-benzamide

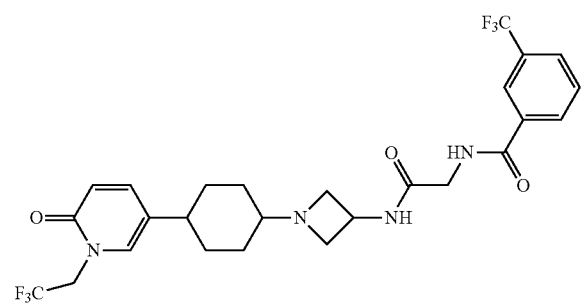

The title compounds were prepared as white solids from the reductive amination of 5-(4-oxo-cyclohexyl)-1-(2,2,2-trifluoro-ethyl)-1H-pyridin-2-one (as prepared in the previous step) and N-(azetidin-3-ylcarbamoylmethyl)-3-trifluoromethyl-benzamide using the procedure described in Step F of Example 1.

42a: Less Polar Isomer,
$^1$H NMR (400 MHz, $d_4$-MeOH) δ 8.25 (s, 1H), 8.14 (d, J=6.2 Hz, 1H), 7.87 (d, J=6.0 Hz, 1H), 7.73 (t, J=6.2 Hz, 1H), 7.65 (d, J=6.4 Hz, 1H), 7.42 (s, 1H), 6.55 (d, J=6.5 Hz, 1H), 4.80 (q, J=9.5 Hz, 2H), 4.45 (m, 1H), 4.08 (s, 2H), 3.70 (t, J=7.5 Hz, 2H), 3.02 (t, J=7.2 Hz, 2H), 2.45 (m, 2H), 1.75 (m, 4H), 1.58 (m, 4H).

42b: More Polar Isomer
$^1$H NMR (400 MHz, $d_4$-MeOH) δ 8.15 (s, 1H), 8.02 (d, J=6.5 Hz, 1H), 7.82 (d, J=5.0 Hz, 1H), 7.65 (t, J=7.2 Hz, 1H), 7.60 (m, 1H), 7.32 (d, J=6.1 Hz, 1H), 6.55 (d, J=6.1 Hz, 1H), 4.63 (q, J=8.5 Hz, 2H), 4.52 (m, 1H), 4.18 (s, 2H), 3.65 (t, J=7.5 Hz, 2H), 3.10 (t, J=7.2 Hz, 2H), 2.85 (m, 1H), 2.30 (m, 3H), 2.21 (m, 2H), 1.65 (m, 2H), 1.42 (m, 2H).

Example 43

N-[(1-{4-[1-(2-Hydroxy-ethyl)-6-oxo-1,6-dihydro-pyridin-3-yl]-cyclohexyl}-azetidin-3-ylcarbamoyl)-methyl]-3-trifluoromethyl-benzamide Step A: 1-[2-(tert-Butyl-dimethyl-silanyloxy)-ethyl]-5-iodo-1H-pyridin-2-one

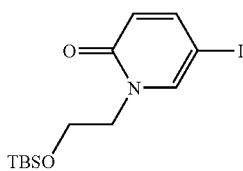

The title compounds were prepared as white solids from the alkylation of 5-iodo-1H-pyridin-2-one with BrCH$_2$CH$_2$OTBS (Aldrich) using the procedure described in Step A of Example 38.

ESI-MS (m/z): Calcd. For $C_{13}H_{22}INO_2Si$, 379. found: 380 (M+H).

Step B: 1-[2-(tert-Butyl-dimethyl-silanyloxy)-ethyl]-5-(1,4-dioxa-spiro[4.5]dec-7-en-8-yl)-1H-pyridin-2-one

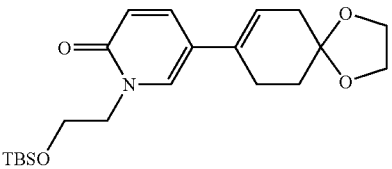

The title compound was prepared as described in Step A of Example 3 from 1-[2-(tert-butyl-dimethyl-silanyloxy)-ethyl]-5-iodo-1H-pyridin-2-one (as prepared in the previous step) as a white solid.

$^1$H NMR (400 MHz, CDCl$_3$) δ 7.55 (d, J=5.5 Hz, 1H), 7.33 (s, 1H), 6.58 (d, J=6.8 Hz, 1H), 5.90 (m, 1H), 4.15 (t, J=4.5 Hz, 2H), 4.10 (s, 4H), 4.02 9t, J=4.6 Hz, 2H), 2.58 (t, J=3.5 Hz, 2H), 2.45 (s, 2H), 1.98 (t, J=6.1 Hz, 2H), 0.92 (s, 9H).

Step C: 1-(2-Hydroxy-ethyl)-5-(4-oxo-cyclohexyl)-1H-pyridin-2-one

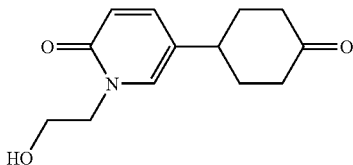

The title compound was prepared as a white solid from the hydrogenation of 1-[2-(tert-Butyl-dimethyl-silanyloxy)-ethyl]-5-(1,4-dioxa-spiro[4.5]dec-7-en-8-yl)-1H-pyridin-2-one (as prepared in the previous step) using the procedure described in Step G of Example 1 followed by de-protection of the corresponding ketal using the procedure described in Step B of Example 2.

ESI-MS (m/z): Calcd. For $C_{13}H_{17}NO_3$, 235. found: 236 (M+H).

Step D: N-[(1-{4-[1-(2-Hydroxy-ethyl)-6-oxo-1,6-dihydro-pyridin-3-yl]-cyclohexyl}-azetidin-3-ylcarbamoyl)-methyl]-3-trifluoromethyl-benzamide

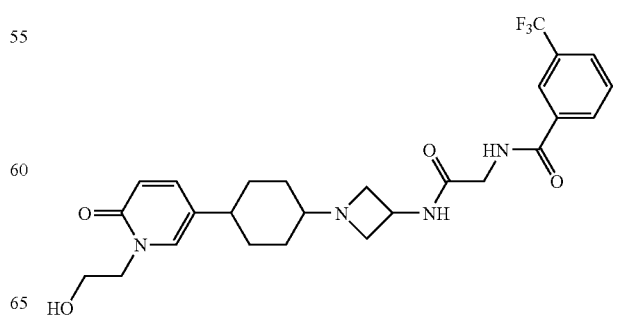

The title compounds were prepared as white solids from the reductive amination of 1-(2-hydroxy-ethyl)-5-(4-oxo-cyclohexyl)-1H-pyridin-2-one (as prepared in the previous step) and N-(azetidin-3-ylcarbamoylmethyl)-3-trifluoromethyl-benzamide using the procedure described in Step F of Example 1.

¹H NMR (400 MHz, d₄-MeOH) δ 8.25 (s, 1H), 8.14 (d, J=6.2 Hz, 1H), 7.87 (d, J=6.0 Hz, 1H), 7.73 (t, J=6.2 Hz, 1H), 7.62 (d, J=6.4 Hz, 1H), 7.42 (s, 1H), 6.50 (d, J=6.5 Hz, 1H), 4.45 (m, 1H), 4.12 (t, J=6.3 Hz, 2H), 4.08 (s, 2H), 3.80 (t, J=5.5 Hz, 2H), 3.61 (m, 2H), 3.43 (m, 1H), 2.98 (t, J=5.2 Hz, 2H), 2.35 (m, 2H), 1.80 (m, 4H), 1.45 (m, 4H).

Example 44

N-({1-[4-(5-Methyl-6-oxo-1,6-dihydro-pyridin-3-yl)-cyclohexyl]-azetidin-3-ylcarbamoyl}-methyl)-3-trifluoromethyl-benzamide Step A: 5-(1,4-Dioxa-spiro[4.5]dec-7-en-8-yl)-3-methyl-1H-pyridin-2-one

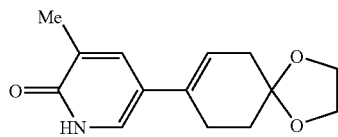

The title compound was prepared as described in Step A of Example 3 from 5-bromo-3-methyl-1H-pyridin-2-one (Aldrich) as a white solid.

ESI-MS (m/z): Calcd. For $C_{14}H_{17}NO_3$, 247. found: 248 (M+H).

Step B: 3-Methyl-5-(4-oxo-cyclohex-1-enyl)-1H-pyridin-2-one

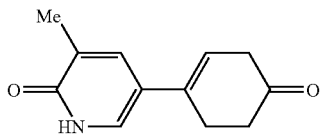

The title compound was prepared as a white solid from the de-protection of 5-(1,4-dioxa-spiro[4.5]dec-7-en-8-yl)-3-methyl-1H-pyridin-2-one (as prepared in the previous step) using the procedure described in Step B of Example 2.

¹H NMR (400 MHz, d₄-MeOH) δ 7.67 (s, 1H), 7.25 (s, 1H), 3.00 (m, 2H), 2.67 (t, J=6.0 Hz, 2H), 2.66 (t, J=6.4 Hz, 2H).

Step C: 3-Methyl-5-(4-oxo-cyclohexyl)-1H-pyridin-2-one

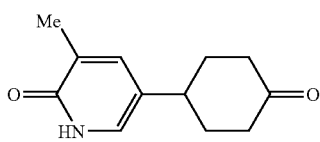

The title compound was prepared as a white solid from the hydrogenation of 3-methyl-5-(4-oxo-cyclohex-1-enyl)-1H-pyridin-2-one (as prepared in the previous step) using the procedure described in Step G of Example 1.

¹H NMR (400 MHz, d₄-MeOH) δ 7.40 (s, 1H), 7.07 (s, 1H), 2.65 (m, 1H), 2.45 (m, 2H), 2.28 (m, 2H), 2.02 (m, 2H), 1.78 (m, 2H).

Step D: N-({1-[4-(5-Methyl-6-oxo-1,6-dihydro-pyridin-3-yl)-cyclohexyl]-azetidin-3-ylcarbamoyl}-methyl)-3-trifluoromethyl-benzamide

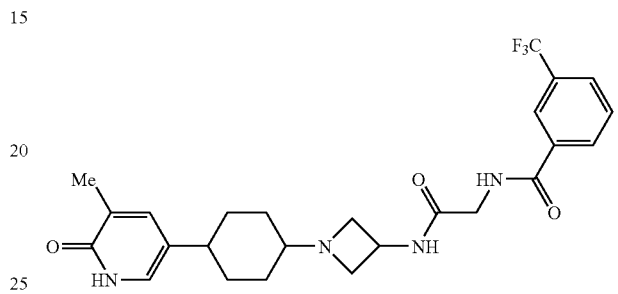

The title compounds were prepared as white solids from the reductive amination of 3-methyl-5-(4-oxo-cyclohexyl)-1H-pyridin-2-one and N-(azetidin-3-ylcarbamoylmethyl)-3-trifluoromethyl-benzamide using the procedure described in Step F of Example 1.

44a: Less Polar Isomer,

¹H NMR (400 MHz, d₄-MeOH) δ 8.25 (s, 1H), 8.14 (d, J=6.6 Hz, 1H), 7.90 (d, J=6.5 Hz, 1H), 7.73 (t, J=6.5 Hz, 1H), 7.52 (s, 1H), 7.12 (s, 1H), 4.48 (m, 1H), 4.02 (s, 2H), 3.68 (t, J=7.1 Hz, 2H), 2.95 (t, J=7.0 Hz, 2H), 2.41 (m, 2H), 2.15 (s, 3H), 1.75 (m 4H), 1.54 (m, 4H).

44b: More Polar Isomer

¹H NMR (400 MHz, CDCl₃) δ 8.20 (s, 1H), 8.18 (d, J=6.5 Hz, 1H), 7.90 (d, J=6.6 Hz, 1H), 7.73 (t, J=6.6 Hz, 1H), 7.45 (s, 1H), 7.10 (s, 1H), 4.45 (m, 1H), 4.05 (s, 2H), 3.70 (m, J=6.5 Hz, 2H), 3.10 (m, J=6.1 Hz, 2H), 2.45 (m, 2H), 2.10 (s, 3H), 2.01 (m, 4H), 1.90 (m 2H), 1.44 (m, 2H), 1.20 (m, 2H).

Example 45

N-({1-[4-(1,5-Dimethyl-6-oxo-1,6-dihydro-pyridin-3-yl)-cyclohexyl]-azetidin-3-ylcarbamoyl}-methyl)-3-trifluoromethyl-benzamide Step A: 1,3-Dimethyl-5-(4-oxo-cyclohexyl)-1H-pyridin-2-one

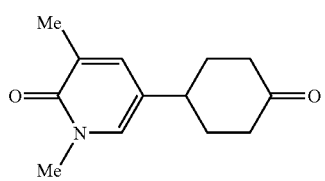

The title compound was prepared as a white solid from the methylation of 3-methyl-5-(4-oxo-cyclohexyl)-1H-pyridin-2-one (as prepared in Example 44, Step C) with MeI using the procedure described in Step B of Example 38.

ESI-MS (m/z): Calcd. For $C_{13}H_{17}NO_2$, 219. found: 220 (M+H).

Step B: N-({1-[4-(1,5-Dimethyl-6-oxo-1,6-dihydro-pyridin-3-yl)-cyclohexyl]-azetidin-3-ylcarbamoyl}-methyl)-3-trifluoromethyl-benzamide

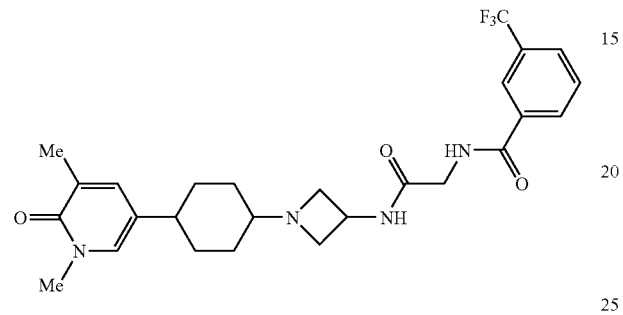

The title compounds were prepared as white solids from the reductive amination of 1,3-dimethyl-5-(4-oxo-cyclohexyl)-1H-pyridin-2-one (as prepared in the previous step) and N-(azetidin-3-ylcarbamoylmethyl)-3-trifluoromethyl-benzamide using the procedure described in Step F of Example 1.

45a: Less Polar Isomer,
$^1$H NMR (400 MHz, CDCl$_3$) δ 8.20 (s, 1H), 8.11 (d, J=6.5 Hz, 1H), 7.99 (m, 1H), 7.72 (d, J=6.6 Hz, 1H), 7.63 (t, J=6.6 Hz, 1H), 7.20 (s, 1H), 4.75 (m, 1H), 4.15 (m, 2H), 4.06 (m, J=6.5 Hz, 2H), 3.55 (s, 3H), 3.21 (s, 1H), 3.10 (m, J=6.1 Hz, 2H), 2.25 (m, 1H), 2.10 (s, 3H), 1.90 (m, 4H), 1.60 (m, 4H).

45b: More Polar Isomer
$^1$H NMR (400 MHz, CDCl$_3$) δ 8.21 (s, 1H), 8.10 (d, J=5.8 Hz, 1H), 7.90 (m, 1H), 7.79 (d, J=6.0 Hz, 1H), 7.75 (d, J=5.5 Hz, 1H), 7.63 (t, J=6.6 Hz, 1H), 7.15 (s, 1H), 4.70 (m, 1H), 4.15 (t, J=4.5 Hz, 2H), 3.80 (t, J=6.5 Hz, 2H), 3.62 (m, 1H), 3.48 (s, 3H), 3.15 (m, 2H), 2.75 (m, 1H), 2.25 (m, 2H), 2.14 (s, 3H), 1.90 (m, 2H), 1.75 (m, 2H), 1.33 (m, 2H).

Example 46

N-({1-[4-(1-Methyl-2-oxo-1,2-dihydro-pyridin-4-yl)-cyclohexyl]-azetidin-3-ylcarbamoyl}-methyl)-3-trifluoromethyl-benzamide Step A:
4-(1,4-Dioxa-spiro[4.5]dec-7-en-8-yl)-pyridine

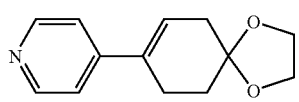

The title compound was prepared as described in Step A of Example 3 from 4-bromo-pyridine as a white solid.

$^1$H NMR (400 MHz, CDCl$_3$) δ 8.52 (d, J=6.8 Hz, 2H), 7.28 (d, J=6.8 Hz, 2H), 6.26 9t, J=3.5 Hz, 1H), 4.10 (s, 4H), 2.80 (m, 2H), 2.58 (m, 2H), 2.05 (t, J=6.0 Hz, 2H).

Step B: 4-(1,4-Dioxa-spiro[4.5]dec-7-en-8-yl)-1-methyl-pyridinium iodide

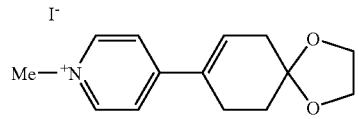

4-(1,4-Dioxa-spiro[4.5]dec-7-en-8-yl)-pyridine (as prepared in the previous step, 1.5 g, 6.91 mmol) in MeI (~10 mL) was heated to reflux until the precipitate was completely dissolved. The reaction was cooled and filtered to collect the brown solid as the title compound.

Step C: 4-(1,4-Dioxa-spiro[4.5]dec-7-en-8-yl)-1-methyl-1H-pyridin-2-one

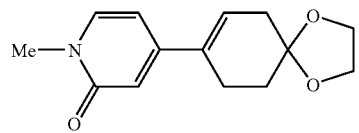

4-(1,4-Dioxa-spiro[4.5]dec-7-en-8-yl)-1-methyl-pyridinium iodide (as prepared in the previous step, 864 mg, 2.40 mmol) in THF (5 mL) and 1N NaOH (5 mL) was treated with K$_3$Fe(CN)$_6$ (Aldrich, 1.58 g, 4.80 mmol) at room temperature for 4 hours. The reaction solution was partitioned between ethyl acetate and water. The organic layer was washed with brine, dried over anhydrous Na$_2$SO$_4$, filtered and concentrated to give a yellow oil, which was then purified by silica gel column on a CombiFlash® system using hexanes and ethyl acetate (from 10% ethyl acetate to 100% ethyl acetate) to afford the title compound as a white solid.

$^1$H NMR (400 MHz, d$_4$-MeOH) δ 7.82 (d, J=7.0 Hz, 1H), 7.45 (d, J=6.0 Hz, 1H), 7.36 (s, 1H), 5.95 (m, 1H), 4.02 (s, 4H), 2.55 (m, 2H), 2.47 (s, br, 2H), 1.90 (t, J=6.5 Hz, 2H).

Step D: 4-(1,4-Dioxa-spiro[4.5]dec-8-yl)-1-methyl-1H-pyridin-2-one

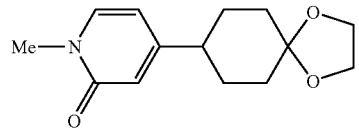

The title compound was prepared as a white solid from the hydrogenation of 4-(1,4-dioxa-spiro[4.5]dec-7-en-8-yl)-1-methyl-1H-pyridin-2-one (as prepared in the previous step) using the procedure described in Step G of Example 1.

$^1$H NMR (400 MHz, CDCl$_3$) δ 7.20 (d, J=6.0 Hz, 1H), 6.40 (s, 1H), 6.08 (d, J=6.5 Hz, 1H), 3.98 (m, 4H), 3.50 (s, 3H), 2.35 (m, 1H), 1.80 (m, 4H), 1.65 (m, 4H).

Step E: 1-Methyl-4-(4-oxo-cyclohexyl)-1H-pyridin-2-one

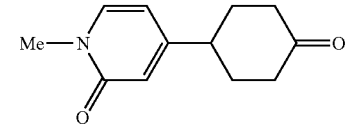

The title compound was prepared as a white solid from the deprotection of 4-(1,4-dioxa-spiro[4.5]dec-8-yl)-1-methyl-1H-pyridin-2-one (as prepared in the previous step) using the procedure described in Step B of Example 2.

¹H NMR (400 MHz, CDCl₃) δ 7.25 (d, J=6.5 Hz, 1H), 6.42 (s, 1H), 6.05 (d, J=6.3 Hz, 1H), 3.48 (s, 3H), 2.45 (m, 4H), 2.20 (m, 2H), 1.82 (m, 2H).

Step F: N-({1-[4-(1-Methyl-2-oxo-1,2-dihydro-pyridin-4-yl)-cyclohexyl]-azetidin-3-ylcarbamoyl}-methyl)-3-trifluoromethyl-benzamide

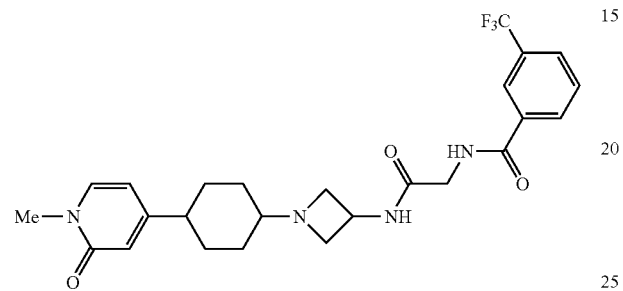

The title compounds were prepared as white solids from the reductive amination of 1-methyl-4-(4-oxo-cyclohexyl)-1H-pyridin-2-one (as prepared in the previous step) and N-(azetidin-3-ylcarbamoylmethyl)-3-trifluoromethyl-benzamide using the procedure described in Step F of Example 1.

46a: Less Polar Isomer,
¹H NMR (400 MHz, d₄-MeOH) δ 8.25 (s, 1H), 8.11 (d, J=6.5 Hz, 1H), 7.82 (d, J=6.0 Hz, 1H), 7.65 (t, J=7.2 Hz, 1H), 7.21 (d, J=6.2 Hz, 1H), 6.25 (s, 1H), 6.22 (d, J=6.5 Hz, 1H), 4.50 (m, 1H), 3.98 (s, 2H), 3.76 (s, 3H), 3.65 (t, J=7.5 Hz, 2H), 2.95 (t, J=7.2 Hz, 2H), 2.30 (m, 2H), 1.65 (m, 4H), 1.42 (m, 4H).

46b: More Polar Isomer
¹H NMR (400 MHz, d₄-MeOH) δ 8.21 (s, 1H), 8.18 (d, J=6.5 Hz, 1H), 7.92 (d, J=6.5 Hz, 1H), 7.73 (t, J=7.0 Hz, 1H), 7.50 (d, J=5.2 Hz, 1H), 6.38 (s, 1H), 6.35 (d, J=6.0 Hz, 1H), 4.72 (m, 1H), 4.52 (m, 2H), 4.20 (m, 2H), 4.01 (s, 2H), 3.65 (s, 3H), 3.02 (m, 1H), 2.20 (m, 2H), 2.01 (m, 2H), 1.85 (m, 2H), 1.62 (m, 2H).

Example 47

N-({1-[4-(6-Oxo-1,6-dihydro-pyridin-2-yl)-cyclohexyl]-azetidin-3-ylcarbamoyl}-methyl)-3-trifluoromethyl-benzamide Step A: 2-Benzyloxy-6-(1,4-dioxa-spiro[4.5]dec-7-en-8-yl)-pyridine

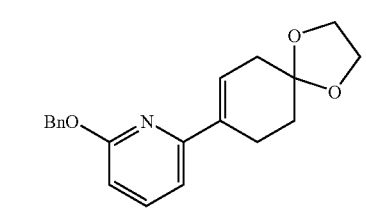

The title compound was prepared as described in Step A of Example 3 from 2-benzyloxy-6-bromo-pyridine (TCI) as a white solid.

¹H NMR (CHLOROFORM-d) δ: 7.43-7.55 (m, 3H), 7.28-7.41 (m, 3H), 6.96 (d, J=7.6 Hz, 1H), 6.71 (s, 1H), 6.64 (d, J=8.1 Hz, 1H), 5.41 (s, 2H), 4.03 (s, 4H), 2.75 (d, J=1.8 Hz, 2H), 2.52 (d, J=1.3 Hz, 2H), 1.94 (t, J=6.4 Hz, 2H); LCMS (ESI, M/Z): 324 (MH+).

Step B: 6-(1,4-Dioxa-spiro[4.5]dec-8-yl)-1H-pyridin-2-one

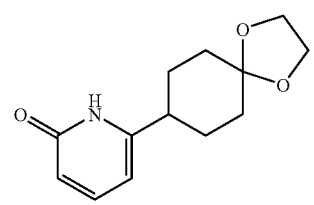

The title compound was prepared as a white solid from the hydrogenation of 2-benzyloxy-6-(1,4-dioxa-spiro[4.5]dec-7-en-8-yl)-pyridine (as prepared in the previous step) using the procedure described in Step G of Example 1.

¹H NMR (DMSO-d₆) δ: 11.26-11.60 (m, 1H), 7.33 (dd, J=9.1, 6.8 Hz, 1H), 6.13 (d, J=9.1 Hz, 1H), 5.97 (d, J=6.6 Hz, 1H), 3.87 (s, 4H), 2.38-2.50 (m, 2H), 1.44-1.90 (m, 8H); LCMS (ESI, M/Z): 236 (MH+).

Step C: 6-(4-Oxo-cyclohexyl)-1H-pyridin-2-one

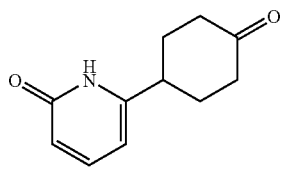

The title compound was prepared as a white solid from the deprotection of 6-(1,4-dioxa-spiro[4.5]dec-8-yl)-1H-pyridin-2-one (as prepared in the previous step) using the procedure described in Step B of Example 2.

LCMS (ESI, M/Z): 192 (MH+).

Step D: N-({1-[4-(6-Oxo-1,6-dihydro-pyridin-2-yl)-cyclohexyl]-azetidin-3-ylcarbamoyl}-methyl)-3-trifluoromethyl-benzamide

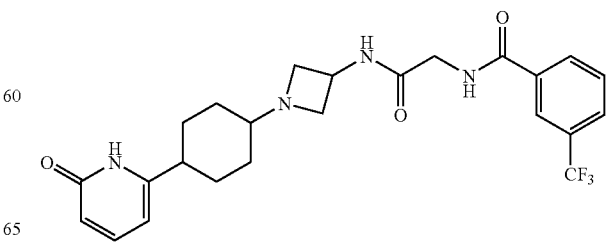

The title compounds were prepared as white solids from the reductive amination of 6-(4-oxo-cyclohexyl)-1H-pyridin-2-one (as prepared in the previous step) and N-(azetidin-3-ylcarbamoylmethyl)-3-trifluoromethyl-benzamide using the procedure described in Step F of Example 1.

$^1$H NMR (DMSO-d$_6$) δ: 9.53-9.72 (m, 1H), 9.06-9.24 (m, 1H), 8.52-8.66 (m, 1H), 8.11-8.28 (m, 2H), 7.87-8.01 (m, 1H), 7.70-7.83 (m, 1H), 7.28-7.47 (m, 1H), 6.13-6.21 (m, 1H), 5.98-6.10 (m, 1H), 4.52-4.68 (m, 1H), 4.37-4.51 (m, 2H), 3.99-4.21 (m, 3H), 3.81-3.98 (m, 3H), 1.69 (none, 8H); LCMS (ESI, M/Z): 477 (MH+).

Example 48

N-({1-[4-(1-Methyl-2-oxo-1,2-dihydro-pyridin-3-yl)-cyclohexyl]-azetidin-3-ylcarbamoyl}-methyl)-3-trifluoromethyl-benzamide Step A: 3-(1,4-Dioxa-spiro[4.5]dec-8-yl)-1-methyl-1H-pyridin-2-one

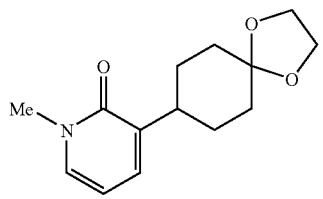

To a mixture of 3-(1,4-Dioxa-spiro[4.5]dec-8-yl)-pyridin-2-ol (as prepared in example 10, Step B, 182 mg, 0.774 mmol) in dry DMF (5 mL) was added cesium carbonate (367 mg, 1.13 mmol) and methyl iodide (80 µL, 1.28 mmol). The reaction mixture was stirred at room temperature for 16 hours, poured onto saturated sodium bicarbonate solution and extracted with ethyl acetate. Purification by flash chromatography (SiO$_2$, 0-10% MeOH/CH$_2$Cl$_2$) afforded 2-(1,4-dioxa-spiro[4.5]dec-8-yl)-1-methyl-1H-pyridin-4-one as the more polar material along with the O-Methyl isomer as the less polar isomer.

LCMS (ESI, M/Z): 250 (MH+).

Step B: 1-Methyl-3-(4-oxo-cyclohexyl)-1H-pyridin-2-one

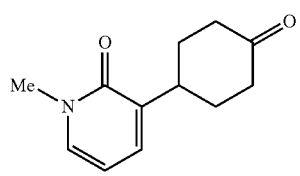

The title compound was prepared as a white solid from the deprotection of 3-(1,4-dioxa-spiro[4.5]dec-8-yl)-1-methyl-1H-pyridin-2-one (as prepared in the previous step) using the procedure described in Step B of Example 2.

LCMS (ESI, M/Z): 206 (MH+).

Step C: N-({1-[4-(1-Methyl-2-oxo-1,2-dihydro-pyridin-3-yl)-cyclohexyl]-azetidin-3-ylcarbamoyl}-methyl)-3-trifluoromethyl-benzamide

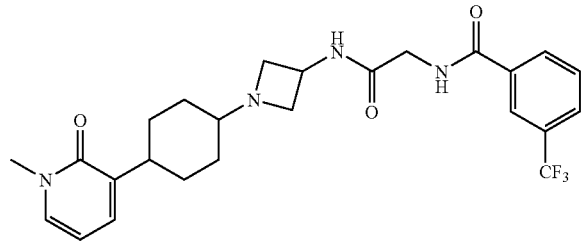

The title compound was prepared as a white solid from the reductive amination of 1-methyl-3-(4-oxo-cyclohexyl)-1H-pyridin-2-one (as prepared in the previous step) and N-(azetidin-3-ylcarbamoylmethyl)-3-trifluoromethyl-benzamide using the procedure described in Step F of Example 1.

LCMS (ESI, M/Z): 477 (MH+).

Example 49

N-({1-[4-(1H-Indol-3-yl)-cyclohexyl]-azetidin-3-ylcarbamoyl}-methyl)-benzamide

Step A: N-(Azetidin-3-ylcarbamoylmethyl)-benzamide TFA salt

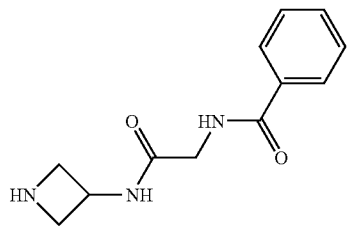

The title compound was prepared as a TFA salt from the EDCI coupling of hippuric acid (Fluka) and 3-amino-azetidine-1-carboxylic acid tert-butyl ester (BetaPharm) followed by the de-protection of N-Boc by TFA using the procedures described in Example 1, steps D and E.

Step B: N-({1-[4-(1H-Indol-3-yl)-cyclohexyl]-azetidin-3-ylcarbamoyl}-methyl-benzamide

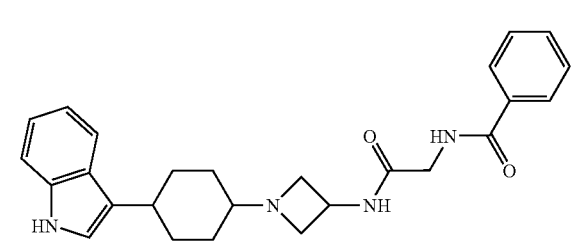

The title compounds were prepared as white solids from the reductive amination of 4-(1H-indol-3-yl)-cyclohexanone (prepared following the procedure described in EP 345808 A119891213) and N-(azetidin-3-ylcarbamoylmethyl)-benzamide TFA salt using the procedure described in Step F of Example 1.

$^1$H NMR (400 MHz, CDCl$_3$) δ 8.20 (s, 1H), 7.85 9d, J=6.5 Hz, 1H), 6.62 (d, J=6.6 Hz, 1H), 6.55 (d, J=6.4 Hz, 1H), 6.48 (t, J=6.8 Hz, 1H), 7.36 (d, J=6.5 Hz, 1H), 7.22 (t, J=6.4 Hz, 1H), 7.10 (t, J=6.6 Hz, 1H), 7.01 (s, 1H), 5.45 (s, br, 1H), 4.52 (m, 1H), 4.15 (d, J=3.0 Hz, 2H), 3.55 (t, J=7.0 Hz, 2H), 2.90 (m, 1H), 2.88 (t, J=7.0 Hz, 2H), 1.98~1.55 (m, 8H).

Example 50

N-({1-[4-(1H-Indol-3-yl)-cyclohexyl]-azetidin-3-ylcarbamoyl}-methyl)-3-trifluoromethyl-benzamide

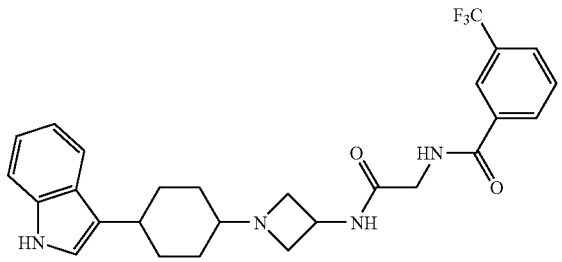

The title compounds were prepared as white solids from the reductive amination of 4-(1H-indol-3-yl)-cyclohexanone (prepared following the procedure described in EP 345808 A119891213) and N-(azetidin-3-ylcarbamoylmethyl)-3-trifluoromethyl-benzamide using the procedure described in Step F of Example 1.

$^1$H NMR (400 MHz, d$_4$-MeOH) δ 8.25 (s, 1H), 8.20 (d, J=7.0 Hz, 1H), 7.88 (d, J=6.5 Hz, 1H), 7.72 (t, J=6.8 Hz, 1H), 7.55 (d, J=6.4 Hz, 1H), 7.42 (d, J=5.8 Hz, 1H), 7.18 (s, 1H), 7.15 (t, J=6.0 Hz, 1H), 7.02 (t, J=6.8 Hz, 1H), 4.68 (m, 1H), 4.32 (t, J=7.4 Hz, 2H), 4.26 (t, J=7.5 Hz, 2H), 4.10 (d, J=3.2 Hz, 2H), 3.50 (m, 1H), 3.20 (m, 1H), 2.05~1.81 (m, 8H).

Example 51

[5-(4-{3-[2-(3-Trifluoromethyl-benzoylamino)-acetylamino]-azetidin-1-yl}-cyclohexyl)-thiazol-2-yl]-carbamic acid methyl ester Step A: [5-(8-Hydroxy-1,4-dioxa-spiro[4.5]dec-8-yl)-thiazol-2-yl]-carbamic acid methyl ester

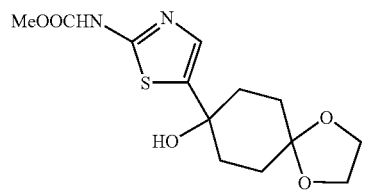

A solution of n-BuLi (2.5 M in hexanes, 28 mL, 70 mmol) was dropped slowly into a solution of thiazol-2-yl-carbamic acid methyl ester (Aldrich, 5.0 g, 31.6 mmol) in THF (100 mL) at −78° C., over 10 min. The reaction was stirred for additional 20 min. at −78° C. A solution of 1,4-dioxa-spiro [4.5]decan-8-one (Aldrich, 7.0 g, 45 mmol) in THF (20 mL) was slowly dropped into the reaction. After addition, the reaction was stirred for an additional 2 hours at −78° C. The reaction was then quenched with diluted NH$_4$Cl solution and warmed to room temperature. The solvent was removed in vacuo and the residue was partitioned between ethyl acetate and water. The organic layer was washed with brine, dried over anhydrous Na$_2$SO$_4$, filtered and concentrated to give a yellow solid, which was then purified by silica gel column on a CombiFlash® system using hexanes and ethyl acetate (from 10% ethyl acetate to 100% ethyl acetate) to afford the title compound as a white solid.

$^1$H NMR (400 MHz, CDCl$_3$) δ 7.21 (s, 1H), 4.02 (m, 4H), 3.87 (s, 3H), 2.10 (m, 2H), 2.05 (m, 4H), 1.72 (m, 2H).

Step B: [5-(1,4-Dioxa-spiro[4.5]dec-8-yl)-thiazol-2-yl]-carbamic acid methyl ester

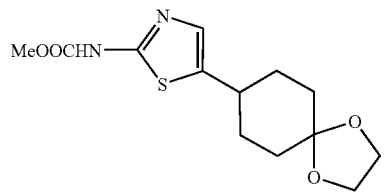

The title compounds were prepared as white solids from Burgess's reagent catalyzed dehydration of [5-(8-Hydroxy-1,4-dioxa-spiro[4.5]dec-8-yl)-thiazol-2-yl]-carbamic acid methyl ester (as prepared in the previous step) using the procedure described in Step C of Example 1 followed by hydrogenation of the corresponding alkene following the procedure described in Step G of Example 1.

$^1$H NMR (400 MHz, CDCl$_3$) δ 7.05 (s, 1H), 3.98 (s, 4H), 3.85 (s, 3H), 2.78 (m, 1H), 2.02 (m, 2H), 1.85 (m, 4H), 1.70 (m, 2H).

Step C: [5-(4-Oxo-cyclohexyl)-thiazol-2-yl]-carbamic acid methyl ester

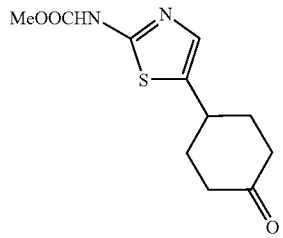

The title compound was prepared as a white solid from the deprotection of [5-(1,4-dioxa-spiro[4.5]dec-8-yl)-thiazol-2-yl]-carbamic acid methyl ester (as prepared in the previous step) using the procedure described in Step B of Example 2.

$^1$H NMR (400 MHz, CDCl$_3$) δ 7.15 (s, 1H), 3.90 (s, 3H), 3.31 (m, 1H), 2.52 (m, 4H), 2.40 (m, 2H), 2.02 (m, 2H).

Step D: [5-(4-{3-[2-(3-Trifluoromethyl-benzoylamino)-acetylamino]-azetidin-1-yl}-cyclohexyl)-thiazol-2-yl]-carbamic acid methyl ester

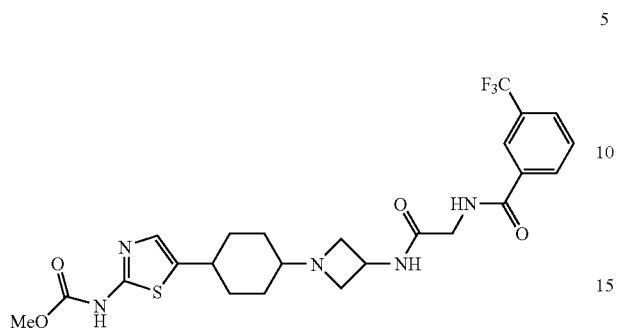

The title compounds were prepared as white solids from the reductive amination of [5-(4-oxo-cyclohexyl)-thiazol-2-yl]-carbamic acid methyl ester (as prepared in the previous step) and N-(azetidin-3-ylcarbamoylmethyl)-3-trifluoromethyl-benzamide using the procedure described in Step F of Example 1.

51a: Less Polar Isomer, $^1$H NMR (400 MHz, d$_4$-MeOH) δ 8.25 (s, 1H), 8.20 (d, J=6.0 Hz, 1H), 7.88 (d, J=6.0 Hz, 1H), 7.69 (t, J=6.0 Hz, 1H), 7.10 (s, 1H), 4.45 (m, 1H), 4.10 (s, 2H), 3.88 (s, 3H), 3.75 (t, J=4.0 Hz, 2H), 3.12 (s, br, 2H), 2.85 (s, br, 1H), 2.35 (m, 1H), 1.90 (m, 2H), 1.82 (m, 2H), 1.62 (m, 4H).

51b: More Polar Isomer $^1$H NMR (400 MHz, d$_4$-MeOH) δ 8.23 (s, 1H), 8.16 (d, J=6.1 Hz, 1H), 7.87 (d, J=5.5 Hz, 1H), 7.72 (t, J=5.5 Hz, 1H), 7.02 (s, 1H), 4.42 (m, 1H), 4.08 (s, 2H), 3.86 (s, 3H), 3.68 (t, J=5.0 Hz, 2H), 3.10 (t, J=5.2 Hz, 2H), 2.52 (m, 1H), 2.10 (m, 2H), 1.95 (m, 2H), 1.54 (m, 2H), 1.21 (m, 2H).

Example 52

5-(4-{3-[2-(3-Trifluoromethyl-benzoylamino)-acetylamino]-azetidin-1-yl}-cyclohexyl)-thiazole-2-carboxylic acid

Step A: 2-(1,4-Dioxa-spiro[4.5]dec-7-en-8-yl)-thiazole

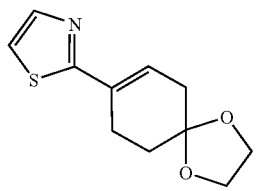

The title compound was prepared as described in Step A of Example 3 from 2-bromo-thiazole (Aldrich) as a white solid.

$^1$H NMR (400 MHz, CDCl$_3$) δ 7.72 (s, 1H), 7.18 (s, 1H), 6.52 (t, J=3.5 Hz, 1H), 4.01 (s, 4H), 2.82 (t, J=4.1 Hz, 2H), 2.50 (m, 2H), 1.92 (t, J=4.0 Hz, 2H).

Step B: 2-(1,4-Dioxa-spiro[4.5]dec-8-yl)-thiazole

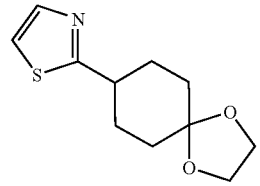

The title compound was prepared as a white solid from the hydrogenation of 2-(1,4-dioxa-spiro[4.5]dec-7-en-8-yl)-thiazole (as prepared in the previous step) using the procedure described in Step G of Example 1.

ESI-MS (m/z): Calcd. For C$_{11}$H$_{15}$NO$_2$S, 225. Found: 226 (M+H).

Step C: 2-(1,4-Dioxa-spiro[4.5]dec-8-yl)-thiazole-5-carboxylic acid

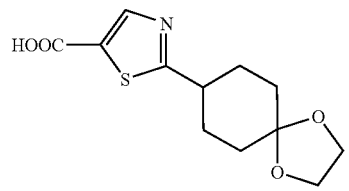

A solution of n-BuLi (2.5 M in hexanes, 5 mL, 12 mmol) was added dropwise into 2-(1,4-dioxa-spiro[4.5]dec-8-yl)-thiazole (2.50 g, 11 mmol) in THF (10 mL) at −78° C. The reaction was kept at −78° C. for 30 min. The solution was added to solid dry ice (~5 g) dropwise. After addition, the reaction was warmed to room temperature slowly over 1 hour and quenched with 1 N NaOH (~10 mL) solution. The solvent was removed and the residue was partitioned between ether and water. The aqueous layer was adjusted to pH=6 with 5% HCl and extracted with ethyl acetate three times. The combined organic layers were washed with brine, dried over anhydrous Na$_2$SO$_4$, filtered and concentrated to give the title compound as white solid.

$^1$H NMR (400 MHz, CDCl$_3$) δ 10.9 (s, br, 1H), 8.38 (s, 1H), 4.01 (s, 4H), 3.15 (m, 1H), 2.21 (m, 2H), 1.95 (m, 4H), 0.76 (m, 2H).

Step D: 5-(4-Oxo-cyclohexyl)-thiazole-2-carboxylic acid

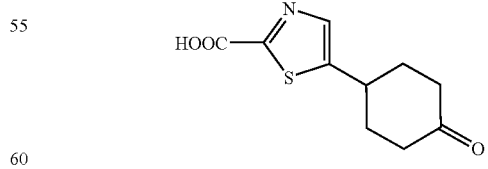

The title compound was prepared as a white solid from the deprotection of 2-(1,4-dioxa-spiro[4.5]dec-8-yl)-thiazole-5-carboxylic acid (as prepared in the previous step) using the procedure described in Step B of Example 2.

ESI-MS (m/z): Calcd. For C$_{10}$H$_{11}$NO$_3$S, 225. found: 226 (M+H).

Step E: 5-(4-{3-[2-(3-Trifluoromethyl-benzoylamino)-acetylamino]-azetidin-1-yl}-cyclohexyl)-thiazole-2-carboxylic acid

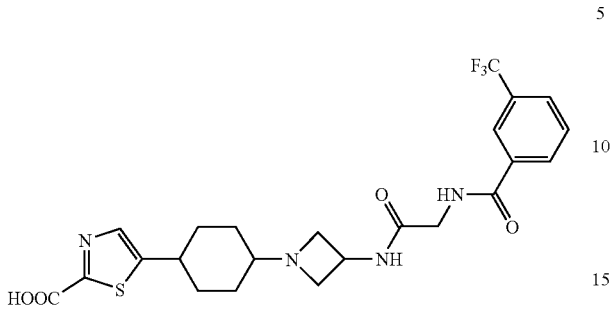

The title compounds were prepared as white solids from the reductive amination of 5-(4-oxo-cyclohexyl)-thiazole-2-carboxylic acid (as prepared in the previous step) and N-(azetidin-3-ylcarbamoylmethyl)-3-trifluoromethyl-benzamide using the procedure described in Step F of Example 1.

52a: Less Polar Isomer,
$^1$H NMR (400 MHz, d$_4$-MeOH) δ 8.25 (s, 1H), 8.20 (d, J=6.0 Hz, 1H), 7.92 (s, 1H), 7.88 (d, J=6.0 Hz, 1H), 7.70 (t, J=6.0 Hz, 1H), 4.62 (m, 1H), 4.20 (t, J=6.0 Hz, 2H), 4.08 (s, 2H), 3.78 (t, J=6.5 Hz, 2H), 3.02 (m, 1H), 2.35 (s, br, 1H), 2.25 (m, 4H), 1.82 (m, 4H).

52b: More Polar Isomer
$^1$H NMR (400 MHz, d$_4$-MeOH) δ 8.20 (s, 1H), 8.16 (d, J=6.5 Hz, 1H), 7.90 (d, J=6.0 Hz, 1H), 7.88 (s, 1H), 7.68 (t, J=6.1 Hz, 1H), 4.70 (m, 1H), 4.23 (t, J=6.8 Hz, 2H), 4.10 (s, 2H), 3.86 (t, J=6.0 Hz, 2H), 3.18 (m, 1H), 2.97 (m, 1H), 2.21 (m, 2H), 1.85 (m, 4H), 1.64 (m, 1H), 1.35 (m, 1H).

Example 53

5-(4-{3-[2-(3-Trifluoromethyl-benzoylamino)-acetylamino]-azetidin-1-yl}-cyclohexyl)-thiazole-2-carboxylic acid amide

Step A: 2-(1,4-Dioxa-spiro[4.5]dec-8-yl)-thiazole-5-carboxylic acid amide

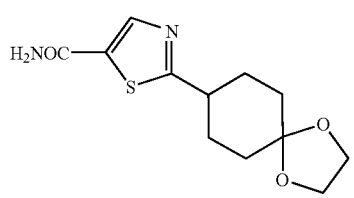

A solution of 2-(1,4-Dioxa-spiro[4.5]dec-8-yl)-thiazole-5-carboxylic acid (as prepared in Example 52, Step C, 700 mg, 2.60 mmol), EDCI (600 mg, 3.12 mmol), HOBT (420 mg, 3.12 mmol) and TEA (490 µL, 3.50 mmol) in DCM (10 mL) were treated with 2N NH$_3$ in dioxane (2 mL) at room temperature overnight. The solvent was removed in vacuo and the residue was purified by a CombiFlash® system using hexanes and ethyl acetate to afford the title compound as a white solid.

$^1$H NMR (400 MHz, CDCl$_3$) δ 8.05 (s, 1H), 5.85 (s, br, 2H), 3.98 (s, 4H), 3.03 (m, 2H), 2.20 (m, 2H), 1.92 (m, 4H), 2.75 (m, 2H).

Step B: 2-(4-Oxo-cyclohexyl)-thiazole-5-carboxylic acid amide

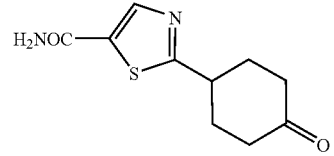

The title compound was prepared as a white solid from the deprotection of 2-(1,4-dioxa-spiro[4.5]dec-8-yl)-thiazole-5-carboxylic acid amide (as prepared in the previous step) using the procedure described in Step B of Example 2.

$^1$H NMR (400 MHz, CDCl$_3$) δ 8.10 (s, 1H), 5.95 (s, br, 2H), 3.38 (m, 1H), 2.51 (m, 4H), 2.15 (m, 2H), 2.00 (m, 2H).

Step C: 5-(4-{3-[2-(3-Trifluoromethyl-benzoylamino)-acetylamino]-azetidin-1-yl}-cyclohexyl)-thiazole-2-carboxylic acid amide

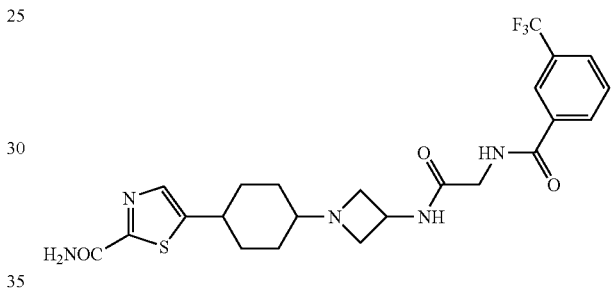

The title compound was prepared as a white solid from the reductive amination of 2-(4-oxo-cyclohexyl)-thiazole-5-carboxylic acid amide (as prepared in the previous step) and N-(azetidin-3-ylcarbamoylmethyl)-3-trifluoromethyl-benzamide using the procedure described in Step F of Example 1.

$^1$H NMR (400 MHz, d$_4$-MeOH) δ 8.18 (s, 1H), 8.15 (s, 1H), 8.05 (d, J=6.3 Hz, 1H), 7.78 (d, J=6.5 Hz, 1H), 7.59 (t, J=6.0 Hz, 1H), 4.37 (m, 1H), 3.99 (s, 2H), 3.58 (t, J=7.0 Hz, 2H), 3.08 (m, 1H), 2.98 (t, J=7.0 Hz, 2H), 2.25 (s, br, 1H), 2.05 (m, 2H), 1.82 (m, 2H), 1.45 (m, 4H).

Example 54

N-({1-[4-(2-Oxo-2,3-dihydro-thiazol-5-yl)-cyclohexyl]-azetidin-3-ylcarbamoyl}-methyl)-3-trifluoromethyl-benzamide

Step A: 8-(2-Methoxy-thiazol-5-yl)-1,4-dioxa-spiro[4.5]decan-8-ol

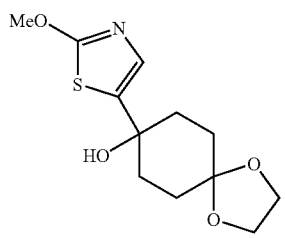

The title compound was prepared as a white solid from 2-methoxy-thiazole (Aldrich) using the procedure described in Step A of Example 51.

$^1$H NMR (400 MHz, CDCl$_3$) δ 6.95 (s, 1H), 4.05 (s, 3H), 3.95 (m, 4H), 2.10 (m, 2H), 2.00 (m, 4H), 1.69 (m, 2H).

Step B: 5-(4-Oxo-cyclohex-1-enyl)-3H-thiazol-2-one

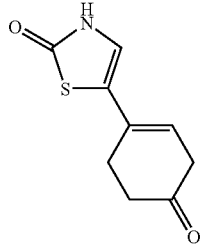

8-(2-Methoxy-thiazol-5-yl)-1,4-dioxa-spiro[4.5]decan-8-ol (as prepared in the previous step, 1.05 g, 3.87 mmol) was treated with 6N HCl (~2 mL) in THF (5 mL) at room temperature for 4 hours. The reaction was neutralized with saturated NaHCO$_3$ solution and the solvent was removed. The residue was partitioned between ethyl acetate and water. The organic layer was washed with brine, dried over anhydrous Na$_2$SO$_4$, filtered and concentrated to give a yellow solid, which was then purified by silica gel column on a CombiFlash® system using hexanes and ethyl acetate (from 10% ethyl acetate to 100% ethyl acetate) to afford the title compound as white solid.

$^1$H NMR (400 MHz, CDCl$_3$) δ 9.78 (s, br, 1H), 6.55 (s, 1H), 5.78 (m, 1H), 2.98 (s, br, 1H), 2.65 (, 2H), 2.58 (m, 2H)

Step C: 5-(4-Oxo-cyclohexyl)-3H-thiazol-2-one

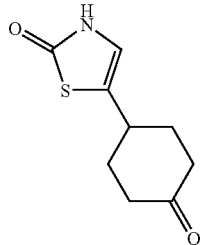

The title compound was prepared as a white solid from the hydrogenation of 5-(4-oxo-cyclohex-1-enyl)-3H-thiazol-2-one (as prepared in the previous step) using the procedure described in Step G of Example 1.

$^1$H NMR (400 MHz, CDCl$_3$) δ 9.65 (s, br, 1H), 6.38 (s, 1H), 2.45 (m, 5H), 2.31 (m, 2H), 1.87 (m, 2H).

Step D: N-({1-[4-(2-Oxo-2,3-dihydro-thiazol-5-yl)-cyclohexyl]-azetidin-3-ylcarbamoyl}-methyl)-3-trifluoromethyl-benzamide

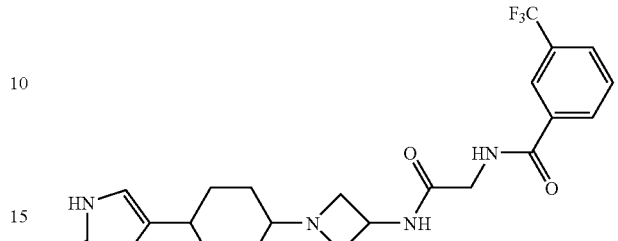

The title compounds were prepared as white solids from the reductive amination of 5-(4-oxo-cyclohexyl)-3H-thiazol-2-one (as prepared in the previous step) and N-(azetidin-3-ylcarbamoylmethyl)-3-trifluoromethyl-benzamide using the procedure described in Step F of Example 1.

$^1$H NMR (400 MHz, CDCl$_3$) δ 9.80 (s, br, 1H), 8.10 (s, 1H), 6.25 (s, 1H), 4.50 (m, 1H), 4.18 (d, J=4.0 Hz, 2H), 3.60 (t, J=7.0 Hz, 2H), 3.05 (d, J=6.5 Hz, 2H), 2.35 (m, 1H), 2.30 (m, 1H), 2.10 (m, 2H), 1.85 (m, 2H), 1.60 (m, 2H), 158 (m, 2H).

Example 55

N-({1-[4-(3,5-Diimino-isoxazolidin-4-yl)-cyclohexyl]-azetidin-3-ylcarbamoyl}-methyl)-3-trifluoromethyl-benzamide Step A:
2-(1,4-Dioxa-spiro[4.5]dec-8-yl)-malononitrile

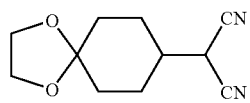

The title compound was prepared by the method of Dunham et al. (Synthesis 2006 (4), 680). 1,4-Cyclohexanedione monoethylene ketal (3.15 g, 20.0 mmol) was dissolved in anhydrous 2-propanol (20 mL), treated with warm malononitrile (Aldrich, 0.70 mL, 11.1 mmol) via syringe, and the reaction was cooled in ice and treated with powdered sodium borohydride (Aldrich, 0.42 g, 11.1 mmol). After stirring for 2 h in ice, the reaction was quenched with water and acidified to pH 6 with 1N aqueous HCl, and the resulting suspension was extracted thrice with dichloromethane. The combined organic layers were washed with brine, dried over Na$_2$SO$_4$, filtered and concentrated in vacuo to give a pale yellow oil, which was purified by flash column chromatography on silica gel (gradient elution, 30 to 80% EtOAc in hexanes) giving the title compound as a pale yellow crystalline solid.

$^1$H NMR (400 MHz, Chloroform-d) δ 3.96 (t, J=3.7 Hz, 4H), 3.59 (d, J=6.8 Hz, 1H), 2.00 (m, 3H), 1.80-1.91 (m, 2H), 1.57-1.73 (m, 4H).

Step B: 4-(1,4-Dioxa-spiro[4.5]dec-8-yl)-isoxazoli-
dine-3,5-diylidenediamine

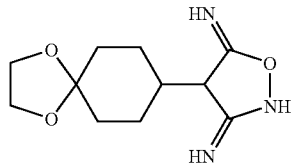

A solution of 2-(1,4-dioxa-spiro[4.5]dec-8-yl)-malononi-
trile (as prepared in the previous step, 0.207 g, 1.00 mmol)
and hydroxylamine hydrochloride (Aldrich, 0.107 g, 1.54
mmol) in anhydrous pyridine (5 mL) were heated to 100° C.
under a reflux condenser for 18 h. After cooling to ambient
temperature and evaporation of the solvent in vacuo, the crude
product was purified by thin layer chromatography on silica
gel (10% methanol in dichloromethane) giving the title com-
pound as an orange solid.
$^1$H NMR (400 MHz, DMSO-d$_6$) δ 7.68 (br. s., 1H), 7.47
(br. s., 1H), 5.70 (s, 1H), 3.84 (s, 4H), 3.58 (d, J=7.1 Hz, 1H),
1.83-2.03 (m, 1H), 1.55-1.83 (m, 4H), 1.25-1.55 (m, 4H).
ESI-MS (m/z): Calcd. For $C_{11}H_{17}N_3O_3$: 239. found: 240
(M+H).

Step C:
4-(3,5-Diimino-isoxazolidin-4-yl)-cyclohexanone

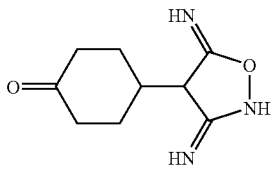

A solution of 4-(1,4-dioxa-spiro[4.5]dec-8-yl)-isoxazoli-
dine-3,5-diylidenediamine (as prepared in the previous step,
0.078 g, 0.326 mmol) in acetonitrile (10 mL) was treated with
1N aqueous HCl (3.2 mL, 3.2 mmol), and stirred at ambient
temperature for 6 h. After removing the MeCN in vacuo, the
reaction was treated with saturated aqueous NaHCO$_3$ (ca. 7
mL), stirred at ambient temperature overnight, and extracted
thrice with EtOAc. The combined organic layers were
washed with brine, dried over Na$_2$SO$_4$, filtered and concen-
trated in vacuo to give the title compound as an orange gum.
$^1$H NMR (400 MHz, ACETONITRILE-d$_3$) δ 6.47 (br. s.,
1H), 6.06 (br. s., 1H), 4.70 (br. s., 0H), 3.52 (d, J=6.6 Hz, 1H),
2.34-2.55 (m, 3H), 2.18-2.34 (m, 2H), 1.97-2.12 (m, 2H),
1.61 (m, 2H). ESI-MS (m/z): Calcd. For $C_9H_{13}N_3O_2$: 195.
found: 196 (M+H).

Step D: N-({1-[4-(3,5-Diimino-isoxazolidin-4-yl)-
cyclohexyl]-azetidin-3-ylcarbamoyl}-methyl)-3-
trifluoromethyl-benzamide

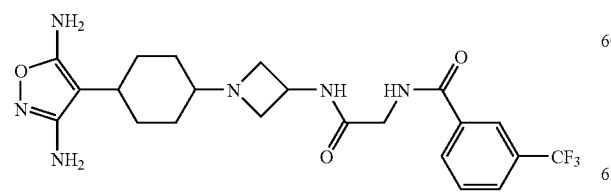

The title compound was prepared as described in Step F of
Example 1 from 4-(3,5-diimino-isoxazolidin-4-yl)-cyclo-
hexanone (as prepared in the previous step) as a pale yellow
solid.
$^1$H NMR (400 MHz, ACETONITRILE-d$_3$) δ 8.06 (s, 1H),
8.01 (d, J=7.8 Hz, 1H), 7.78 (d, J=7.8 Hz, 1H), 7.60 (t, J=7.8
Hz, 1H), 7.48 (br. s., 1H), 6.93 (d, J=5.8 Hz, 1H), 6.40 (br. s.,
1H), 5.97 (br. s., 1H), 4.26 (sxt, J=7.0 Hz, 1H), 3.86 (d, J=5.8
Hz, 2H), 3.48 (t, J=7.3 Hz, 2H), 3.32 (d, J=7.3 Hz, 1H), 2.72
(t, J=7.1 Hz, 2H), 2.16-2.23 (m, 1 H), 1.37-1.60 (m, 5H),
1.22-1.37 (m, 3H). ESI-MS (m/z): Calcd. For
$C_{22}H_{27}N_6O_3F_3$: 480. found: 481 (M+H).

Example 56

N-({1-[4-(1-Methyl-2,4-dioxo-1,2,3,4-tetrahydro-
pyrimidin-5-yl)-cyclohexyl]-azetidin-3-ylcarbam-
oyl}-methyl)-3-trifluoromethyl-benzamide

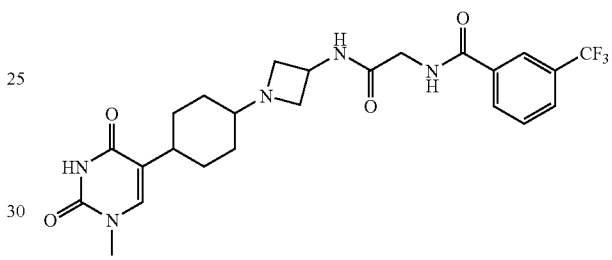

The title compound was prepared as described in Example
3: Steps A-D from 5-bromo-1-methyl-1H-pyrimidine-2,4-di-
one (Aldrich) as a white solid.
$^1$H NMR (400 MHz, DMSO-d$_6$) δ ppm 11.15 (br. s., 1H),
9.00 (br. s., 1H), 8.35 (d, J=7.3 Hz, 1H), 8.22 (s, 1H), 8.18 (d,
J=7.8 Hz, 1H), 7.93 (d, J=7.8 Hz, 1H), 7.74 (t, J=7.8 Hz, 1H),
7.33 (s, 1H), 4.24 (br. s., 1H), 3.87 (d, J=5.6 Hz, 2H), 3.49 (br.
s., 2H), 3.23 (s, 3H), 2.74 (br. s., 2H), 2.20-2.43 (m, 2H),
1.57-1.71 (m, 2H), 1.27-1.57 (m, 5H). ESI-MS (m/z): Calcd.
For $C_{25}H_{29}N_4O_3F_3$: 490. found: 491 (M+H).

Example 57

N-({1-[4-(5-Oxo-4,5-dihydro-[1,2,4]oxadiazol-3-yl)-
cyclohexyl]-azetidin-3-ylcarbamoyl}-methyl)-3-
trifluoromethyl-benzamide Step A: N-{[1-(4-Cyano-cyclohexyl)-azetidin-3-
ylcarbamoyl]-methyl}-3-trifluoromethyl-benzamide

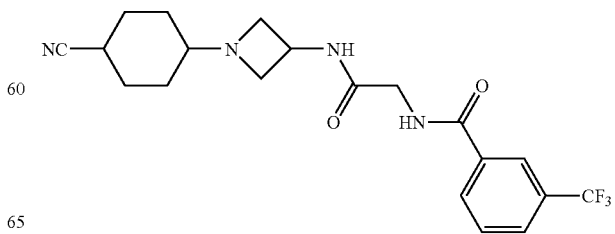

The title compound was prepared from 4-oxo-cyclohexanecarbonitrile (prepared according to the procedure from Tremblay, Maxime, PCT Int. Appl. (2007), WO 2007013848) according to the general reductive amination procedure in Step F of Example 1.

A mixture of cis/trans isomers. LC/MS: 409.0 [M+H].

Step B: N-({1-[4-(N-Hydroxycarbamimidoyl)-cyclohexyl]-azetidin-3-ylcarbamoyl}-methyl)-3-trifluoromethyl-benzamide

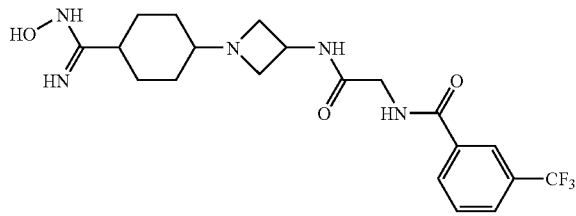

A mixture of the above intermediate from Step A (1 g, 2.4 mmol), hydroxylamine hydrochloride (Aldrich, 0.51 g, 7.32 mmol) and $K_2CO_3$ (0.67 g, 4.88 mmol) in ethanol (10 mL) in a sealed tube was heated to 86° C. for 18 h. After removal of organic solvent by evaporation, the residue was dissolved in water, extracted with EtOAc and dried over $Na_2SO_4$. Filtration and evaporation to dryness gave the product as a mixture of cis/trans isomers.
LC/MS: 442.2 [M+H].

Step C: N-({1-[4-(5-Oxo-4,5-dihydro-[1,2,4]oxadiazol-3-yl)-cyclohexyl]-azetidin-3-ylcarbamoyl}-methyl)-3-trifluoromethyl-benzamide

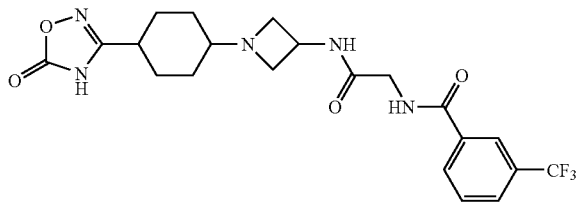

A mixture of the above intermediate from Step B (0.044 g, 0.1 mmol), 1,1'-carbonyldiimidazole (Aldrich, 0.0178 g, 0.11 mmol), DBU (Acros, 0.06 mL, 0.4 mmol) in $CH_3CN$ (1 mL) was stirred at rt overnight. The crude product was purified by HPLC to give a TFA salt as a yellowish solid.
LC/MS: 468.2 [M+H].

Example 58

N-({1-[4-(5-Trichloromethyl-[1,2,4]oxadiazol-3-yl)-cyclohexyl]-azetidin-3-ylcarbamoyl}-methyl)-3-trifluoromethyl-benzamide Step A: N-Hydroxy-1,4-dioxa-spiro[4.5]decane-8-carboxamidine

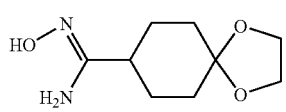

A mixture of 1,4-dioxa-spiro[4.5]decane-8-carbonitrile (0.40 g, 2.4 mmol, prepared according to the procedure from Tremblay, Maxime, PCT Int. Appl. (2007), WO 2007013848) and hydroxylamine (Aldrich, 50% in $H_2O$, 0.7 mL, 9.6 mmol) in ethanol (1.5 mL) in a sealed tube was heated to 80° C. for 6 h. After removal of organic solvent by evaporation, the residue was dissolved in water, extracted with EtOAc and dried over $Na_2SO_4$. Filtration and evaporation to dryness gave the product as a white solid.

$^1$H NMR (400 MHz, $CDCl_3$): δ 4.5 (2H, br s), 3.92-3.97 (4H, m), 2.13-2.20 (1H, m), 1.57-1.90 (8H, m).

Step B: 3-(1,4-Dioxa-spiro[4.5]dec-8-yl)-5-trichloromethyl-[1,2,4]oxadiazole and 4-(5-Trichloromethyl-[1,2,4]oxadiazol-3-yl)-cyclohexanone

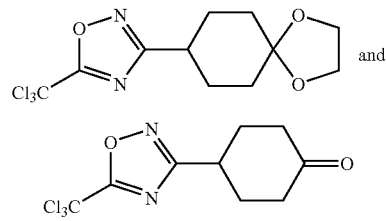

To a mixture of the above intermediate from Step A (0.34 g, 1.7 mmol) in toluene (11 mL) was added trichloroacetic anhydride (Fluka, 0.36 mL, 1.97 mmol) dropwise under Ar. The resulting mixture was then heated to reflux at 80° C. for 2 h. After the reaction was cooled to room temperature, it was then poured into an ice-diluted $NaHCO_3$ solution and separated. The aqueous phase was extracted with EtOAc, the combined organic layers were dried over $Na_2SO_4$. Purification by column chromatography (eluent: 10% to 30% EtOAc in hexanes) gave the ketal, as well as the deprotected ketone as the title compound.

The Ketal $^1$H NMR (400 MHz, $CDCl_3$): δ 3.96-3.99 (4H, m), 2.88-2.96 (1H, m), 2.10-2.14 (2H, m), 1.86-2.03 (4H, m), 1.64-1.72 (2H, m).

4-(5-Trichloromethyl-[1,2,4]oxadiazol-3-yl)-cyclohexanone $^1$H NMR (400 MHz, $CDCl_3$): δ 3.33-3.40 (1H, m), 2.37-2.63 (6H, m), 2.15-2.26 (2H, m).

Step C: {1-[4-(5-Trichloromethyl-[1,2,4]oxadiazol-3-yl)-cyclohexyl]-azetidin-3-yl}-carbamic acid tent-butyl ester

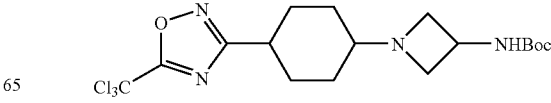

The title compound was prepared from 4-(5-trichloromethyl-[1,2,4]oxadiazol-3-yl)-cyclohexanone (as prepared in the previous step) and azetidine-3-yl-carbonic acid tert-butyl ester (Beta Pharma) according to the general reductive amination procedure described in Step F of Example 1.

A mixture of cis/trans isomers: LC/MS: 439.2 [M+H].

Step D: 1-[4-(5-Trichloromethyl-[1,2,4]oxadiazol-3-yl)-cyclohexyl]-azetidin-3-ylamine

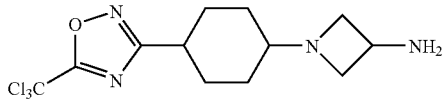

{1-[4-(5-Trichloromethyl-[1,2,4]oxadiazol-3-yl)-cyclohexyl]-azetidin-3-yl}-carbamic acid tert-butyl ester (as prepared in the previous step) was treated with 1:1 ratio of DCM and TFA at room temperature. After 2 hours, the solvent was removed in vacuo and the residue was dried overnight to give the title compound as TFA salt (colorless oil).

A mixture of cis/trans isomers: LC/MS: 339.0 [M+H].

Step E: N-({1-[4-(5-Trichloromethyl-[1,2,4]oxadiazol-3-yl)-cyclohexyl]-azetidin-3-ylcarbamoyl}-methyl)-3-trifluoromethyl-benzamide

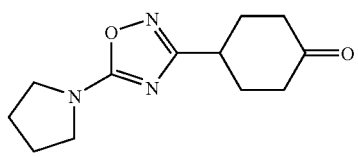

The title compound was prepared by the EDCI coupling of 1-[4-(5-trichloromethyl-[1,2,4]oxadiazol-3-yl)-cyclohexyl]-azetidin-3-ylamine (as prepared in the previous step) and (3-trifluoromethyl-benzoylamino)-acetic acid (Bionet Building Blocks). Purification by HPLC gave cis and trans isomers.
LC/MS: 568.0 [M+H].

Example 59

N-({1-[4-(5-Pyrrolidin-1-yl-[1,2,4]oxadiazol-3-yl)-cyclohexyl]-azetidin-3-ylcarbamoyl}-methyl)-3-trifluoromethyl-benzamide Step A: 4-(5-Pyrrolidin-1-yl-[1,2,4]oxadiazol-3-yl)-cyclohexanone A solution of the intermediate 3-(1,4-dioxa-spiro[4.5]dec-8-yl)-5-trichloromethyl-[1,2,4]oxadiazole from Example 58, Step B (0.2 g, 0.6 mmol) and pyrrolidine (Aldrich, 0.45 mL, 5.4 mmol) in methanol (30 mL) was stirred at rt for 2 days. After evaporation of solvents, the residue was purified by column chromatography (eluent: EtOAc to 10% MeOH in DCM) and gave 0.08 g of the ketal, which was dissolved in CH₃CN (5 mL) and 2N HCl (5 mL), stirred at rt overnight. Removal of volatiles by evaporation gave the product as a HCl salt.

LC/MS: 236.0 [M+H].

Step B: N-({1-[4-(5-Pyrrolidin-1-yl-[1,2,4]oxadiazol-3-yl)-cyclohexyl]-azetidin-3-ylcarbamoyl}-methyl)-3-trifluoromethyl-benzamide

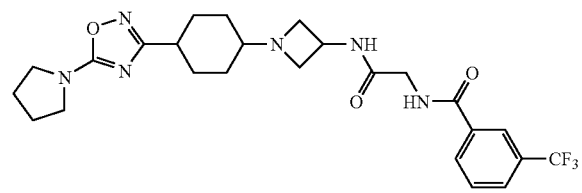

The title compound was prepared from 4-(5-pyrrolidin-1-yl-[1,2,4]oxadiazol-3-yl)-cyclohexanone (as prepared in the previous step) according to the general reductive amination procedure in Step F of Example 1.

A mixture of cis/trans (1:1) isomers. LC/MS: 521.3 [M+H].

Example 60

N-({1-[4-(4-Methyl-6-oxo-1,6-dihydro-pyrimidin-2-yl)-cyclohexyl]-azetidin-3-ylcarbamoyl}-methyl)-3-trifluoromethyl-benzamide Step A: [1-(4-Cyano-cyclohexyl)-azetidin-3-yl]-carbamic acid tert-butyl ester

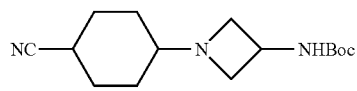

To a solution of 4-oxo-cyclohexanecarbonitrile (2.66 g, 21.5 mmol, prepared according to the procedure from Tremblay, Maxime, PCT Int. Appl. (2007), WO 2007013848) and azetidine-3-yl-carbonic acid tert-butyl ester (Beta Pharma, 3.70 g, 21.5 mmol) in DCM (20 mL) was added NaBH(OAc)₃ (Aldrich, 6.84 g, 32.25 mmol). The resulting mixture was stirred at rt for 6 h and quenched with saturated NaHCO₃. Workup and purification by column chromatograph (eluent:

80% EtOAc in hexanes to EtOAc only) gave the product as a mixture of cis/trans isomers. LC/MS: 280.2 [M+H].

Step B: {1-[4-(N-Hydroxycarbamimidoyl)-cyclohexyl]-azetidin-3-yl}-carbamic acid tert-butyl ester

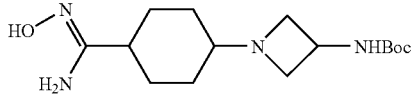

A mixture of the above intermediate (1.68 g, 6 mmol) and hydroxylamine (Aldrich, 50% in H₂O, 1.75 mL, 24 mmol) in ethanol (4 mL) in a sealed tube was heated at 86° C. for 6 h. After removal of organic solvent by evaporation, the residue was dissolved in water, extracted with EtOAc and dried over Na₂SO₄. Filtration and evaporation to dryness gave the mixture of cis/trans isomers as a white solid.
LC/MS: 313.3 [M+H].

Step C: [1-(4-Carbamimidoyl-cyclohexyl)-azetidin-3-yl]-carbamic acid tert-butyl ester

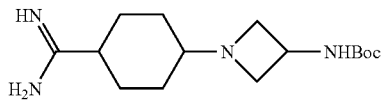

A mixture of the above intermediate (1.30 g, 4.16 mmol) and 10% Pd—C (0.1 g) in HOAc (14 mL) and acetic anhydride (0.6 mL) was hydrogenated on Parr shaker at 55 psi at rt overnight. Filtration and evaporation to dryness gave the mixture of cis/trans isomers as an HOAc salt.
LC/MS: 270.2 [M+H].

Step D: {1-[4-(4-Methyl-6-oxo-1,6-dihydro-pyrimidin-2-yl)-cyclohexyl]-azetidin-3-yl}-carbamic acid tert-butyl ester

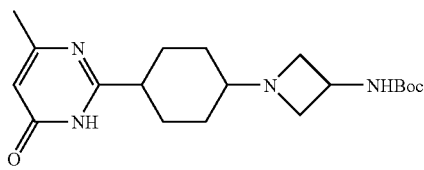

A mixture of the above intermediate (0.2 mmol), ethyl acetoacetate (Fluka, 0.025 mL, 0.2 mmol) and NaOH (0.018 g, 0.44 mmol) in ethanol (6 mL) in a sealed tube was heated at 80° C. for 8 h. After removal of organic solvent by evaporation, the residue was dissolved in water, extracted with EtOAc and dried over Na₂SO₄. Filtration and evaporation to dryness gave the product as a mixture of cis/trans isomers.
LC/MS: 363.3 [M+H].

Step E: N-({1-[4-(4-Methyl-6-oxo-1,6-dihydro-pyrimidin-2-yl)-cyclohexyl]-azetidin-3-ylcarbamoyl}-methyl)-3-trifluoromethyl-benzamide

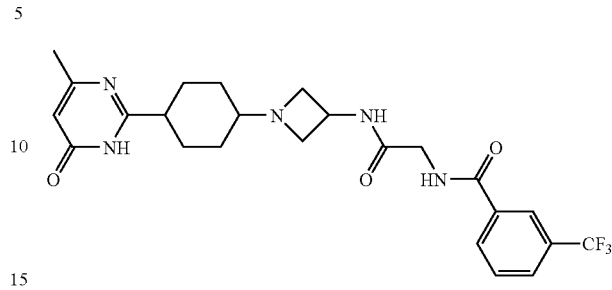

The title compound was prepared from {1-[4-(4-methyl-6-oxo-1,6-dihydro-pyrimidin-2-yl)-cyclohexyl]-azetidin-3-yl}-carbamic acid tert-butyl ester (as prepared in the previous step) according to the de-protection and coupling procedure described in Steps D and E of Example 58.
The TFA salt, a mixture of cis/trans (1:1) isomers: LC/MS: 492.3 [M+H].

Example 61

N-({1-[4-(4-Oxo-3,4,5,6,7,8-hexahydro-quinazolin-2-yl)-cyclohexyl]-azetidin-3-ylcarbamoyl}-methyl)-3-trifluoromethyl-benzamide Step A: {1-[4-(4-Oxo-3,4,5,6,7,8-hexahydro-quinazolin-2-yl)-cyclohexyl]-azetidin-3-yl}-carbamic acid tent-butyl ester

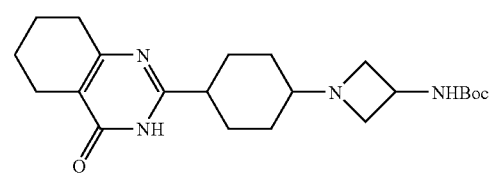

The title compound was prepared according to the procedure described in Example 60, Step D by using ethyl 2-cyclohexanone carboxylate (Aldrich, 0.1 mL, 0.6 mmol), the intermediate [1-(4-Carbamimidoyl-cyclohexyl)-azetidin-3-yl]-carbamic acid tert-butyl ester (prepared as described in Example 60, Step C, 0.6 mmol), NaOH (0.53 g, 1.32 mmol) in ethanol (16 mL).
LC/MS: 403.3 [M+H].

Step B: N-({1-[4-(4-Oxo-3,4,5,6,7,8-hexahydro-quinazolin-2-yl)-cyclohexyl]-azetidin-3-ylcarbamoyl}-methyl)-3-trifluoromethyl-benzamide

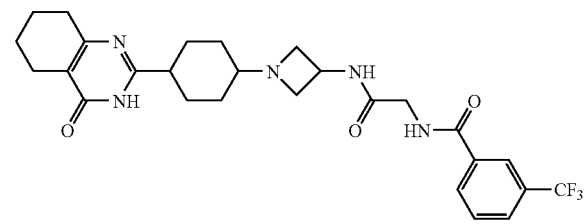

The title compound was prepared from {1-[4-(4-oxo-3,4,5,6,7,8-hexahydro-quinazolin-2-yl)-cyclohexyl]-azetidin-3-yl}-carbamic acid tert-butyl ester (as prepared in the previous step) according to the general de-protection and coupling procedure in Step D and E of Example 58.

The TFA salt, a mixture of cis/trans (1:1) isomers: LC/MS: 532.3 [M+H].

Example 62

N-({1-[4-(5-Chloro-[1,2,4]thiadiazol-3-yl)-cyclohexyl]-azetidin-3-ylcarbamoyl}-methyl)-3-trifluoromethyl-benzamide Step A: 5-Chloro-3-(1,4-dioxa-spiro[4.5]dec-8-yl)-[1,2,4]thiadiazole

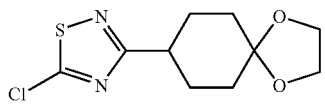

To a stirred suspension of NH$_4$Cl (0.29 g, 5.4 mmol) in dry toluene (2 mL) at 5° C. was slowly added a solution of trimethylaluminium in toluene (Aldrich, 2M, 2.5 mL, 5 mmol) under Ar. After the addition, the mixture was warmed to rt and stirred for 2 h until gas evolution had ceased. Then a solution of the intermediate 1,4-dioxa-spiro[4.5]decane-8-carbonitrile (0.50 g, 3 mmol, prepared according to the procedure from Tremblay, Maxime, PCT Int. Appl. (2007)) in toluene (1 mL) was added and the mixture was heated to 80° C. for 18 h. The reaction mixture was slowly poured into a slurry of silica gel (1.5 g) in CHCl$_3$ (5 mL) and stirred for 5 min. The silical gel was filtered and washed with methanol. The filtrate was condensed to ⅓ volume and filtered again. The filtrate was evaporated to dryness to give the crude intermediate as an HCl salt, which was dissolved in a NaOH solution (5N, 3.48 mL, 17.4 mmol) and cooled to 0° C., followed by addition of a solution of perchloromethyl mercaptan (Aldrich, 0.39 mL, 3.6 mmol). The mixture was vigorously stirred at rt overnight. Aqueous workup and purification by column chromatography (eluent: EtOAc/hexanes, 1:6) gave the product.

$^1$H NMR (400 MHz, CDCl$_3$): δ 3.95-3.97 (4H, m), 2.98-3.03 (1H, m), 2.08-2.14 (2H, m), 1.98-2.04 (2H, m), 1.83-1.88 (2H, m), 1.53-1.70 (2H, m).

Step B: 4-(5-Chloro-[1,2,4]thiadiazol-3-yl)-cyclohexanone

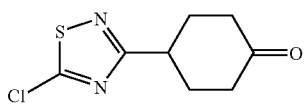

The above intermediate ketal (0.08 g, 0.3 mmol) was dissolved in CH$_3$CN (6 mL) and added to an 8N HCl solution (6 mL). The resulting solution was stirred at rt for 3 h and carefully neutralized with NaOH to pH ~7, and condensed. The aqueous phase was extracted with EtOAc and dried over Na$_2$SO$_4$. Filtration and evaporation to dryness gave the title compound as a HCl salt.
LC/MS: 217.0 [M+H].

Step C: N-({1-[4-(5-Chloro-[1,2,4]thiadiazol-3-yl)-cyclohexyl]-azetidin-3-ylcarbamoyl}-methyl)-3-trifluoromethyl-benzamide

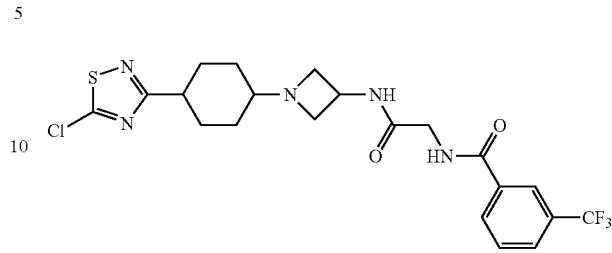

The title compound was prepared from 4-(5-chloro-[1,2,4]thiadiazol-3-yl)-cyclohexanone (as prepared in the previous step) according to the general reductive amination procedure described in Step F of Example 1.
A mixture of cis/trans isomers. LC/MS: 502.0 [M+H].

Example 63

N-({1-[4-(5,6,7,8-Tetrahydro-[1,2,4]-triazolo[1,5-a]pyridin-2-yl)-cyclohexyl]-azetidin-3-ylcarbamoyl}-methyl)-3-trifluoromethyl-benzamide Step A: 4-(5,6,7,8-Tetrahydro-[1,2,4]triazolo[1,5-a]pyridin-2-yl)-cyclohexanone

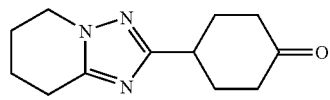

A solution of 2-(1,4-dioxa-spiro[4.5]dec-8-yl)-5,6,7,8-tetrahydro-[1,2,4]triazolo[1,5-a]pyridine (1.05 g, 4 mmol, prepared according to the literature procedure: Quanrui Wang, Atef Amer, Susanne Mohr, Eveline Ertel, Johannes C. Jochims, Tetrahedron, 1993, 49(44), 9973-9986) in CH$_3$CN (20 mL) and 2N HCl (30 mL) was stirred at rt for 2 h. Evaporation to dryness gave the intermediate as a HCl salt.
LC/MS: 220.0 [M+H].

Step B: N-({1-[4-(5,6,7,8-Tetrahydro-[1,2,4]triazolo[1,5-a]pyridin-2-yl)-cyclohexyl]-azetidin-3-ylcarbamoyl}-methyl)-3-trifluoromethyl-benzamide

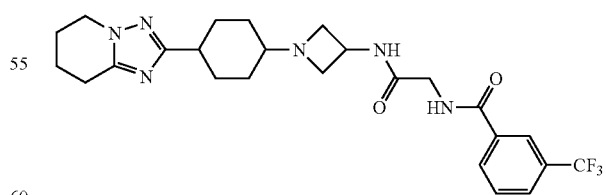

The title compound was prepared from 4-(5,6,7,8-tetrahydro-[1,2,4]triazolo[1,5-a]pyridin-2-yl)-cyclohexanone (as prepared in the previous step) according to the general reductive amination procedure described in Step F of Example 1.
A mixture of cis/trans (1:3) isomers. LC/MS: 505.3 [M+H].

Example 64

N-({1-[4-Fluoro-4-(6-methoxy-pyridin-3-yl)-cyclohexyl]-azetidin-3-ylcarbamoyl}-methyl)-3-trifluoromethyl-benzamide Step A: N-({1-[4-Hydroxy-4-(6-methoxy-pyridin-3-yl)-cyclohexyl]-azetidin-3-ylcarbamoyl}-methyl)-3-trifluoromethyl-benzamide

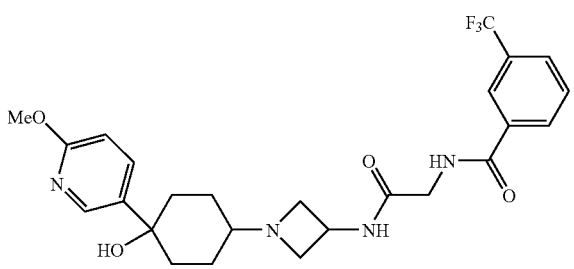

A solution of 4-hydroxy-4-(6-methoxy-pyridin-3-yl)-cyclohexanone (300 mg, 1.36 mmol) and N-(azetidin-3-ylcarbamoylmethyl)-3-trifluoromethyl-benzamide HCl salt (460 mg, 1.36 mmol) in DCM (5 mL) was treated with TEA (1 mL, 7.12 mmol) for 10 min followed by NaBH(OAc)$_3$ (860 mg, 4.07 mmol) for another 4 hours at room temperature. The reaction was quenched with saturated sodium bicarbonate. The organic layer was separated and the aqueous layer was extracted 3 times with a chloroform/IPA "cocktail" (~3:1, v/v). The combined organic layers were dried over anhydrous Na$_2$SO$_4$, filtered and concentrated to give the crude product, and purified by a CombiFlash® system using ethyl acetate and 7N NH$_3$ in MeOH as eluent (from pure ethyl acetate to 5% 7N NH$_3$ in MeOH in ethyl acetate) to afford the two title compounds as white solids:

Less Polar Isomer from Silica Gel Column, $^1$H NMR (400 MHz, CDCl$_3$) δ 8.28 (s, 1H), 8.11 (s, 1H), 8.05 (d, J=5.8 Hz, 1H), 7.78 (d, J=6.5 Hz, 1H), 7.70 (d, J=6.5 Hz, 1H), 7.57 (t, J=6.8 Hz, 1H), 6.70 (d, J=6.5 Hz, 1H), 4.51 (m, 1H), 4.20 (d, J=3.2 Hz, 2H), 3.88 (s, 3H), 3.65 (t, J=6.0 Hz, 2H), 2.92 (t, J=5.8 Hz, 2H), 2.20 (m, 2H), 1.85 (m, 2H), 1.56 (m, 2H), 1.45 (m, 2H).

More Polar Isomer from Silica Gel Column $^1$H NMR (400 MHz, CDCl$_3$) δ 8.25 (s, 1H), 8.10 (s, 1H), 8.05 (d, J=6.5 Hz, 1H), 7.80 (d, J=6.4 Hz, 1H), 7.71 (d, J=6.5 Hz, 1H), 7.62 (d, J=6.5 Hz, 1H), 7.60 (t, J=6.8 Hz, 1H), 7.37 (d, J=6.2 Hz, 1H), 6.70 (d, J=6.8 Hz, 1H), 4.55 (m, 1H), 4.20 (d, J=3.5 hz, 2H), 3.65 (t, J=6.5 Hz, 2H), 3.08 (t, J=6.5 Hz, 2H), 1.85-1.50 (m, 8H).

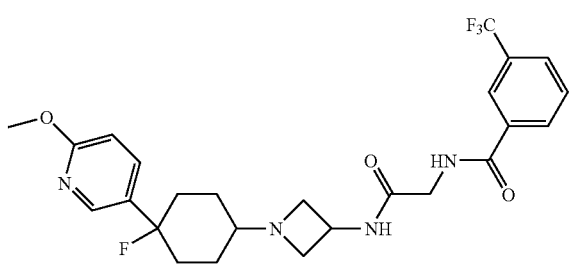

A solution of N-({1-[4-hydroxy-4-(6-methoxy-pyridin-3-yl)-cyclohexyl]-azetidin-3-ylcarbamoyl}-methyl)-3-trifluoromethyl-benzamide (300 mg, 0.60 mmol) in DCM (5 mL) was treated with DAST (Aldrich, 292 μL, 3.0 mmol) dropwise at −78° C. for 4 hours. The reaction was quenched with MeOH, warmed to room temperature and partitioned between DCM and water. The organic layer was washed with brine, dried over anhydrous Na$_2$SO$_4$, filtered, concentrated and the residue was purified by a CombiFlash® system using ethyl acetate and 7N NH$_3$ in MeOH as eluent (from pure ethyl acetate to 5% 7N NH$_3$ in MeOH in ethyl acetate) to afford the two title compounds as white solids.

64a: Less Polar Fraction from Silica Gel Column, $^1$H NMR (400 MHz, CDCl$_3$) δ 8.20 (s, 1H), 8.15 (s, 1H), 8.05 (d, J=6.4 Hz, 1H), 7.80 (d, J=6.6 Hz, 1H), 7.68 (m, 1H), 7.65 (d, J=6.4 Hz, 1H), 7.55 (t, J=7.1 Hz, 1H), 7.28 (d, J=6.5 Hz 1H), 6.72 (d, J=6.8 Hz, 1H), 4.51 (m, 1H), 4.20 (d, J=3.0 Hz, 2H), 3.90 (s, 3H), 3.62 (t, J=6.8 Hz, 2H), 2.90 (t, J=6.6 Hz, 2H), 2.20~2.01 (m, 2H), 1.80 (m, 4H), 1.55 (d, J=6.0 Hz, 2H).

64b: More Polar Fraction from Silica Gel Column $^1$H NMR (400 MHz, CDCl$_3$) δ 8.15 (s, 2H), 8.05 (d, J=6.0 Hz, 1H), 7.80 (d, J=6.2 Hz, 1H), 7.65 (m, 2H), 7.24 (d, J=6.5 Hz, 1H), 6.72 (d, J=6.6 Hz, 1H), 4.55 (m, 1H), 4.21 (d, J=3.0 Hz, 2H), 3.95 (s, 3H), 3.70 (t, J=6.9 Hz, 2H), 3.02 (t, J=6.8 Hz, 2H), 2.10 (m, 3H), 1.75 (m, 3H), 1.55 (m, 2H).

Example 65

In Vitro Biological Data

Compounds of the invention were subjected to various representative biological tests. The results of these tests are intended to illustrate the invention in a non-limiting fashion.

MCP-1 Receptor Binding Assay in THP-1 Cells

Human monocytic cell line THP-1 cells were obtained from American Type Culture Collection (Manassas, Va., USA). The THP-1 cells were grown in RPMI-1640 (RPMI: Roswell Park Memorial Institute Medium-cell culture growth media) supplemented with 10% fetal bovine serum in a humidified 5% CO$_2$ atmosphere at 37° C. The cell density was maintained between 0.5×10$^6$ cells/mL.

THP-1 (cells were incubated with 0.5 nM $^{125}$I labeled MCP-1 (Perkin-Elmer Life Sciences, Inc. Boston, Mass.) in the presence of varying concentrations of either unlabeled MCP-1 (R & D Systems, Minneapolis, Minn.) or test compound for 2 hours at 30° C. in a 96 well plate. Cells were then harvested onto a filter plate, dried, and 20 μL of Microscint 20 was added to each well. Plates were counted in a TopCount NXT, Microplate Scintillation & Luminescence Counter (Perkin-Elmer Life Sciences, Inc. Boston, Mass.). Blank values (buffer only) were subtracted from all values and drug treated values were compared to vehicle treated values. 1 μM cold MCP-1 was used for nonspecific binding.

Table 1 lists IC$_{50}$ values for inhibition of MCP-1 binding to CCR2 obtained for test compounds of the invention. Where an IC$_{50}$ value was not obtained for a particular compound, the percent inhibition is provided at a test concentration of 25 μM.

TABLE 1

| Inhibition of MCP-1 Binding IC$_{50}$ | |
|---|---|
| Example | CCR2 Binding (nM) |
| 1a | 7.0 |
| 2 | 210 |
| 3 | 24 |
| 4 | 13 |
| 5 | 260 |

TABLE 1-continued

Inhibition of MCP-1 Binding IC$_{50}$

| Example | CCR2 Binding (nM) |
|---|---|
| 6 | 50 |
| 7 | 32 |
| 8 | 25 |
| 9 | 52 |
| 10 | 970 |
| 11 | 460 |
| 12 | >25,000 |
| 13 | 90 |
| 14 | 280 |
| 15 | 230 |
| 16 | 95 |
| 17 | 920 |
| 18 | 380 |
| 19 | 1,900 |
| 20 | 43 |
| 21 | 85 |
| 22a | 25 |
| 23a | 72 |
| 24 | 60 |
| 25 | 210 |
| 26 | 840 |
| 27a | 2,700 |
| 28 | 89 |
| 29a | 1,200 |
| 29b | 10,000 |
| 30a | 189 |
| 31a | 150 |
| 32 | 320 |
| 33 | 250 |
| 34 | 120 |
| 35a | 44 |
| 36a | 31 |
| 37a | 170 |
| 38a | 46 |
| 39a | 37 |
| 40a | 330 |
| 41 | 130 |
| 42a | 150 |
| 43 | 330 |
| 44a | 250 |
| 45a | 61 |
| 46a | 550 |
| 47 | 180 |
| 48 | 630 |
| 49 | >25,000 |
| 50 | 920 |
| 51a | 340 |
| 52a | 2,800 |
| 53 | 1,000 |
| 54 | 340 |
| 55 | 125 |
| 56 | 5,800 |
| 57 | 1,100 |
| 58 | 510 |
| 59 | 400 |
| 60 | 3,900 |
| 61 | 4,000 |
| 62 | 390 |
| 63 | 1,500 |
| 64a | 110 |

Example 66

Animals

Mouse CCR2 knock-out/human CCR2 knock-in mice were generated using targeted 129Sv/Evbrd embryonic stem cell clones injected into C57BL/6 mice. Expression of the hCCR2 transcript was confirmed by quantitative reverse transcription-polymerase chain reaction performed on spleen and blood total RNA from homozygous hCCR2 knock-in mice. Backcrossing into C57BL/6 genetic background continued to the eighth generation. Transgenic mice were housed in a specific-pathogen-free, temperature-controlled facility that maintained a 12-hour light/12-hour dark cycle. Mice had free access to water and food. Experimental procedures were carried out in accordance with institutional standards for animal care and were approved by the institute's animal care and use committee.

Example 67

Murine In Vivo Cell Migration Assay

Animals are orally dosed with vehicle or CCR2 antagonists at 3, 10 and 30 mg/kg bid. Animals undergo anesthesia and laparotomy. A distal loop of small bowel (5 cm in length) is gently eventrated onto moist sterile gauze. Synthetic human MCP-1 (1 mg/100 ml sterile PBS) or PBS alone is administered drop-wise onto the serosa of the eventrated loop. A suture knot is placed into the mesentery to mark the terminus of the treated area. Twenty-four hours later, the animal is sacrificed and the segment of bowel plus the adjacent region is removed. The tissue is opened along the mesenteric border, pinned flat and the mucosa removed. The remaining muscle layer is fixed briefly in 100% EtOH and then stained using Hanker-Yates reagent to detect myeloperoxidase-containing immune cells. At 10 mpk, P.O. bid, a compound is deemed efficacious if the inhibition of cell migration reaches 30% compared with vehicle-treated animals.

Example 68

Thiolycollate-Induced Peritonitis in Mice

Animals are orally dosed with vehicle or CCR2 antagonists at 3, 10, 30 and 100 mg/kg bid). One hour later, the animals are intraperiponeally injected with sterile thioglycollate (25 mL/kg, ip, Sigma) for induction of peritonitis. Animals are orally treated twice daily with vehicle or CCR2 antagonists. At the 72-hour time point, perinoteal cavities are lavaged with 10 mL of sterile saline. Total cell counts in the peritoneal lavage fluid are performed using a microscope and cell differentiation is performed using cytospin analysis after Giemsa staining (Hema Tek 2000). Percent inhibition of the thioglycollate-induced peritonitis is calculated by comparing the change in number of leukocytes of CCR2 antagonist treated mice to the vehicle-treated mice.

Example 69

MCP-1-Induced Monocyte Recruitment to Airway of Mice

Animals are orally treated with vehicle or CCR2 antagonists at 3, 10, and 30 mg/kg po bid). One hour later, the animals are intranasally dosed with 4 μg of MCP-1 in sterile saline. The animals are orally treated twice daily with vehicle or CCR2 antagonists. After 48 h, mice are euthanized by intraperitoneal injection of anesthesia solution (Sleepaway-Sodium pentobarbital). Whole bronchoalveolar lavage (BAL) is performed using 1.4 ml of ice-cold PBS containing 3 mM EDTA. Total cell counts in the BAL lavage fluid are performed using a microscope and cell differentiation is performed using cytospin analysis after Giemsa staining (Hema Tek 2000). Percent inhibition is calculated by comparing the change in number of total leukocyte counts (including monocytes/macrophages and lymphocytes) of compound-treated mice to the vehicle-treated mice. Compounds are deemed efficacious if percent inhibition reaches 30%.

Example 70

High-fat Diet Induced Obesity and Insulin Resistance in Mice

Obesity is induced by a high-fat diet that derived approximately 60% calories from lipids (D-12492; Research Diets Inc.) in animals for 10-24 weeks at age of 7 weeks. Prior to age 7 weeks, animals are fed a standard pellet diet, in which 5% of calories were provided as fat. Obese animals were randomized by body weight and fat mass. The obese animals are orally treated with vehicle or CCR2 antagonists at 3, 10 and 30 mg/kg, po bid. Body weight and food intake and were fasting blood glucose levels monitored. Body mass was determined by a NMR analyzer (Burker MiniSpec). Insulin tolerance test is carried out in animals that were fasted for 3 hours. After an intraperitoneal bolus injection of recombinant human insulin (1.5 U/kg), blood glucose concentrations are measured using a Glucometer before and 15, 30, 45, 60, 90 and 120 minutes after injection. Glucose tolerance tests are performed after an overnight (17-hour) fast. Blood glucose concentrations are measured before and after 15, 30, 60, 90, 120 minutes after an oral dose of glucose dissolved in water (1 g/kg). Energy expenditure analysis was monitored by a complete laboratory animal monitor system. After 40 days treatment with vehicle or CCR2 antagonists, the animals are sacrificed by $CO_2$ asphyxiation. Percent of weight loss is calculated by comparing the body weight changes of the compound-treated mice with the vehicle-treated mice.

Example 71

Mouse Model of Allergic Asthma

Animals are sensitized by intraperitoneal injection of 10 μg chicken egg albumin (OVA) absorbed to 1 mg Imject® in 100 μL phosphate-buffered saline (PBS) on days 0 and 5. Control animals received PBS ip. OVA-immunized animals were challenged by inhalation of 0.5% OVA aerosol for 10 minutes by an ultrasonic nebulizer on days 12, 16 and 20. Control animals were challenged with PBS in similar fashion. The OVA-sensitized animals receive vehicle (0.5% Methocel) or CCR2 antagonists orally at 3, 10, mg/kg twice daily from days 9-20 and once daily on Day 21, 2 hours before sacrifice. Dexamethason (5 mg/kg) and Montelukast (1 mg/kg) are given orally once a day. On day 21, 2 hours post the last dose of CCR2 compounds, bronchial reactivity to aerosolized methacholine is measured using a Buxco whole body plethysmograph. On day 21, the animals are sacrificed. Bronchoalveolar lavage fluid is collected (1 mL) and total cells counted. The numbers of eosinophils, lymphocytes, monocytes and neutrophils are determined using cytospin analysis after Giemsa staining (Hema Tek 2000). Percent inhibition of total BAL leukocyte count (and eosinophil count) is calculated by comparing the compound-treated mice with vehicle-treated mice. Compounds are deemed efficacious if the inhibition reaches 30%.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

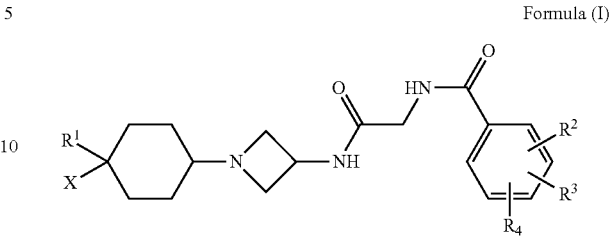

Formula (I)

wherein:
X is F, $NH_2$, or H;
$R^1$ is

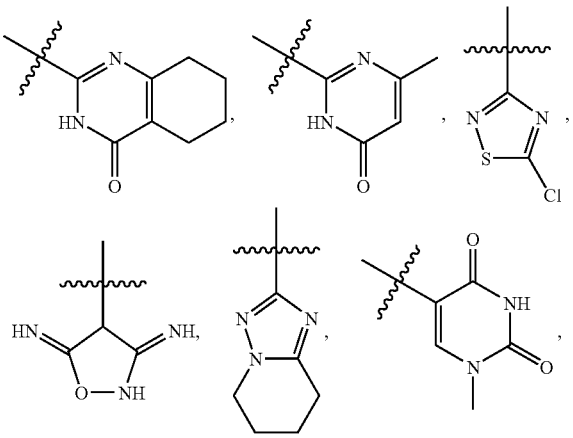

pyridyl, pyridyl-N-oxide, pyridin-2-onyl, indolyl, pyrazinyl, 3-H-thiazol-2-onyl, pyrimidyl, benzooxazolyl, oxazolyl, thiazolyl, isothiazolyl, pyrazolyl, imidazolyl, thiophenyl, furyl, [1,2,4]oxadiazolyl or [1,3,4]thiadiazolyl;

wherein said pyridyl, pyridyl-N-oxide, pyrimidyl, pyrazolyl, imidazolyl, thiophenyl, or thiazolyl is optionally substituted with one substituent selected from the group consisting of $OC_{(1-4)}$alkyl, $OC_{(3-6)}$cycloalkyl, $OCH_2CF_3$, $OCH_2Ph$, F, CN, Cl, $OCF_3$, $CF_3$, $CH_2CN$, $C_{(1-4)}$alkyl, $CH_2CF_3$, $N(C_{(1-4)}$alkyl$)_2$, $C_{(1-4)}$alkylOH, $Si(CH_3)_3$, —C≡CH, $SCH_3$, $S(O)CH_3$, $SO_2CH_3$, pyrrolidinyl, OH, $NH_2$, NHCN, $CO_2H$, $CONH_2$, $NHCO_2C_{(1-4)}$alkyl, $N(SO_2CH_3)_2$, $NHSO_2CH_3$, $NHC(O)CF_3$, $NHC_{(1-4)}$alkyl, $NHCO_2H$, $NHCO_2C_{(1-4)}$alkyl, $NHCOC_{(1-4)}$alkyl, $NHCONH_2$, $NHCONHC_{(1-4)}$alkyl, and Br; or said pyridyl may be substituted with one $OCH_3$ group and one $CH_3$; wherein said pyrimidyl is optionally substituted on any carbon atom with one $N(C_{(1-4)}$alkyl$)_2$ group; or said pyrimidinyl is substituted on any two carbon atoms with two substituents independently selected from the group consiting of OH, $OCH_3$, and $CH_3$; wherein said thiazolyl is substituted with $CO_2H$, $CONH_2$, $NHCO_2C_{(1-4)}$alkyl, or OH; or said thiazolyl is optionally substituted on two adjacent carbon atoms to form a fused bicyclic system benzothiazol-2-yl, wherein said benzothiazol-2-yl is optionally substituted with Br or $OCH_3$; wherein said pyridin-2-onyl is optionally substituted with one substituent selected from the group consisting of CH$_2$CN, C$_{(1-4)}$alkyl, CH$_2$CF$_3$, and CH$_2$CH$_2$OH, or said pyridin-2-onyl is substituted with 2 methyl groups; wherein said [1,2,4]oxadiazolyl is optionally substituted on any carbon atom with OH, CCl$_3$, or pyrrolidinyl;

R$^2$ is C$_{(1-4)}$alkyl, NH$_2$, NO$_2$, NHCH$_2$CH$_2$OH, N(C$_{(1-4)}$alkyl)$_2$, N(SO$_2$CH$_3$)$_2$, CN, F, Cl, Br, CF$_3$, C$_{(3-6)}$cycloalkyl, heterocyclyl, OCF$_3$, OCF$_2$H, CF$_2$H, or OC$_{(1-4)}$alkyl;

R$^3$ is H, F, Cl, CF$_3$, or OC$_{(1-4)}$alkyl; alternatively, R$^2$ and R$^3$ may be taken together with their attached phenyl to form a benzo[1,3]dioxolyl, 2,3-dihydro-benzofuranyl, or 2,3-dihydro-benzo[1,4]dioxinyl group;

R$^4$ is H, OC$_{(1-4)}$alkyl, or F;

and hydrates, tautomers, and pharmaceutically acceptable salts thereof.

2. A compound of claim 1 wherein:
R$^1$ is

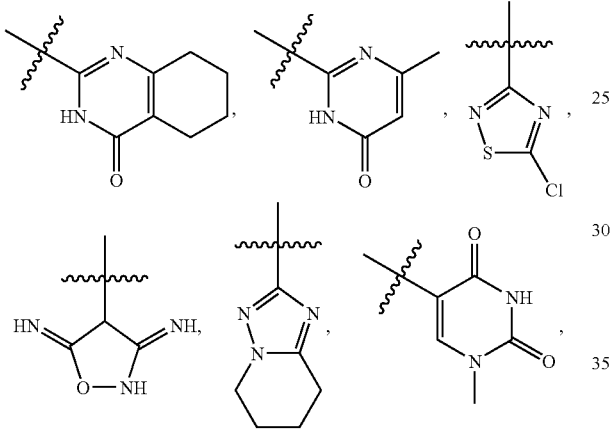

pyridyl, pyridyl-N-oxide, pyridin-2-onyl, indolyl, pyrazinyl, 3-H-thiazol-2-onyl, pyrimidyl, methyl substituted imidazolyl, methyl substituted pyrazolyl optionally substituted with Br, thiophenyl optionally substituted with Br, benzooxazolyl, oxazolyl, thiazolyl, isothiazolyl, [1,2,4]oxadiazolyl or [1,3,4]thiadiazolyl; wherein said pyridyl, pyridyl-N-oxide, or thiazolyl is optionally substituted with one substituent selected from the group consisting of OC$_{(1-4)}$alkyl, OC$_{(3-6)}$cycloalkyl, OCH$_2$CF$_3$, OCH$_2$Ph, F, CN, CH$_2$CN, C$_{(1-4)}$alkyl, CH$_2$CF$_3$, N(C$_{(1-4)}$alkyl)$_2$, C$_{(1-4)}$alkylOH, Si(CH$_3$)$_3$, —C≡CH, SCH$_3$, S(O)CH$_3$, SO$_2$CH$_3$, pyrrolidinyl, OH, NH$_2$, NHCN, CO$_2$H, CONH$_2$, NHCO$_2$C$_{(1-4)}$alkyl, N(SO$_2$CH$_3$)$_2$, NHSO$_2$CH$_3$, NHC(O)CH$_3$, NHC(O)CF$_3$, NHC$_{(1-4)}$alkyl, and Br; or said pyridyl may be substituted with one OCH$_3$ group and one CH$_3$; wherein said pyrimidyl is optionally substituted on any carbon atom with one N(C$_{(1-4)}$alkyl)$_2$ group; or said pyrimidinyl is substituted on any two carbon atoms with one OH group and one CH$_3$; wherein said thiazolyl is substituted with CO$_2$H, CONH$_2$, NHCO$_2$C$_{(1-4)}$alkyl, or OH; or said thiazolyl is optionally substituted on two adjacent carbon atoms to form a fused bicyclic system benzothiazol-2-yl, wherein said benzothiazol-2-yl is optionally substituted with Br or OCH$_3$; wherein said pyridin-2-onyl is optionally substituted with one substituent selected from the group consisting of CH$_2$CN, C$_{(1-4)}$alkyl, CH$_2$CF$_3$, and CH$_2$CH$_2$OH, or said pyridin-2-onyl is substituted with 2 methyl groups; wherein said [1,2,4]oxadiazolyl is optionally substituted on any carbon atom with OH, CCl$_3$, or pyrrolidinyl;

R$^2$ is C$_{(1-4)}$alkyl, NH$_2$, NO$_2$, NHCH$_2$CH$_2$OH, N(C$_{(1-4)}$alkyl)$_2$, N(SO$_2$CH$_3$)$_2$, CN, F, Cl, Br, CF$_3$, pyrrolidinyl, OCF$_3$, OCF$_2$H, CF$_2$H, or OC$_{(1-4)}$alkyl;

R$^3$ is H, F, Cl, CF$_3$, or OC$_{(1-4)}$alkyl; alternatively, R$^2$ and R$^3$ may be taken together with their attached phenyl to form a benzo[1,3]dioxolyl group;

R$^4$ is H, OCH$_3$, or F;

and hydrates, tautomers, and pharmaceutically acceptable salts thereof.

3. A compound of claim 2 wherein:
R$^1$ is

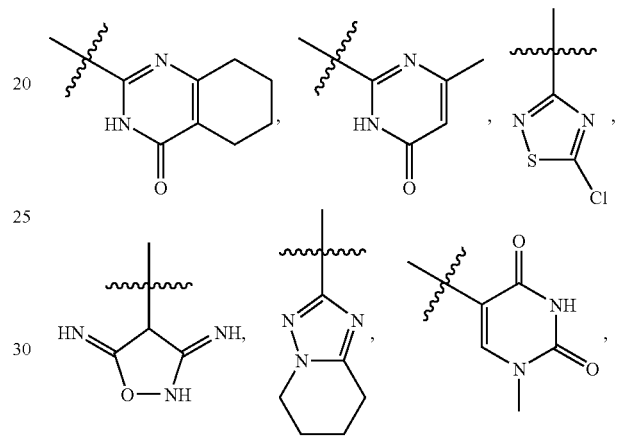

indolyl, pyridyl, pyridyl-N-oxide, pyridin-2-onyl, pyrimidyl, pyrazinyl, methyl substituted imidazolyl, methyl substituted pyrazolyl optionally substituted with Br, thiophenyl optionally substituted with Br, benzooxazolyl, oxazolyl, thiazolyl, [1,2,4]oxadiazolyl, isothiazolyl, or [1,3,4]thiadiazolyl; wherein said pyridyl, pyridyl-N-oxide, or thiazolyl is optionally substituted with one substituent selected from the group consisting of OH, OC$_{(1-4)}$alkyl, NHC(O)CH$_3$, N(SO$_2$CH$_3$)$_2$, NHSO$_2$CH$_3$, NHC(O)CF$_3$, NHC$_{(1-4)}$alkyl, OC$_{(3-6)}$cycloalkyl, OCH$_2$CF$_3$, OCH$_2$Ph, F, CN, C$_{(1-4)}$alkyl, N(C$_{(1-4)}$alkyl)$_2$, C$_{(1-4)}$alkylOH, Si(CH$_3$)$_3$, —C≡CH, SCH$_3$, S(O)CH$_3$, SO$_2$CH$_3$, pyrrolidinyl, NH$_2$, NHCN, and Br; or said pyridyl may be substituted with one OCH$_3$ group and one CH$_3$; wherein said pyrimidyl is optionally substituted on any carbon atom with one N(C$_{(1-4)}$alkyl)$_2$ group; or said pyrimidinyl is substituted on any two carbon atoms with one OH group and one CH$_3$; wherein said pyridin-2-onyl is optionally substituted with one substituent selected from the group consisting of CH$_2$CN, C$_{(1-4)}$alkyl, CH$_2$CF$_3$, and CH$_2$CH$_2$OH, or said pyridin-2-onyl is substituted with 2 methyl groups; wherein said thiazolyl is substituted with CO$_2$H, CONH$_2$, NHCO$_2$C$_{(1-4)}$alkyl, or OH; or said thiazolyl is optionally substituted on two adjacent carbon atoms to form a fused bicyclic system benzothiazol-2-yl, wherein said benzothiazol-2-yl is optionally substituted with Br or OCH$_3$; wherein said [1,2,4]oxadiazolyl is optionally substituted on any carbon atom with OH, CCl$_3$, or pyrrolidinyl;

R$^2$ is NH$_2$, NO$_2$, NHCH$_2$CH$_2$OH, N(CH$_3$)$_2$, N(SO$_2$CH$_3$)$_2$, CN, F, Cl, Br, CF$_3$, pyrrolidinyl, or OCH$_3$;

153

R³ is H, F, Cl, CF₃, or OCH₃; alternatively, R² and R³ may be taken together with their attached phenyl to form a benzo[1,3]dioxolyl group;

R⁴ is H, or F;

and hydrates, tautomers, and pharmaceutically acceptable salts thereof.

4. A compound of claim 3 wherein:

R¹ is

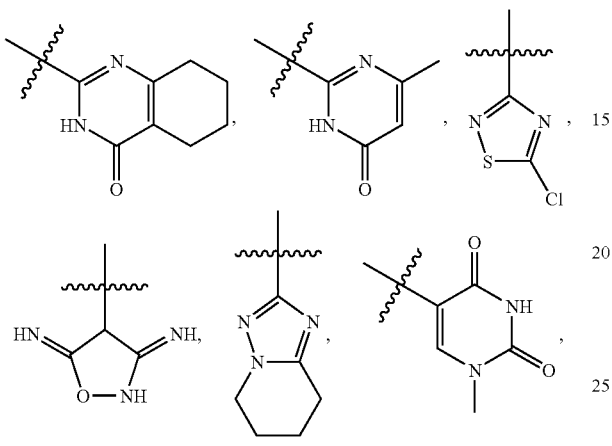

indolyl, pyrimidyl, pyridin-2-onyl, pyrazinyl, thiazolyl, [1,2,4]oxadiazolyl, or pyridyl, wherein said pyridyl is optionally substituted on any carbon atom with one substituent selected from the group consisting of OH, OC₍₁₋₄₎alkyl, NHC(O)CH₃, N(SO₂CH₃)₂, NHSO₂CH₃, NHC(O)CF₃, NH₂, NHC₍₁₋₄₎alkyl, N(CH₃)₂, NHCN, SO₂CH₃; or said pyridyl is optionally substituted on any two carbon atoms with one OH group and one CH₃; wherein said pyrimidinyl is optionally substituted on any carbon atom with one N(CH₃)₂ group; or said pyrimidinyl is substituted on any two carbon atoms with one OH group and one CH₃; wherein said pyridin-2-onyl is optionally substituted with one substituent selected from the group consisting of CH₂CN, C₍₁₋₄₎alkyl, CH₂CF₃, and CH₂CH₂OH, or said pyridin-2-onyl is substituted with 2 methyl groups;

wherein said thiazolyl is substituted with CO₂H, CONH₂, NHCO₂C₍₁₋₄₎alkyl, or OH; wherein said [1,2,4]oxadiazolyl is optionally substituted on any carbon atom with OH, CCl₃, or pyrrolidinyl;

R² is CF₃, CN, F, or Cl;

R³ is H, Cl, CF₃, or F;

R⁴ is H, or F;

and hydrates, tautomers, and pharmaceutically acceptable salts thereof.

154

5. A compound of claim 4 wherein:

X is F, or H;

R¹ is

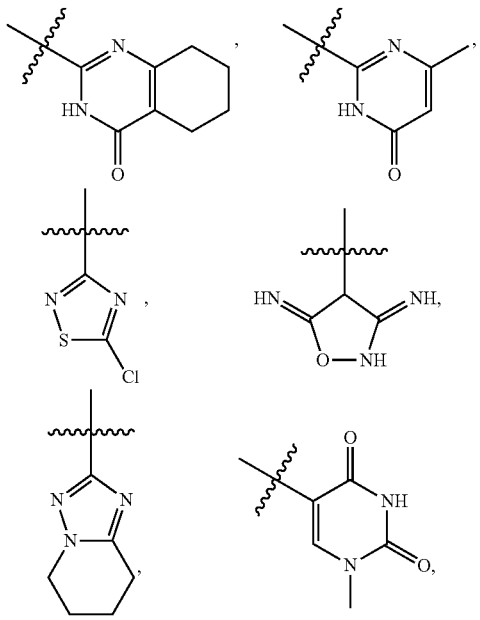

indolyl, pyrimidyl, pyridin-2-onyl, methyl pyridin-2-onyl, pyrazinyl, thiazolyl, [1,2,4]oxadiazolyl, or pyridyl, wherein said pyridyl is optionally substituted on any carbon atom with one substituent selected from the group consisting of OH, OCH₃, NHC(O)CH₃, N(SO₂CH₃)₂, NHSO₂CH₃, NHC(O)CF₃, NH₂, NHCH₃, N(CH₃)₂, NHCN, SO₂CH₃; or said pyridyl is optionally substituted on any two carbon atoms with one OH group and one CH₃; wherein said pyrimidinyl is substituted on any carbon atom with one N(CH₃)₂ group;

wherein said pyridin-2-onyl is N substituted with one substituent selected from the group consisting of CH₂CN, C₍₁₋₄₎alkyl, CH₂CF₃, and CH₂CH₂OH, or said pyridin-2-onyl is substituted with 2 methyl groups;

wherein said thiazolyl is substituted with CO₂H, CONH₂, NHCO₂CH₃, or OH; wherein said [1,2,4]oxadiazolyl is optionally substituted on any carbon atom with OH, CCl₃, or pyrrolidinyl;

R² is CF₃;

R³ is H, or F;

R⁴ is H;

and hydrates, tautomers, and pharmaceutically acceptable salts thereof.

6. A compound selected from the group consisting of:

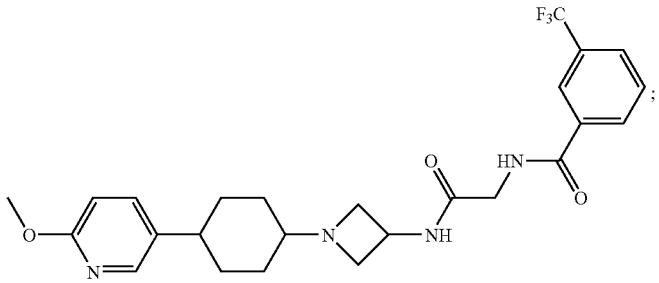

-continued
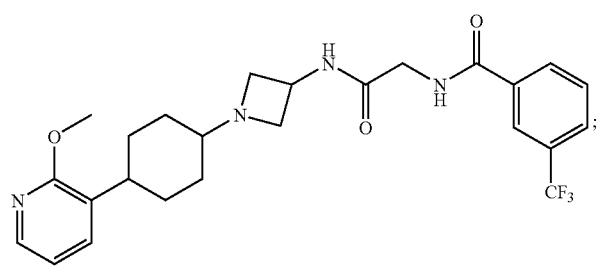
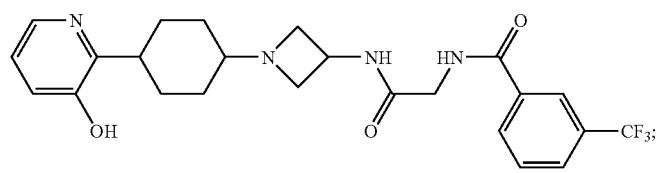
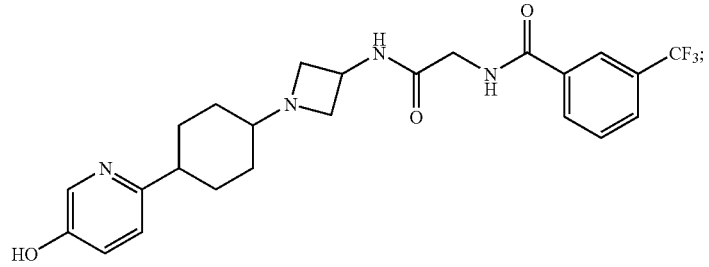
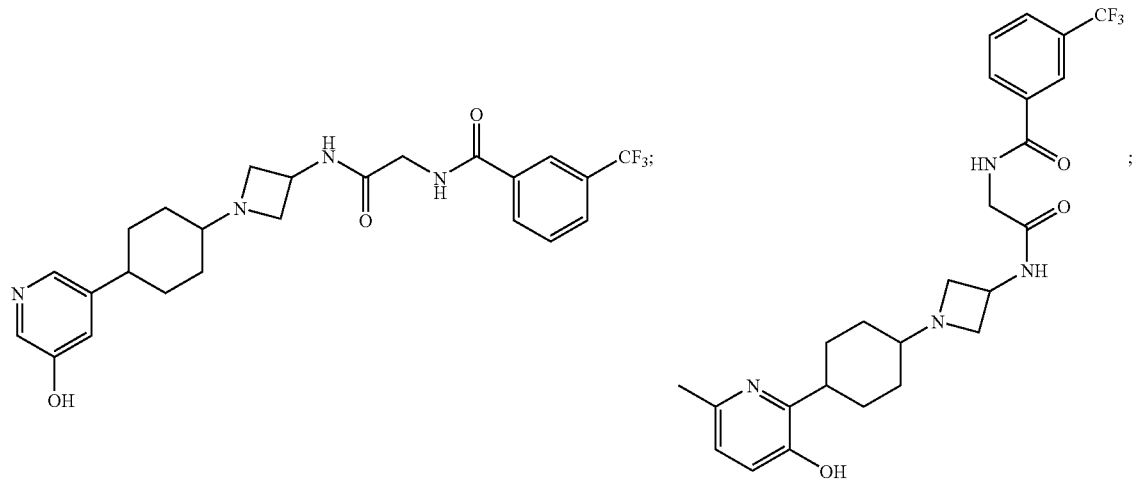
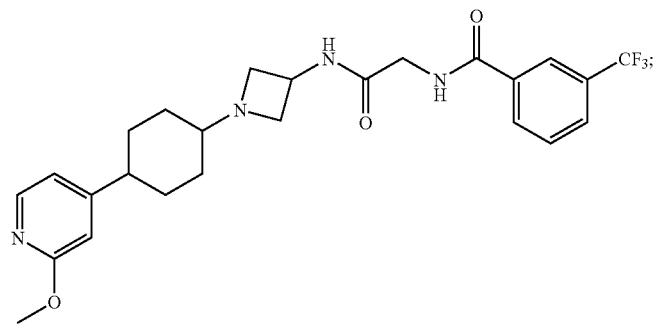

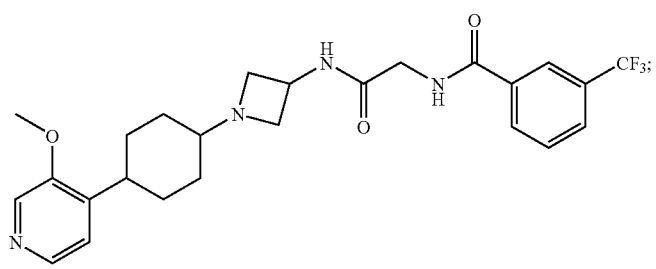
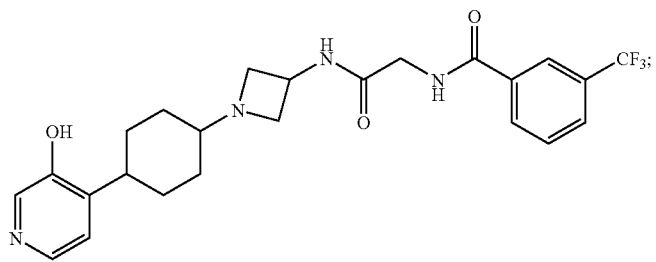
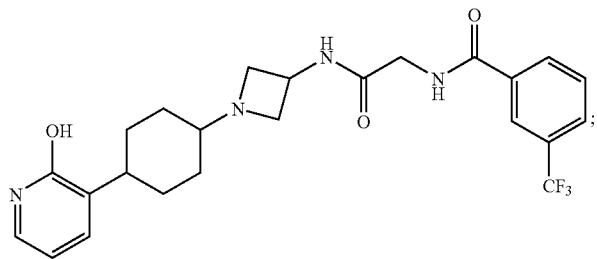
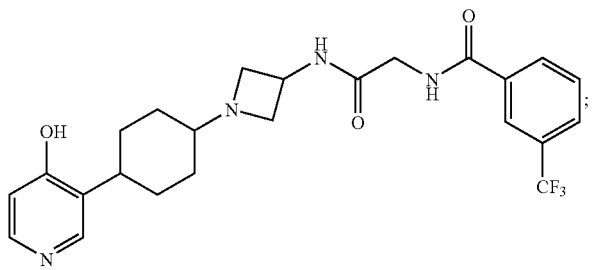
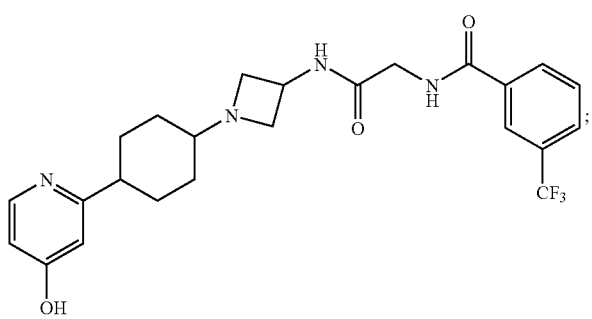
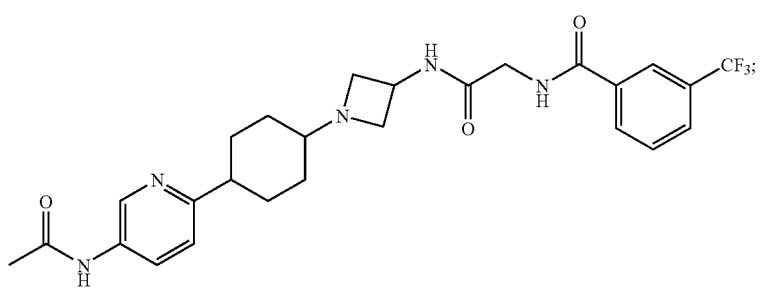

-continued
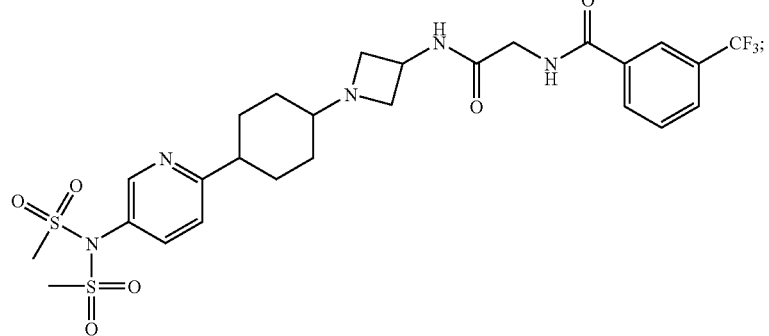
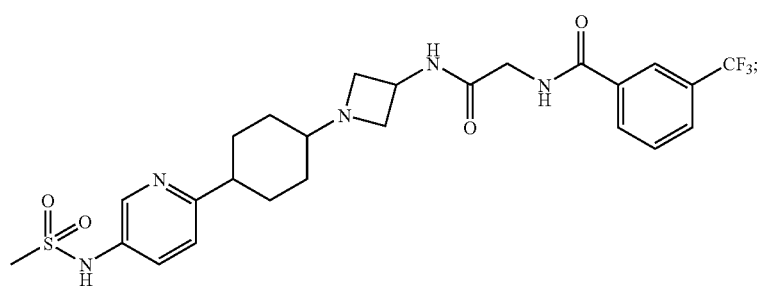
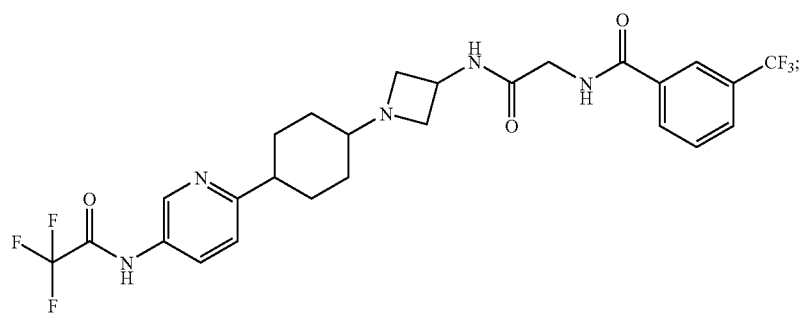
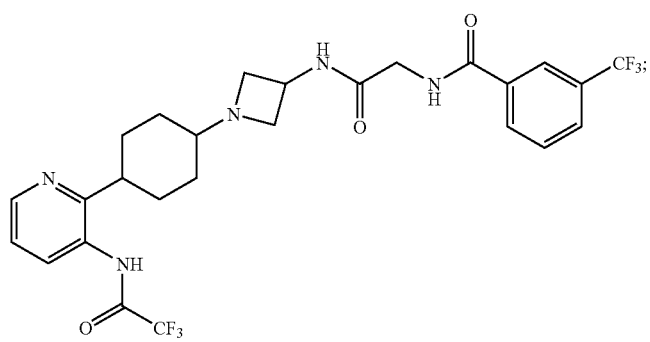
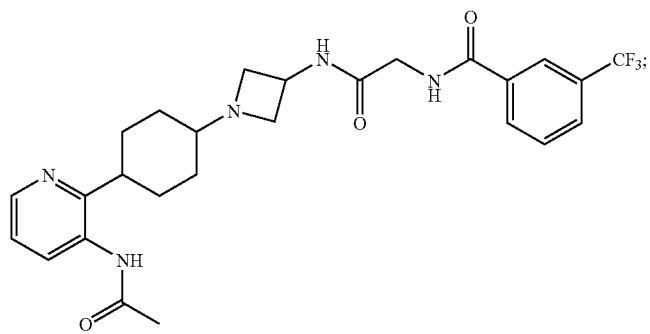

-continued
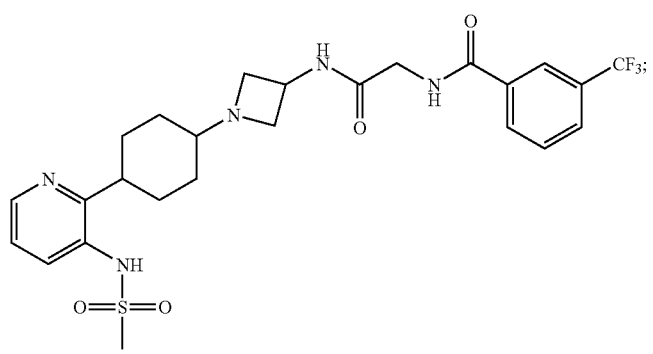
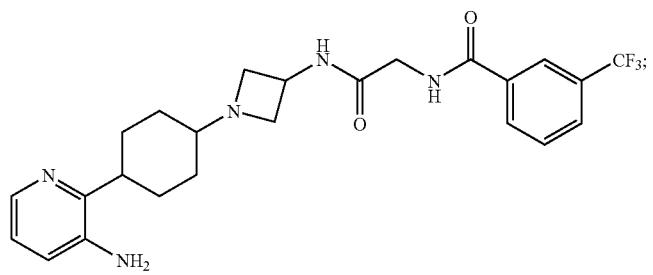
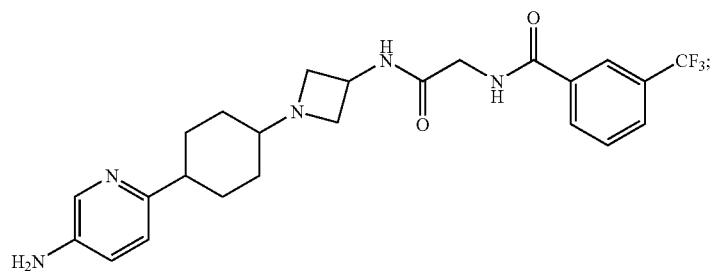
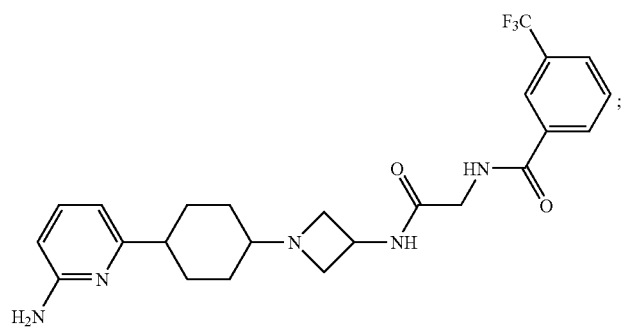
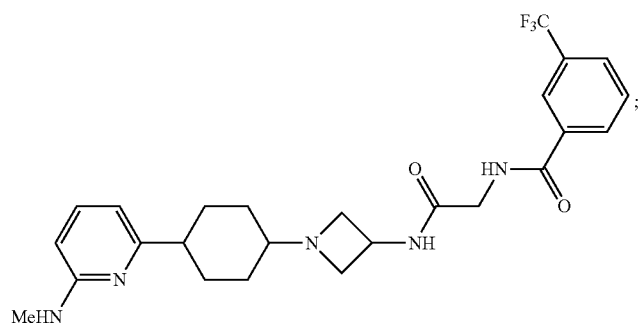

-continued
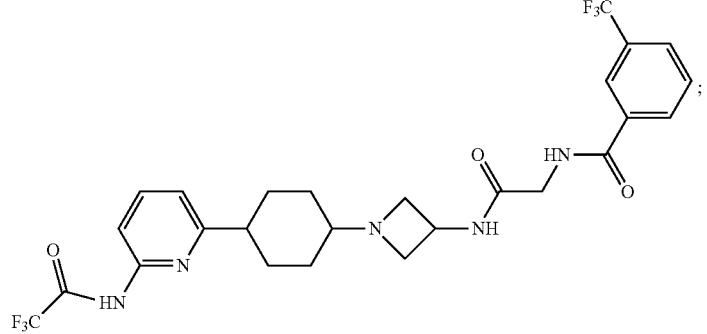
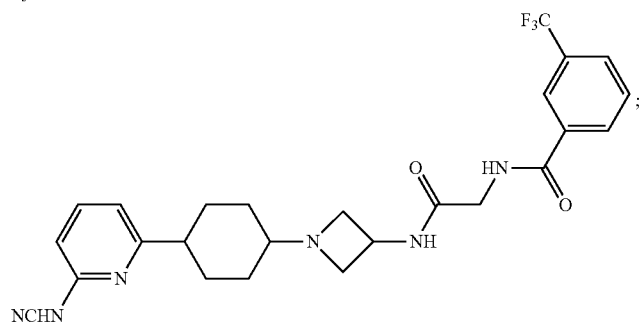
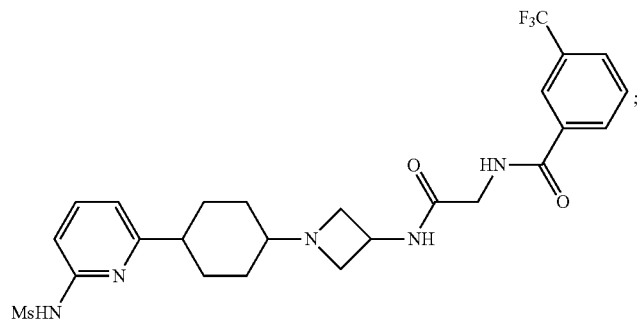
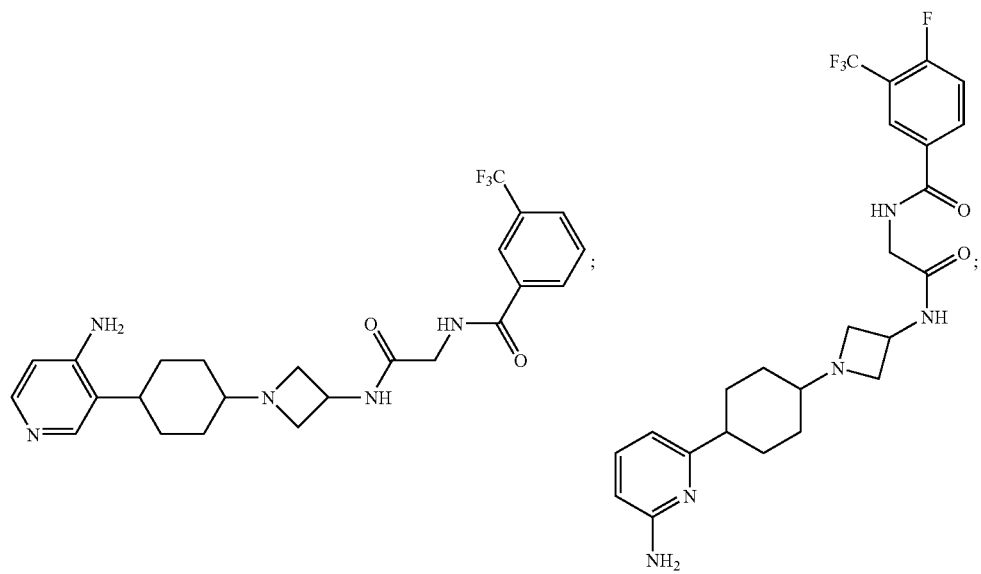

-continued
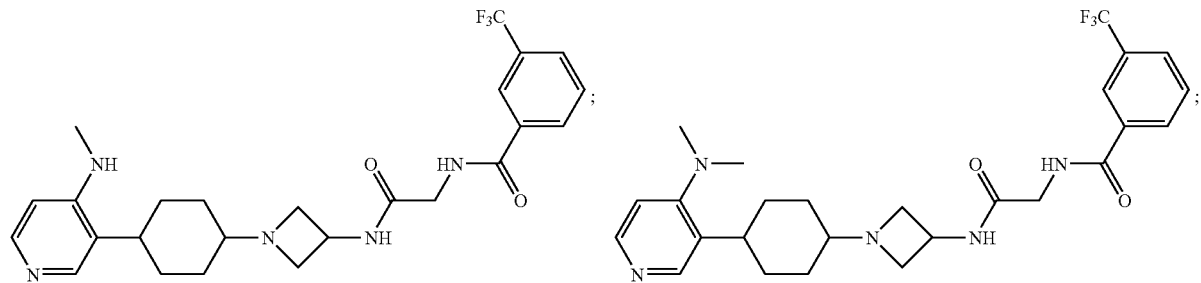
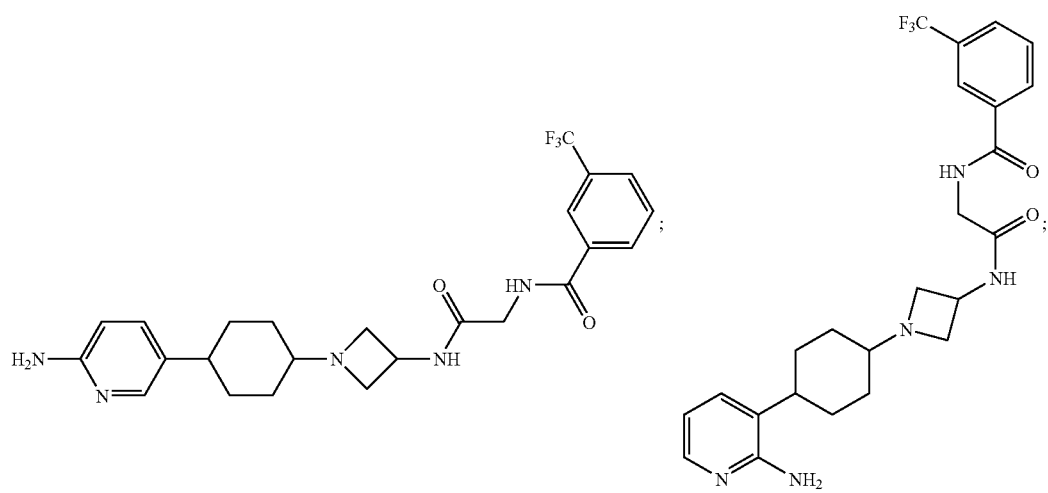
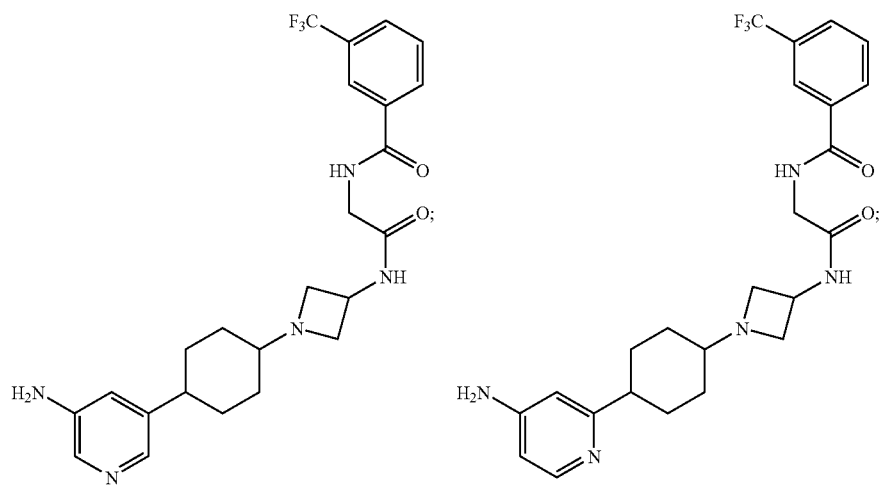

167
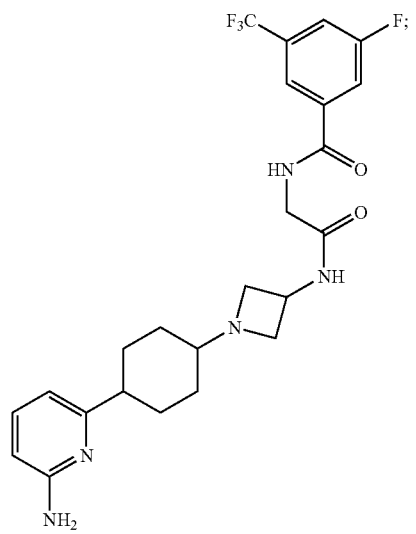
168
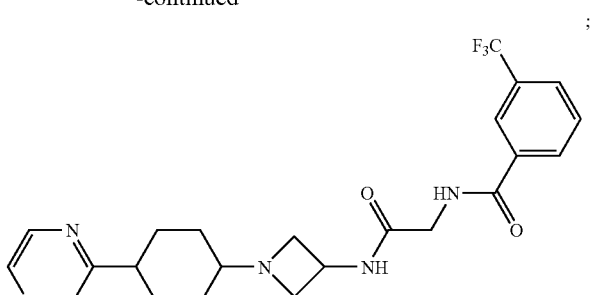
-continued
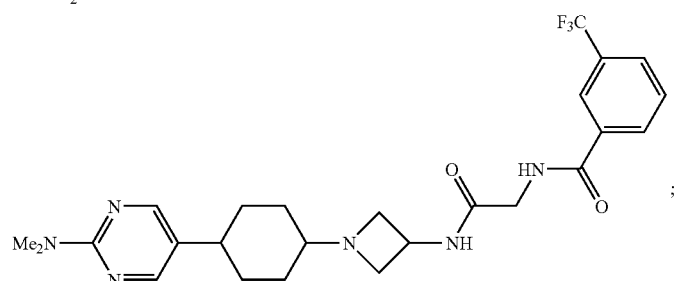
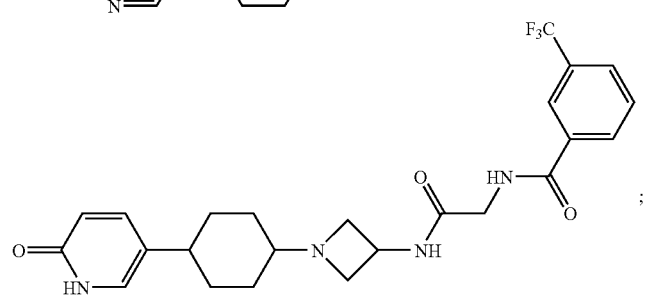
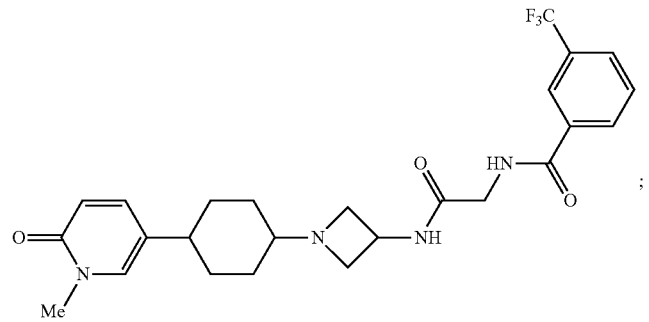
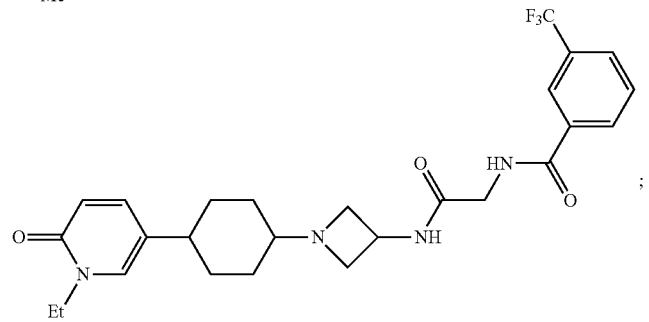

-continued
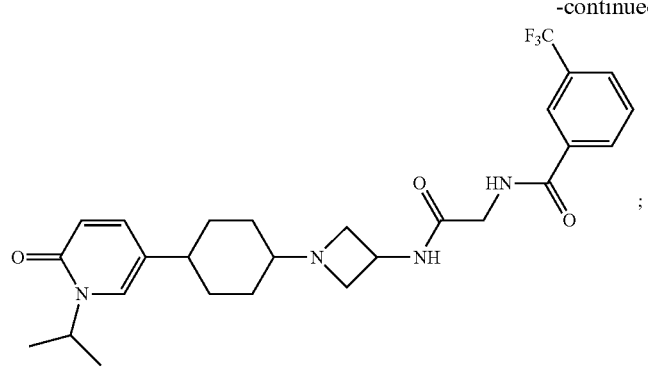
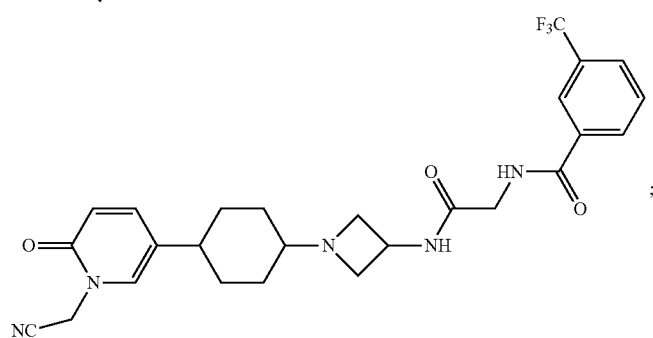
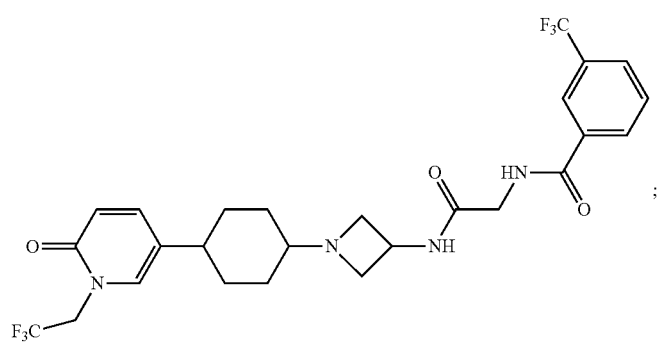
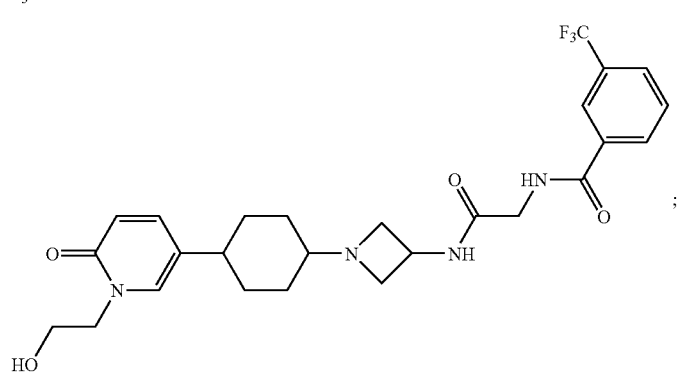
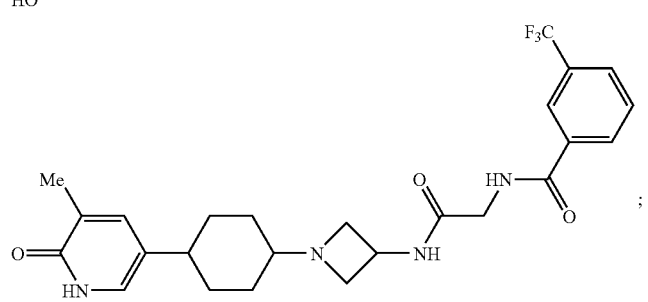

-continued
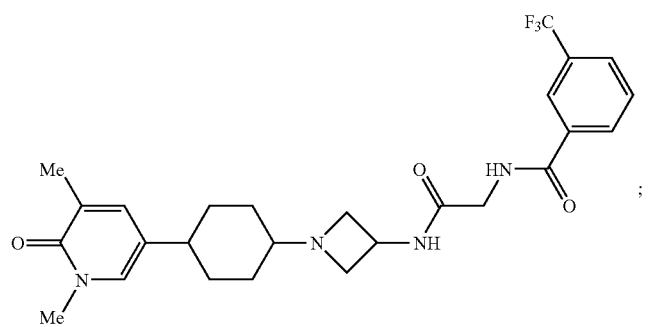
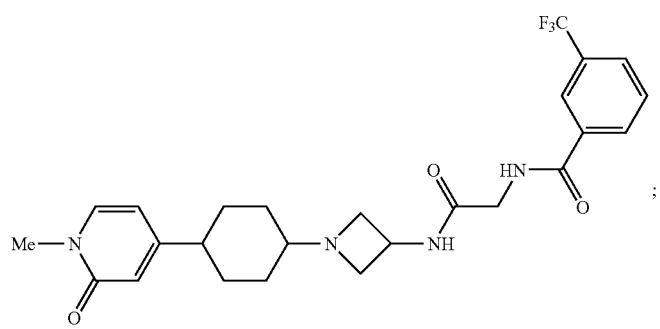
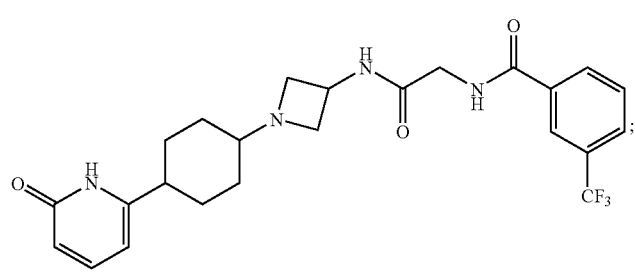
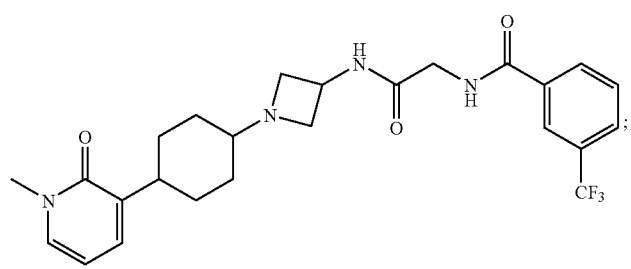
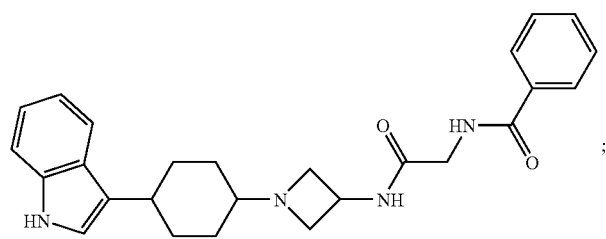
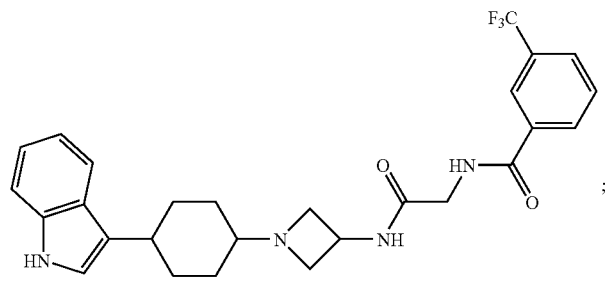

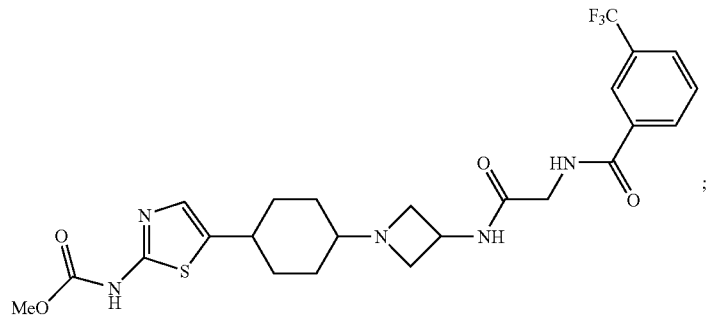
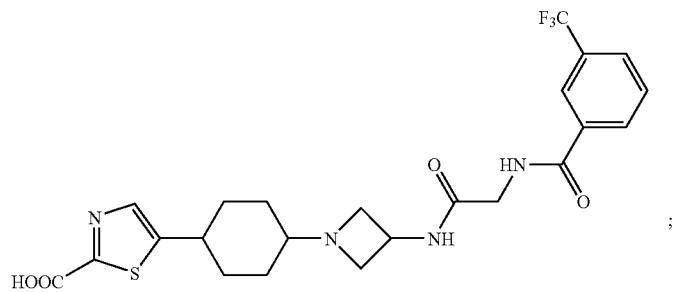
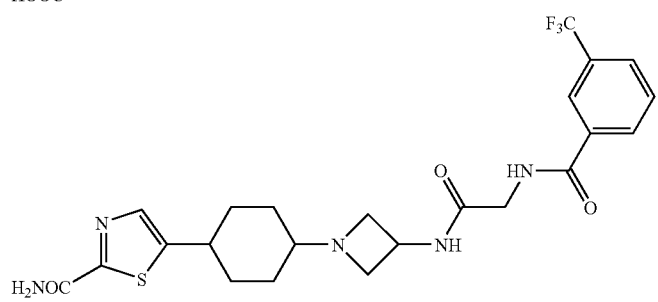
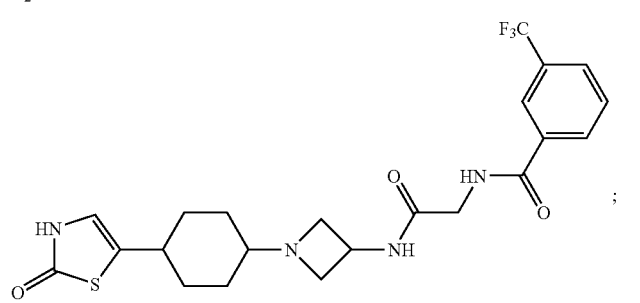
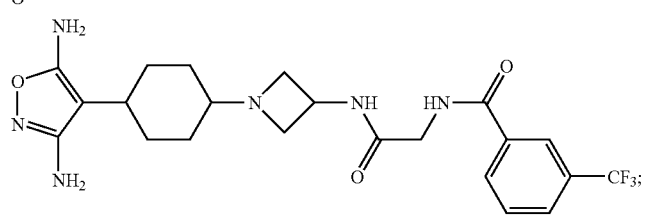
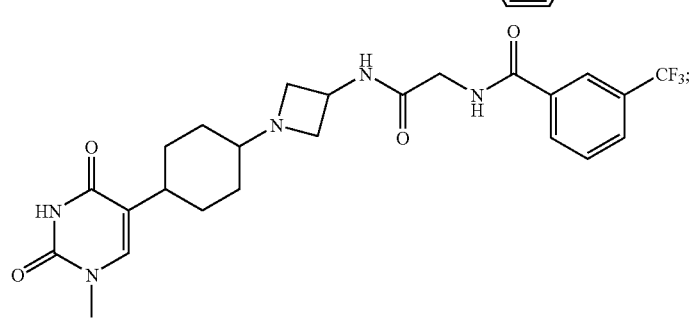

-continued
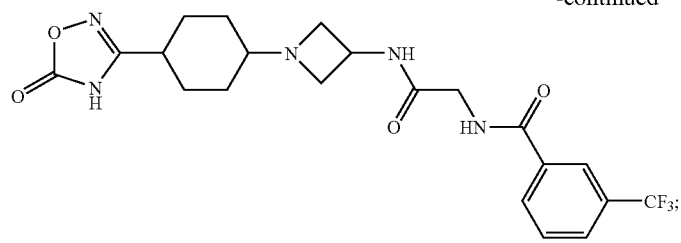
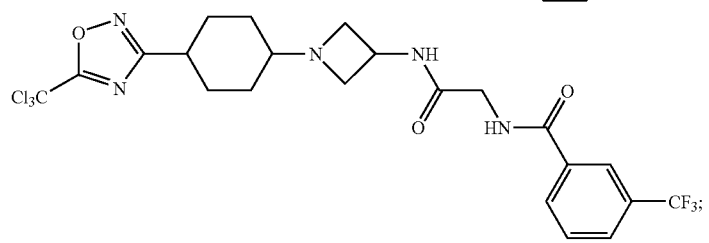
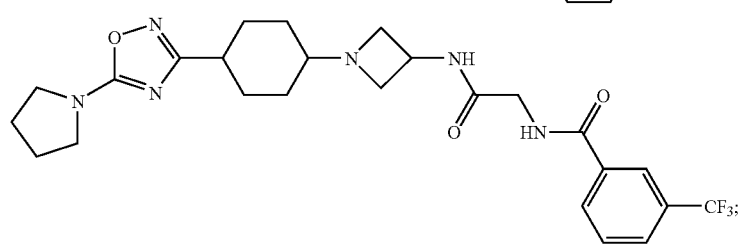
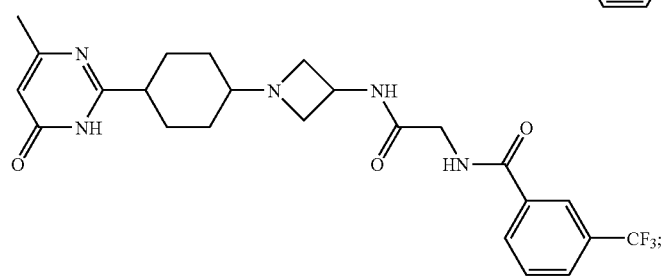
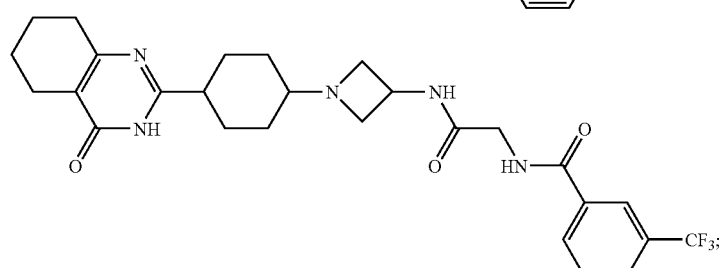
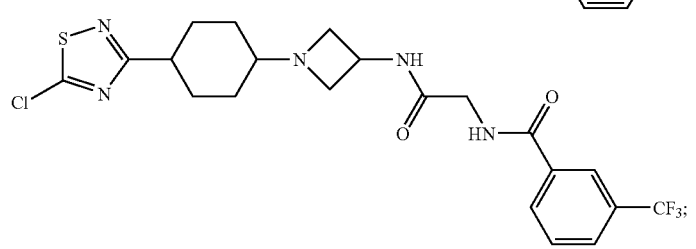
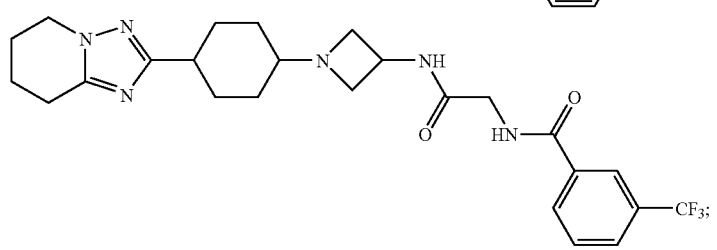

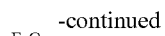
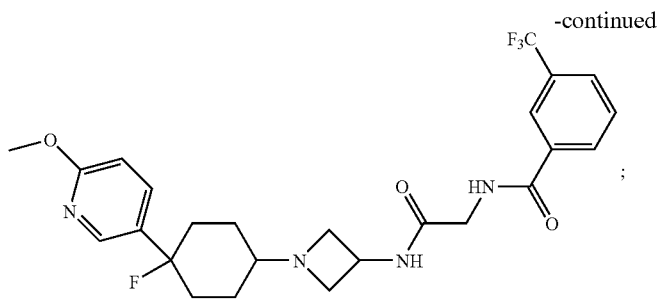
and hydrates, tautomers, and pharmaceutically acceptable salts thereof.
7. A compound of claim 6 selected from the group consisting of:
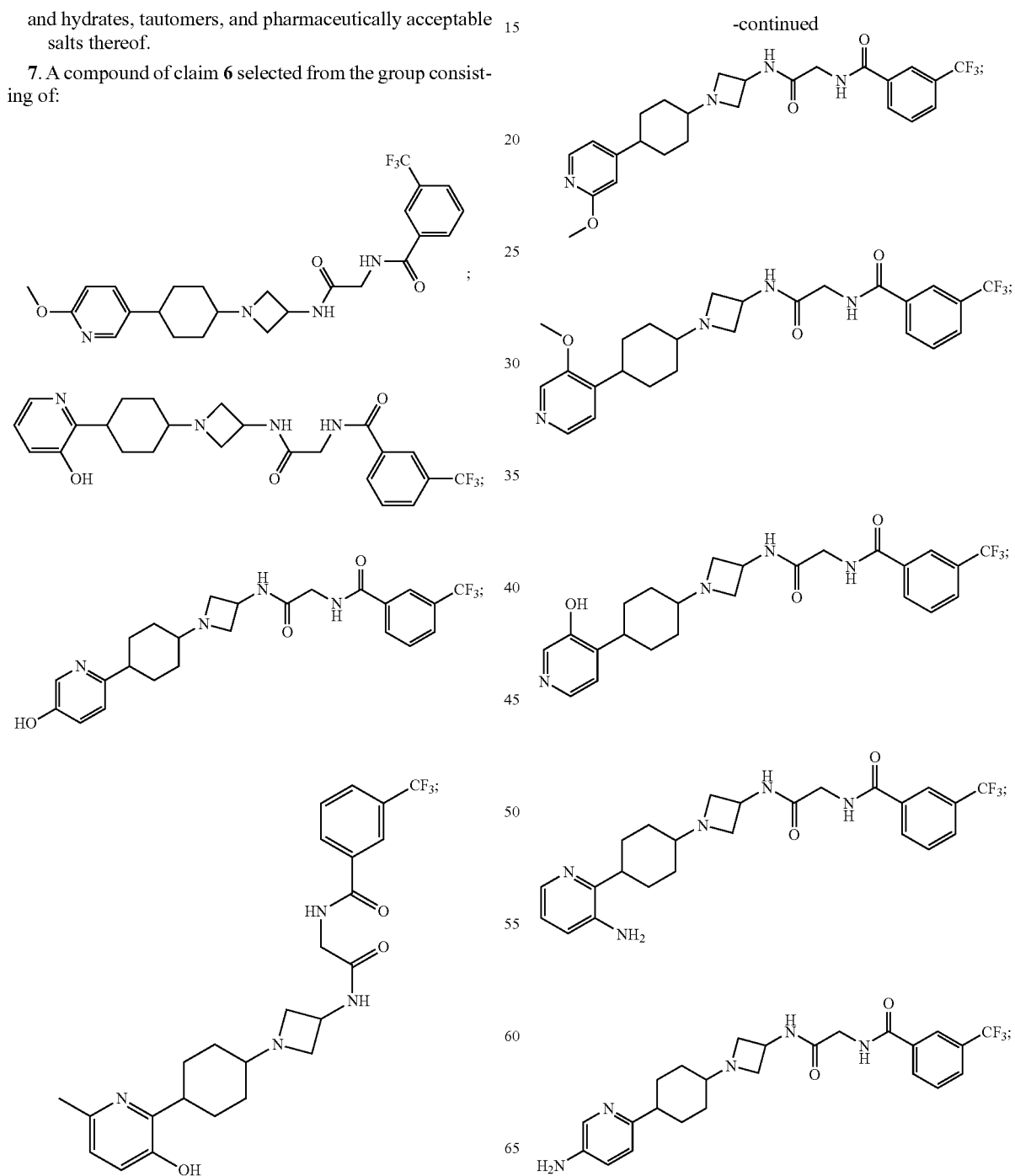

-continued

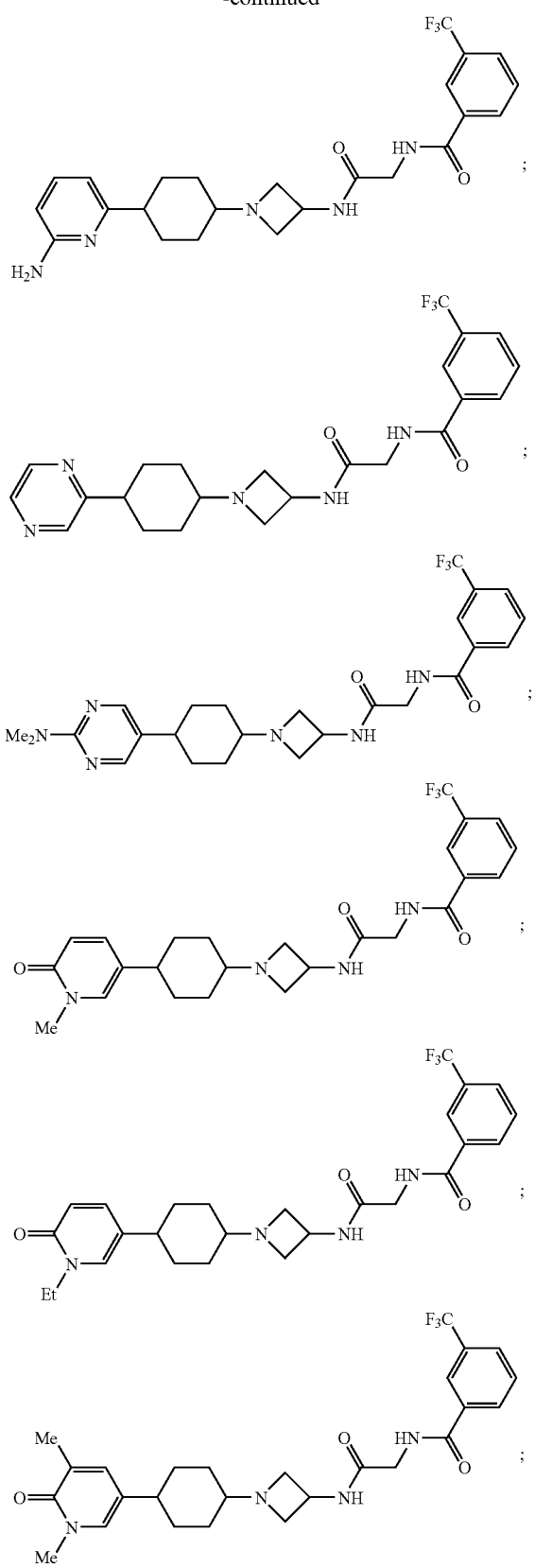

and hydrates, tautomers, and pharmaceutically acceptable salts thereof.

8. A compound of claim 7, which is

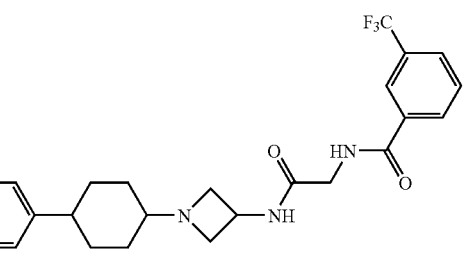

and hydrates, tautomers, and pharmaceutically acceptable salts thereof.

9. A pharmaceutical composition, comprising a compound of claim 1 and a pharmaceutically acceptable carrier.

10. A pharmaceutical composition made by mixing a compound of claim 1 and a pharmaceutically acceptable carrier.

11. A process for making a pharmaceutical composition comprising mixing a compound of claim 1 and a pharmaceutically acceptable carrier.

12. A process for the preparation of a compound of Formula (I) of claim 1, comprising reacting a compound of Formula (V)

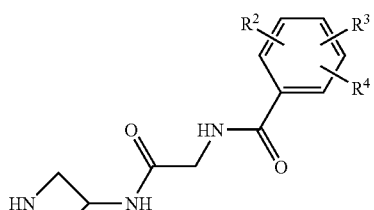

with a compound of Formula (VI)

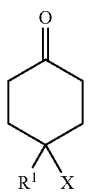

in the presence of a reducing agent to provide the compound of Formula (I).

13. A product made by the process of claim 12.

14. A process for the preparation of a compound of Formula (I) of claim 1, comprising reacting a compound of Formula (XIII)

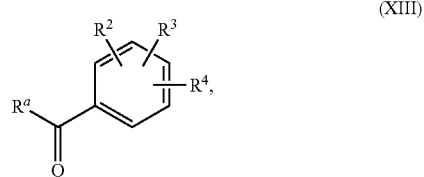

(XIII)

where $R_a$ is OH or Cl, with

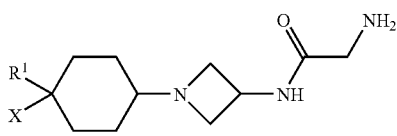

in the presence of HOBt/EDCI or $Et_3N$ to provide the compound of Formula (I).

15. A product made by the process of claim 14.

16. A method of treating a disorder or disease selected from the group consisting of type II diabetes, diabetic complications, diabetic nephropathy, diabetic retinopathy, diabetic retinitis, obesity, asthma, and allergic asthma, comprising administering to a subject in need thereof a therapeutically effective amount of a compound of claim 1.

17. A method of treating a disorder or disease selected from the group consisting of type II diabetes, obesity, and asthma, comprising administering to a subject in need thereof a therapeutically effective amount of a compound of claim 1.

* * * * *